US011897956B2

(12) United States Patent
Blanusa et al.

(10) Patent No.: US 11,897,956 B2
(45) Date of Patent: Feb. 13, 2024

(54) ANTI-ILT4 ANTIBODIES AND ANTIGEN-BINDING FRAGMENTS

(71) Applicants: Merck Sharp & Dohme LLC, Rahway, NJ (US); Agenus Inc., Lexington, MA (US)

(72) Inventors: Milan Blanusa, Jena (DE); Barbara Joyce-Shaikh, San Jose, CA (US); Andrea Claudia Schuster, Jena (DE); Kornelia Schultze, Jena (DE); Luis A. Zuniga, Mountain View, CA (US)

(73) Assignees: Merck Sharp & Dohme LLC, Rahway, NJ (US); Agenus Inc., Lexington, MS (US)

( * ) Notice: Subject to any disclaimer, the term of this patent is extended or adjusted under 35 U.S.C. 154(b) by 264 days.

(21) Appl. No.: 17/338,566

(22) Filed: Jun. 3, 2021

(65) Prior Publication Data
US 2022/0002403 A1     Jan. 6, 2022

Related U.S. Application Data

(62) Division of application No. 15/945,779, filed on Apr. 5, 2018, now Pat. No. 11,053,315.

(60) Provisional application No. 62/483,019, filed on Apr. 7, 2017.

(51) Int. Cl.
    C07K 16/28     (2006.01)
    A61P 35/00     (2006.01)
    A61K 39/00     (2006.01)

(52) U.S. Cl.
    CPC .......... *C07K 16/2803* (2013.01); *A61P 35/00* (2018.01); *C07K 16/2818* (2013.01); *C07K 16/2896* (2013.01); *A61K 2039/505* (2013.01); *C07K 2317/21* (2013.01); *C07K 2317/33* (2013.01); *C07K 2317/56* (2013.01); *C07K 2317/565* (2013.01); *C07K 2317/76* (2013.01); *C07K 2317/92* (2013.01)

(58) Field of Classification Search
    None
    See application file for complete search history.

(56) References Cited

U.S. PATENT DOCUMENTS

| | | | |
|---|---|---|---|
| 4,439,196 A | 3/1984 | Higuchi |
| 4,447,224 A | 5/1984 | DeCant, Jr. et al. |
| 4,447,233 A | 5/1984 | Mayfield |
| 4,487,603 A | 12/1984 | Harris |
| 4,596,556 A | 6/1986 | Morrow et al. |
| 4,790,824 A | 12/1988 | Morrow et al. |
| 4,816,567 A | 3/1989 | Cabilly et al. |
| 4,941,880 A | 7/1990 | Burns |
| 5,064,413 A | 11/1991 | McKinnon et al. |
| 5,312,335 A | 5/1994 | McKinnon et al. |
| 5,383,851 A | 1/1995 | McKinnon, Jr. et al. |
| 5,399,163 A | 3/1995 | Peterson et al. |
| 5,624,821 A | 4/1997 | Winter et al. |
| 5,648,260 A | 7/1997 | Winter et al. |
| 5,677,425 A | 10/1997 | Bodmer et al. |
| 5,714,350 A | 2/1998 | Co et al. |
| 5,869,046 A | 2/1999 | Presta et al. |
| 6,096,002 A | 8/2000 | Landau |
| 6,121,022 A | 9/2000 | Presta et al. |
| 6,165,745 A | 12/2000 | Ward et al. |
| 6,194,551 B1 | 2/2001 | Idusogie et al. |
| 6,277,375 B1 | 8/2001 | Ward |
| 6,350,861 B1 | 2/2002 | Co et al. |
| 6,620,135 B1 | 9/2003 | Weston et al. |
| 6,946,292 B2 | 9/2005 | Kanda et al. |
| 6,998,267 B1 | 2/2006 | Seki et al. |
| 7,029,872 B2 | 4/2006 | Gerngross |
| 7,214,775 B2 | 5/2007 | Hanai et al. |
| 7,388,081 B2 | 6/2008 | Seki et al. |
| 7,449,308 B2 | 11/2008 | Gerngross et al. |
| 7,632,983 B2 | 12/2009 | Dickey et al. |
| 7,795,002 B2 | 9/2010 | Davidson et al. |
| 9,970,007 B2 | 5/2018 | Chau |
| 9,987,314 B2 | 6/2018 | Champion et al. |
| 10,000,554 B2 | 6/2018 | Sekiguchi et al. |
| 10,005,845 B2 | 6/2018 | Loustau et al. |
| 2004/0110704 A1 | 6/2004 | Yamane et al. |
| 2007/0179086 A1 | 8/2007 | Gliniak et al. |

FOREIGN PATENT DOCUMENTS

| | | |
|---|---|---|
| EP | 0154316 A2 | 9/1985 |
| EP | 0401384 A1 | 12/1990 |
| EP | 1176195 A1 | 4/2000 |
| EP | 2295588 A1 | 3/2011 |
| EP | 3144389 B1 | 5/2018 |
| WO | 199429351 A2 | 12/1994 |
| WO | 199848017 A1 | 10/1998 |

(Continued)

OTHER PUBLICATIONS

Rouet, 2015, J. Biol. Chem. vol. 292: 11905-11917.*
Frenzel, 2013, Front. Immunol. vol. 4: 1-20.*
Holt, 2003, Trends Biotech. vol. 21: 484-490.*
Wang, Chunyan et al., Preparation and Preliminary Identification of Monoclonal Antibody against Human ILT, Chin J Cell Mol Immunol, 2008, 238-239, 24(3).
Wang, Chunyan et al., Preparation and preliminary identification of monoclonal antibody against human ILT-4, Chin J Cell Mol Immunol, 2008, 238-239, 24(3).
Xu, H. et al., Research progress of ILT receptor in the mechanism of HLA-G involvement in immune tolerance, Chinese Bulletin of Life Sciences, 2012, 640-645, 24(7).
Xu, Hui-Hui et al., Roles of immunolglobulin-like transcript family receptors and HLA-G binding in immune tolerogenic regulation, Chinese Bulletin of Life Sciences, 2012, 640-645, 24(7).
U.S. Appl. No. 15/945,779, filed Apr. 5, 2018.

(Continued)

*Primary Examiner* — Amy E Juedes
(74) *Attorney, Agent, or Firm* — Nichole M. Valeyko; Alysia Finnegan

(57) ABSTRACT

The present invention provides antibodies and antigen-binding fragments thereof that bind to ILT4 (immunoglobulin-like transcript 4) and combinations thereof, e.g., with an anti-PD1 antibody. Also provided are methods of use thereof, for example, for treating or preventing cancer in a subject; and methods of making such antibodies and fragments.

18 Claims, 23 Drawing Sheets

Specification includes a Sequence Listing.

(56) References Cited

FOREIGN PATENT DOCUMENTS

| | | |
|---|---|---|
| WO | 199954342 A1 | 10/1999 |
| WO | 2003000199 A2 | 1/2003 |
| WO | 2003035835 A2 | 5/2003 |
| WO | 2003041650 A2 | 5/2003 |
| WO | 2003086310 A2 | 10/2003 |
| WO | 2005009465 A1 | 2/2005 |
| WO | 2005120571 A2 | 12/2005 |
| WO | 2006005772 A1 | 1/2006 |
| WO | 2006089231 A2 | 8/2006 |
| WO | 2007146968 A2 | 12/2007 |
| WO | 2008061019 | 5/2008 |
| WO | 2012151578 A1 | 11/2012 |
| WO | 2013043569 A1 | 3/2013 |
| WO | 2013066765 A1 | 5/2013 |
| WO | 2013181438 A2 | 12/2013 |
| WO | 2014006063 A2 | 1/2014 |
| WO | 2014164519 A1 | 10/2014 |
| WO | 2015179633 A1 | 11/2015 |
| WO | 2016028672 A1 | 2/2016 |
| WO | 2016044022 A1 | 3/2016 |
| WO | 2016111947 A2 | 7/2016 |
| WO | 2016127247 | 8/2016 |
| WO | 2016144728 A2 | 9/2016 |
| WO | 2017042816 | 3/2017 |
| WO | 2018013534 A1 | 1/2018 |
| WO | 2018022881 A2 | 2/2018 |
| WO | 2018027197 A1 | 2/2018 |
| WO | 2018035503 A1 | 2/2018 |
| WO | 2018035710 A1 | 3/2018 |
| WO | 2018039097 A1 | 3/2018 |
| WO | 2018061012 A1 | 4/2018 |
| WO | 2019126514 A2 | 6/2019 |
| WO | 2020014132 A2 | 1/2020 |

OTHER PUBLICATIONS

Agaugue et al., Role of HLA G in tumor escape through expansion of myeloid derived suppressor cells and cytokinic balance in favor of Th2 versus Th1 and Th17, Blood, 2011, pp. 7021-7031, 117.

Al-Lazikani et al., Standard conformations for the canocial structures of immunoglobulins, J. Mol. Biol., 1997, pp. 927-948, 273.

Allan et al., Tetrameric complexes of human histocompatibility leukocyte antigen HLA G bind to peripheral blood myelomonocytic cells, J. Exp. Med., 1999, No. 7, pp. 1149-1155, 189.

Angal et al., A Single Amino Acid Substitution Abolishes the Heterogeneity of Chimeric Mouse/Human (IgG4) Antibody, Molecular Immunology, 1993, pp. 105-108, vol. 30(1).

Apps et al., A homodimeric complex of HLA G on normal trophoblast cells modulates antigen presenting cells via LILRB1, Eur. J. Immunol., 2007, Section 7, pp. 1924-1937, 37.

Baert et al., Influence of Immunogenicity on the long term efficacy of Infliximab in Crohns disease, New England Journal Med., 2003, pp. 601-608, 348.

Balermpas et al., Head and neck cancer relapse after chemoradiotherapy correlates with CD163 plus macrophages in primary tumour and CD11b plus myeloid cells in recurrences, Br. J. Cancer, 2014, Section 8, pp. 1509-1518, 111.

Beniaminovitz et al., Prevention of rejection in cardiac transplantation by blockade of the interleukin 2 receptor with a monoclonal antibody, New England Journal of Medicine, 2000, pp. 613-619, 342.

Bergamini et al., Downregulaiton of immunoglobulin like transcript ILT4 in patients with psoriatic arthritis, PLoS One, 2014, Section 3, p. e92018, 9.

Breous-Nystroma et al., Retrocyte display technology. Generation and screening of a high diversity cellular antibody library, Methods, 2014, Section 1, pp. 57-67, 65.

Bronkhorst et al., Detection of M2 macrophages in unveal melanoma and relation with survival, Invest. Opthamol. Vis. Sci., 2011, Section 2, pp. 643-650, 52.

Burt et al., Circulating and tumor infiltrating myeloid cells predict survival in human pleural mesothelioma, Cancer, 2011, Section 22, pp. 5234-5244, 117.

Choi, Byung-Kwon et al., Use of combinatorial genetic libraries to humanize N-linked glycosylation in the yeast *Pichia pastoris*, Proc Natl Acad Sci USA, 2003, 5022-5027, 100(9).

Chothia and Lesk et al, Canonical Structures for the Hypervariable Regions of Immunoglobins, J. Mol. Biol., 1987, 901-917, 196.

Chothia, Cyrus et al., Conformations of immunoglobulin hypervariable regions, Nature, 1989, 878-883, 342.

Clackson et al., Making Antibody Fragments Using Phage Display Libraries, Nature, 1991, pp. 624-628, vol. 352.

Colonna et al., Cutting edge human myelomonocyte cells express an inhibitory receptor for classical and nonclassical MHC class 1 molecules, J. Immunol., 1998, pp. 3096-3100, 160.

Curigliano et al., Molecular Pathways Human Leukocyte Antigen G HLA G, Clin. Cancer Research, 2013, No. 20, pp. 5564-5571, 19.

Dannenmann et al., Tumor associated macrophages subvert T cell function and correlate with reduced survival in clear cell renal cell carcinoma, Oncoimmunology, 2013, Section 3, p. e23562, 2.

David, Protein iodination with solid state lactoperoxidase, Biochemistry, 1974, p. 1014, 13.

Deng et al., A motif in LILRB2 critical for Angptl 2 binding and activation, Blood, 2014, Section 6, pp. 924-935, 124.

Fujiwara et al., Macrophage infiltration predicts a poor prognosis for human ewing sarcoma, Am. J. Pathol., 2011, Section 3, pp. 1157-1170, 179.

Ghosh et al., Natalizumab for active Crohns disease, New England J. Med., 2003, pp. 24-32, 348.

Gonzales et al., The immunosuppressive molecule HLA G and its clinical implications, Critical Reviews in Clinical Laboratory Sciences, 2012, No. 3, pp. 63-84, 49.

Hamilton, Stephen R. et al., Glycosylation engineering in yeast: the advent of fully humanized yeast, Current Opinion in Biotechnology, 2007, 387-392, 18.

Hamilton, Stephen R. et al., Humanization of Yeast to Produce Complex Terminally Sialylated Glycoproteins, Science, 2006, 1441-1443, 313.

Hamilton, Stephen R. et al., Production of Complex Human Glycoproteins in Yeast, Science, 2003, 1244-1246, 301.

Human LILRB2/CD85d/ILT4 Antibody. Revision Oct. 23, 2019The whole documentCitation not enclosed due to copyright restrictions. A copy may be obtained from the URL athttps://resources.rndsystems.com/pdfs/datasheets/af2078.pdf?v=20210221 (2 pages).

Hunter et al., Preparation of iodine 131 labelled human growth hormone of high specific activity, Nature, 1962, p. 945, 144.

Kabat, The Structural Basis of Antibody Complementarity, Adv. Prot. Chem., 1978, 1-75, 32.

Kabat, Unusual Distributions of Amino Acids in Complementarity-determining (Hypervriable) Segment of Heavy and Light Chains of Immunoglobulins and Their Possible Roles in Specificity of Antibody-combining Sites, J. Biol. Chem., 1977, 6609-6616, 252.

Kohler et al., Continuous Cultures of Fused Cells Secreting Antibody of Predefined Specificity, Nature, 1975, pp. 495-497, vol. 256.

Lee et al., Prolonged circulating lives of single chain Fv proteins conjugated with polyethylene glycol. A comparison of conjugation chemistries and compounds, Bioconj. Chem., 1999, pp. 973-981, 10.

Li, Huijuan et al., Optimization of humanized IgGs in glycoengineered Pichia pastoris, Nature Biotechnology, 2006, 210-215, 24(2).

Li, Y. et al., A Mini-Review for Cancer Immunotherapy: Molecular Understanding of PD-1/PD-L1 Pathway & Translational Blockade of Immune Checkpoints, Int J Mol Sci, 2016, 1-22, vol. 17, No. 7(1151).

Liang et al., Mobilizing dendritic cells for tolerance by engagement of immune inhibitory receptors for HLA G, Hum. Immunol., 2003, Section 11, pp. 1025-1032, 64.

Liang et al., Modulation of dendritic cell differentiation by HLA G and ILT4 requires the IL6 STAT3 signaling pathway, PNAS, 2008, No. 24, pp. 8357-8362, 105.

Lin et al., Human leukocyte antigen G HLA G expression in cancers roles in immune evasion metastasis and target for therapy, Molecular Medicine, 2015, pp. 782-791, 21.

(56) References Cited

OTHER PUBLICATIONS

Lin et al., Multiple steps of HLA G in ovarian carcinoma metastasis. Alter NK cytotoxicity and induce matrix metalloproteinase 15 MMP 15 expression, Hum. Immunol., 2013, pp. 439-446, 74.

Lipsky et al., Infliximab and methotrexate in the treatment of rheumatoid arthritis, New England Journal of Medicine, 2000, pp. 1594-1602, 343.

Loumange et al., In vivo evidence that secretion of HLA G by immunogenic tumor cells allow their evasion from immunosurveillance, International Journal of Cancer, 2014, pp. 2107-2117, 135.

Manavalan et al., High expression of ILT3 and ILT4 is a general feature of tolerogenic dendritic cells, Transplant Immunol., 2003, Sections 3-4, pp. 245-258, 11.

Marks et al., By passing Immunization, J. Mol. Biol., 1991, pp. 581-597, 222.

Milgrom et al., Treatment of allergic asthma with monoclonal anti IgE antibody, New England Journal Med., 1999, pp. 1966-1973, 341.

Morandi et al., The emerging role of soluble HLA G in the control of chemotaxis, Cytokine and growth factor reviews, 2014, pp. 327-335, 25.

Morea et al., Antibody Modeling: Implications for Engineering and Design, Methods, 2000, pp. 267-279, vol. 20.

Nett, Juergen H. et al., A combinatorial genetic library approach to target heterologous glycosylation enzymes to the endoplasmic reticulum or the Golgi apparatus of Pichia pastoris, Yeast, 2011, 237-252, 28.

Nygren et al., Conjugation of Horseradish Peroxidase to Fab Fragments with Different Homobifunctional and Heterobifunctional cross linking reagents, The Journal of Histochemistry and Cytochem., 1982, No. 5, pp. 407-412, 30.

Pain et al., Preparation of protein A peroxidase monoconjugate using a heterobifunctional reagent and its use in enzyme immunoassays, J. Immunol. Meth., 1981, p. 219, 40.

Presta, Leonard G. et al., Selection, design, and engineering of therapeutic antibodies, J. Allergy Clin. Immunol., 2005, 731-736, 116(4).

Ristich et al., Tolerization of dendritic cells by HLA G, Eur. J. Immunol., 2005, pp. 1133-1142, 35.

Rouas-Freiss et al., The dual role of HLA G in cancer, J. Immunol. Res., 2014, p. 359748, 1.

Schuurman et al., The inter-heavy chain disulfide bonds of IgG4 are in equilibrium with intra-chain disulfide bonds, Molecular Immunology, 2001, pp. 1-8. vol. 38.

Shields et al., Lack of fucose on human IgG1 N linked oligosaccharide improves binding to human Fc gamma RIII and antibody dependent cellular toxicity, J. Biol. Chem., 2002, pp. 26733-26740, 277.

Shields, Robert L. et al., High Resolution Mapping of the Bidning Site on Human IgG1 for FcγRI, FcγRII, FcγRIII, and ReRn and Design of IgG1 Variants with Improved Binding to the FcγR*, The Journal of Biological Chemistry, 2001, 6591-6604, 276(9).

Shinkawa et al., The absence of fucose but not the presence of galactose or bisecting N acetylglucosamine of human IgG1 complex type oligosaccharide shows the critical role of enhancing antibody dependent cellular cytotoxicity, J. Biol. Chem., 2003, pp. 3466-3473, 278.

Shiroishi et al., Structural basis for recognition of the nonclassical MHC molecule HLA G by the leukocyte IG like receptor B2, PNAS USA, 2006, No. 44, pp. 16412-16417, 103.

Silva, J-P et al., The S228P mutation prevents in vivo and in vitro IgG4 Fab-arm exchange as demonstrated using a combination of novel quantitative immunoassays and physiological matrix preparation, J Biol Chem, 2015, 5462-5469, vol. 290, No. 9.

Slamon et al., Use of chemotherapy plus a monoclonal antibody against HER2 for metastatic breast cancer that overexpresses HER2, New England J. Med., 2001, pp. 783-792, 344.

Steidl et al., Tumor associated macrophages and survival in classic hodgkins lymphoma, N. Engl. J. Med., 2010, pp. 875-885, 362.

Tarentino et al., The isolation and structure of the core oligosaccharide sequences of IgM, Biochem., 1975, pp. 5516-5523, 14.

Umana et al., Engineered glycoforms of an antineuroblastoma IgG1 with optimized antibody dependent cellular cytotoxic activity, Nature Biotechnology, 1999, pp. 176-180, 17.

Watson et al., The fine structure of bacterial and phage genes, Molecular biology of the gene, 1987, pp. 224-238, 4.

Wen et al., Polyethylene glycol conjugated anti EGF receptor antibody C225 with radiometal chelator attached to teh termini of polymer chains, Bioconj. Chem., 2001, pp. 545-553, 12.

Wilcox et al., Crystal structure of LIR2 ILT4 at 1.8A differences from LIR I ILT2 in regions implicated in teh binding of the human cytomegalovirus class I MHC homolog UL18, BMC Structural Biology, 2002, pp. 1-9, 2.

Wu et al., Multiplex bead based immunoassay for the free soluble forms of the HLA G receptors ILT2 and ILT4, Human Immunology, 2016, No. 9, pp. 720-726, 77.

Yamane-Ohnuki et al., Establishment of FUT 8 knockout Chinese hamster ovary cells. An ideal host cell line for producing completely defucosylated antibodies with enhanced antibody dependent cellular cytotoxicity, Biotechno.l Bioeng., 2004, pp. 614-622, 87.

Zha, D., Glycoengineered Pichia-Based Expression of Monoclonal Antibodies, Methods Mol. Biol., 2013, pp. 31-43, 988.

Zha, D., Glycoengineered Yeast as an Alternative Monoclonal Antibody Discovery and Production Platform, Glycosylation, InTech, 2017, 420-436, Chapter 18.

Zhang et al., Co expression of ILT4 HLA in human non small cell lung cancer correlates with poor prognosis and ILT4 HLAG interaction activates ERK signaling, Tumour Biol., 2016, pp. 11187-11198, 37.

Zhang et al., Prognostic significance as tumor associated macrophages in solid tumor. A meta analysis of the literature, PLoS One, 2012, Section 12, p. e50946, 7.

Zheng et al., Inhibitory receptors bind ANGPTLs and support blood stem cells and leukemia development, Nature, 2012, pp. 656-660, 485.

Rudikoff, S et al., Single amino acid substitution altering antigen-binding specificity, PNAS, 1982, pp. 1979-1983, 79.

Tamura, Midori et al., Structural Correlates of an Anticarcinoma Antibody: Identification of Specificity-Determining Residues (SDRs) and Development of a Minimally Immunogenic Antibody Variant by Retention of SDRs Only, Journal of Immunology, 2000, 1432-1441, 164(3).

Wang, Linlin, Expression of ILT4 in breast cancer and its clinical significance, Chinese Masters' Theses Full text Database, Medicine and Health Science, 2009, 3 pages (Abstract only), No. 4, E072-272 (Abstract).

* cited by examiner

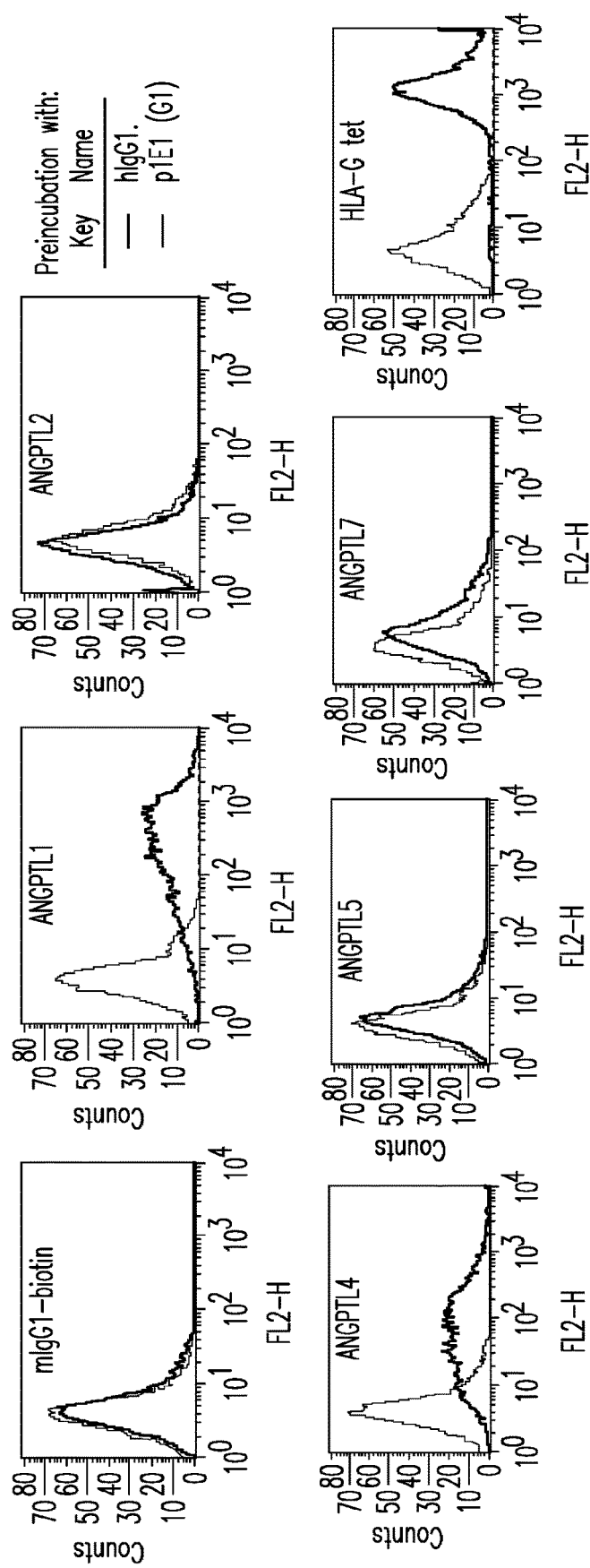
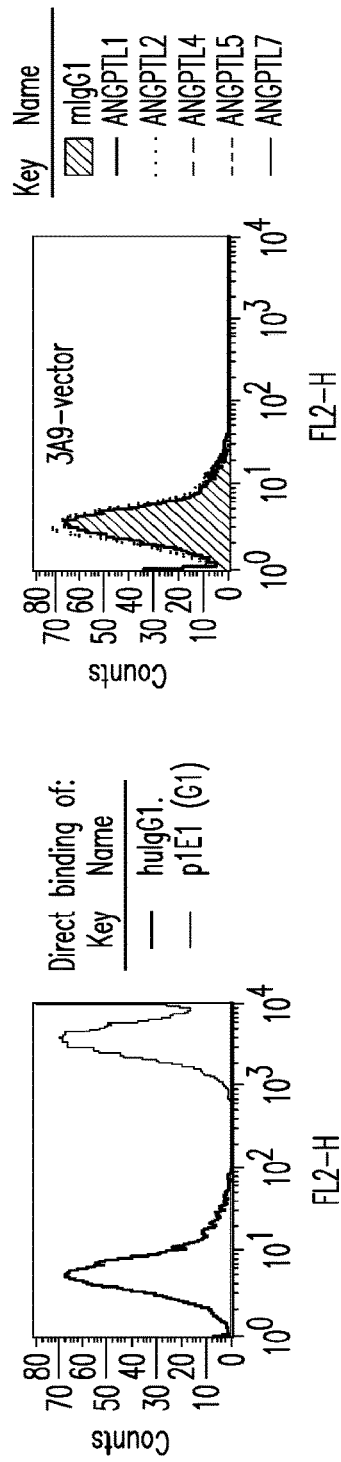
FIG.5A
FIG.5B
FIG.5C

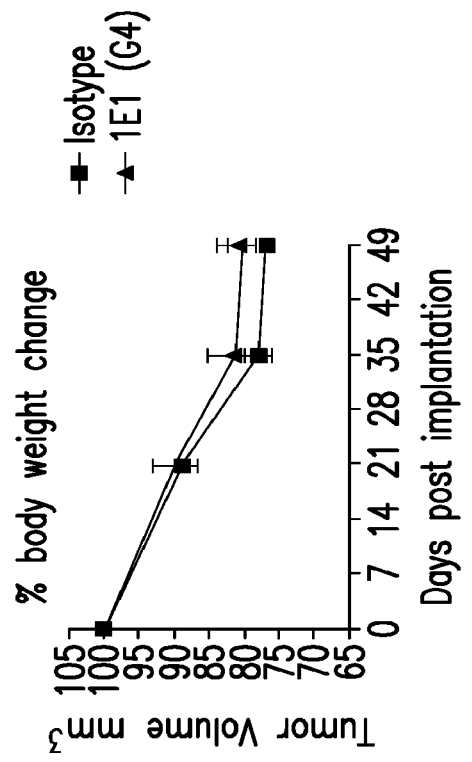
FIG.12A
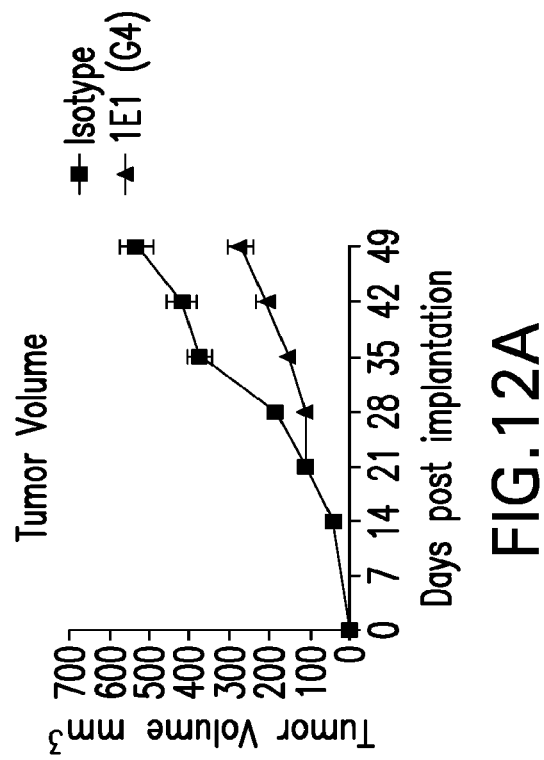
FIG.12C
FIG.12B
FIG.12D

```
SEQUENCE LISTING

<160> NUMBER OF SEQ ID NOS: 90

<210> SEQ ID NO 1
<211> LENGTH: 448
<212> TYPE: PRT
<213> ORGANISM: Artificial Sequence
<220> FEATURE:
<223> OTHER INFORMATION: HC of 1E1 (Q1E)

<400> SEQUENCE: 1
```

-continued

Glu Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Leu Pro Thr Arg Trp Val Thr Thr Arg Tyr Phe Asp Leu Trp Gly
            100                 105                 110

Arg Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
                420                 425                 430

Leu His Asn His Tyr Thr Gln Lys Ser Leu Ser Leu Ser Leu Gly Lys
        435                 440                 445

<210> SEQ ID NO 2
<211> LENGTH: 448
<212> TYPE: PRT
<213> ORGANISM: Artificial Sequence
<220> FEATURE:
<223> OTHER INFORMATION: HC of 1E1 (Q1E, S54A)

<400> SEQUENCE: 2

Glu Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ala Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Leu Pro Thr Arg Trp Val Thr Thr Arg Tyr Phe Asp Leu Trp Gly
            100                 105                 110

Arg Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

```
Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445

<210> SEQ ID NO 3
<211> LENGTH: 217
<212> TYPE: PRT
<213> ORGANISM: Artificial Sequence
<220> FEATURE:
<223> OTHER INFORMATION: LC of 1E1 (Q1E)

<400> SEQUENCE: 3

Glu Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Val Ser Lys Ser Gly Ala Ser Ala Ser Leu Ala Ile Thr Gly Leu
65                  70                  75                  80

Gln Ala Glu Asp Glu Ala Asp Tyr Tyr Cys Gln Ser Phe Asp Asn Ser
                85                  90                  95

Leu Ser Ala Tyr Val Phe Gly Gly Gly Thr Gln Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215

<210> SEQ ID NO 4
<211> LENGTH: 217
<212> TYPE: PRT
<213> ORGANISM: Artificial Sequence
<220> FEATURE:
```

<223> OTHER INFORMATION: LC of 1E1 (Q1E, S54A)

<400> SEQUENCE: 4

Glu Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ala Asn Arg Pro Ser Gly Val Pro Asp Arg Phe
    50                  55                  60

Ser Val Ser Lys Ser Gly Ala Ser Ala Ser Leu Ala Ile Thr Gly Leu
65                  70                  75                  80

Gln Ala Glu Asp Glu Ala Asp Tyr Tyr Cys Gln Ser Phe Asp Asn Ser
                85                  90                  95

Leu Ser Ala Tyr Val Phe Gly Gly Gly Thr Gln Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215

<210> SEQ ID NO 5
<211> LENGTH: 217
<212> TYPE: PRT
<213> ORGANISM: Artificial Sequence
<220> FEATURE:
<223> OTHER INFORMATION: LC of 1E1 (Q1E, N53Q)

<400> SEQUENCE: 5

Glu Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Gln Ser Asn Arg Pro Ser Gly Val Pro Asp Arg Phe
    50                  55                  60

Ser Val Ser Lys Ser Gly Ala Ser Ala Ser Leu Ala Ile Thr Gly Leu
65                  70                  75                  80

Gln Ala Glu Asp Glu Ala Asp Tyr Tyr Cys Gln Ser Phe Asp Asn Ser
                85                  90                  95

Leu Ser Ala Tyr Val Phe Gly Gly Gly Thr Gln Leu Thr Val Leu Gly
            100                 105                 110

Gln Pro Lys Ala Ala Pro Ser Val Thr Leu Phe Pro Pro Ser Ser Glu
        115                 120                 125

```
Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
                180                 185                 190

His Arg Ser Tyr Ser Cys Gln Val Thr His Glu Gly Ser Thr Val Glu
            195                 200                 205

Lys Thr Val Ala Pro Thr Glu Cys Ser
    210                 215

<210> SEQ ID NO 6
<211> LENGTH: 217
<212> TYPE: PRT
<213> ORGANISM: Artificial Sequence
<220> FEATURE:
<223> OTHER INFORMATION: LC of 1E1 (Q1E, N53E)

<400> SEQUENCE: 6

Glu Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
                20                  25                  30

Tyr Asp Val His Trp Tyr Gln Gln Leu Pro Gly Thr Ala Pro Lys Leu
            35                  40                  45

Leu Ile Tyr Gly Glu Ser Asn Arg Pro Ser Gly Val Pro Asp Arg Phe
    50                  55                  60

Ser Val Ser Lys Ser Gly Ala Ser Ala Ser Leu Ala Ile Thr Gly Leu
65                  70                  75                  80

Gln Ala Glu Asp Glu Ala Asp Tyr Tyr Cys Gln Ser Phe Asp Asn Ser
                85                  90                  95

Leu Ser Ala Tyr Val Phe Gly Gly Gly Thr Gln Leu Thr Val Leu Gly
                100                 105                 110

Gln Pro Lys Ala Ala Pro Ser Val Thr Leu Phe Pro Pro Ser Ser Glu
            115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
                180                 185                 190

His Arg Ser Tyr Ser Cys Gln Val Thr His Glu Gly Ser Thr Val Glu
            195                 200                 205

Lys Thr Val Ala Pro Thr Glu Cys Ser
    210                 215

<210> SEQ ID NO 7
<211> LENGTH: 217
<212> TYPE: PRT
<213> ORGANISM: Artificial Sequence
<220> FEATURE:
<223> OTHER INFORMATION: LC of 1E1 (Q1E, N53D)
```

```
<400> SEQUENCE: 7

Glu Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asp Ser Asn Arg Pro Ser Gly Val Pro Asp Arg Phe
    50                  55                  60

Ser Val Ser Lys Ser Gly Ala Ser Ala Ser Leu Ala Ile Thr Gly Leu
65                  70                  75                  80

Gln Ala Glu Asp Glu Ala Asp Tyr Tyr Cys Gln Ser Phe Asp Asn Ser
                85                  90                  95

Leu Ser Ala Tyr Val Phe Gly Gly Gly Thr Gln Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
        210                 215

<210> SEQ ID NO 8
<211> LENGTH: 451
<212> TYPE: PRT
<213> ORGANISM: Artificial Sequence
<220> FEATURE:
<223> OTHER INFORMATION: HC of 2A6 (Q1E)

<400> SEQUENCE: 8

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Phe Asp Ser Ser Gly Trp Tyr Lys Gly Gly Ala Phe Asp
            100                 105                 110

Ile Trp Gly Gln Gly Thr Met Val Thr Val Ser Ser Ala Ser Thr Lys
        115                 120                 125

Gly Pro Ser Val Phe Pro Leu Ala Pro Cys Ser Arg Ser Thr Ser Glu
```

```
                130              135              140
Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Leu Gly Thr Lys Thr Tyr Thr Cys Asn
            195                 200                 205

Val Asp His Lys Pro Ser Asn Thr Lys Val Asp Lys Arg Val Glu Ser
    210                 215                 220

Lys Tyr Gly Pro Pro Cys Pro Pro Cys Pro Ala Pro Glu Phe Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser Gln
                260                 265                 270

Glu Asp Pro Glu Val Gln Phe Asn Trp Tyr Val Asp Gly Val Glu Val
            275                 280                 285

His Asn Ala Lys Thr Lys Pro Arg Glu Glu Gln Phe Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Gly Leu Pro Ser Ser Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Gln Glu Glu Met Thr Lys Asn Gln Val Ser
            355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Arg Leu Thr Val
                405                 410                 415

Asp Lys Ser Arg Trp Gln Glu Gly Asn Val Phe Ser Cys Ser Val Met
                420                 425                 430

His Glu Ala Leu His Asn His Tyr Thr Gln Lys Ser Leu Ser Leu Ser
            435                 440                 445

Leu Gly Lys
450

<210> SEQ ID NO 9
<211> LENGTH: 451
<212> TYPE: PRT
<213> ORGANISM: Artificial Sequence
<220> FEATURE:
<223> OTHER INFORMATION: HC of 2A6 (Q1E, S102A, M119L)

<400> SEQUENCE: 9

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
```

```
                35                  40                  45
Gly Gly Ile Ile Pro Ile Phe Gly Thr Ala Asn Tyr Ala Gln Lys Phe
 50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Tyr Phe Asp Ala Ser Gly Trp Tyr Lys Gly Gly Ala Phe Asp
                100                 105                 110

Ile Trp Gly Gln Gly Thr Leu Val Thr Val Ser Ser Ala Ser Thr Lys
                115                 120                 125

Gly Pro Ser Val Phe Pro Leu Ala Pro Cys Ser Arg Ser Thr Ser Glu
130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
                180                 185                 190

Val Thr Val Pro Ser Ser Ser Leu Gly Thr Lys Thr Tyr Thr Cys Asn
                195                 200                 205

Val Asp His Lys Pro Ser Asn Thr Lys Val Asp Lys Arg Val Glu Ser
210                 215                 220

Lys Tyr Gly Pro Pro Cys Pro Pro Cys Pro Ala Pro Glu Phe Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser Gln
                260                 265                 270

Glu Asp Pro Glu Val Gln Phe Asn Trp Tyr Val Asp Gly Val Glu Val
                275                 280                 285

His Asn Ala Lys Thr Lys Pro Arg Glu Glu Gln Phe Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Gly Leu Pro Ser Ser Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Gln Glu Glu Met Thr Lys Asn Gln Val Ser
                355                 360                 365

Leu Thr Cys Leu Val Lys Gly Phe Tyr Pro Ser Asp Ile Ala Val Glu
                370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Arg Leu Thr Val
                405                 410                 415

Asp Lys Ser Arg Trp Gln Glu Gly Asn Val Phe Ser Cys Ser Val Met
                420                 425                 430

His Glu Ala Leu His Asn His Tyr Thr Gln Lys Ser Leu Ser Leu Ser
                435                 440                 445

Leu Gly Lys
450
```

<210> SEQ ID NO 10
<211> LENGTH: 451
<212> TYPE: PRT
<213> ORGANISM: Artificial Sequence
<220> FEATURE:
<223> OTHER INFORMATION: HC of 2A6 (Q1E, D101S, M119L)

<400> SEQUENCE: 10

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Phe Ser Ser Gly Trp Tyr Lys Gly Gly Ala Phe Asp
                100                 105                 110

Ile Trp Gly Gln Gly Thr Leu Val Thr Val Ser Ser Ala Ser Thr Lys
            115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Lys Thr Tyr Thr Cys Asn
        195                 200                 205

Val Asp His Lys Pro Ser Asn Thr Lys Val Asp Lys Arg Val Glu Ser
    210                 215                 220

Lys Tyr Gly Pro Pro Cys Pro Pro Cys Pro Ala Pro Glu Phe Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser Gln
            260                 265                 270

Glu Asp Pro Glu Val Gln Phe Asn Trp Tyr Val Asp Gly Val Glu Val
        275                 280                 285

His Asn Ala Lys Thr Lys Pro Arg Glu Glu Gln Phe Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Gly Leu Pro Ser Ser Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Gln Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Arg Leu Thr Val
            405                 410                 415

Asp Lys Ser Arg Trp Gln Glu Gly Asn Val Phe Ser Cys Ser Val Met
            420                 425                 430

His Glu Ala Leu His Asn His Tyr Thr Gln Lys Ser Leu Ser Leu Ser
        435                 440                 445

Leu Gly Lys
    450

<210> SEQ ID NO 11
<211> LENGTH: 221
<212> TYPE: PRT
<213> ORGANISM: Artificial Sequence
<220> FEATURE:
<223> OTHER INFORMATION: LC of 2A6

<400> SEQUENCE: 11

Gln Ser Val Leu Thr Gln Pro Ser Ser Leu Ser Ala Ser Pro Gly Ala
1               5                   10                  15

Ser Ala Ser Leu Thr Cys Thr Leu Arg Ser Gly Ile Asn Val Asp Thr
            20                  25                  30

Tyr Arg Ile His Trp Tyr Gln Gln Lys Pro Gly Ser Pro Pro Gln Tyr
        35                  40                  45

Leu Leu Arg Tyr Lys Ser Asp Ser Asp Lys His Gln Gly Ser Gly Val
    50                  55                  60

Pro Ser Arg Phe Ser Gly Ser Lys Asp Pro Ser Ala Asn Ala Gly Ile
65                  70                  75                  80

Leu Leu Ile Ser Gly Leu Gln Ser Glu Asp Glu Ala Asp Tyr Tyr Cys
                85                  90                  95

Ala Ile Trp Tyr Ser Ser Thr Trp Val Phe Gly Gly Gly Thr Gln Leu
            100                 105                 110

Thr Val Leu Gly Gln Pro Lys Ala Ala Pro Ser Val Thr Leu Phe Pro
        115                 120                 125

Pro Ser Ser Glu Glu Leu Gln Ala Asn Lys Ala Thr Leu Val Cys Leu
    130                 135                 140

Ile Ser Asp Phe Tyr Pro Gly Ala Val Thr Val Ala Trp Lys Ala Asp
145                 150                 155                 160

Ser Ser Pro Val Lys Ala Gly Val Glu Thr Thr Thr Pro Ser Lys Gln
                165                 170                 175

Ser Asn Asn Lys Tyr Ala Ala Ser Ser Tyr Leu Ser Leu Thr Pro Glu
            180                 185                 190

Gln Trp Lys Ser His Arg Ser Tyr Ser Cys Gln Val Thr His Glu Gly
        195                 200                 205

Ser Thr Val Glu Lys Thr Val Ala Pro Thr Glu Cys Ser
    210                 215                 220

<210> SEQ ID NO 12
<211> LENGTH: 449
<212> TYPE: PRT
<213> ORGANISM: Artificial Sequence
<220> FEATURE:
<223> OTHER INFORMATION: HC of 3G7 (Q1E)

```
<400> SEQUENCE: 12

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Gly Glu Trp Ile Gln Leu Trp Ser Pro Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415
```

```
Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
            435                 440                 445

Lys

<210> SEQ ID NO 13
<211> LENGTH: 214
<212> TYPE: PRT
<213> ORGANISM: Artificial Sequence
<220> FEATURE:
<223> OTHER INFORMATION: LC of 3G7

<400> SEQUENCE: 13

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Phe Leu Ile
        35                  40                  45

Tyr Ala Ala Ser Ser Leu Gln Ser Gly Val Pro Ser Lys Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Pro
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 14
<211> LENGTH: 456
<212> TYPE: PRT
<213> ORGANISM: Artificial Sequence
<220> FEATURE:
<223> OTHER INFORMATION: HC of 2C1 (Q1E)

<400> SEQUENCE: 14

Glu Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Met His Trp Val Arg Gln Ala Pro Gly Lys Gly Leu Glu Trp Met
        35                  40                  45
```

```
Gly Gly Phe Asp Pro Glu Asp Gly Glu Thr Ile Tyr Ala Gln Lys Phe
 50                  55                  60
Gln Gly Arg Val Thr Met Thr Glu Asp Thr Ser Thr Asp Thr Ala Tyr
 65                  70                  75                  80
Met Glu Leu Ser Ser Leu Arg Ser Glu Asp Thr Ala Val Tyr Tyr Cys
                 85                  90                  95
Ala Arg Ala Gly Pro Leu Tyr Thr Ile Phe Gly Val Val Ile Ile Pro
            100                 105                 110
Asp Asn Trp Phe Asp Pro Trp Gly Gln Gly Thr Leu Val Thr Val Ser
            115                 120                 125
Ser Ala Ser Thr Lys Gly Pro Ser Val Phe Pro Leu Ala Pro Cys Ser
130                 135                 140
Arg Ser Thr Ser Glu Ser Thr Ala Ala Leu Gly Cys Leu Val Lys Asp
145                 150                 155                 160
Tyr Phe Pro Glu Pro Val Thr Val Ser Trp Asn Ser Gly Ala Leu Thr
                165                 170                 175
Ser Gly Val His Thr Phe Pro Ala Val Leu Gln Ser Ser Gly Leu Tyr
            180                 185                 190
Ser Leu Ser Ser Val Val Thr Val Pro Ser Ser Ser Leu Gly Thr Lys
            195                 200                 205
Thr Tyr Thr Cys Asn Val Asp His Lys Pro Ser Asn Thr Lys Val Asp
210                 215                 220
Lys Arg Val Glu Ser Lys Tyr Gly Pro Pro Cys Pro Pro Cys Pro Ala
225                 230                 235                 240
Pro Glu Phe Leu Gly Gly Pro Ser Val Phe Leu Phe Pro Pro Lys Pro
                245                 250                 255
Lys Asp Thr Leu Met Ile Ser Arg Thr Pro Glu Val Thr Cys Val Val
            260                 265                 270
Val Asp Val Ser Gln Glu Asp Pro Glu Val Gln Phe Asn Trp Tyr Val
            275                 280                 285
Asp Gly Val Glu Val His Asn Ala Lys Thr Lys Pro Arg Glu Glu Gln
290                 295                 300
Phe Asn Ser Thr Tyr Arg Val Val Ser Val Leu Thr Val Leu His Gln
305                 310                 315                 320
Asp Trp Leu Asn Gly Lys Glu Tyr Lys Cys Lys Val Ser Asn Lys Gly
                325                 330                 335
Leu Pro Ser Ser Ile Glu Lys Thr Ile Ser Lys Ala Lys Gly Gln Pro
            340                 345                 350
Arg Glu Pro Gln Val Tyr Thr Leu Pro Pro Ser Gln Glu Glu Met Thr
            355                 360                 365
Lys Asn Gln Val Ser Leu Thr Cys Leu Val Lys Gly Phe Tyr Pro Ser
370                 375                 380
Asp Ile Ala Val Glu Trp Glu Ser Asn Gly Gln Pro Glu Asn Asn Tyr
385                 390                 395                 400
Lys Thr Thr Pro Pro Val Leu Asp Ser Asp Gly Ser Phe Phe Leu Tyr
                405                 410                 415
Ser Arg Leu Thr Val Asp Lys Ser Arg Trp Gln Glu Gly Asn Val Phe
            420                 425                 430
Ser Cys Ser Val Met His Glu Ala Leu His Asn His Tyr Thr Gln Lys
            435                 440                 445
Ser Leu Ser Leu Ser Leu Gly Lys
450                 455
```

<210> SEQ ID NO 15
<211> LENGTH: 219
<212> TYPE: PRT
<213> ORGANISM: Artificial Sequence
<220> FEATURE:
<223> OTHER INFORMATION: LC of 2C1 (Q1E)

<400> SEQUENCE: 15

Glu Ser Val Leu Thr Gln Pro Pro Ser Val Ser Gly Ala Pro Gly Gln
1               5                   10                  15

Arg Val Thr Ile Ser Cys Thr Gly Ser Ser Asn Ile Gly Ala Gly
            20                  25                  30

Tyr Asp Val His Trp Tyr Gln Gln Leu Pro Gly Thr Ala Pro Lys Leu
            35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Ser Gly Val Val Phe Gly Gly Thr Gln Leu Ile Ile
            100                 105                 110

Leu Gly Gln Pro Lys Ala Ala Pro Ser Val Thr Leu Phe Pro Pro Ser
        115                 120                 125

Ser Glu Glu Leu Gln Ala Asn Lys Ala Thr Leu Val Cys Leu Ile Ser
    130                 135                 140

Asp Phe Tyr Pro Gly Ala Val Thr Val Ala Trp Lys Ala Asp Ser Ser
145                 150                 155                 160

Pro Val Lys Ala Gly Val Glu Thr Thr Thr Pro Ser Lys Gln Ser Asn
                165                 170                 175

Asn Lys Tyr Ala Ala Ser Ser Tyr Leu Ser Leu Thr Pro Glu Gln Trp
            180                 185                 190

Lys Ser His Arg Ser Tyr Ser Cys Gln Val Thr His Glu Gly Ser Thr
        195                 200                 205

Val Glu Lys Thr Val Ala Pro Thr Glu Cys Ser
    210                 215

<210> SEQ ID NO 16
<211> LENGTH: 5
<212> TYPE: PRT
<213> ORGANISM: Artificial Sequence
<220> FEATURE:
<223> OTHER INFORMATION: CDR-H1, 1E1

<400> SEQUENCE: 16

Gly Tyr Tyr Trp Ser
1               5

<210> SEQ ID NO 17
<211> LENGTH: 16
<212> TYPE: PRT
<213> ORGANISM: Artificial Sequence
<220> FEATURE:
<223> OTHER INFORMATION: CDR-H2, 1E1
<220> FEATURE:
<221> NAME/KEY: MISC_FEATURE
<222> LOCATION: (5)..(5)
<223> OTHER INFORMATION: X is S or A

<400> SEQUENCE: 17

Glu Ile Asn His Xaa Gly Ser Thr Asn Tyr Asn Pro Ser Leu Lys Ser
1               5                   10                  15

<210> SEQ ID NO 18
<211> LENGTH: 13
<212> TYPE: PRT
<213> ORGANISM: Artificial Sequence
<220> FEATURE:
<223> OTHER INFORMATION: CDR-H3, 1E1

<400> SEQUENCE: 18

Leu Pro Thr Arg Trp Val Thr Thr Arg Tyr Phe Asp Leu
1               5                   10

<210> SEQ ID NO 19
<211> LENGTH: 14
<212> TYPE: PRT
<213> ORGANISM: Artificial Sequence
<220> FEATURE:
<223> OTHER INFORMATION: CDR-L1, 1E1

<400> SEQUENCE: 19

Thr Gly Ser Ser Ser Asn Ile Gly Ala Gly Tyr Asp Val His
1               5                   10

<210> SEQ ID NO 20
<211> LENGTH: 7
<212> TYPE: PRT
<213> ORGANISM: Artificial Sequence
<220> FEATURE:
<223> OTHER INFORMATION: CDR-L2, 1E1
<220> FEATURE:
<221> NAME/KEY: MISC_FEATURE
<222> LOCATION: (2)..(2)
<223> OTHER INFORMATION: X is N, Q, E or D
<220> FEATURE:
<221> NAME/KEY: MISC_FEATURE
<222> LOCATION: (3)..(3)
<223> OTHER INFORMATION: X is S or A

<400> SEQUENCE: 20

Gly Xaa Xaa Asn Arg Pro Ser
1               5

<210> SEQ ID NO 21
<211> LENGTH: 11
<212> TYPE: PRT
<213> ORGANISM: Artificial Sequence
<220> FEATURE:
<223> OTHER INFORMATION: CDR-L3, 1E1

<400> SEQUENCE: 21

Gln Ser Phe Asp Asn Ser Leu Ser Ala Tyr Val
1               5                   10

<210> SEQ ID NO 22
<211> LENGTH: 5
<212> TYPE: PRT
<213> ORGANISM: Artificial Sequence
<220> FEATURE:
<223> OTHER INFORMATION: CDR-H1, 2A6

<400> SEQUENCE: 22

Ser Tyr Ala Ile Ser
1               5

<210> SEQ ID NO 23
<211> LENGTH: 17

```
<212> TYPE: PRT
<213> ORGANISM: Artificial Sequence
<220> FEATURE:
<223> OTHER INFORMATION: CDR-H2, 2A6

<400> SEQUENCE: 23

Gly Ile Ile Pro Ile Phe Gly Thr Ala Asn Tyr Ala Gln Lys Phe Gln
1               5                   10                  15

Gly

<210> SEQ ID NO 24
<211> LENGTH: 15
<212> TYPE: PRT
<213> ORGANISM: Artificial Sequence
<220> FEATURE:
<223> OTHER INFORMATION: CDR-H3, 2A6
<220> FEATURE:
<221> NAME/KEY: MISC_FEATURE
<222> LOCATION: (3)..(3)
<223> OTHER INFORMATION: X is D or S
<220> FEATURE:
<221> NAME/KEY: MISC_FEATURE
<222> LOCATION: (4)..(4)
<223> OTHER INFORMATION: X is S or A

<400> SEQUENCE: 24

Tyr Phe Xaa Xaa Ser Gly Trp Tyr Lys Gly Gly Ala Phe Asp Ile
1               5                   10                  15

<210> SEQ ID NO 25
<211> LENGTH: 14
<212> TYPE: PRT
<213> ORGANISM: Artificial Sequence
<220> FEATURE:
<223> OTHER INFORMATION: CDR-L1, 2A6

<400> SEQUENCE: 25

Thr Leu Arg Ser Gly Ile Asn Val Asp Thr Tyr Arg Ile His
1               5                   10

<210> SEQ ID NO 26
<211> LENGTH: 11
<212> TYPE: PRT
<213> ORGANISM: Artificial Sequence
<220> FEATURE:
<223> OTHER INFORMATION: CDR-L2, 2A6

<400> SEQUENCE: 26

Tyr Lys Ser Asp Ser Asp Lys His Gln Gly Ser
1               5                   10

<210> SEQ ID NO 27
<211> LENGTH: 9
<212> TYPE: PRT
<213> ORGANISM: Artificial Sequence
<220> FEATURE:
<223> OTHER INFORMATION: CDR-L3, 2A6

<400> SEQUENCE: 27

Ala Ile Trp Tyr Ser Ser Thr Trp Val
1               5

<210> SEQ ID NO 28
<211> LENGTH: 5
<212> TYPE: PRT
<213> ORGANISM: Artificial Sequence
<220> FEATURE:
<223> OTHER INFORMATION: CDR-H1, 3G7
```

```
<400> SEQUENCE: 28

Ser Tyr Ala Met His
1               5

<210> SEQ ID NO 29
<211> LENGTH: 17
<212> TYPE: PRT
<213> ORGANISM: Artificial Sequence
<220> FEATURE:
<223> OTHER INFORMATION: CDR-H2, 3G7

<400> SEQUENCE: 29

Val Ile Ser Tyr Asp Gly Ser Asn Lys Tyr Tyr Ala Asp Ser Val Lys
1               5                   10                  15

Gly

<210> SEQ ID NO 30
<211> LENGTH: 13
<212> TYPE: PRT
<213> ORGANISM: Artificial Sequence
<220> FEATURE:
<223> OTHER INFORMATION: CDR-H3, 3G7

<400> SEQUENCE: 30

Val Gly Glu Trp Ile Gln Leu Trp Ser Pro Phe Asp Tyr
1               5                   10

<210> SEQ ID NO 31
<211> LENGTH: 11
<212> TYPE: PRT
<213> ORGANISM: Artificial Sequence
<220> FEATURE:
<223> OTHER INFORMATION: CDR-L1, 3G7

<400> SEQUENCE: 31

Arg Ala Ser Gln Gly Ile Ser Ser Trp Leu Ala
1               5                   10

<210> SEQ ID NO 32
<211> LENGTH: 7
<212> TYPE: PRT
<213> ORGANISM: Artificial Sequence
<220> FEATURE:
<223> OTHER INFORMATION: CDR-L2, 3G7

<400> SEQUENCE: 32

Ala Ala Ser Ser Leu Gln Ser
1               5

<210> SEQ ID NO 33
<211> LENGTH: 9
<212> TYPE: PRT
<213> ORGANISM: Artificial Sequence
<220> FEATURE:
<223> OTHER INFORMATION: CDR-L3, 3G7

<400> SEQUENCE: 33

Gln Gln Tyr Asn Ser Tyr Pro Pro Thr
1               5

<210> SEQ ID NO 34
<211> LENGTH: 5
<212> TYPE: PRT
<213> ORGANISM: Artificial Sequence
<220> FEATURE:
```

```
<223> OTHER INFORMATION: CDR-H1, 2C1

<400> SEQUENCE: 34

Glu Leu Ser Met His
1               5

<210> SEQ ID NO 35
<211> LENGTH: 17
<212> TYPE: PRT
<213> ORGANISM: Artificial Sequence
<220> FEATURE:
<223> OTHER INFORMATION: CDR-H2, 2C1

<400> SEQUENCE: 35

Gly Phe Asp Pro Glu Asp Gly Glu Thr Ile Tyr Ala Gln Lys Phe Gln
1               5                   10                  15

Gly

<210> SEQ ID NO 36
<211> LENGTH: 20
<212> TYPE: PRT
<213> ORGANISM: Artificial Sequence
<220> FEATURE:
<223> OTHER INFORMATION: CDR-H3, 2C1

<400> SEQUENCE: 36

Ala Gly Pro Leu Tyr Thr Ile Phe Gly Val Val Ile Ile Pro Asp Asn
1               5                   10                  15

Trp Phe Asp Pro
            20

<210> SEQ ID NO 37
<211> LENGTH: 14
<212> TYPE: PRT
<213> ORGANISM: Artificial Sequence
<220> FEATURE:
<223> OTHER INFORMATION: CDR-L1, 2C1

<400> SEQUENCE: 37

Thr Gly Ser Ser Ser Asn Ile Gly Ala Gly Tyr Asp Val His
1               5                   10

<210> SEQ ID NO 38
<211> LENGTH: 7
<212> TYPE: PRT
<213> ORGANISM: Artificial Sequence
<220> FEATURE:
<223> OTHER INFORMATION: CDR-L2, 2C1

<400> SEQUENCE: 38

Gly Asn Ser Asn Arg Pro Ser
1               5

<210> SEQ ID NO 39
<211> LENGTH: 13
<212> TYPE: PRT
<213> ORGANISM: Artificial Sequence
<220> FEATURE:
<223> OTHER INFORMATION: CDR-L3, 2C1

<400> SEQUENCE: 39

Gln Ser Tyr Asp Ser Ser Leu Ser Gly Ser Gly Val Val
1               5                   10

<210> SEQ ID NO 40
```

-continued

```
<211> LENGTH: 598
<212> TYPE: PRT
<213> ORGANISM: Homo sapiens

<400> SEQUENCE: 40

Met Thr Pro Ile Val Thr Val Leu Ile Cys Leu Gly Leu Ser Leu Gly
1               5                   10                  15

Pro Arg Thr His Val Gln Thr Gly Thr Ile Pro Lys Pro Thr Leu Trp
            20                  25                  30

Ala Glu Pro Asp Ser Val Ile Thr Gln Gly Ser Pro Val Thr Leu Ser
        35                  40                  45

Cys Gln Gly Ser Leu Glu Ala Gln Glu Tyr Arg Leu Tyr Arg Glu Lys
    50                  55                  60

Lys Ser Ala Ser Trp Ile Thr Arg Ile Arg Pro Glu Leu Val Lys Asn
65                  70                  75                  80

Gly Gln Phe His Ile Pro Ser Ile Thr Trp Glu His Thr Gly Arg Tyr
                85                  90                  95

Gly Cys Gln Tyr Tyr Ser Arg Ala Arg Trp Ser Glu Leu Ser Asp Pro
            100                 105                 110

Leu Val Leu Val Met Thr Gly Ala Tyr Pro Lys Pro Thr Leu Ser Ala
        115                 120                 125

Gln Pro Ser Pro Val Val Thr Ser Gly Gly Arg Val Thr Leu Gln Cys
    130                 135                 140

Glu Ser Gln Val Ala Phe Gly Gly Phe Ile Leu Cys Lys Glu Gly Glu
145                 150                 155                 160

Glu Glu His Pro Gln Cys Leu Asn Ser Gln Pro His Ala Arg Gly Ser
                165                 170                 175

Ser Arg Ala Ile Phe Ser Val Gly Pro Val Ser Pro Asn Arg Arg Trp
            180                 185                 190

Ser His Arg Cys Tyr Gly Tyr Asp Leu Asn Ser Pro Tyr Val Trp Ser
        195                 200                 205

Ser Pro Ser Asp Leu Leu Glu Leu Leu Val Pro Gly Val Ser Lys Lys
    210                 215                 220

Pro Ser Leu Ser Val Gln Pro Gly Pro Val Val Ala Pro Gly Glu Ser
225                 230                 235                 240

Leu Thr Leu Gln Cys Val Ser Asp Val Gly Tyr Asp Arg Phe Val Leu
                245                 250                 255

Tyr Lys Glu Gly Glu Arg Asp Leu Arg Gln Leu Pro Gly Arg Gln Pro
            260                 265                 270

Gln Ala Gly Leu Ser Gln Ala Asn Phe Thr Leu Gly Pro Val Ser Arg
        275                 280                 285

Ser Tyr Gly Gly Gln Tyr Arg Cys Tyr Gly Ala His Asn Leu Ser Ser
    290                 295                 300

Glu Cys Ser Ala Pro Ser Asp Pro Leu Asp Ile Leu Ile Thr Gly Gln
305                 310                 315                 320

Ile Arg Gly Thr Pro Phe Ile Ser Val Gln Pro Gly Pro Thr Val Ala
                325                 330                 335

Ser Gly Glu Asn Val Thr Leu Leu Cys Gln Ser Trp Arg Gln Phe His
            340                 345                 350

Thr Phe Leu Leu Thr Lys Ala Gly Ala Ala Asp Ala Pro Leu Arg Leu
        355                 360                 365

Arg Ser Ile His Glu Tyr Pro Lys Tyr Gln Ala Glu Phe Pro Met Ser
    370                 375                 380

Pro Val Thr Ser Ala His Ala Gly Thr Tyr Arg Cys Tyr Gly Ser Leu
```

-continued

```
                385                 390                 395                 400
        Asn Ser Asp Pro Tyr Leu Leu Ser His Pro Ser Glu Pro Leu Glu Leu
                        405                 410                 415

Val Val Ser Gly Pro Ser Met Gly Ser Ser Pro Pro Thr Gly Pro
                    420                 425                 430

Ile Ser Thr Pro Ala Gly Pro Glu Asp Gln Pro Leu Thr Pro Thr Gly
                        435                 440                 445

Ser Asp Pro Gln Ser Gly Leu Gly Arg His Leu Gly Val Val Ile Gly
                    450                 455                 460

Ile Leu Val Ala Val Val Leu Leu Leu Leu Leu Leu Leu Leu Leu Phe
        465                 470                 475                 480

Leu Ile Leu Arg His Arg Arg Gln Gly Lys His Trp Thr Ser Thr Gln
                        485                 490                 495

Arg Lys Ala Asp Phe Gln His Pro Ala Gly Ala Val Gly Pro Glu Pro
                    500                 505                 510

Thr Asp Arg Gly Leu Gln Trp Arg Ser Ser Pro Ala Ala Asp Ala Gln
                        515                 520                 525

Glu Glu Asn Leu Tyr Ala Ala Val Lys Asp Thr Gln Pro Glu Asp Gly
                    530                 535                 540

Val Glu Met Asp Thr Arg Ala Ala Ala Ser Glu Ala Pro Gln Asp Val
        545                 550                 555                 560

Thr Tyr Ala Gln Leu His Ser Leu Thr Leu Arg Arg Lys Ala Thr Glu
                        565                 570                 575

Pro Pro Pro Ser Gln Glu Arg Glu Pro Pro Ala Glu Pro Ser Ile Tyr
                    580                 585                 590

Ala Thr Leu Ala Ile His
                595

<210> SEQ ID NO 41
<211> LENGTH: 19
<212> TYPE: PRT
<213> ORGANISM: Artificial Sequence
<220> FEATURE:
<223> OTHER INFORMATION: Signal peptide

<400> SEQUENCE: 41

Met Glu Trp Ser Trp Val Phe Leu Phe Phe Leu Ser Val Thr Thr Gly
1               5                   10                  15

Val His Ser

<210> SEQ ID NO 42
<211> LENGTH: 20
<212> TYPE: PRT
<213> ORGANISM: Artificial Sequence
<220> FEATURE:
<223> OTHER INFORMATION: Signal peptide

<400> SEQUENCE: 42

Met Ser Val Pro Thr Gln Val Leu Gly Leu Leu Leu Leu Trp Leu Thr
1               5                   10                  15

Asp Ala Arg Cys
            20

<210> SEQ ID NO 43
<211> LENGTH: 597
<212> TYPE: PRT
<213> ORGANISM: Macaca fascicularis

<400> SEQUENCE: 43
```

-continued

```
Met Thr Pro Ile Leu Met Val Leu Ile Cys Leu Gly Leu Ser Leu Gly
1               5                   10                  15

Pro Arg Thr His Val Gln Ala Gly Ile Leu Pro Lys Pro Thr Leu Trp
                20                  25                  30

Ala Glu Pro Gly Ser Val Ile Ser Glu Gly Ser Pro Val Thr Leu Arg
            35                  40                  45

Cys Gln Gly Ser Leu Gln Val Gln Glu Tyr His Leu Tyr Arg Glu Lys
    50                  55                  60

Asn Pro Ala Ser Trp Val Arg Gln Ile Arg Gln Glu Leu Val Lys Lys
65                  70                  75                  80

Gly Tyr Phe Ala Ile Gly Phe Ile Thr Trp Glu His Thr Gly Gln Tyr
                85                  90                  95

Arg Cys Gln Tyr Tyr Ser His Ser Trp Trp Ser Glu Pro Ser Asp Pro
            100                 105                 110

Leu Glu Leu Val Val Thr Gly Ala Tyr Ser Lys Pro Thr Leu Ser Ala
    115                 120                 125

Leu Pro Ser Pro Val Val Ala Ser Gly Gly Asn Val Thr Leu Gln Cys
130                 135                 140

Asp Ser Gln Val Ala Phe Asp Ser Phe Thr Leu Cys Lys Glu Gly Glu
145                 150                 155                 160

Asp Glu His Pro Gln Arg Leu Asn Cys Gln Ser His Ala Arg Gly Trp
                165                 170                 175

Ser Trp Ala Val Phe Ser Val Gly Pro Val Ser Pro Ser Arg Arg Trp
            180                 185                 190

Ser Tyr Arg Cys Tyr Gly Tyr Ile Ser Ser Ala Pro Asn Val Trp Ser
        195                 200                 205

Leu Pro Ser Asp Leu Leu Glu Leu Leu Val Pro Gly Val Ser Lys Lys
210                 215                 220

Pro Ser Leu Ser Val Gln Pro Gly Pro Val Val Ala Pro Gly Asp Lys
225                 230                 235                 240

Leu Thr Leu Gln Cys Gly Ser Asp Ala Gly Tyr Asp Arg Phe Ala Leu
                245                 250                 255

Tyr Lys Glu Gly Glu Gly Asp Phe Leu Gln Arg Pro Val Arg Gln Pro
            260                 265                 270

Gln Ala Gly Leu Ser Gln Ala Asn Phe Leu Leu Gly Pro Val Ser Arg
        275                 280                 285

Ser His Gly Gly Gln Tyr Arg Cys Ser Gly Ala His Asn Leu Ser Ser
    290                 295                 300

Glu Trp Ser Ala Pro Ser Asp Pro Leu Asp Ile Leu Ile Ala Gly Gln
305                 310                 315                 320

Ile Arg Gly Arg Pro Phe Leu Ser Val Gln Pro Gly Pro Lys Val Val
                325                 330                 335

Ser Gly Glu Asn Val Thr Leu Leu Cys Gln Ser Ser Trp Gln Phe His
            340                 345                 350

Ala Phe Leu Leu Thr Gln Ala Gly Ala Ala Asp Ala His Leu His Leu
        355                 360                 365

Arg Ser Met Tyr Lys Tyr Pro Lys Tyr Gln Ala Glu Phe Pro Met Ser
    370                 375                 380

Pro Val Thr Ser Ala His Ala Gly Thr Tyr Arg Cys Tyr Gly Ser Arg
385                 390                 395                 400

Ser Ser Asn Pro Tyr Leu Leu Ser Val Pro Ser Asp Pro Leu Glu Leu
                405                 410                 415
```

```
Val Val Ser Gly Pro Ser Gly Gly Pro Ser Ser Pro Thr Thr Gly Pro
            420             425             430

Thr Ser Thr Cys Gly Pro Glu Asp Gln Pro Leu Thr Pro Thr Gly Ser
            435             440             445

Ala Pro Gln Ser Gly Leu Gly Arg His Leu Gly Val Val Thr Gly Val
        450             455             460

Leu Val Ala Phe Val Leu Leu Phe Leu Leu Leu Leu Leu Leu Phe Leu
465             470             475             480

Val Leu Arg Tyr Arg Arg Gln Gly Lys Arg Trp Thr Ser Ala Gln Arg
                485             490             495

Lys Ala Asp Phe Gln His Pro Ala Gly Ala Val Glu Pro Glu Pro Arg
            500             505             510

Asp Arg Gly Leu Gln Arg Ser Ser Pro Ala Ala Asp Thr Gln Glu
            515             520             525

Glu Asn Leu Tyr Ala Ala Val Lys Asp Thr Gln Pro Glu Asp Gly Val
        530             535             540

Glu Leu Asp Ser Arg Ala Ala Ser Glu Asp Pro Gln Asp Val Thr
545             550             555             560

Tyr Ala Gln Leu Gln Ser Leu Thr Leu Arg Arg Glu Ala Thr Glu Pro
            565             570             575

Pro Pro Ser Gln Glu Arg Ala Pro Pro Val Glu Ser Ser Ile Tyr Ala
            580             585             590

Thr Leu Thr Ile His
            595

<210> SEQ ID NO 44
<211> LENGTH: 451
<212> TYPE: PRT
<213> ORGANISM: Artificial Sequence
<220> FEATURE:
<223> OTHER INFORMATION: HC of p1E1 (G1)

<400> SEQUENCE: 44

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Leu Pro Thr Arg Trp Val Thr Thr Arg Tyr Phe Asp Leu Trp Gly
            100                 105                 110

Arg Gly Thr Leu Val Thr Val Ser Ala Ser Thr Lys Gly Pro Ser
            115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175
```

```
Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Arg Val Glu Pro Lys Ser Cys
        210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 45
<211> LENGTH: 217
<212> TYPE: PRT
<213> ORGANISM: Artificial Sequence
<220> FEATURE:
<223> OTHER INFORMATION: LC of p1E1 (G1)

<400> SEQUENCE: 45

Gln Ser Val Leu Thr Gln Pro Pro Ser Val Ser Gly Ala Pro Gly Gln
1               5                   10                  15

Arg Val Thr Ile Ser Cys Thr Gly Ser Ser Asn Ile Gly Ala Gly
                20                  25                  30

Tyr Asp Val His Trp Tyr Gln Gln Leu Pro Gly Thr Ala Pro Lys Leu
            35                  40                  45

Leu Ile Tyr Gly Asn Ser Asn Arg Pro Ser Gly Val Pro Asp Arg Phe
        50                  55                  60

Ser Val Ser Lys Ser Gly Ala Ser Ala Ser Leu Ala Ile Thr Gly Leu
65                  70                  75                  80
```

```
Gln Ala Glu Asp Glu Ala Asp Tyr Tyr Cys Gln Ser Phe Asp Asn Ser
                85                  90                  95

Leu Ser Ala Tyr Val Phe Gly Gly Gly Thr Gln Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215

<210> SEQ ID NO 46
<211> LENGTH: 16
<212> TYPE: PRT
<213> ORGANISM: Artificial Sequence
<220> FEATURE:
<223> OTHER INFORMATION: Signal peptide

<400> SEQUENCE: 46

Met Pro Leu Leu Leu Leu Leu Pro Leu Leu Trp Ala Gly Ala Leu Ala
1               5                   10                  15

<210> SEQ ID NO 47
<211> LENGTH: 16
<212> TYPE: PRT
<213> ORGANISM: Artificial Sequence
<220> FEATURE:
<223> OTHER INFORMATION: CDR-H2, variant 1

<400> SEQUENCE: 47

Glu Ile Asn His Ser Gly Ser Thr Asn Tyr Asn Pro Ser Leu Lys Ser
1               5                   10                  15

<210> SEQ ID NO 48
<211> LENGTH: 16
<212> TYPE: PRT
<213> ORGANISM: Artificial Sequence
<220> FEATURE:
<223> OTHER INFORMATION: CDR-H2, variant 2

<400> SEQUENCE: 48

Glu Ile Asn His Ala Gly Ser Thr Asn Tyr Asn Pro Ser Leu Lys Ser
1               5                   10                  15

<210> SEQ ID NO 49
<211> LENGTH: 7
<212> TYPE: PRT
<213> ORGANISM: Artificial Sequence
<220> FEATURE:
<223> OTHER INFORMATION: CDR-L2, variant 1

<400> SEQUENCE: 49

Gly Asn Ser Asn Arg Pro Ser
1               5
```

```
<210> SEQ ID NO 50
<211> LENGTH: 7
<212> TYPE: PRT
<213> ORGANISM: Artificial Sequence
<220> FEATURE:
<223> OTHER INFORMATION: CDR-L2, variant 2

<400> SEQUENCE: 50

Gly Gln Ser Asn Arg Pro Ser
1               5

<210> SEQ ID NO 51
<211> LENGTH: 7
<212> TYPE: PRT
<213> ORGANISM: Artificial Sequence
<220> FEATURE:
<223> OTHER INFORMATION: CDR-L2, variant 3

<400> SEQUENCE: 51

Gly Glu Ser Asn Arg Pro Ser
1               5

<210> SEQ ID NO 52
<211> LENGTH: 7
<212> TYPE: PRT
<213> ORGANISM: Artificial Sequence
<220> FEATURE:
<223> OTHER INFORMATION: CDR-L2, variant 4

<400> SEQUENCE: 52

Gly Asp Ser Asn Arg Pro Ser
1               5

<210> SEQ ID NO 53
<211> LENGTH: 7
<212> TYPE: PRT
<213> ORGANISM: Artificial Sequence
<220> FEATURE:
<223> OTHER INFORMATION: CDR-L2, variant 5

<400> SEQUENCE: 53

Gly Asn Ala Asn Arg Pro Ser
1               5

<210> SEQ ID NO 54
<211> LENGTH: 7
<212> TYPE: PRT
<213> ORGANISM: Artificial Sequence
<220> FEATURE:
<223> OTHER INFORMATION: CDR-L2, variant 6

<400> SEQUENCE: 54

Gly Gln Ala Asn Arg Pro Ser
1               5

<210> SEQ ID NO 55
<211> LENGTH: 7
<212> TYPE: PRT
<213> ORGANISM: Artificial Sequence
<220> FEATURE:
<223> OTHER INFORMATION: CDR-L2, variant 7

<400> SEQUENCE: 55

Gly Glu Ala Asn Arg Pro Ser
1               5
```

```
<210> SEQ ID NO 56
<211> LENGTH: 7
<212> TYPE: PRT
<213> ORGANISM: Artificial Sequence
<220> FEATURE:
<223> OTHER INFORMATION: CDR-L2, variant 8

<400> SEQUENCE: 56

Gly Asp Ala Asn Arg Pro Ser
1               5

<210> SEQ ID NO 57
<211> LENGTH: 121
<212> TYPE: PRT
<213> ORGANISM: Artificial Sequence
<220> FEATURE:
<223> OTHER INFORMATION: VH of 1E1(G4)

<400> SEQUENCE: 57

Glu Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ala Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Leu Pro Thr Arg Trp Val Thr Arg Tyr Phe Asp Leu Trp Gly
            100                 105                 110

Arg Gly Thr Leu Val Thr Val Ser Ser
        115                 120

<210> SEQ ID NO 58
<211> LENGTH: 111
<212> TYPE: PRT
<213> ORGANISM: Artificial Sequence
<220> FEATURE:
<223> OTHER INFORMATION: VL of 1E1(G4)

<400> SEQUENCE: 58

Glu Ser Val Leu Thr Gln Pro Pro Ser Val Ser Gly Ala Pro Gly Gln
1               5                   10                  15

Arg Val Thr Ile Ser Cys Thr Gly Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asp Ser Asn Arg Pro Ser Gly Val Pro Asp Arg Phe
    50                  55                  60

Ser Val Ser Lys Ser Gly Ala Ser Ala Ser Leu Ala Ile Thr Gly Leu
65                  70                  75                  80

Gln Ala Glu Asp Glu Ala Asp Tyr Tyr Cys Gln Ser Phe Asp Asn Ser
                85                  90                  95

Leu Ser Ala Tyr Val Phe Gly Gly Gly Thr Gln Leu Thr Val Leu
            100                 105                 110

<210> SEQ ID NO 59
```

```
<211> LENGTH: 10
<212> TYPE: PRT
<213> ORGANISM: Homo sapiens

<400> SEQUENCE: 59

Leu Tyr Arg Glu Lys Lys Ser Ala Ser Trp
1               5                   10

<210> SEQ ID NO 60
<211> LENGTH: 7
<212> TYPE: PRT
<213> ORGANISM: Homo sapiens

<400> SEQUENCE: 60

Thr Arg Ile Arg Pro Glu Leu
1               5

<210> SEQ ID NO 61
<211> LENGTH: 4
<212> TYPE: PRT
<213> ORGANISM: Homo sapiens

<400> SEQUENCE: 61

Asn Gly Gln Phe
1

<210> SEQ ID NO 62
<211> LENGTH: 8
<212> TYPE: PRT
<213> ORGANISM: Homo sapiens

<400> SEQUENCE: 62

His Thr Gly Arg Tyr Gly Cys Gln
1               5

<210> SEQ ID NO 63
<211> LENGTH: 121
<212> TYPE: PRT
<213> ORGANISM: Artificial Sequence
<220> FEATURE:
<223> OTHER INFORMATION: VH of 1E1 (Q1E)

<400> SEQUENCE: 63

Glu Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Leu Pro Thr Arg Trp Val Thr Thr Arg Tyr Phe Asp Leu Trp Gly
            100                 105                 110

Arg Gly Thr Leu Val Thr Val Ser Ser
            115                 120

<210> SEQ ID NO 64
<211> LENGTH: 124
```

```
<212> TYPE: PRT
<213> ORGANISM: Artificial Sequence
<220> FEATURE:
<223> OTHER INFORMATION: VH of 2A6 (Q1E)

<400> SEQUENCE: 64

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Phe Asp Ser Ser Gly Trp Tyr Lys Gly Gly Ala Phe Asp
            100                 105                 110

Ile Trp Gly Gln Gly Thr Met Val Thr Val Ser Ser
        115                 120

<210> SEQ ID NO 65
<211> LENGTH: 124
<212> TYPE: PRT
<213> ORGANISM: Artificial Sequence
<220> FEATURE:
<223> OTHER INFORMATION: VH of 2A6 (Q1E, S102A, M119L)

<400> SEQUENCE: 65

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Phe Asp Ala Ser Gly Trp Tyr Lys Gly Gly Ala Phe Asp
            100                 105                 110

Ile Trp Gly Gln Gly Thr Leu Val Thr Val Ser Ser
        115                 120

<210> SEQ ID NO 66
<211> LENGTH: 124
<212> TYPE: PRT
<213> ORGANISM: Artificial Sequence
<220> FEATURE:
<223> OTHER INFORMATION: VH of 2A6 (Q1E, D101S, M119L)

<400> SEQUENCE: 66

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
```

```
                    20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Phe Ser Ser Ser Gly Trp Tyr Lys Gly Gly Ala Phe Asp
            100                 105                 110

Ile Trp Gly Gln Gly Thr Leu Val Thr Val Ser Ser
        115                 120

<210> SEQ ID NO 67
<211> LENGTH: 122
<212> TYPE: PRT
<213> ORGANISM: Artificial Sequence
<220> FEATURE:
<223> OTHER INFORMATION: VH of 3G7 (Q1E)

<400> SEQUENCE: 67

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Gly Glu Trp Ile Gln Leu Trp Ser Pro Phe Asp Tyr Trp
            100                 105                 110

Gly Gln Gly Thr Leu Val Thr Val Ser Ser
        115                 120

<210> SEQ ID NO 68
<211> LENGTH: 129
<212> TYPE: PRT
<213> ORGANISM: Artificial Sequence
<220> FEATURE:
<223> OTHER INFORMATION: VH of 2C1 (Q1E)

<400> SEQUENCE: 68

Glu Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Met His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Glu Asp Thr Ser Thr Asp Thr Ala Tyr
65                  70                  75                  80
```

```
Met Glu Leu Ser Ser Leu Arg Ser Glu Asp Thr Ala Val Tyr Tyr Cys
                85                  90                  95

Ala Arg Ala Gly Pro Leu Tyr Thr Ile Phe Gly Val Val Ile Ile Pro
            100                 105                 110

Asp Asn Trp Phe Asp Pro Trp Gly Gln Gly Thr Leu Val Thr Val Ser
        115                 120                 125

Ser

<210> SEQ ID NO 69
<211> LENGTH: 121
<212> TYPE: PRT
<213> ORGANISM: Artificial Sequence
<220> FEATURE:
<223> OTHER INFORMATION: VH of p1E1(G1)

<400> SEQUENCE: 69

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Leu Pro Thr Arg Trp Val Thr Thr Arg Tyr Phe Asp Leu Trp Gly
            100                 105                 110

Arg Gly Thr Leu Val Thr Val Ser Ser
        115                 120

<210> SEQ ID NO 70
<211> LENGTH: 111
<212> TYPE: PRT
<213> ORGANISM: Artificial Sequence
<220> FEATURE:
<223> OTHER INFORMATION: VL of 1E1 (Q1E)

<400> SEQUENCE: 70

Glu Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Val Ser Lys Ser Gly Ala Ser Ala Ser Leu Ala Ile Thr Gly Leu
65                  70                  75                  80

Gln Ala Glu Asp Glu Ala Asp Tyr Tyr Cys Gln Ser Phe Asp Asn Ser
                85                  90                  95

Leu Ser Ala Tyr Val Phe Gly Gly Gly Thr Gln Leu Thr Val Leu
            100                 105                 110

<210> SEQ ID NO 71
<211> LENGTH: 111
```

<212> TYPE: PRT
<213> ORGANISM: Artificial Sequence
<220> FEATURE:
<223> OTHER INFORMATION: VL of 1E1 (Q1E, S54A)

<400> SEQUENCE: 71

Glu Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ala Asn Arg Pro Ser Gly Val Pro Asp Arg Phe
    50                  55                  60

Ser Val Ser Lys Ser Gly Ala Ser Ala Ser Leu Ala Ile Thr Gly Leu
65                  70                  75                  80

Gln Ala Glu Asp Glu Ala Asp Tyr Tyr Cys Gln Ser Phe Asp Asn Ser
                85                  90                  95

Leu Ser Ala Tyr Val Phe Gly Gly Gly Thr Gln Leu Thr Val Leu
            100                 105                 110

<210> SEQ ID NO 72
<211> LENGTH: 111
<212> TYPE: PRT
<213> ORGANISM: Artificial Sequence
<220> FEATURE:
<223> OTHER INFORMATION: VL of 1E1 (Q1E, N53Q)

<400> SEQUENCE: 72

Glu Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Gln Ser Asn Arg Pro Ser Gly Val Pro Asp Arg Phe
    50                  55                  60

Ser Val Ser Lys Ser Gly Ala Ser Ala Ser Leu Ala Ile Thr Gly Leu
65                  70                  75                  80

Gln Ala Glu Asp Glu Ala Asp Tyr Tyr Cys Gln Ser Phe Asp Asn Ser
                85                  90                  95

Leu Ser Ala Tyr Val Phe Gly Gly Gly Thr Gln Leu Thr Val Leu
            100                 105                 110

<210> SEQ ID NO 73
<211> LENGTH: 111
<212> TYPE: PRT
<213> ORGANISM: Artificial Sequence
<220> FEATURE:
<223> OTHER INFORMATION: VL of 1E1 (Q1E, N53E)

<400> SEQUENCE: 73

Glu Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Glu Ser Asn Arg Pro Ser Gly Val Pro Asp Arg Phe

```
                50              55              60
Ser Val Ser Lys Ser Gly Ala Ser Ala Ser Leu Ala Ile Thr Gly Leu
 65              70              75              80

Gln Ala Glu Asp Glu Ala Asp Tyr Tyr Cys Gln Ser Phe Asp Asn Ser
                85                  90                  95

Leu Ser Ala Tyr Val Phe Gly Gly Gly Thr Gln Leu Thr Val Leu
                100                 105                 110

<210> SEQ ID NO 74
<211> LENGTH: 115
<212> TYPE: PRT
<213> ORGANISM: Artificial Sequence
<220> FEATURE:
<223> OTHER INFORMATION: VL of 2A6

<400> SEQUENCE: 74

Gln Ser Val Leu Thr Gln Pro Ser Ser Leu Ser Ala Ser Pro Gly Ala
 1               5                  10                  15

Ser Ala Ser Leu Thr Cys Thr Leu Arg Ser Gly Ile Asn Val Asp Thr
                20                  25                  30

Tyr Arg Ile His Trp Tyr Gln Gln Lys Pro Gly Ser Pro Pro Gln Tyr
            35                  40                  45

Leu Leu Arg Tyr Lys Ser Asp Ser Asp Lys His Gln Gly Ser Gly Val
 50                  55                  60

Pro Ser Arg Phe Ser Gly Ser Lys Asp Pro Ser Ala Asn Ala Gly Ile
 65                  70                  75                  80

Leu Leu Ile Ser Gly Leu Gln Ser Glu Asp Glu Ala Asp Tyr Tyr Cys
                85                  90                  95

Ala Ile Trp Tyr Ser Ser Thr Trp Val Phe Gly Gly Gly Thr Gln Leu
                100                 105                 110

Thr Val Leu
        115

<210> SEQ ID NO 75
<211> LENGTH: 107
<212> TYPE: PRT
<213> ORGANISM: Artificial Sequence
<220> FEATURE:
<223> OTHER INFORMATION: VL of 3G7

<400> SEQUENCE: 75

Asp Ile Gln Met Thr Gln Ser Pro Ser Ser Val Ser Ala Ser Val Gly
 1               5                  10                  15

Asp Arg Val Thr Ile Thr Cys Arg Ala Ser Gln Gly Ile Ser Ser Trp
                20                  25                  30

Leu Ala Trp Tyr Gln Gln Lys Pro Gly Lys Ala Pro Lys Phe Leu Ile
            35                  40                  45

Tyr Ala Ala Ser Ser Leu Gln Ser Gly Val Pro Ser Lys Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser Tyr Pro Pro
                85                  90                  95

Thr Phe Gly Gly Gly Thr Lys Val Glu Ile Lys
                100                 105

<210> SEQ ID NO 76
<211> LENGTH: 113
```

```
<212> TYPE: PRT
<213> ORGANISM: Artificial Sequence
<220> FEATURE:
<223> OTHER INFORMATION: VL of 2C1

<400> SEQUENCE: 76
```

Glu Ser Val Leu Thr Gln Pro Pro Ser Val Ser Gly Ala Pro Gly Gln
1               5                   10                  15

Arg Val Thr Ile Ser Cys Thr Gly Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Ser Gly Val Val Phe Gly Gly Thr Gln Leu Ile Ile
            100                 105                 110

Leu

```
<210> SEQ ID NO 77
<211> LENGTH: 111
<212> TYPE: PRT
<213> ORGANISM: Artificial Sequence
<220> FEATURE:
<223> OTHER INFORMATION: VL of 1E1

<400> SEQUENCE: 77
```

Gln Ser Val Leu Thr Gln Pro Pro Ser Val Ser Gly Ala Pro Gly Gln
1               5                   10                  15

Arg Val Thr Ile Ser Cys Thr Gly Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Val Ser Lys Ser Gly Ala Ser Ala Ser Leu Ala Ile Thr Gly Leu
65                  70                  75                  80

Gln Ala Glu Asp Glu Ala Asp Tyr Tyr Cys Gln Ser Phe Asp Asn Ser
                85                  90                  95

Leu Ser Ala Tyr Val Phe Gly Gly Gly Thr Gln Leu Thr Val Leu
            100                 105                 110

```
<210> SEQ ID NO 78
<211> LENGTH: 577
<212> TYPE: PRT
<213> ORGANISM: Homo sapiens

<400> SEQUENCE: 78
```

Gln Thr Gly Thr Ile Pro Lys Pro Thr Leu Trp Ala Glu Pro Asp Ser
1               5                   10                  15

Val Ile Thr Gln Gly Ser Pro Val Thr Leu Ser Cys Gln Gly Ser Leu
            20                  25                  30

Glu Ala Gln Glu Tyr Arg Leu Tyr Arg Glu Lys Lys Ser Ala Ser Trp
        35                  40                  45

Ile Thr Arg Ile Arg Pro Glu Leu Val Lys Asn Gly Gln Phe His Ile

```
            50                  55                  60
Pro Ser Ile Thr Trp Glu His Thr Gly Arg Tyr Gly Cys Gln Tyr Tyr
 65                  70                  75                  80

Ser Arg Ala Arg Trp Ser Glu Leu Ser Asp Pro Leu Val Leu Val Met
                 85                  90                  95

Thr Gly Ala Tyr Pro Lys Pro Thr Leu Ser Ala Gln Pro Ser Pro Val
                100                 105                 110

Val Thr Ser Gly Gly Arg Val Thr Leu Gln Cys Glu Ser Gln Val Ala
            115                 120                 125

Phe Gly Gly Phe Ile Leu Cys Lys Glu Gly Glu Glu His Pro Gln
130                 135                 140

Cys Leu Asn Ser Gln Pro His Ala Arg Gly Ser Ser Arg Ala Ile Phe
145                 150                 155                 160

Ser Val Gly Pro Val Ser Pro Asn Arg Arg Trp Ser His Arg Cys Tyr
                165                 170                 175

Gly Tyr Asp Leu Asn Ser Pro Tyr Val Trp Ser Ser Pro Ser Asp Leu
            180                 185                 190

Leu Glu Leu Leu Val Pro Gly Val Ser Lys Lys Pro Ser Leu Ser Val
            195                 200                 205

Gln Pro Gly Pro Val Val Ala Pro Gly Glu Ser Leu Thr Leu Gln Cys
210                 215                 220

Val Ser Asp Val Gly Tyr Asp Arg Phe Val Leu Tyr Lys Glu Gly Glu
225                 230                 235                 240

Arg Asp Leu Arg Gln Leu Pro Gly Arg Gln Pro Gln Ala Gly Leu Ser
                245                 250                 255

Gln Ala Asn Phe Thr Leu Gly Pro Val Ser Arg Ser Tyr Gly Gly Gln
            260                 265                 270

Tyr Arg Cys Tyr Gly Ala His Asn Leu Ser Ser Glu Cys Ser Ala Pro
            275                 280                 285

Ser Asp Pro Leu Asp Ile Leu Ile Thr Gly Gln Ile Arg Gly Thr Pro
290                 295                 300

Phe Ile Ser Val Gln Pro Gly Pro Thr Val Ala Ser Gly Glu Asn Val
305                 310                 315                 320

Thr Leu Leu Cys Gln Ser Trp Arg Gln Phe His Thr Phe Leu Leu Thr
                325                 330                 335

Lys Ala Gly Ala Ala Asp Ala Pro Leu Arg Leu Arg Ser Ile His Glu
            340                 345                 350

Tyr Pro Lys Tyr Gln Ala Glu Phe Pro Met Ser Pro Val Thr Ser Ala
            355                 360                 365

His Ala Gly Thr Tyr Arg Cys Tyr Gly Ser Leu Asn Ser Asp Pro Tyr
370                 375                 380

Leu Leu Ser His Pro Ser Glu Pro Leu Glu Leu Val Val Ser Gly Pro
385                 390                 395                 400

Ser Met Gly Ser Ser Pro Pro Thr Gly Pro Ile Ser Thr Pro Ala
                405                 410                 415

Gly Pro Glu Asp Gln Pro Leu Thr Pro Thr Gly Ser Asp Pro Gln Ser
            420                 425                 430

Gly Leu Gly Arg His Leu Gly Val Val Ile Gly Ile Leu Val Ala Val
            435                 440                 445

Val Leu Leu Leu Leu Leu Leu Leu Phe Leu Ile Leu Arg His
450                 455                 460

Arg Arg Gln Gly Lys His Trp Thr Ser Thr Gln Arg Lys Ala Asp Phe
465                 470                 475                 480
```

-continued

```
Gln His Pro Ala Gly Ala Val Gly Pro Glu Pro Thr Asp Arg Gly Leu
            485                 490                 495

Gln Trp Arg Ser Ser Pro Ala Ala Asp Ala Gln Glu Glu Asn Leu Tyr
        500                 505                 510

Ala Ala Val Lys Asp Thr Gln Pro Glu Asp Gly Val Glu Met Asp Thr
            515                 520                 525

Arg Ala Ala Ala Ser Glu Ala Pro Gln Asp Val Thr Tyr Ala Gln Leu
    530                 535                 540

His Ser Leu Thr Leu Arg Arg Lys Ala Thr Glu Pro Pro Ser Gln
545                 550                 555                 560

Glu Arg Glu Pro Pro Ala Glu Pro Ser Ile Tyr Ala Thr Leu Ala Ile
            565                 570                 575

His

<210> SEQ ID NO 79
<211> LENGTH: 447
<212> TYPE: PRT
<213> ORGANISM: Artificial Sequence
<220> FEATURE:
<223> OTHER INFORMATION: HC of 1E1 (Q1E) without C-terminal K

<400> SEQUENCE: 79

Glu Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
            85                  90                  95

Arg Leu Pro Thr Arg Trp Val Thr Arg Tyr Phe Asp Leu Trp Gly
            100                 105                 110

Arg Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
        180                 185                 190

Pro Ser Ser Ser Leu Gly Thr Lys Thr Tyr Thr Cys Asn Val Asp His
    195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
            245                 250                 255
```

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly
        435                 440                 445

<210> SEQ ID NO 80
<211> LENGTH: 447
<212> TYPE: PRT
<213> ORGANISM: Artificial Sequence
<220> FEATURE:
<223> OTHER INFORMATION: HC of 1E1 (Q1E, S54A) without C-terminal K

<400> SEQUENCE: 80

Glu Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ala Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Leu Pro Thr Arg Trp Val Thr Thr Arg Tyr Phe Asp Leu Trp Gly
            100                 105                 110

Arg Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

```
Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
        260                 265                 270

Glu Val Gln Phe Asn Trp Tyr Val Asp Gly Val Glu Val His Asn Ala
    275                 280                 285

Lys Thr Lys Pro Arg Glu Glu Gln Phe Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly
        435                 440                 445

<210> SEQ ID NO 81
<211> LENGTH: 450
<212> TYPE: PRT
<213> ORGANISM: Artificial Sequence
<220> FEATURE:
<223> OTHER INFORMATION: HC of p1E1(G1) without C-terminal K

<400> SEQUENCE: 81

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95
```

```
Arg Leu Pro Thr Arg Trp Val Thr Thr Arg Tyr Phe Asp Leu Trp Gly
            100                 105                 110

Arg Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450

<210> SEQ ID NO 82
<211> LENGTH: 450
<212> TYPE: PRT
<213> ORGANISM: Artificial Sequence
<220> FEATURE:
<223> OTHER INFORMATION: HC of 2A6 (Q1E) without C-terminal K

<400> SEQUENCE: 82
```

```
Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Phe Asp Ser Ser Gly Trp Tyr Lys Gly Gly Ala Phe Asp
                100                 105                 110

Ile Trp Gly Gln Gly Thr Met Val Thr Val Ser Ser Ala Ser Thr Lys
            115                 120                 125

Gly Pro Ser Val Phe Pro Leu Ala Pro Cys Ser Arg Ser Thr Ser Glu
        130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
                180                 185                 190

Val Thr Val Pro Ser Ser Ser Leu Gly Thr Lys Thr Tyr Thr Cys Asn
            195                 200                 205

Val Asp His Lys Pro Ser Asn Thr Lys Val Asp Lys Arg Val Glu Ser
        210                 215                 220

Lys Tyr Gly Pro Pro Cys Pro Pro Cys Pro Ala Pro Glu Phe Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser Gln
            260                 265                 270

Glu Asp Pro Glu Val Gln Phe Asn Trp Tyr Val Asp Gly Val Glu Val
        275                 280                 285

His Asn Ala Lys Thr Lys Pro Arg Glu Glu Gln Phe Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Gly Leu Pro Ser Ser Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Gln Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Arg Leu Thr Val
                405                 410                 415

Asp Lys Ser Arg Trp Gln Glu Gly Asn Val Phe Ser Cys Ser Val Met
```

-continued

```
                420                 425                 430

His Glu Ala Leu His Asn His Tyr Thr Gln Lys Ser Leu Ser Leu Ser
            435                 440                 445

Leu Gly
    450

<210> SEQ ID NO 83
<211> LENGTH: 450
<212> TYPE: PRT
<213> ORGANISM: Artificial Sequence
<220> FEATURE:
<223> OTHER INFORMATION: HC of 2A6 (Q1E, S102A, M119L) without C-
      terminal K

<400> SEQUENCE: 83

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Phe Asp Ala Ser Gly Trp Tyr Lys Gly Gly Ala Phe Asp
            100                 105                 110

Ile Trp Gly Gln Gly Thr Leu Val Thr Val Ser Ser Ala Ser Thr Lys
        115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Lys Thr Tyr Thr Cys Asn
        195                 200                 205

Val Asp His Lys Pro Ser Asn Thr Lys Val Asp Lys Arg Val Glu Ser
    210                 215                 220

Lys Tyr Gly Pro Pro Cys Pro Pro Cys Pro Ala Pro Glu Phe Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser Gln
            260                 265                 270

Glu Asp Pro Glu Val Gln Phe Asn Trp Tyr Val Asp Gly Val Glu Val
        275                 280                 285

His Asn Ala Lys Thr Lys Pro Arg Glu Glu Gln Phe Asn Ser Thr Tyr
    290                 295                 300

Arg Val Val Ser Val Leu Thr Val Leu His Gln Asp Trp Leu Asn Gly
305                 310                 315                 320
```

Lys Glu Tyr Lys Cys Lys Val Ser Asn Lys Gly Leu Pro Ser Ser Ile
                    325                 330                 335

Glu Lys Thr Ile Ser Lys Ala Lys Gly Gln Pro Arg Glu Pro Gln Val
            340                 345                 350

Tyr Thr Leu Pro Pro Ser Gln Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Arg Leu Thr Val
                405                 410                 415

Asp Lys Ser Arg Trp Gln Glu Gly Asn Val Phe Ser Cys Ser Val Met
                420                 425                 430

His Glu Ala Leu His Asn His Tyr Thr Gln Lys Ser Leu Ser Leu Ser
            435                 440                 445

Leu Gly
    450

<210> SEQ ID NO 84
<211> LENGTH: 450
<212> TYPE: PRT
<213> ORGANISM: Artificial Sequence
<220> FEATURE:
<223> OTHER INFORMATION: HC of 2A6 (Q1E, D101S, M119L) without C-
      terminal K

<400> SEQUENCE: 84

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Phe Ser Ser Gly Trp Tyr Lys Gly Gly Ala Phe Asp
            100                 105                 110

Ile Trp Gly Gln Gly Thr Leu Val Thr Val Ser Ser Ala Ser Thr Lys
        115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Lys Thr Tyr Thr Cys Asn
        195                 200                 205

Val Asp His Lys Pro Ser Asn Thr Lys Val Asp Lys Arg Val Glu Ser
    210                 215                 220

```
Lys Tyr Gly Pro Pro Cys Pro Pro Cys Pro Ala Pro Glu Phe Leu Gly
225                 230                 235                 240

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser Gln
            260                 265                 270

Glu Asp Pro Glu Val Gln Phe Asn Trp Tyr Val Asp Gly Val Glu Val
            275                 280                 285

His Asn Ala Lys Thr Lys Pro Arg Glu Glu Gln Phe Asn Ser Thr Tyr
        290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Gly Leu Pro Ser Ser Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Gln Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Arg Leu Thr Val
                405                 410                 415

Asp Lys Ser Arg Trp Gln Glu Gly Asn Val Phe Ser Cys Ser Val Met
            420                 425                 430

His Glu Ala Leu His Asn His Tyr Thr Gln Lys Ser Leu Ser Leu Ser
        435                 440                 445

Leu Gly
    450

<210> SEQ ID NO 85
<211> LENGTH: 448
<212> TYPE: PRT
<213> ORGANISM: Artificial Sequence
<220> FEATURE:
<223> OTHER INFORMATION: HC of 3G7 (Q1E) without C-terminal K

<400> SEQUENCE: 85

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Gly Glu Trp Ile Gln Leu Trp Ser Pro Phe Asp Tyr Trp
            100                 105                 110

Gly Gln Gly Thr Leu Val Thr Val Ser Ser Ala Ser Thr Lys Gly Pro
        115                 120                 125
```

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

<210> SEQ ID NO 86
<211> LENGTH: 455
<212> TYPE: PRT
<213> ORGANISM: Artificial Sequence
<220> FEATURE:
<223> OTHER INFORMATION: HC of 2C1 (Q1E) without C-terminal K

<400> SEQUENCE: 86

Glu Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Met His Trp Val Arg Gln Ala Pro Gly Lys Gly Leu Glu Trp Met
        35                  40                  45

-continued

```
Gly Gly Phe Asp Pro Glu Asp Gly Glu Thr Ile Tyr Ala Gln Lys Phe
 50                  55                  60
Gln Gly Arg Val Thr Met Thr Thr Glu Asp Thr Ser Thr Asp Thr Ala Tyr
 65                      70                  75                  80
Met Glu Leu Ser Ser Leu Arg Ser Glu Asp Thr Ala Val Tyr Tyr Cys
                 85                  90                  95
Ala Arg Ala Gly Pro Leu Tyr Thr Ile Phe Gly Val Ile Ile Pro
             100                 105                 110
Asp Asn Trp Phe Asp Pro Trp Gly Gln Gly Thr Leu Val Thr Val Ser
             115                 120                 125
Ser Ala Ser Thr Lys Gly Pro Ser Val Phe Pro Leu Ala Pro Cys Ser
130                 135                 140
Arg Ser Thr Ser Glu Ser Thr Ala Ala Leu Gly Cys Leu Val Lys Asp
145                 150                 155                 160
Tyr Phe Pro Glu Pro Val Thr Val Ser Trp Asn Ser Gly Ala Leu Thr
                 165                 170                 175
Ser Gly Val His Thr Phe Pro Ala Val Leu Gln Ser Ser Gly Leu Tyr
             180                 185                 190
Ser Leu Ser Ser Val Val Thr Val Pro Ser Ser Ser Leu Gly Thr Lys
         195                 200                 205
Thr Tyr Thr Cys Asn Val Asp His Lys Pro Ser Asn Thr Lys Val Asp
    210                 215                 220
Lys Arg Val Glu Ser Lys Tyr Gly Pro Pro Cys Pro Pro Cys Pro Ala
225                 230                 235                 240
Pro Glu Phe Leu Gly Gly Pro Ser Val Phe Leu Phe Pro Pro Lys Pro
                 245                 250                 255
Lys Asp Thr Leu Met Ile Ser Arg Thr Pro Glu Val Thr Cys Val Val
             260                 265                 270
Val Asp Val Ser Gln Glu Asp Pro Glu Val Gln Phe Asn Trp Tyr Val
         275                 280                 285
Asp Gly Val Glu Val His Asn Ala Lys Thr Lys Pro Arg Glu Glu Gln
    290                 295                 300
Phe Asn Ser Thr Tyr Arg Val Val Ser Val Leu Thr Val Leu His Gln
305                 310                 315                 320
Asp Trp Leu Asn Gly Lys Glu Tyr Lys Cys Lys Val Ser Asn Lys Gly
                 325                 330                 335
Leu Pro Ser Ser Ile Glu Lys Thr Ile Ser Lys Ala Lys Gly Gln Pro
             340                 345                 350
Arg Glu Pro Gln Val Tyr Thr Leu Pro Pro Ser Gln Glu Glu Met Thr
         355                 360                 365
Lys Asn Gln Val Ser Leu Thr Cys Leu Val Lys Gly Phe Tyr Pro Ser
    370                 375                 380
Asp Ile Ala Val Glu Trp Glu Ser Asn Gly Gln Pro Glu Asn Asn Tyr
385                 390                 395                 400
Lys Thr Thr Pro Pro Val Leu Asp Ser Asp Gly Ser Phe Phe Leu Tyr
                 405                 410                 415
Ser Arg Leu Thr Val Asp Lys Ser Arg Trp Gln Glu Gly Asn Val Phe
             420                 425                 430
Ser Cys Ser Val Met His Glu Ala Leu His Asn His Tyr Thr Gln Lys
         435                 440                 445
Ser Leu Ser Leu Ser Leu Gly
    450                 455
```

<210> SEQ ID NO 87
<211> LENGTH: 1404
<212> TYPE: DNA
<213> ORGANISM: Artificial Sequence
<220> FEATURE:
<223> OTHER INFORMATION: Nucleotide sequence for HC of 1E1(G4)

<400> SEQUENCE: 87

```
atgaagcacc tgtggttctt cctgctgctg gtggctgctc ccaggtgggt gctgtccgag      60
gtgcagctgc agcagtgggg agctggcctg ctgaagccct ccgaaaccct gtccctgacc     120
tgcgctgtgt acggcggctc cttttccggc tactactgga gctggatcag gcagcctcct     180
ggcaagggcc tggaatggat cggcgagatc aaccacgccg gctccaccaa ctacaacccc     240
tccctgaagt cccgggtgac catctccgtg gacacctcca agaaccagtt ctccctgaag     300
ctgtcctccg tgacagccgc cgacacagcc gtgtactact gtgccaggct gcccaccagg     360
tgggtgacca ccaggtactt tgacctgtgg ggcaggggaa ccctggtgac cgtgtcctcc     420
gctagcacca agggcccatc cgtcttcccc ctggcgccct gctccaggag cacctccgag     480
agcacagccg ccctgggctg cctggtcaag gactacttcc ccgaaccggt gacggtgtcg     540
tggaactcag gcgccctgac cagcggcgtg cacaccttcc cggctgtcct acagtcctca     600
ggactctact ccctcagcag cgtggtgacc gtgccctcca gcagcttggg cacgaagacc     660
tacacctgca acgtagatca caagcccagc aacaccaagg tggacaagag agttgagtcc     720
aaatatggtc cccatgccca ccatgcccag gcacctgagt tcctggggg accatcagtc     780
ttcctgttcc ccccaaaacc caaggacact ctcatgatct cccggacccc tgaggtcacg     840
tgcgtggtgg tggacgtgag ccaggaagac cccgaggtcc agttcaactg gtacgtggat     900
ggcgtggagg tgcataatgc caagacaaag ccgcgggagg agcagttcaa cagcacgtac     960
cgtgtggtca gcgtcctcac cgtcctgcac caggactggc tgaacggcaa ggagtacaag    1020
tgcaaggtct ccaacaaagg cctcccgtcc tccatcgaga aaaccatctc caaagccaaa    1080
gggcagcccc gagagccaca ggtgtacacc ctgcccccat cccaggagga gatgaccaag    1140
aaccaggtca gcctgacctg cctggtcaaa ggcttctacc ccagcgacat cgccgtggag    1200
tgggagagca atgggcagcc ggagaacaac tacaagacca cgcctcccgt gctggactcc    1260
gacggctcct tcttcctcta cagcaggcta accgtggaca agagcaggtg gcaggagggg    1320
aatgtcttct catgctccgt gatgcatgag gctctgcaca accactacac acagaagagc    1380
ctctccctgt ctctgggtaa atga                                            1404
```

<210> SEQ ID NO 88
<211> LENGTH: 711
<212> TYPE: DNA
<213> ORGANISM: Artificial Sequence
<220> FEATURE:
<223> OTHER INFORMATION: Nucleotide sequence for LC of 1E1(G4)

<400> SEQUENCE: 88

```
atggcctgga gccctctgct gctgaccctg ctggcccact gtaccggaag ctgggccgag      60
agcgtgctga cacagcctcc tagcgtgagc ggcgctcctg acaaagggt gaccatcagc     120
tgcaccggct cctccagcaa cattggcgcc ggctacgacg tgcactggta ccagcagctg     180
cctggcaccg ccctaagct gctgatctac ggcgactcca caggccctc cggagtgcct     240
gacaggttct ccgtgtccaa gtccggagct tccgccagcc tggccattac cggactgcag     300
gctgaggacg aggccgacta ctactgccag tccttcgaca cagcctgag cgcctacgtg     360
```

```
ttcggcggag gcacccagct gacagtgctg ggacagccca aagccgcccc ttccgtgacc    420
ctgtttcccc cctcctccga ggagctgcag gctaacaagg ccacactggt gtgtctgatc    480
agcgacttct atcccggagc cgtgaccgtc gcctggaaag ctgatagcag ccccgtgaag    540
gccggagtgg agaccaccac ccccagcaag cagtccaaca caagtacgc cgcctcctcc     600 tacctgtccc tgaccctga gcagtggaag tcccacaggt cctactcctg ccaggtgacc     660
catgagggaa gcacagtgga gaagaccgtg gctcccaccg agtgcagctg a             711

<210> SEQ ID NO 89
<211> LENGTH: 327
<212> TYPE: PRT
<213> ORGANISM: Homo sapiens

<400> SEQUENCE: 89
```

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser

Leu Ser Leu Ser Leu Gly Lys
305                310
                        325

<210> SEQ ID NO 90
<211> LENGTH: 106
<212> TYPE: PRT
<213> ORGANISM: Homo sapiens

<400> SEQUENCE: 90

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

ANTI-ILT4 ANTIBODIES AND ANTIGEN-BINDING FRAGMENTS

CROSS REFERENCE TO RELATED APPLICATIONS

This application is a divisional application of U.S. Non-provisional application Ser. No. 15/945,779, filed Apr. 5, 2018, which claims the benefit of priority to U.S. Provisional Application No. 62/483,019, filed on Apr. 7, 2017, the disclosure of which is incorporated herein by its entirety.

FIELD OF THE INVENTION

The present invention relates to antibodies and antigen-binding fragments thereof that bind to immunoglobulin-like transcript 4 (ILT4) as well as methods of making and using such antibodies and antigen-binding fragments, for example, to treat diseases such as cancer.

REFERENCE TO SEQUENCE LISTING SUBMITTED ELECTRONICALLY

The sequence listing of the present application is submitted electronically via EFS-Web as an ASCII formatted sequence listing with a file name 24443USDIV1-SEQLIST-03JUN2021.txt, creation date of Jun. 3, 2021 and a size of 125 kb. This sequence listing submitted via EFS-Web is part of the specification and is herein incorporated by reference in its entirety.

BACKGROUND OF THE INVENTION

A common strategy used by tumor cells to escape innate and adaptive immune response is associated with aberrant expression of human leukocyte antigen (HLA)-G (Curigliano et al. Clin Cancer Res. 2013 and Gonzalez et al. Crit Rev Clin Lab Sci. 2012). HLA-G can directly inhibit immune cell function through receptor binding and/or through trogocytosis and impairment of chemotaxis (Morandi et al. Cytokine Growth Factor Review. 2014 and Lin et al. Mol Med. 2015). Its high expression in multiple tumor types, including for example, colorectal, pancreatic, endometrial, lung, breast, ovarian, and gastric cancer, is associated with advanced disease stage, tumor invasiveness, metastatic potential and an unfavorable prognosis (Lin et al. Mol Med. 2015. and Loumange et al. Int J Cancer. 2014). Antibody-mediated blockade of HLA-G function in transgenic mouse models has been shown to inhibit tumor development and block expansion of myeloid-derived suppressor cells (MDSC) (Loumange et al. Int J Cancer. 2014, Lin et al. Hum Immunol. 2013, and Agaugue et al. Blood. 2011). HLA-G binding to ILT4 can directly inhibit the function of monocytes, dendritic cells, and neutrophils, thus impairing the innate immune anti-tumor response. The interaction between HLA-G and monocytes due to ILT4 inhibits maturation of human monocyte-derived antigen-presenting cells (APCs) resulting in a reduced expression of MHC class II antigens and co-stimulatory molecules through Stat3 activation (Colonna et al. J Immunol. 1998; Allan et al. J Exp Med. 1999, and Liang et al. Proc Natl Sci USA. 2008). Using human monocyte-derived dendritic cells (DCs) and ILT4-transgenic mice, HLA-G was shown to induce the development of tolerogenic APCs with arrest maturation/activation of myeloid DCs, and the induction of tolerogenic DCs by HLA-G was through disrupting the MHC class II presentation pathway (Ristich et al. Eur J Immunol. 2005).

An unmet medical need exists for patients that do not respond to T-cell therapy but may benefit from relief of tissue associated-macrophage/MDSC-mediated tumor tolerance (e.g. myeloid "rich" tumors). ILT4 blockade would fill this need and would differentiate from current T-cell-targeted antibodies (e.g. anti-PD1, anti-TIGIT) by relieving suppression of tolerogenic myeloid cells in the tumor microenvironment.

SUMMARY OF THE INVENTION

The present invention provides antibodies or antigen-binding fragments thereof that bind to human ILT4. In certain embodiments, the antibody or antigen-binding fragment thereof binds to one or more amino acid residues in a human ILT4 epitope selected from the group consisting of LYREKKSASW (SEQ ID NO:59), TRIRPEL (SEQ ID NO:60), NGQF (SEQ ID NO:61), and HTGRYGCQ (SEQ ID NO:62). In certain embodiments, the antibody or antigen-binding fragment thereof protects the epitope from deuterium exchange with a deuterium source, such as $D_2O$. In one embodiment, the antibody or antigen-binding fragment thereof binds to one or more amino acid residues in the epitope LYREKKSASW (SEQ ID NO:59). In another embodiment, the antibody or antigen-binding fragment thereof binds to one or more amino acid residues in the epitope TRIRPEL (SEQ ID NO:60). In yet another embodiment, the antibody or antigen-binding fragment thereof binds to one or more amino acid residues in the epitope NGQF (SEQ ID NO:61). In still another embodiment, the antibody or antigen-binding fragment thereof binds to one or more amino acid residues in the epitope HTGRYGCQ (SEQ ID NO:62). In yet still another embodiment, the antibody or antigen-binding fragment thereof binds to one or more amino acid residues in two, three, or four ILT4 epitopes selected from the group consisting of LYREKKSASW (SEQ ID NO:59), TRIRPEL (SEQ ID NO:60), NGQF (SEQ ID NO:61), and HTGRYGCQ (SEQ ID NO:62). In one embodiment, the antibody or antigen-binding fragment thereof binds to one or more amino acid residues in the epitope LYREKKSASW (SEQ ID NO:59) and protects the epitope from deuterium exchange with a deuterium source such as $D_2O$. In another embodiment, the antibody or antigen-binding fragment thereof binds to one or more amino acid residues in the epitope TRIRPEL (SEQ ID NO:60) and protects the epitope from deuterium exchange with a deuterium source such as $D_2O$. In yet another embodiment, the antibody or antigen-binding fragment thereof binds to one or more amino acid residues in the epitope NGQF (SEQ ID NO:61) and protects the epitope from deuterium exchange with a deuterium source such as $D_2O$. In still another embodiment, the antibody or antigen-binding fragment thereof binds to one or more amino acid residues in the epitope HTGRYGCQ (SEQ ID NO:62) and protects the epitope from deuterium exchange with a deuterium source such as $D_2O$. In yet still another embodiment, the antibody or antigen-binding fragment thereof binds to one or more amino acid residues in two, three, or four ILT4 epitopes selected from the group consisting of LYREKKSASW (SEQ ID NO:59), TRIRPEL (SEQ ID NO:60), NGQF (SEQ ID NO:61), and HTGRYGCQ (SEQ ID NO:62) and protects the epitopes from deuterium exchange with a deuterium source such as $D_2O$.

The present invention also provides an antibody or antigen-binding fragment thereof that binds to the same epitope of human ILT4 as any antibody or antigen-binding fragment thereof disclosed herein. In certain embodiments, the antibody or antigen-binding fragment thereof binds to the same epitope of human ILT4 as an antibody or antigen-binding fragment thereof comprising the heavy chain and light chain amino acid sequences set forth in SEQ ID NOs:1 and 3; 2 and 4; 2 and 5; 2 and 6; 2 and 7; 2 and 3; 8 and 11; 9 and 11; 10 and 11; 12 and 13; 14 and 15; 79 and 3; 80 and 4; 80 and 5; 80 and 6; 80 and 7; 80 and 3; 82 and 11; 83 and 11; 84 and 11; 85 and 13; and 86 and 15; respectively. In some embodiments, the antibody or antigen-binding fragment thereof binds to the same epitope of human ILT4 as an antibody or antigen-binding fragment thereof comprising the heavy chain variable domain and light chain variable domain amino acid sequences set forth in SEQ ID NOs:63 and 70; 57 and 71; 57 and 72; 57 and 73; 57 and 58; 57 and 70; 64 and 74; 65 and 74; 66 and 74; 67 and 75; 68 and 76; respectively.

The present invention further provides an antibody or antigen-binding fragment thereof that competes for binding to human ILT4 with an antibody or antigen-binding fragment thereof disclosed herein. In certain embodiments, the antibody or antigen-binding fragment thereof competes for binding to human ILT4 with an antibody or fragment comprising the heavy chain and light chain amino acid sequences set forth in SEQ ID NOs:1 and 3; 2 and 4; 2 and 5; 2 and 6; 2 and 7; 2 and 3; 8 and 11; 9 and 11; 10 and 11; 12 and 13; 14 and 15; 79 and 3; 80 and 4; 80 and 5; 80 and 6; 80 and 7; 80 and 3; 82 and 11; 83 and 11; 84 and 11; 85 and 13; and 86 and 15; respectively. In some embodiments, the antibody or antigen-binding fragment thereof competes for binding to human ILT4 with an antibody or fragment comprising the heavy chain variable domain and light chain variable domain amino acid sequences set forth in SEQ ID NOs:63 and 70; 57 and 71; 57 and 72; 57 and 73; 57 and 58; 57 and 70; 64 and 74; 65 and 74; 66 and 74; 67 and 75; 68 and 76; respectively.

In addition, the present invention provides an antibody or antigen-binding fragment thereof that binds human ILT4, comprising: (a) the complementarity determining region-L1 (CDR-L1), complementarity determining region-L2 (CDR-L2), and complementarity determining region-L3 (CDR-L3) of a light chain variable ($V_L$) domain of an immunoglobulin chain that comprises the amino acid sequence set forth in SEQ ID NO: 3-7, 11, 13, 15, or 45; and/or (b) the complementarity determining region-H1 (CDR-H1), complementarity determining region-H2 (CDR-H2), and complementarity determining region-H3 (CDR-H3) of a heavy chain variable ($V_H$) domain of an immunoglobulin chain that comprises the amino acid sequence set forth in SEQ ID NO: 1, 2, 8-10, 12, 14, 44, or 79-86.

In an embodiment of the invention, the antibody or antigen-binding fragment thereof comprises: (1) a $V_H$ domain comprising: CDR-H1: GYYWS (SEQ ID NO: 16), CDR-H2: EINHXGSTNYNPSLKS wherein X is S or A (SEQ ID NO: 17); and CDR-H3: LPTRWVTTRYFDL (SEQ ID NO: 18); and/or, a $V_L$ domain comprising: CDR-L1: TGSSSNIGAGYDVH (SEQ ID NO: 19), CDR-L2: GX$_1$X$_2$NRPS, wherein X$_1$ is S or A and X$_2$ is N, Q, E or D (SEQ ID NO: 20); and CDR-L3: QSFDNSLSAYV (SEQ ID NO: 21); (2) a $V_H$ domain comprising: CDR-H1: SYAIS (SEQ ID NO: 22); CDR-H2: GIIPIFGTANYAQKFQG (SEQ ID NO: 23); and CDR-H3: YFX$_1$X$_2$SGWYKGGAFDI, wherein X$_1$ is D or S and X$_2$ is S or A (SEQ ID NO: 24); and/or, a $V_L$ domain comprising: CDR-L1: TLRSGINVDTYRIH (SEQ ID NO: 25); CDR-L2: YKSDSDKHQGS (SEQ ID NO: 26); and CDR-L3: AIWYSSTWV (SEQ ID NO: 27); (3) a $V_H$ domain comprising: CDR-H1: SYAMH (SEQ ID NO: 28); CDR-H2: VISYDGSNKYYADSVKG (SEQ ID NO: 29); and CDR-H3: VGEWIQLWSPFDY (SEQ ID NO: 30); and/or, a $V_L$ domain comprising: CDR-L1: RASQGISSWLA (SEQ ID NO: 31); CDR-L2: AASSLQS (SEQ ID NO: 32); and CDR-L3: QQYNSYPPT (SEQ ID NO: 33); and/or (4) a $V_H$ domain comprising: CDR-H1: ELSMH (SEQ ID NO: 34); CDR-H2: GFDPEDGETIYAQKFQG (SEQ ID NO: 35); and CDR-H3: AGPLYTIFGVVIIPDNWFDP (SEQ ID NO: 36); and/or, a $V_L$ domain comprising: CDR-L1: TGSSSNIGAGYDVH (SEQ ID NO: 37); CDR-L2: GNSNRPS (SEQ ID NO: 38); and CDR-L3: QSYDSSLSGSGVV (SEQ ID NO: 39).

In one embodiment, the antibody or antigen-binding fragment comprises: a $V_H$ domain comprising: CDR-H1: GYYWS (SEQ ID NO: 16), CDR-H2: EINHXGSTNYNPSLKS (SEQ ID NO: 47), and CDR-H3: LPTRWVTTRYFDL (SEQ ID NO: 18); and/or, a $V_L$ domain comprising: CDR-L1: TGSSSNIGAGYDVH (SEQ ID NO: 19), CDR-L2: GNSNRPS(SEQ ID NO: 49), and CDR-L3: QSFDNSLSAYV (SEQ ID NO: 21).

In another embodiment, the antibody or antigen-binding fragment comprises: a $V_H$ domain comprising: CDR-H1: GYYWS (SEQ ID NO: 16), CDR-H2: EINHSGSTNYNPSLKS (SEQ ID NO: 47), and CDR-H3: LPTRWVTTRYFDL (SEQ ID NO: 18); and/or, a $V_L$ domain comprising: CDR-L1: TGSSSNIGAGYDVH (SEQ ID NO: 19), CDR-L2: GQSNRPS(SEQ ID NO: 50), and CDR-L3: QSFDNSLSAYV (SEQ ID NO: 21).

In yet another embodiment, the antibody or antigen-binding fragment thereof comprises: a $V_H$ domain comprising: CDR-H1: GYYWS (SEQ ID NO: 16), CDR-H2: EINHSGSTNYNPSLKS (SEQ ID NO: 47), and CDR-H3: LPTRWVTTRYFDL (SEQ ID NO: 18); and/or, a $V_L$ domain comprising: CDR-L1: TGSSSNIGAGYDVH (SEQ ID NO: 19), CDR-L2: GESNRPS(SEQ ID NO: 51), and CDR-L3: QSFDNSLSAYV (SEQ ID NO: 21).

In still another embodiment, the antibody or antigen-binding fragment thereof comprises: a $V_H$ domain comprising: CDR-H1: GYYWS (SEQ ID NO: 16), CDR-H2: EINHSGSTNYNPSLKS (SEQ ID NO: 47), and CDR-H3: LPTRWVTTRYFDL (SEQ ID NO: 18); and/or, a $V_L$ domain comprising: CDR-L1: TGSSSNIGAGYDVH (SEQ ID NO: 19), CDR-L2: GDSNRPS(SEQ ID NO: 52), and CDR-L3: QSFDNSLSAYV (SEQ ID NO: 21).

In one embodiment, the antibody or antigen-binding fragment thereof comprises: a $V_H$ domain comprising: CDR-H1: GYYWS (SEQ ID NO: 16), CDR-H2: EINHSGSTNYNPSLKS (SEQ ID NO: 47), and CDR-H3: LPTRWVTTRYFDL (SEQ ID NO: 18); and/or, a $V_L$ domain comprising: CDR-L1: TGSSSNIGAGYDVH (SEQ ID NO: 19), CDR-L2: GNANRPS(SEQ ID NO: 53), and CDR-L3: QSFDNSLSAYV (SEQ ID NO: 21).

In another embodiment, the antibody or antigen-binding fragment thereof comprises: a $V_H$ domain comprising: CDR-H1: GYYWS (SEQ ID NO: 16), CDR-H2: EINHSGSTNYNPSLKS (SEQ ID NO: 47), and CDR-H3: LPTRWVTTRYFDL (SEQ ID NO: 18); and/or, a $V_L$ domain comprising: CDR-L1: TGSSSNIGAGYDVH (SEQ ID NO: 19), CDR-L2: GQANRPS(SEQ ID NO: 54), and CDR-L3: QSFDNSLSAYV (SEQ ID NO: 21).

In yet another embodiment, the antibody or antigen-binding fragment thereof comprises: a $V_H$ domain comprising: CDR-H1: GYYWS (SEQ ID NO: 16), CDR-H2: EINHSGSTNYNPSLKS (SEQ ID NO: 47), and CDR-H3: LPTRWVTTRYFDL (SEQ ID NO: 18); and/or, a $V_L$ domain comprising: CDR-L1: TGSSSNIGAGYDVH (SEQ ID NO:

19), CDR-L2: GEANRPS(SEQ ID NO: 55), and CDR-L3: QSFDNSLSAYV (SEQ ID NO: 21).

In still another embodiment, the antibody or antigen-binding fragment thereof comprises: a $V_H$ domain comprising: CDR-H1: GYYWS (SEQ ID NO: 16), CDR-H2: EINHSGSTNYNPSLKS (SEQ ID NO: 47), and CDR-H3: LPTRWVTTRYFDL (SEQ ID NO: 18); and/or, a $V_L$ domain comprising: CDR-L1: TGSSSNIGAGYDVH (SEQ ID NO: 19), CDR-L2: GDANRPS(SEQ ID NO: 56), and CDR-L3: QSFDNSLSAYV (SEQ ID NO: 21).

In one embodiment, the antibody or antigen-binding fragment thereof comprises: a $V_H$ domain comprising: CDR-H1: GYYWS (SEQ ID NO: 16), CDR-H2: EINHAGSTNYNPSLKS (SEQ ID NO: 48), and CDR-H3: LPTRWVTTRYFDL (SEQ ID NO: 18); and/or, a $V_L$ domain comprising: CDR-L1: TGSSSNIGAGYDVH (SEQ ID NO: 19), CDR-L2: GNSNRPS(SEQ ID NO: 49), and CDR-L3: QSFDNSLSAYV (SEQ ID NO: 21).

In another embodiment, the antibody or antigen-binding fragment thereof comprises: a $V_H$ domain comprising: CDR-H1: GYYWS (SEQ ID NO: 16), CDR-H2: EINHAGSTNYNPSLKS (SEQ ID NO: 48), and CDR-H3: LPTRWVTTRYFDL (SEQ ID NO: 18); and/or, a $V_L$ domain comprising: CDR-L1: TGSSSNIGAGYDVH (SEQ ID NO: 19), CDR-L2: GQSNRPS(SEQ ID NO: 50), and CDR-L3: QSFDNSLSAYV (SEQ ID NO: 21).

In yet another embodiment, the antibody or antigen-binding fragment thereof comprises: a $V_H$ domain comprising: CDR-H1: GYYWS (SEQ ID NO: 16), CDR-H2: EINHAGSTNYNPSLKS (SEQ ID NO: 48), and CDR-H3: LPTRWVTTRYFDL (SEQ ID NO: 18); and/or, a $V_L$ domain comprising: CDR-L1: TGSSSNIGAGYDVH (SEQ ID NO: 19), CDR-L2: GESNRPS(SEQ ID NO: 51), and CDR-L3: QSFDNSLSAYV (SEQ ID NO: 21).

In still another embodiment, the antibody or antigen-binding fragment thereof comprises: a $V_H$ domain comprising: CDR-H1: GYYWS (SEQ ID NO: 16), CDR-H2: EINHAGSTNYNPSLKS (SEQ ID NO: 48), and CDR-H3: LPTRWVTTRYFDL (SEQ ID NO: 18); and/or, a $V_L$ domain comprising: CDR-L1: TGSSSNIGAGYDVH (SEQ ID NO: 19), CDR-L2: GDSNRPS(SEQ ID NO: 52), and CDR-L3: QSFDNSLSAYV (SEQ ID NO: 21).

In one embodiment, the antibody or antigen-binding fragment thereof comprises: a $V_H$ domain comprising: CDR-H1: GYYWS (SEQ ID NO: 16), CDR-H2: EINHAGSTNYNPSLKS (SEQ ID NO: 48), and CDR-H3: LPTRWVTTRYFDL (SEQ ID NO: 18); and/or, a $V_L$ domain comprising: CDR-L1: TGSSSNIGAGYDVH (SEQ ID NO: 19), CDR-L2: GNANRPS(SEQ ID NO: 53), and CDR-L3: QSFDNSLSAYV (SEQ ID NO: 21).

In another embodiment, the antibody or antigen-binding fragment thereof comprises: a $V_H$ domain comprising: CDR-H1: GYYWS (SEQ ID NO: 16), CDR-H2: EINHAGSTNYNPSLKS (SEQ ID NO: 48), and CDR-H3: LPTRWVTTRYFDL (SEQ ID NO: 18); and/or, a $V_L$ domain comprising: CDR-L1: TGSSSNIGAGYDVH (SEQ ID NO: 19), CDR-L2: GQANRPS(SEQ ID NO: 54), and CDR-L3: QSFDNSLSAYV (SEQ ID NO: 21).

In yet another embodiment, the antibody or antigen-binding fragment thereof comprises: a $V_H$ domain comprising: CDR-H1: GYYWS (SEQ ID NO: 16), CDR-H2: EINHAGSTNYNPSLKS (SEQ ID NO: 48), and CDR-H3: LPTRWVTTRYFDL (SEQ ID NO: 18); and/or, a $V_L$ domain comprising: CDR-L1: TGSSSNIGAGYDVH (SEQ ID NO: 19), CDR-L2: GEANRPS(SEQ ID NO: 55), and CDR-L3: QSFDNSLSAYV (SEQ ID NO: 21).

In still another embodiment, the antibody or antigen-binding fragment thereof comprises: a $V_H$ domain comprising: CDR-H1: GYYWS (SEQ ID NO: 16), CDR-H2: EINHAGSTNYNPSLKS (SEQ ID NO: 48), and CDR-H3: LPTRWVTTRYFDL (SEQ ID NO: 18); and/or, a $V_L$ domain comprising: CDR-L1: TGSSSNIGAGYDVH (SEQ ID NO: 19), CDR-L2: GDANRPS(SEQ ID NO: 56), and CDR-L3: QSFDNSLSAYV (SEQ ID NO: 21).

In certain embodiments, the antibody or antigen-binding fragment thereof comprises a light chain immunoglobulin, a heavy chain immunoglobulin, or both a light and heavy chain immunoglobulin, wherein the light chain immunoglobulin has at least 90% amino acid sequence identity to the amino acid sequence set forth in SEQ ID NO:3, 4, 5, 6, 7, 11, 13, 15, or 45, and/or the heavy chain immunoglobulin has at least 90% amino acid sequence identity to the amino acid sequence set forth in SEQ ID NO:1, 2, 8, 9, 10, 12, 14, 44, 79, 80, 81, 82, 83, 84, 85, or 86.

In some embodiments, the antibody or antigen-binding fragment thereof comprises a light chain immunoglobulin, a heavy chain immunoglobulin, or both a light and heavy chain immunoglobulin, wherein the light chain immunoglobulin comprises a light chain variable domain having at least 90% amino acid sequence identity to the amino acid sequence set forth in SEQ ID NO:70, 71, 72, 73, 58, 74, 75, 76, or 77, and/or the heavy chain immunoglobulin comprises a heavy chain variable domain having at least 90% amino acid sequence identity to the amino acid sequence set forth in SEQ ID NO:63, 57, 64, 65, 66, 67, 68, or 69.

In still other embodiments, the antibody or antigen-binding fragment thereof comprises a light chain immunoglobulin, a heavy chain immunoglobulin, or both a light and heavy chain immunoglobulin, wherein the light chain immunoglobulin comprises the amino acid sequence set forth in SEQ ID NO:3, 4, 5, 6, 7, 11, 13, 15, or 45; and/or the heavy chain immunoglobulin comprises the amino acid sequence set forth in SEQ ID NO: 1, 2, 8, 9, 10, 12, 14, 44, 79, 80, 81, 82, 83, 84, 85, or 86.

In yet still other embodiments, the antibody or antigen-binding fragment thereof comprises a light chain immunoglobulin, a heavy chain immunoglobulin, or both a light and heavy chain immunoglobulin, wherein the light chain variable domain comprises the amino acid sequence set forth in SEQ ID NO:70, 71, 72, 73, 58, 74, 75, 76, or 77, and/or the heavy chain variable domain comprise the amino acid sequence set forth in SEQ ID NO:63, 57, 64, 65, 66, 67, 68, or 69.

Further provided is an antibody or antigen-binding fragment thereof comprising any of the following sets of heavy chain immunoglobulins and light chain immunoglobulins: (1) a heavy chain immunoglobulin comprising the amino acid sequence set forth in SEQ ID NO:1; a light chain immunoglobulin comprising the amino acid sequence set forth in SEQ ID NO:3; (2) a heavy chain immunoglobulin comprising the amino acid sequence set forth in SEQ ID NO:2; a light chain immunoglobulin comprising the amino acid sequence set forth in SEQ ID NO:4; (3) a heavy chain immunoglobulin comprising the amino acid sequence set forth in SEQ ID NO:2; a light chain immunoglobulin comprising the amino acid sequence set forth in SEQ ID NO:5; (4) a heavy chain immunoglobulin comprising the amino acid sequence set forth in SEQ ID NO:2; a light chain immunoglobulin comprising the amino acid sequence set forth in SEQ ID NO:6; (5) a heavy chain immunoglobulin comprising the amino acid sequence set forth in SEQ ID NO:2; a light chain immunoglobulin comprising the amino acid sequence set forth in SEQ ID NO:7; (6) a heavy chain immunoglobulin comprising the amino acid sequence set forth in SEQ ID NO:2; a light chain immunoglobulin comprising the amino acid sequence set forth in SEQ ID NO:3; (7) a heavy chain immunoglobulin comprising the amino acid sequence set forth in SEQ ID NO:8; a light chain immunoglobulin comprising the amino acid sequence set forth in SEQ ID NO:11; (8) a heavy chain immunoglobulin comprising the amino acid sequence set forth in SEQ ID NO:9; a light chain immunoglobulin comprising the amino acid sequence set forth in SEQ ID NO:11; (9) a heavy chain immunoglobulin comprising the amino acid sequence set forth in SEQ ID NO:10; a light chain immunoglobulin comprising the amino acid sequence set forth in SEQ ID NO:11; (10) a heavy chain immunoglobulin comprising the amino acid sequence set forth in SEQ ID NO:12; a light chain immunoglobulin comprising the amino acid sequence set forth in SEQ ID NO:13; (11) a heavy chain immunoglobulin comprising the amino acid sequence set forth in SEQ ID NO:14; a light chain immunoglobulin comprising the amino acid sequence set forth in SEQ ID NO:15; (12) a heavy chain immunoglobulin comprising the amino acid sequence set forth in SEQ ID NO:79; a light chain immunoglobulin comprising the amino acid sequence set forth in SEQ ID NO:3; (13) a heavy chain immunoglobulin comprising the amino acid sequence set forth in SEQ ID NO:80; a light chain immunoglobulin comprising the amino acid sequence set forth in SEQ ID NO:4; (14) a heavy chain immunoglobulin comprising the amino acid sequence set forth in SEQ ID NO:80; a light chain immunoglobulin comprising the amino acid sequence set forth in SEQ ID NO:5; (15) a heavy chain immunoglobulin comprising the amino acid sequence set forth in SEQ ID NO:80; a light chain immunoglobulin comprising the amino acid sequence set forth in SEQ ID NO:6; (16) a heavy chain immunoglobulin comprising the amino acid sequence set forth in SEQ ID NO:80; a light chain immunoglobulin comprising the amino acid sequence set forth in SEQ ID NO:7; (17) a heavy chain immunoglobulin comprising the amino acid sequence set forth in SEQ ID NO:80; a light chain immunoglobulin comprising the amino acid sequence set forth in SEQ ID NO:3; (18) a heavy chain immunoglobulin comprising the amino acid sequence set forth in SEQ ID NO:82; a light chain immunoglobulin comprising the amino acid sequence set forth in SEQ ID NO:11; (19) a heavy chain immunoglobulin comprising the amino acid sequence set forth in SEQ ID NO:83; a light chain immunoglobulin comprising the amino acid sequence set forth in SEQ ID NO:11; (20) a heavy chain immunoglobulin comprising the amino acid sequence set forth in SEQ ID NO:84; a light chain immunoglobulin comprising the amino acid sequence set forth in SEQ ID NO:11; (21) a heavy chain immunoglobulin comprising the amino acid sequence set forth in SEQ ID NO:85; a light chain immunoglobulin comprising the amino acid sequence set forth in SEQ ID NO:13; or (22) a heavy chain immunoglobulin comprising the amino acid sequence set forth in SEQ ID NO:86; a light chain immunoglobulin comprising the amino acid sequence set forth in SEQ ID NO:15.

In addition, provided herein is an antibody or antigen-binding fragment thereof comprising any of the following sets of heavy chain variable domain and light chain variable domain: (1) a heavy chain variable domain comprising the amino acid sequence set forth in SEQ ID NO:63; and a light chain variable domain comprising the amino acid sequence set forth in SEQ ID NO:70; (2) a heavy chain variable domain comprising the amino acid sequence set forth in SEQ ID NO:57; and a light chain variable domain comprising the amino acid sequence set forth in SEQ ID NO:71; (3) a heavy chain variable domain comprising the amino acid sequence set forth in SEQ ID NO:57; and a light chain variable domain comprising the amino acid sequence set forth in SEQ ID NO:72; (4) a heavy chain variable domain comprising the amino acid sequence set forth in SEQ ID NO:57; and a light chain variable domain comprising the amino acid sequence set forth in SEQ ID NO:73; (5) a heavy chain variable domain comprising the amino acid sequence set forth in SEQ ID NO:57; and a light chain variable domain comprising the amino acid sequence set forth in SEQ ID NO:58; (6) a heavy chain variable domain comprising the amino acid sequence set forth in SEQ ID NO:57; and a light chain variable domain comprising the amino acid sequence set forth in SEQ ID NO:70; (7) a heavy chain variable domain comprising the amino acid sequence set forth in SEQ ID NO:64; and a light chain variable domain comprising the amino acid sequence set forth in SEQ ID NO:74; (8) a heavy chain variable domain comprising the amino acid sequence set forth in SEQ ID NO:65; and a light chain variable domain comprising the amino acid sequence set forth in SEQ ID NO:74; (9) a heavy chain variable domain comprising the amino acid sequence set forth in SEQ ID NO:66; and a light chain variable domain comprising the amino acid sequence set forth in SEQ ID NO:74; (10) a heavy chain variable domain comprising the amino acid sequence set forth in SEQ ID NO:67; and a light chain variable domain comprising the amino acid sequence set forth in SEQ ID NO:75; or (11) a heavy chain variable domain comprising the amino acid sequence set forth in SEQ ID NO:68; and a light chain variable domain comprising the amino acid sequence set forth in SEQ ID NO:76.

In one preferred embodiment, the antibody or antigen-binding fragment thereof comprises a $V_H$ domain comprising the amino acid sequence set forth in SEQ ID NO:57; and a $V_L$ domain comprising the amino acid sequence set forth in SEQ ID NO:58.

In another preferred embodiment, the antibody or antigen-binding fragment thereof comprises: a heavy chain immunoglobulin comprising the amino acid sequence set forth in SEQ ID NO:2; and a light chain immunoglobulin comprising the amino acid sequence set forth in SEQ ID NO:7.

In yet another preferred embodiment, the antibody or antigen-binding fragment thereof comprises: a heavy chain immunoglobulin comprising the amino acid sequence set forth in SEQ ID NO:80; and a light chain immunoglobulin comprising the amino acid sequence set forth in SEQ ID NO:7.

In one embodiment, the antibody consists of two heavy chains and two light chains, wherein each light chain comprises the amino acid sequence set forth in SEQ ID NO:58 and each heavy chain comprises the amino acid sequence set forth in SEQ ID NO:57.

In another embodiment, the antibody consists of two heavy chains and two light chains, wherein each light chain comprises the amino acid sequence set forth in SEQ ID NO:58 and each heavy chain comprises the amino acid sequence set forth in SEQ ID NO:57, wherein the light chain further comprises the amino acid sequence set forth in SEQ ID NO:90.

In yet another embodiment, the antibody consists of two heavy chains and two light chains, wherein each light chain comprises the amino acid sequence set forth in SEQ ID NO:58 and each heavy chain comprises the amino acid sequence set forth in SEQ ID NO:57, wherein the heavy chain further comprises the amino acid sequence set forth in SEQ ID NO:89.

In still another embodiment, the antibody consists of two heavy chains and two light chains, wherein each light chain comprises the amino acid sequence set forth in SEQ ID NO:58 and each heavy chain comprises the amino acid sequence set forth in SEQ ID NO:57, wherein the light chain further comprises the amino acid sequence set forth in SEQ ID NO:90 and the heavy chain further comprises the amino acid sequence set forth in SEQ ID NO:89.

In one embodiment, the antibody consists of two heavy chains and two light chains, wherein each light chain comprises the amino acid sequence set forth in SEQ ID NO:7 and each heavy chain comprises the amino acid sequence set forth in SEQ ID NO:2.

In another embodiment, the antibody consists of two heavy chains and two light chains, wherein each light chain consists of the amino acid sequence set forth in SEQ ID NO:7 and each heavy chain consists of the amino acid sequence set forth in SEQ ID NO:2.

In an embodiment of the invention, the antibody or antigen-binding fragment thereof is glycosylated, e.g., with engineered yeast N-linked glycans or Chinese hamster ovary (CHO) cell N-linked glycans. In an embodiment of the invention, the antibody or antigen-binding fragment thereof is an antibody.

The present invention also provides a pharmaceutical composition comprising an antibody or antigen-binding fragment thereof disclosed herein. In certain embodiments, the composition further comprises a therapeutic agent (e.g., pembrolizumab). In some embodiments, the composition further comprises a pharmaceutically acceptable carrier. In other embodiments, the composition further comprises a therapeutic agent (e.g., pembrolizumab) and a pharmaceutically acceptable carrier.

In one embodiment, the pharmaceutical composition comprises: (i) an antibody that consists of two heavy chains and two light chains, wherein each light chain consists of the amino acid sequence set forth in SEQ ID NO:7 and each heavy chain consists of the amino acid sequence set forth in SEQ ID NO:2, and (ii) pembrolizumab.

The present invention further provides a polypeptide (e.g., an isolated polypeptide) which includes the immunoglobulin light chain and/or immunoglobulin heavy chain or a variable domain thereof of any antibody or antigen-binding fragment thereof disclosed herein. For example, in an embodiment of the invention, the polypeptide comprises an amino acid sequence selected from the group consisting of SEQ ID NOs: 1-39, 44, 45, 47-58, 63-77, and 79-86. Also provided by the present invention is any polynucleotide (e.g., DNA or RNA) that encodes any polypeptide disclosed herein. In another aspect, provided is a vector comprising the polynucleotide disclosed herein. The present invention also provides a host cell (e.g., a CHO cell) comprising the polynucleotide or the vector disclosed herein.

The present invention provides a method for blocking binding of ILT4 to HLA-G, HLA-A, HLA-B, and/or HLA-F, e.g., in vitro or in vivo, for example, in the body of a subject (e.g., a human subject) in need thereof, comprising administering to the subject an effective amount of the antibody or antigen-binding fragment thereof disclosed herein. In certain embodiments, the method for blocking binding of ILT4 to HLA-G, HLA-A, HLA-B, and/or HLA-F further comprises performing a therapeutic procedure (e.g., anti-cancer radiation therapy or surgical tumorectomy) to the subject. In some embodiments, the method for blocking binding of ILT4 to HLA-G, HLA-A, HLA-B, and/or HLA-F further comprises administering a therapeutic agent (e.g., pembrolizumab) to the subject. In other embodiments, the method for blocking binding of ILT4 to HLA-G, HLA-A, HLA-B, and/or HLA-F further comprises performing a therapeutic procedure (e.g., anti-cancer radiation therapy or surgical tumorectomy) and administering a therapeutic agent (e.g., pembrolizumab) to the subject.

The present invention also provides a method of treating a cancer in a subject (e.g., a human subject), comprising administering to the subject an effective amount of the antibody or antigen-binding fragment thereof disclosed herein. In certain embodiments, the method of treating a cancer further comprises performing a therapeutic procedure (e.g., anti-cancer radiation therapy or surgical tumorectomy) to the subject. In some embodiments, the method of treating a cancer further comprises administering a therapeutic agent (e.g., pembrolizumab) to the subject. In other embodiments, the method of treating a cancer further comprises performing a therapeutic procedure (e.g., anti-cancer radiation therapy or surgical tumorectomy) and administering a therapeutic agent (e.g., pembrolizumab) to the subject.

The present invention also provides a method of producing the antibody or antigen-binding fragment thereof of the present invention or an immunoglobulin chain thereof (e.g., a $V_H$ and/or $V_L$ thereof), comprising culturing a host cell (e.g., a CHO cell) comprising a polynucleotide (e.g., wherein the polynucleotide is in a vector and/or is integrated into one or more chromosomes of the host cell) encoding the antibody or antigen-binding fragment thereof or an immunoglobulin chain thereof to express the antibody or antigen-binding fragment thereof or an immunoglobulin chain thereof.

Also provided is a method of producing the antibody or antigen-binding fragment thereof of the present invention or an immunoglobulin chain thereof (e.g., a $V_H$ and/or $V_L$ thereof), comprising: expressing a polynucleotide encoding the antibody or antigen-binding fragment thereof or an immunoglobulin chain thereof.

An antibody or antigen-binding fragment thereof that binds human ILT4 or an immunoglobulin chain thereof which is a product of said method is also part of the present invention.

A method for detecting the presence of an ILT4 peptide or a fragment thereof in a sample also forms part of the present invention. The method comprises contacting the sample with an antibody or antigen-binding fragment of the present invention and detecting the presence of a complex between the antibody or antigen-binding fragment and the ILT4 peptide or fragment thereof, wherein detection of the complex indicates the presence of the ILT4 peptide or fragment thereof. In an embodiment of the invention, the method is performed in vitro, e.g., in a biological sample, e.g., surgical section or blood sample, of a subject. In another embodiment, the method is performed in vivo, e.g., in the body of a subject. In yet another embodiment, the subject is a human being.

BRIEF DESCRIPTION OF THE FIGURES

FIG. 2A depicts the deuterium labeling levels mapped onto the structure of human ILT4. FIG. 2B shows the crystal structure of domains 1 and 2 of human ILT4 complexed with HLA-G. ILT4, HLA-G heavy chain, and beta-2-microglobulin are indicated. The human ILT4 epitopes, having residues LYREKKSASW (SEQ ID NO:59), TRIRPEL (SEQ ID NO:60), NGQF (SEQ ID NO:61), and HTGRYGCQ (SEQ ID NO:62), are indicated.

FIG. 3A. 1E1(G4) or hIgG4 was detected with fluorochrome labeled goat anti-human F(ab)$_2$ and detected by flow cytometry. FIG. 3B. Following 1E1(G4) pre-treatment, cells were incubated with 2 ug/mL biotinylated HLA-Fc or control Fc (mVISTA-Fc). Fc binding was detected with PE conjugated streptavidin and detected by flow cytometry. Plots shown are representative of 3 independent experiments. IC50 and EC50 values shown are the average of these experiments +/−standard deviation.

FIGS. 5A-5C. ANGPTL binding to ILT4 and p1E1(G1) blockade. FIG. 5A. Biotinylated ANGPTL proteins were preincubated for 20 min. with p1E1(G1) or human IgG1, the final concentration of each was 20 ug/mL. Solutions were then added to mouse 3A9 T cells transfected with human ILT4 and were incubated for an additional 30 minutes. ANGPTL binding was detected with PE conjugated streptavidin and analyzed by flow cytometry. PE labeled HLA-G tetramer was also added as a positive ILT4 binding/blocking control. ANGPTL proteins were purchased from R&D SYSTEMS and biotinylated; FIG. 5B. Mouse 3A9 T cells transfected with human ILT4 were blocked with Fc block, then incubated with 20 ug/mL of p1E1(G1) or hIgG1 isotype control. Following incubation, p1E1 (G1) or hIgG1 was detected with fluorochrome labeled goat anti-human F(ab')2 and analyzed by flow cytometry; FIG. 5C. Vector control 3A9 T-cells were used as a negative control for ANGPTL binding. Cells were treated as described in (A) except no treatment with antibody was performed.

FIG. 11A shows mean tumor volume (mm$^3$)+/−SD over time for both groups, and FIGS. 11B and 11C show individual mouse tumor volumes (mm$^3$) over time for isotype treated and p1E1(G4), respectively. FIG. 11D shows tumor weight in individual mice treated with isotype control or p1E1(G4) as followed over time; FIG. 11E shows weight loss of each treatment group was also measured over time. Following study completion, mice were sacrificed and tumors were harvested and weighed.

FIGS. 12A-12D demonstrate that 1E1(G4) treatment led to tumor growth inhibition in a humanized mouse SK-MEL-5 tumor model. FIG. 12A shows mean tumor volume (mm$^3$)+/−SD over time for both 1E1(G4)-treated mice and IgG4 isotype control-treated mice. FIG. 12B shows body weight change over time for both groups. FIG. 12C shows endpoint tumor weight in individual mice treated with isotype control or 1E1(G4). FIG. 12D shows endpoint spleen weight in individual mice treated with isotype control or 1E1(G4).

FIG. 14A depicts ILT4 RNA expression in various tumor types according to the TOGA database. FIG. 14B depicts ILT4 RNA expression in various cell types according to the Blueprint database.

DETAILED DESCRIPTION OF THE INVENTION

Figure 1:
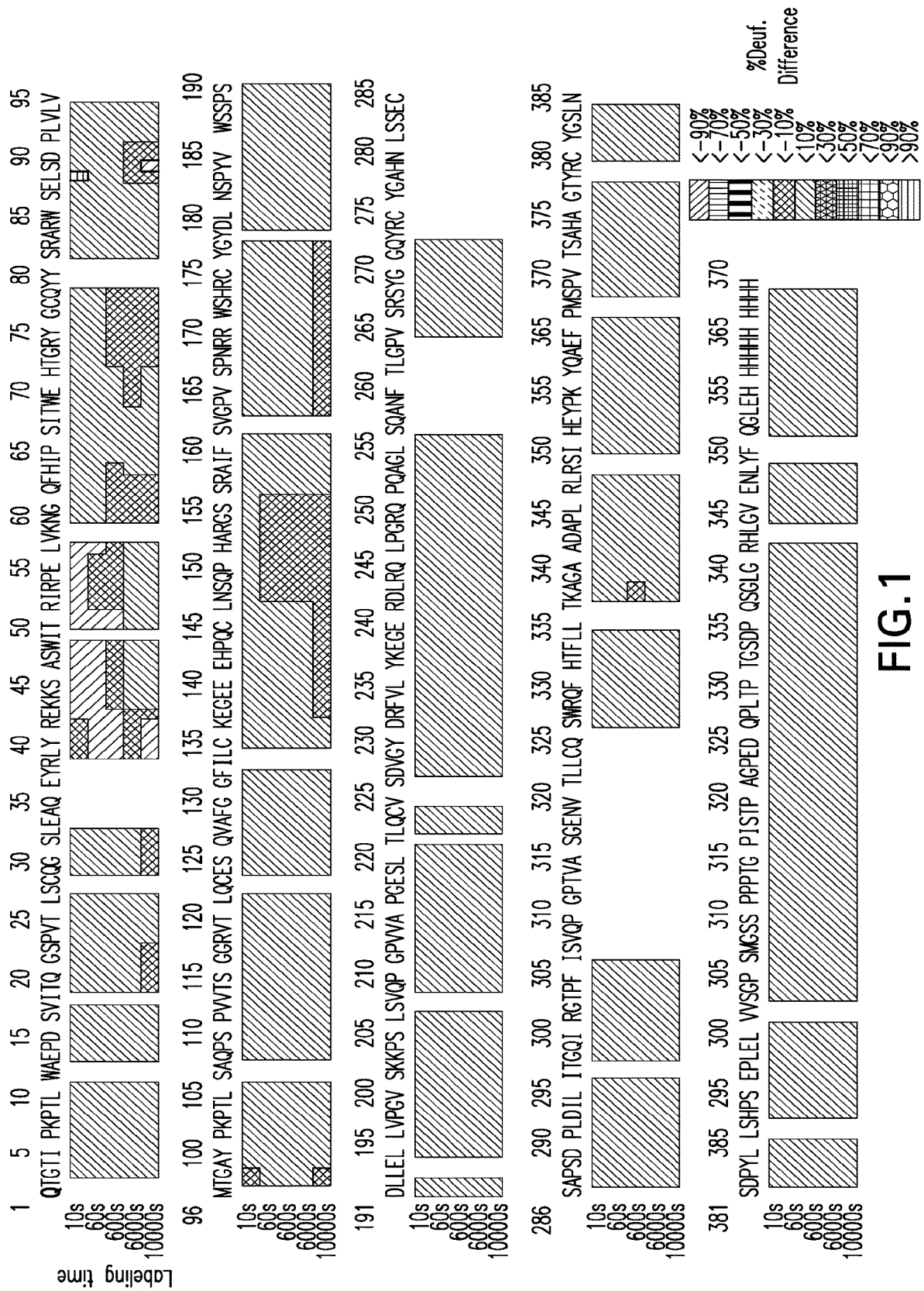
FIG. 1. Deuterium labeling Heatmap of p1E1(G1) binding to ILT4-His.

So that the invention may be more readily understood, certain technical and scientific terms are specifically defined below. Unless specifically defined elsewhere in this document, all other technical and scientific terms used herein have the meaning commonly understood by one of ordinary skill in the art to which this invention belongs.

As used herein, including the appended claims, the singular forms of words such as "a," "an," and "the," include their corresponding plural references unless the context clearly dictates otherwise.

"Affinity" refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_D$). Affinity can be measured by common methods known in the art, including KinExA and Biacore.

As used herein, the term "antibody" includes, but is not limited to, monoclonal antibodies, polyclonal antibodies, multispecific antibodies (e.g., bispecific antibodies), fully human antibodies, and chimeric antibodies.

As used herein, unless otherwise indicated, "antigen-binding fragment" refers to antigen-binding fragments of antibodies, i.e. antibody fragments that retain the ability to bind to the antigen bound by the full-length antibody, e.g. fragments that retain one or more CDR regions. Examples of antibody binding fragments include, but are not limited to, Fab, Fab', F(ab')$_2$, Fv fragments and individual antibody heavy chains or light chains, and individual heavy chain or light chain variable regions.

A "Fab fragment" is comprised of one light chain and the CH1 and variable regions of one heavy chain. The heavy chain of a Fab molecule cannot form a disulfide bond with another heavy chain molecule. An "Fab fragment" can be the product of papain cleavage of an antibody.

An "Fc" region contains two heavy chain fragments comprising the CH1 and CH2 domains of an antibody. The two heavy chain fragments are held together by two or more disulfide bonds and by hydrophobic interactions of the CH3 domains.

A "Fab' fragment" contains one light chain and a portion or fragment of one heavy chain that contains the $V_H$ domain and the CH1 domain and also the region between the CH1 and CH2 domains, such that an interchain disulfide bond can be formed between the two heavy chains of two Fab' fragments to form a F(ab')$_2$ molecule.

A "F(ab')$_2$ fragment" contains two light chains and two heavy chains containing a portion of the constant region between the CH1 and CH2 domains, such that an interchain disulfide bond is formed between the two heavy chains. A F(ab')$_2$ fragment thus is composed of two Fab' fragments that are held together by a disulfide bond between the two heavy chains. An "F(ab')$_2$ fragment" can be the product of pepsin cleavage of an antibody.

The "Fv region" comprises the variable regions from both the heavy and light chains, but lacks the constant regions.

"Isolated antibody" refers to the purification status and in such context means the molecule is substantially free of other biological molecules such as nucleic acids, proteins, lipids, carbohydrates, or other material such as cellular debris and growth media. Generally, the term "isolated" is not intended to refer to a complete absence of such material or to an absence of water, buffers, or salts, unless they are present in amounts that substantially interfere with experimental or therapeutic use of the binding compound as described herein.

The term "monoclonal antibody", as used herein, refers to a population of substantially homogeneous antibodies, i.e., the antibody molecules comprising the population are identical in amino acid sequence except for possible naturally occurring mutations that may be present in minor amounts. In contrast, conventional (polyclonal) antibody preparations typically include a multitude of different antibodies having different amino acid sequences in their variable domains that are often specific for different epitopes. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al. (1975) Nature 256: 495, or may be made by recombinant DNA methods (see, e.g., U.S. Pat. No. 4,816,567). The "monoclonal antibodies" may also be isolated from phage antibody libraries using the techniques described in Clackson et al. (1991) Nature 352: 624-628 and Marks et al. (1991) J. Mol. Biol. 222: 581-597, for example. See also Presta (2005) J. Allergy Clin. Immunol. 116:731.

The term "fully human antibody" refers to an antibody that comprises human immunoglobulin protein sequences only. A fully human antibody may contain murine carbohydrate chains if produced in a mouse, in a mouse cell, or in a hybridoma derived from a mouse cell. Similarly, "mouse antibody" refers to an antibody that comprises mouse immunoglobulin sequences only. Alternatively, a fully human antibody may contain rat carbohydrate chains if produced in a rat, in a rat cell, or in a hybridoma derived from a rat cell. Similarly, "rat antibody" refers to an antibody that comprises rat immunoglobulin sequences only.

In general, the basic "antibody" structural unit comprises a tetramer. In an monospecific antibody, each tetramer includes two identical pairs of polypeptide chains, each pair having one "light" (about 25 kDa) and one "heavy" chain (about 50-70 kDa). The amino-terminal portion of each chain includes a "variable region" or "variable domain" of about 100 to 110 or more amino acids primarily responsible for antigen recognition. The carboxy-terminal portion of the heavy chain may define a constant region primarily responsible for effector function.

Typically, human constant light chains are classified as kappa and lambda light chains. Furthermore, human constant heavy chains are typically classified as mu, delta, gamma, alpha, or epsilon, and define the antibody's isotype as IgM, IgD, IgG, IgA, and IgE, respectively. Subtypes of these IgG include, for example, IgG1 and IgG4. The present invention includes anti-ILT4 antibodies and antigen-binding fragments comprising any of these light and/or heavy constant chains.

"Variable region," "variable domain," "V region," or "V chain" as used herein means the segment of IgG chains which is variable in sequence between different antibodies. A "variable region" of an antibody refers to the variable region of the antibody light chain or the variable region of the antibody heavy chain, either alone or in combination. The variable region of the heavy chain may be referred to as "$V_H$." The variable region of the light chain may be referred to as "$V_L$." Typically, the variable regions of both the heavy and light chains comprise three hypervariable regions, also called complementarity determining regions (CDRs), which are located within relatively conserved framework regions (FR). The CDRs are usually aligned by the framework regions, enabling binding to a specific epitope. In general, from N-terminal to C-terminal, both light and heavy chains variable domains comprise FR1, CDR1, FR2, CDR2, FR3, CDR3, and FR4. The assignment of amino acids to each domain is, generally, in accordance with the definitions of Sequences of Proteins of Immunological Interest, Kabat, et al.; National Institutes of Health, Bethesda, Md.; 5th ed.; NIH Publ. No. 91-3242 (1991); Kabat (1978) Adv. Prot. Chem. 32:1-75; Kabat, et al., (1977) J. Biol. Chem. 252: 6609-6616; Chothia, et al., (1987) J Mol. Biol. 196:901-917 or Chothia, et al., (1989) Nature 342:878-883.

A "CDR" refers to one of three hypervariable regions (H1, H2, or H3) within the non-framework region of the antibody $V_H$ β-sheet framework, or one of three hypervariable regions (L1, L2, or L3) within the non-framework region of the antibody $V_L$ β-sheet framework. Accordingly, CDRs are variable region sequences interspersed within the framework region sequences. CDR regions are well known to those skilled in the art and have been defined by, for example, Kabat as the regions of most hypervariability within the antibody variable domains. CDR region sequences also have been defined structurally by Chothia as those residues that are not part of the conserved β-sheet framework, and thus are able to adapt to different conformation. Both terminologies are well recognized in the art. CDR region sequences have also been defined by AbM, Contact, and IMGT. The positions of CDRs within a canonical antibody variable region have been determined by comparison of numerous structures (Al-Lazikani et al., 1997, J. Mol. Biol. 273:927-48; Morea et al., 2000, Methods 20:267-79). Because the number of residues within a hypervariable region varies in different antibodies, additional residues relative to the canonical positions are conventionally numbered with a, b, c and so forth next to the residue number in the canonical variable region numbering scheme (Al-Lazikani et al., supra). Such nomenclature is similarly well known to those skilled in the art. Correspondence between the numbering system, including, for example, the Kabat numbering and the IMGT unique numbering system, is well known to one skilled in the art and shown below in Table 1. In some embodiments, the CDRs are as defined by the Kabat numbering system. In other embodiments, the CDRs are as defined by the IMGT numbering system. In yet other embodiments, the CDRs are as defined by the AbM numbering system. In still other embodiments, the CDRs are as defined by the Chothia numbering system. In yet other embodiments, the CDRs are as defined by the Contact numbering system.

TABLE 1

Correspondence between the CDR Numbering Systems

| | Kabat + Chothia | IMGT | Kabat | AbM | Chothia | Contact |
|---|---|---|---|---|---|---|
| $V_H$ CDR1 | 26-35 | 27-38 | 31-35 | 26-35 | 26-32 | 30-35 |
| $V_H$ CDR2 | 50-65 | 56-65 | 50-65 | 50-58 | 52-56 | 47-58 |
| $V_H$ CDR3 | 95-102 | 105-117 | 95-102 | 95-102 | 95-102 | 93-101 |
| $V_L$ CDR1 | 24-34 | 27-38 | 24-34 | 24-34 | 24-34 | 30-36 |
| $V_L$ CDR2 | 50-56 | 56-65 | 50-56 | 50-56 | 50-56 | 46-55 |
| $V_L$ CDR3 | 89-97 | 105-117 | 89-97 | 89-97 | 89-97 | 89-96 |

Sequence identity refers to the degree to which the amino acids of two polypeptides are the same at equivalent positions when the two sequences are optimally aligned.

Sequence similarity includes identical residues and non-identical, biochemically related amino acids. Biochemically related amino acids that share similar properties and may be interchangeable are discussed above.

"Conservatively modified variants" or "conservative substitution" refers to substitutions of amino acids in a protein with other amino acids having similar characteristics (e.g. charge, side-chain size, hydrophobicity/hydrophilicity, backbone conformation and rigidity, etc.), such that the changes can frequently be made without altering the biological activity of the protein. Those of skill in this art recognize that, in general, single amino acid substitutions in non-essential regions of a polypeptide do not substantially alter biological activity (see, e.g., Watson et al. (1987) Molecular Biology of the Gene, The Benjamin/Cummings Pub. Co., p. 224 (4th Ed.)). In addition, substitutions of structurally or functionally similar amino acids are less likely to disrupt biological activity. Exemplary conservative substitutions are set forth in Table 2.

TABLE 2

Exemplary Conservative Amino Acid Substitutions

| Original residue | Conservative substitution |
|---|---|
| Ala (A) | Gly; Ser |
| Arg (R) | Lys; His |
| Asn (N) | Gln; His |
| Asp (D) | Glu; Asn |
| Cys (C) | Ser; Ala |
| Gln (Q) | Asn |
| Glu (E) | Asp; Gln |

TABLE 2-continued

Exemplary Conservative Amino Acid Substitutions

| Original residue | Conservative substitution |
|---|---|
| Gly (G) | Ala |
| His (H) | Asn; Gln |
| Ile (I) | Leu; Val |
| Leu (L) | Ile; Val |
| Lys (K) | Arg; His |
| Met (M) | Leu; Ile; Tyr |
| Phe (F) | Tyr; Met; Leu |
| Pro (P) | Ala |
| Ser (S) | Thr |
| Thr (T) | Ser |
| Trp (W) | Tyr; Phe |
| Tyr (Y) | Trp; Phe |
| Val (V) | Ile; Leu |

The term "epitope," as used herein, refers to an area or region on an antigen to which an antibody or antigen-binding fragment binds. Binding of an antibody or antigen-binding fragment thereof disclosed herein to an epitope means that the antibody or antigen-binding fragment thereof binds to one or more amino acid residues within the epitope.

"Isolated" nucleic acid molecule or polynucleotide means a DNA or RNA, e.g., of genomic, mRNA, cDNA, or synthetic origin or some combination thereof which is not associated with all or a portion of a polynucleotide in which the isolated polynucleotide is found in nature, or is linked to a polynucleotide to which it is not linked in nature. For purposes of this disclosure, it should be understood that "a polynucleotide comprising" (or the like) a particular nucleotide sequence does not encompass intact chromosomes. Isolated polynucleotides "comprising" specified nucleic acid sequences may include, in addition to the specified sequences, coding sequences for up to ten or even up to twenty or more other proteins or portions or fragments thereof, or may include operably linked regulatory sequences that control expression of the coding region of the recited nucleic acid sequences, and/or may include vector sequences.

The phrase "control sequences" refers to polynucleotide sequences necessary or helpful for the expression of an operably linked coding sequence in a particular host organism. The control sequences that are suitable for prokaryotes, for example, include a promoter, optionally an operator sequence, and a ribosome binding site. Eukaryotic cells are known to use promoters, polyadenylation signals, and enhancers. In an embodiment of the invention, the polynucleotide is operably linked to a promoter such as a viral promoter, a CMV promoter, an SV40 promoter or a non-viral promoter or an elongation factor (EF)-1 promotor; and/or an intron.

A nucleic acid is "operably linked" when it is placed into a functional relationship with another polynucleotide. For example, DNA for a pre-sequence or secretory leader is operably linked to DNA for a polypeptide if it is expressed as a pre-protein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, but not always, "operably linked" means that the polynucleotide sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that not all progeny will have precisely identical DNA content, due to deliberate or inadvertent mutations. Mutant progeny that have the same function or biological activity as screened for in the originally transformed cell are included. Where distinct designations are intended, it will be clear from the context.

Host cells include eukaryotic and prokaryotic host cells, including mammalian cells. Host cells may be used as hosts for expression of the anti-ILT4 antibodies and antigen-binding fragments thereof. Host cells include, inter alia, Chinese hamster ovary (CHO) cells, NSO, SP2 cells, HeLa cells, baby hamster kidney (BHK) cells, monkey kidney cells (COS), human hepatocellular carcinoma cells (e.g., Hep G2), A549 cells, 3T3 cells and HEK-293 cells. Mammalian host cells include human, mouse, rat, dog, monkey, pig, goat, bovine, horse and hamster cells. Other cell lines that may be used are insect cell lines (e.g., *Spodoptera frugiperda* or *Trichoplusia ni*), amphibian cells, bacterial cells, plant cells and fungal cells. Fungal cells include yeast and filamentous fungus cells including, for example, *Pichia pastoris*, *Pichia finlandica*, *Pichia trehalophila*, *Pichia koclamae*, *Pichia membranaefaciens*, *Pichia minuta* (*Ogataea minuta*, *Pichia lindneri*), *Pichia opuntiae*, *Pichia thermotolerans*, *Pichia salictaria*, *Pichia guercuum*, *Pichia pijperi*, *Pichia stiptis*, *Pichia methanolica*, *Pichia* sp., *Saccharomyces cerevisiae*, *Saccharomyces* sp., *Hansenula polymorpha*, *Kluyveromyces* sp., *Kluyveromyces lactis*, *Candida albicans*, *Aspergillus nidulans*, *Aspergillus niger*, *Aspergillus oryzae*, *Trichoderma reesei*, *Chrysosporium lucknowense*, *Fusarium* sp., *Fusarium gramineum*, *Fusarium venenatum*, *Physcomitrella patens* and *Neurospora crassa*. *Pichia* sp., any *Saccharomyces* sp., *Hansenula polymorpha*, any *Kluyveromyces* sp., *Candida albicans*, any *Aspergillus* sp., *Trichoderma reesei*, *Chrysosporium lucknowense*, any *Fusarium* sp., *Yarrowia lipolytica*, and *Neurospora crassa*. The present invention includes any host cell (e.g., a CHO cell or *Pichia* cell, e.g., *Pichia pastoris*) containing an anti-ILT4 antibody or antigen-binding fragment thereof or containing a polynucleotide encoding such an antibody or fragment or containing a vector that contains the polynucleotide.

"Treat" or "treating" means to administer anti-ILT4 antibodies or antigen-binding fragments thereof of the present invention, to a subject having one or more symptoms of a disease for which the anti-ILT4 antibodies and antigen-binding fragments are effective, e.g., in the treatment of a subject having cancer or an infectious disease, or being suspected of having cancer or infectious disease, for which the agent has therapeutic activity. Typically, the antibody or fragment is administered in an "effective amount" or "effective dose" which will alleviate one or more symptoms (e.g., of cancer or infectious disease) in the treated subject or population, whether by inducing the regression or elimination of such symptoms or by inhibiting the progression of such symptom(s), e.g., cancer symptoms such as tumor growth or metastasis, by any clinically measurable degree. The effective amount of the antibody or fragment may vary according to factors such as the disease stage, age, and weight of the patient, and the ability of the drug to elicit a desired response in the subject.

As used herein, "an anti-ILT4 antibody or antigen-binding fragment thereof" refers to an antibody or antigen-binding fragment thereof that binds to human ILT4.

The present invention includes antibodies and antigen-binding fragments thereof set forth herein that bind specifically to ILT4. An antibody or antigen-binding fragment binds "specifically" to a polypeptide comprising a given sequence (e.g., human ILT4) if it binds to polypeptides comprising the sequence with a $K_D$ of about 20 nM or a higher affinity (e.g., about 17 nM, 10 nM, 5 nM, 1 nM, 100 pM, or 1 pM), but does not bind to proteins lacking the sequence. For example, an antibody or antigen-binding fragment that specifically binds to a polypeptide comprising human ILT4 may bind to a FLAG®-tagged form of human ILT4 but will not bind to other FLAG®-tagged proteins that lack ILT4 sequences.

ILT4

In an embodiment of the invention, the amino acid sequence of human ILT4 comprises the amino acid sequence:

```
MTPIVTVLIC LGLSLGPRTH VQTGTIPKPT LWAEPDSVIT QGSPVTLSCQ GSLEAQEYRL    60

YREKKSASWI TRIRPELVKN GQFHIPSITW EHTGRYGCQY YSRARWSELS DPLVLVMTGA   120

YPKPTLSAQP SPVVTSGGRV TLQCESQVAF GGFILCKEGE EEHPQCLNSQ PHARGSSRAI   180

FSVGPVSPNR RWSHRCYGYD LNSPYVWSSP SDLLELLVPG VSKKPSLSVQ PGPVVAPGES   240

LTLQCVSDVG YDRFVLYKEG ERDLRQLPGR QPQAGLSQAN FTLGPVSRSY GGQYRCYGAH   300

NLSSECSAPS DPLDILITGQ IRGTPFISVQ PGPTVASGEN VTLLCQSWRQ FHTFLLTKAG   360

AADAPLRLRS IHEYPKYQAE FPMSPVTSAH AGTYRCYGSL NSDPYLLSHP SEPLELVVSG   420

PSMGSSPPPT GPISTPAGPE DQPLTPTGSD PQSGLGRHLG VVIGILVAVV LLLLLLLLLF   480

LILRHRRQGK HWTSTQRKAD FQHPAGAVGP EPTDRGLQWR SSPAADAQEE NLYAAVKDTQ   540

PEDGVEMDTR AAASEAPQDV TYAQLHSLTL RRKATEPPPS QEREPPAEPS IYATLAIH    598
(SEQ ID NO: 40, signal sequence underscored) See Uniprot accession
no. Q8N423.
```

In another embodiment of the invention, the amino acid sequence of human ILT4 comprises the following amino acid sequence without the signal sequence:

```
                                                        (SEQ ID NO: 78)
           QTGTIPKPT LWAEPDSVIT QGSPVTLSCQ GSLEAQEYRL    39

YREKKSASWI TRIRPELVKN GQFHIPSITW EHTGRYGCQY YSRARWSELS DPLVLVMTGA    99

YPKPTLSAQP SPVVTSGGRV TLQCESQVAF GGFILCKEGE EEHPQCLNSQ PHARGSSRAI   159

FSVGPVSPNR RWSHRCYGYD LNSPYVWSSP SDLLELLVPG VSKKPSLSVQ PGPVVAPGES   219

LTLQCVSDVG YDRFVLYKEG ERDLRQLPGR QPQAGLSQAN FTLGPVSRSY GGQYRCYGAH   279

NLSSECSAPS DPLDILITGQ IRGTPFISVQ PGPTVASGEN VTLLCQSWRQ FHTFLLTKAG   339

AADAPLRLRS IHEYPKYQAE FPMSPVTSAH AGTYRCYGSL NSDPYLLSHP SEPLELVVSG   399

PSMGSSPPPT GPISTPAGPE DQPLTPTGSD PQSGLGRHLG VVIGILVAVV LLLLLLLLLF   459

LILRHRRQGK HWTSTQRKAD FQHPAGAVGP EPTDRGLQWR SSPAADAQEE NLYAAVKDTQ   519

PEDGVEMDTR AAASEAPQDV TYAQLHSLTL RRKATEPPPS QEREPPAEPS IYATLAIH    577.
```

In an embodiment of the invention, the amino acid sequence of cynomolgous monkey ILT4 comprises the amino acid sequence:

```
MTPILMVLIC LGLSLGPRTH VQAGILPKPT LWAEPGSVIS EGSPVTLRCQ GSLQVQEYHL    60

YREKNPASWV RQIRQELVKK GYFAIGFITW EHTGQYRCQY YSHSWWSEPS DPLELVVTGA   120

YSKPTLSALP SPVVASGGNV TLQCDSQVAF DSFTLCKEGE DEHPQRLNCQ SHARGWSWAV   180

FSVGPVSPSR RWSYRCYGYI SSAPNVWSLP SDLLELLVPG VSKKPSLSVQ PGPVVAPGDK   240

LTLQCGSDAG YDRFALYKEG EGDFLQRPVR QPQAGLSQAN FLLGPVSRSH GGQYRCSGAH   300
```

-continued

```
NLSSEWSAPS DPLDILIAGQ IRGRPFLSVQ PGPKVVSGEN VTLLCQSSWQ FHAFLLTQAG    360

AADAHLHLRS MYKYPKYQAE FPMSPVTSAH AGTYRCYGSR SSNPYLLSVP SDPLELVVSG    420

PSGGPSSPTT GPTSTCGPED QPLTPTGSAP QSGLGRHLGV VTGVLVAFVL LLFLLLLLFL    480

VLRYRRQGKR WTSAQRKADF QHPAGAVEPE PRDRGLQRRS SPAADTQEEN LYAAVKDTQP    540

EDGVELDSRA AASEDPQDVT YAQLQSLTLR REATEPPPSQ ERAPPVESSI YATLTIH       597
(SEQ ID NO: 43, signal sequence underscored). See NCBI refseq
XP_005590753.
```

In an embodiment of the invention, the signal sequence for expression of ILT4 or any other polypeptide set forth herein is MTPILMVLICLGLSLGPRTHV (amino acids 1-21 of SEQ ID NO:40) or MTPIVTVLICLGLSLGPRTHV (amino acids 1-21 of SEQ ID NO:43) or MPLLLLLPLL-WAGALA (SEQ ID NO:46).

In an embodiment of the invention, an anti-ILT4 antibody or antigen-binding fragment thereof of the present invention binds to the extracellular domain of ILT4:

```
QTGTIPKPTLWAEPDSVITQGSPVTLSCQGSLEAQEYRLYREKKSASWIT

RIRPELVKNGQFHIPSITWEHTGRYGCQYYSRARWSELSDPLVLVMTGAY

PKPTLSAQPSPVVTSGGRVTLQCESQVAFGGFILCKEGEEEHPQCLNSQP

HARGSSRAIFSVGPVSPNRRWSHRCYGYDLNSPYVWSSPSDLLELLVPGV

SKKPSLSVQPGPVVAPGESLTLQCVSDVGYDRFVLYKEGERDLRQLPGRQ

PQAGLSQANFTLGPVSRSYGGQYRCYGAHNLSSECSAPSDPLDILITGQI

RGTPFISVQPGPTVASGENVTLLCQSWRQFHTFLLTKAGAADAPLRLRSI

HEYPKYQAEFPMSPVTSAHAGTYRCYGSLNSDPYLLSHPSEPLELVVSGP

SMGSSPPPTGPISTPAGPEDQPLTPTGSDPQSGLGRHLGV
(amino acids 22-461 of SEQ ID NO: 40)
``` or an immunoglobulin-fusion thereof (e.g., IgG1 or IgG4) or a cell surface transmembrane (TM) form which is expressed on the surface of a cell:

```
QTGTIPKPTLWAEPDSVITQGSPVTLSCQGSLEAQEYRLYREKKSASWIT

RIRPELVKNGQFHIPSITWEHTGRYGCQYYSRARWSELSDPLVLVMTGAY

PKPTLSAQPSPVVTSGGRVTLQCESQVAFGGFILCKEGEEEHPQCLNSQP

HARGSSRAIFSVGPVSPNRRWSHRCYGYDLNSPYVWSSPSDLLELLVPGV

SKKPSLSVQPGPVVAPGESLTLQCVSDVGYDRFVLYKEGERDLRQLPGRQ

PQAGLSQANFTLGPVSRSYGGQYRCYGAHNLSSECSAPSDPLDILITGQI

RGTPFISVQPGPTVASGENVTLLCQSWRQFHTFLLTKAGAADAPLRLRSI

HEYPKYQAEFPMSPVTSAHAGTYRCYGSLNSDPYLLSHPSEPLELVVSGP

SMGSSPPPTGPISTPAGPEDQPLTPTGSDPQSGLGRHLGVVIGILVAVVL

LLLLLLLLFLILRHRRQGKH
(amino acids 22-491 of SEQ ID NO: 40).
```

Antibodies and Antigen-Binding Fragments

The present invention provides antibodies and antigen-binding fragments thereof (e.g., fully human antibodies) that bind to ILT4 (herein referred to as "anti-ILT4") and methods of use of the antibodies or antigen-binding fragments thereof in the treatment or prevention of disease. In one embodiment, the invention provides for antagonistic anti-ILT4 antibodies and methods of use of the antibodies or antigen-binding fragments thereof in the treatment or prevention of disease.

In one aspect, the present application includes anti-ILT4 antibodies and antigen-binding fragments thereof as set forth herein having one or more of the properties set forth below:

binds human ILT4 at one or more amino acid residues in LYREKKSASW (SEQ ID NO:59), TRIRPEL (SEQ ID NO:60), NGQF (SEQ ID NO:61), and/or HTGRYGCQ (SEQ ID NO:62), and/or protects LYREKKSASW (SEQ ID NO:59), TRIRPEL (SEQ ID NO:60), NGQF (SEQ ID NO:61), and/or HTGRYGCQ (SEQ ID NO:62) from deuterium (e.g., $D_2O$) exchange, e.g., as determined by hydrogen-deuterium exchange mass spectrometry and/or binds to ILT4 with a heat map essentially as shown in FIG. 1;

binds human ILT4 at domain 1 (see Wilcox et al. BMC Structural Biology 2:6 (2002));

binds human ILT4 extracellular domain or TM form of ILT4 expressed on a cell surface, e.g., a pre-B cell, Chinese hamster ovary cell, U937 cell, or Jurkat JE6 cell.

calculated pI~7.29 (e.g., 7.29 or 7.30);

experimentally determined pI~7.2;

is characterized by a thermogram having Tm onset>60° C., Tm1~65.2° C. and Tm2~78.8° C.;

binds human ILT4 with a $K_D$ of about $1.7 \times 10^{-8}$ M (e.g., as determined by surface plasmon resonance, e.g., binding of anti-ILT4 to polyhistidine tagged human ILT4);

Ka=$5.5 \times 10^5$ $M^{-1}$ $s^{-1}$ (e.g., as determined by surface plasmon resonance, e.g., binding of anti-ILT4 to polyhistidine tagged human ILT4);

Kd=$9 \times 10^{-3} s^{-1}$ (e.g., as determined by surface plasmon resonance, e.g., binding of anti-ILT4 to polyhistidine tagged human ILT4);

blocks binding of HLA-G (e.g., Fc fused HLA-G) to human ILT4 (e.g., ILT4 on mouse 3A9 T cells transfected with and expressing ILT4), e.g., with an $IC_{50}$ of about 0.25 micrograms/ml (±0.06 micrograms/ml), e.g., as determined by surface plasmon resonance;

blocks binding of HLA-A, HLA-B (e.g., fluorochrome labeled dexamers of HLA-A, such as HLA*A2:01 or HLA-B such as HLA*B7:02), and/or HLA-F (e.g., fluorochrome labeled tetramers of HLA-F) to ILT4 (e.g., ILT4 on mouse 3A9 T cells transfected with and expressing ILT4), e.g., as determined by surface plasmon resonance;

blocks ILT4 (e.g., ILT4 on mouse 3A9 T cells transfected with and expressing ILT4), binding to ANGPTL1, ANGPTL4, and/or ANGPTL7 (e.g., biotinylated ANGPTL proteins), e.g., as determined by surface plasmon resonance;

does not bind to ILT2, ILT3, ILT5, LILRB5, LILRA1, LILRA2, ILT7, ILT8, and/or ILT11, reverses ILT4-mediated suppression of 1L2 in ILT4 transfected 3A9 cells, e.g., with an $EC_{50}$ of 0.43 micrograms/ml (±0.14 micrograms/ml);

rescues ILT4:HLA-G induced suppression of mast cell degranulation (e.g., In the presence of plate-bound HLA-G tetramer), for example, wherein the mast cells express ILT4 and CD200RLa and are stimulated, for example, with antibody-mediated cross-linking of CD200RLa, enhances lipopolysaccharide (LPS)-induced expression of proinflammatory myeloid cytokines, for example, GM-CSF and/or TNFalpha, from a peripheral blood mononuclear cell (PBMC);

enhances anti-CD3-induced expression of pro-inflammatory myeloid cytokines for example, GM-CSF and/or TNFalpha, from a peripheral blood mononuclear cell (PBMC);

inhibits tumor growth in humans or, for example, in other mammals such as mice (e.g., Immuno-deficient NSG mice) which were reconstituted with human hematopoietic stem cells, for example, which harbor peripheral human CD45+ immune cells, for example, wherein the tumor is a human skin melanoma tumor such as from the cell line SKMEL5;

relieves macrophage/myeloid-derived suppressor cell (MDSC)-mediated tumor tolerance in the body of a subject (e.g., human subject) with a tumor;

does not bind to cynomolgous monkey ILT4 and/or mouse pirB; and/or stains CD14 +human monocytes and/or CD11B+ human granulocytes binds to one or more (e.g., 1, 2, 3, 4, 5, 6, 7, 8, 9 or all 10) of the human ILT4 haplotypes set forth in Table 7.

Antibody 1E1 (Q1E) Heavy Chain (IgG4)
Heavy Chain

EVQLQQWGAGLLKPSETLSLTCAVYGGSFSGYYWSWIRQPPGKGLEWIGE

INHSGSTNYNPSLKSRVTISVDTSKNQFSLKLSSVTAADTAVYYCARLPT

RWVTTRYFDLWGRGTLVTVSSASTKGPSVFPLAPCSRSTSESTAALGCLV

KDYFPEPVTVSWNSGALTSGVHTFPAVLQSSGLYSLSSVVTVPSSSLGTK

TYTCNVDHKPSNTKVDKRVESKYGPPCPPCPAPEFLGGPSVFLFPPKPKD

TLMISRTPEVTCVVVDVSQEDPEVQFNWYVDGVEVHNAKTKPREEQFNST

YRVVSVLTVLHQDWLNGKEYKCKVSNKGLPSSIEKTISKAKGQPREPQVY

TLPPSQEEMTKNQVSLTCLVKGFYPSDIAVEWESNGQPENNYKTTPPVLD

SDGSFFLYSRLTVDKSRWQEGNVFSCSVMHEALHNHYTQKSLSLSLGK
(SEQ ID NO: 1; variable domain underscored;
CDRs double underscored)

Heavy Chain Variable Domain (SEQ ID NO: 63)
EVQLQQWGAGLLKPSETLSLTCAVYGGSFSGYYWSWIRQPPGKGLEWIGE

INHSGSTNYNPSLKSRVTISVDTSKNQFSLKLSSVTAADTAVYYCARLPT

RWVTTRYFDLWGRGTLVTVSS

Antibody 1E1 (Q1E, S54A) Heavy Chain (IgG4)
Heavy Chain

EVQLQQWGAGLLKPSETLSLTCAVYGGSFSGYYWSWIRQPPGKGLEWIGE

INHAGSTNYNPSLKSRVTISVDTSKNQFSLKLSSVTAADTAVYYCAR

RWVTTRYFDLWGRGTLVTVSSASTKGPSVFPLAPCSRSTSESTAALG

CLVKDYFPEPVTVSWNSGALTSGVHTFPAVLQSSGLYSLSSVVTVPSSSL

GTKTYTCNVDHKPSNTKVDKRVESKYGPPCPPCPAPEFLGGPSVFLFPPK

PKDTLMISRTPEVTCVVVDVSQEDPEVQFNWYVDGVEVHNAKTKPREEQF

NSTYRVVSVLTVLHQDWLNGKEYKCKVSNKGLPSSIEKTISKAKGQPREP

QVYTLPPSQEEMTKNQVSLTCLVKGFYPSDIAVEWESNGQPENNYKTTPP

VLDSDGSFFLYSRLTVDKSRWQEGNVESCSVMHEALHNHYTQKSLSLSLGK
(SEQ ID NO: 2; variable domain underscored;
CDRs double underscored)

Heavy Chain Variable Domain (SEQ ID NO: 57)
EVQLQQWGAGLLKPSETLSLTCAVYGGSFSGYYWSWIRQPPGKGLEWIGE

INHAGSTNYNPSLKSRVTISVDTSKNQSLKLSSVTAADTAVYYCARLPTR

WVTTRYFDLWGRGTLVTVSS

Antibody 1E1 Heavy Chain (IgG1)
Heavy Chain

QVQLQQWGAGLLKPSETLSLTCAVYGGSFSGYYWSWIRQPPGKGLEWIGE

INHSGSTNYNPSLKSRVTISVDTSKNQFSLKLSSVTAADTAVYYCARLPT

RWVTTRYFDLWGRGTLVTVSSASTKGPSVFPLAPSSKSTSGGTAALGCLV

KDYFPEPVTVSWNSGALTSGVHTFPAVLQSSGLYSLSSVVTVPSSSLGTQ

TYICNVNHKPSNTKVDKRVEPKSCDKTHTCPPCPAPELLGGPSVFLFPPK

PKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREP

QVYTLPPSREEMTKNQVSLTCLVKGFYPSDIAVEWESNGQPENNYKTTPP

VLDSDGSFFLYSKLTVDKSRWQQGNVESCSVMHEALHNHYTQKSLSLSPG

K
(SEQ ID NO: 44, variable domain underscored;
CDRs double underscored)

Heavy chain variable domain (SEQ ID NO: 69)
QVQLQQWGAGLLKPSETLSLTCAVYGGSFSGYYWSWIRQPPGKGLEWIGE

INHSGSTNYNPSLKSRVTISVDTSKNQFSLKLSSVTAADTAVYYCARLPT

RWVTTRYFDLWGRGTLVTVSS

1E1 Heavy Chain CDRs

CDR-H1:
(SEQ ID NO: 16)
GYYWS

CDR-H2:
(SEQ ID NO: 17)
EINHXGSTNYNPSLKS wherein X is S or A (e.g., EINHSGSTNYNPSLKS or EINHAGSTNYNPSLKS)

CDR-H3:
(SEQ ID NO: 18)
LPTRWVTTRYFDL

Antibody 1E1 (Q1E) Light Chain (Lambda)
Light Chain (SEQ ID NO: 3)
ESVLTQPPSVSGAPGQRVTISCTGSSSNIGAGYDVHWYQQLPGTAPKLL
IYGNSNRPSGVPDRFSVSKSGASASLAITGLQAEDEADYYCQSFDNSLS
AYVFGGGTQLTVLGQPKAAPSVTLFPPSSEELQANKATLVCLISDFYPG
AVTVAWKADSSPVKAGVETTTPSKQSNNKYAASSYLSLTPEQWKSHRSY
SCQVTHEGSTVEKTVAPTECS (SEQ ID NO: 3; variable domain underscored; CDRs double underscored)

Light Chain Variable Domain (SEQ ID NO: 70)
ESVLTQPPSVSGAPGQRVTISCTGSSSNIGAGYDVHWYQQLPGTAPKLL
IYGNSNRPSGVPDRFSVSKSGASASLAITGLQAEDEADYYCQSFDNSLS
AYVFGGGTQLTVL

Antibody 1E1 (Q1E, S54A) Light Chain (Lambda)
Light Chain

ESVLTQPPSVSGAPGQRVTISCTGSSSNIGAGYDVHWYQQLPGTAPKLL
IYGNANRPSGVPDRFSVSKSGASASLAITGLQAEDEADYYCQSFDNSLS
AYVFGGGTQLTVLGQPKAAPSVTLFPPSSEELQANKATLVCLISDFYPG
AVTVAWKADSSPVKAGVETTTPSKQSNNKYAASSYLSLTPEQWKSHRSY
SCQVTHEGSTVEKTVAPTECS (SEQ ID NO: 4; variable domain underscored; CDRs double underscored)

Light Chain Variable Domain (SEQ ID NO: 71)
ESVLTQPPSVSGAPGQRVTISCTGSSSNIGAGYDVHWYQQLPGTAPKLL
IYGNANRPSGVPDRFSVSKSGASASLAITGLQAEDEADYYCQSFDNSLS
AYVFGGGTQLTVL

Antibody 1E1 (Q1E, N53Q) Light Chain (Lambda)
Light Chain

ESVLTQPPSVSGAPGQRVTISCTGSSSNIGAGYDVHWYQQLPGTAPKLL
IYGQSNRPSGVPDRFSVSKSGASASLAITGLQAEDEADYYCQSFDNSLS
AYVFGGGTQLTVLGQPKAAPSVTLFPPSSEELQANKATLVCLISDFYPG
AVTVAWKADSSPVKAGVETTTPSKQSNNKYAASSYLSLTPEQWKSHRSY
SCQVTHEGSTVEKTVAPTECS (SEQ ID NO: 5; variable domain underscored; CDRs double underscored)

Light Chain Variable Domain (SEQ ID NO: 72)
ESVLTQPPSVSGAPGQRVTISCTGSSSNIGAGYDVHWYQQLPGTAPKLL
IYGQSNRPSGVPDRFSVSKSGASASLAITGLQAEDEADYYCQSFDNSLS
AYVFGGGTQLTVL

Antibody 1E1 (Q1E, N53E) Light Chain (Lambda)
Light Chain

ESVLTQPPSVSGAPGQRVTISCTGSSSNIGAGYDVHWYQQLPGTAPKLL
IYGESNRPSGVPDRFSVSKSGASASLAITGLQAEDEADYYCQSFDNSLS
AYVFGGGTQLTVLGQPKAAPSVTLFPPSSEELQANKATLVCLISDFYPG
AVTVAWKADSSPVKAGVETTTPSKQSNNKYAASSYLSLTPEQWKSHRSY
SCQVTHEGSTVEKTVAPTECS (SEQ ID NO: 6; variable domain underscored; CDRs double underscored)

Light Chain Variable Domain (SEQ ID NO: 73)
ESVLTQPPSVSGAPGQRVTISCTGSSSNIGAGYDVHWYQQLPGTAPKLL
IYGESNRPSGVPDRFSVSKSGASASLAITGLQAEDEADYYCQSFDNSLS
AYVFGGGTQLTVL

Antibody 1E1 (Q1E, N53D) Light Chain (Lambda)
Light Chain

ESVLTQPPSVSGAPGQRVTISCTGSSSNIGAGYDVHWYQQLPGTAPKLL
IYGDSNRPSGVPDRFSVSKSGASASLAITGLQAEDEADYYCQSFDNSLS
AYVFGGGTQLTVLGQPKAAPSVTLFPPSSEELQANKATLVCLISDFYPG
AVTVAWKADSSPVKAGVETTTPSKQSNNKYAASSYLSLTPEQWKSHRSY
SCQVTHEGSTVEKTVAPTECS (SEQ ID NO: 7; variable domain underscored; CDRs double underscored)

Light Chain Variable Domain (SEQ ID NO: 58)
ESVLTQPPSVSGAPGQRVTISCTGSSSNIGAGYDVHWYQQLPGTAPKLL
IYGDSNRPSGVPDRFSVSKSGASASLAITGLQAEDEADYYCQSFDNSLS
AYVFGGGTQLTVL

Antibody 1E1 Light Chain (Lambda)
Light Chain

QSVLTQPPSVSGAPGQRVTISCTGSSSNIGAGYDVHWYQQLPGTAPKLL
IYGNSNRPSGVPDRFSVSKSGASASLAITGLQAEDEADYYCQSFDNSLS
AYVFGGGTQLTVLGQPKAAPSVTLFPPSSEELQANKATLVCLISDFYPG

-continued

```
AVTVAWKADSSPVKAGVETTTPSKQSNNKYAASSYLSLTPEQWKSHRSY
SCQVTHEGSTVEKTVAPTECS (SEQ ID NO: 45, variable
domain underscored; CDRs double underscored)
```

Light Chain Variable Domain

```
                                      (SEQ ID NO: 77)
QSVLTQPPSVSGAPGQRVTISCTGSSSNIGAGYDVHWYQQLPGTAPKLL
IYGNSNRPSGVPDRFSVSKSGASASLAITGLQAEDEADYYCQSFDNSLS
AYVFGGGTQLTVL
```

1E1 Light Chain CDRs

```
CDR-L1:
                                      (SEQ ID NO: 19)
TGSSSNIGAGYDVH

CDR-L2:
                                      (SEQ ID NO: 20)
GX1X2NRPS, wherein X1 is N,Q,E or D and X2 is S or
A (e.g., GNSNRPS, GNANRPS, GQSNRPS, GESNRPS or
GDSNRPS)

CDR-L3:
                                      (SEQ ID NO: 21)
QSFDNSLSAYV
```

Antibodies and antigen-binding fragments thereof including the 1E1 heavy and light chain CDRs or the 1E1 $V_H$ and $V_L$ or the 1E1 heavy chain and light chain (or a variant thereof, e.g., as set forth herein) may be referred to as "1E1."

Antibody 2A6 (Q1E) Heavy Chain (IgG4)
Heavy Chain

```
EVQLVQSGAEVKKPGSSVKVSCKASGGTFSSYAISWVRQAPGQGLEWMG
GIIPIFGTANYAQKFQGRVTITADESTSTAYMELSSLRSEDTAVYYCAR
YFDSSGWYKGGAFDIWGQGTMVTVSSASTKGPSVFPLAPCSRSTSESTA
ALGCLVKDYFPEPVTVSWNSGALTSGVHTFPAVLQSSGLYSLSSVVTVP
SSSLGTKTYTCNVDHKPSNTKVDKRVESKYGPPCPPCPAPEFLGGPSVF
LFPPKPKDTLMISRTPEVTCVVVDVSQEDPEVQFNWYVDGVEVHNAKTK
PREEQFNSTYRVVSVLTVLHQDWLNGKEYKCKVSNKGLPSSIEKTISKA
KGQPREPQVYTLPPSQEEMTKNQVSLTCLVKGFYPSDIAVEWESNGQPE
NNYKTTPPVLDSDGSFFLYSRLTVDKSRWQEGNVFSCSVMHEALHNHYT
QKSLSLSLGK (SEQ ID NO: 8; variable domain
underscored; CDRs double underscored)
```

Heavy Chain Variable Domain

```
                                      (SEQ ID NO: 64)
EVQLVQSGAEVKKPGSSVKVSCKASGGTFSSYAISWVRQAPGQGLEWMG
GIIPIFGTANYAQKFQGRVTITADESTSTAYMELSSLRSEDTAVYYCAR
YFDSSGWYKGGAFDIWGQGTMVTVSS
```

Antibody 2A6 (Q1E, S102A, M119L) Heavy Chain (IgG4)
Heavy Chain

```
EVQLVQSGAEVKKPGSSVKVSCKASGGTFSSYAISWVRQAPGQGLEWMG
GIIPIFGTANYAQKFQGRVTITADESTSTAYMELSSLRSEDTAVYYCAR
YFDASGWYKGGAFDIWGQGTLVTVSSASTKGPSVFPLAPCSRSTSESTA
ALGCLVKDYFPEPVTVSWNSGALTSGVHTFPAVLQSSGLYSLSSVVTVP
SSSLGTKTYTCNVDHKPSNTKVDKRVESKYGPPCPPCPAPEFLGGPSVF
LFPPKPKDTLMISRTPEVTCVVVDVSQEDPEVQFNWYVDGVEVHNAKTK
PREEQFNSTYRVVSVLTVLHQDWLNGKEYKCKVSNKGLPSSIEKTISKA
KGQPREPQVYTLPPSQEEMTKNQVSLTCLVKGFYPSDIAVEWESNGQPE
NNYKTTPPVLDSDGSFFLYSRLTVDKSRWQEGNVFSCSVMHEALHNHYT
QKSLSLSLGK (SEQ ID NO: 9; variable domain
underscored; CDRs double underscored)
```

Heavy Chain Variable Domain

```
                                      (SEQ ID NO: 65)
EVQLVQSGAEVKKPGSSVKVSCKASGGTFSSYAISWVRQAPGQGLEWMG
GIIPIFGTANYAQKFQGRVTITADESTSTAYMELSSLRSEDTAVYYCAR
YFDASGWYKGGAFDIWGQGTLVTVSS
```

Antibody 2A6 (Q1E, D101S, M119L) Heavy Chain (IgG4)
Heavy Chain

```
EVQLVQSGAEVKKPGSSVKVSCKASGGTFSSYAISWVRQAPGQGLEWMG
GIIPIFGTANYAQKFQGRVTITADESTSTAYMELSSLRSEDTAVYYCAR
YFSSSGWYKGGAFDIWGQGTLVTVSSASTKGPSVFPLAPCSRSTSESTA
ALGCLVKDYFPEPVTVSWNSGALTSGVHTFPAVLQSSGLYSLSSVVTVP
SSSLGTKTYTCNVDHKPSNTKVDKRVESKYGPPCPPCPAPEFLGGPSVF
LFPPKPKDTLMISRTPEVTCVVVDVSQEDPEVQFNWYVDGVEVHNAKTK
PREEQFNSTYRVVSVLTVLHQDWLNGKEYKCKVSNKGLPSSIEKTISKA
KGQPREPQVYTLPPSQEEMTKNQVSLTCLVKGFYPSDIAVEWESNGQPE
NNYKTTPPVLDSDGSFFLYSRLTVDKSRWQEGNVFSCSVMHEALHNHYT
QKSLSLSLGK (SEQ ID NO: 10, variable domain
underscored; CDRs double underscored)
```

Heavy Chain Variable Domain

```
                                      (SEQ ID NO: 66)
EVQLVQSGAEVKKPGSSVKVSCKASGGTFSSYAISWVRQAPGQGLEWMG
GIIPIFGTANYAQKFQGRVTITADESTSTAYMELSSLRSEDTAVYYCAR
YFSSSGWYKGGAFDIWGQGTLVTVSS
```

The present invention includes antibodies and antigen-binding fragments thereof wherein residue 1 of SEQ ID NO:8, 9, 10, 64, 65, or 66 is Q instead of E.

2A6 Heavy Chain CDRs

CDR-H1:
(SEQ ID NO: 22)
SYAIS

CDR-H2:
(SEQ ID NO: 23)
GIIPIFGTANYAQKFQG

CDR-H3:
(SEQ ID NO: 24)
YFX₁X₂SGWYKGGAFDI, wherein X₁ is D or S and X₂ is S or A (e.g., YFDSSGWYKGGAFDI, YFDASGWYKGGAFDI or YFSSSGWYKGGAFDI)

Antibody 2A6 Light Chain (Lambda)
Light Chain

QSVLTQPSSLSASPGASASLTCTLRSGINVDTYRIHWYQQKPGSPPQYL
LRYKSDSDKHQGSGVPSRFSGSKDPSANAGILLISGLQSEDEADYYC
WYSSTWVFGGGTQLTVLGQPKAAPSVTLEPPSSEELQANKATLVCLISD
FYPGAVTVAWKADSSPVKAGVETTTPSKQSNNKYAASSYLSLTPEQWKS
HRSYSCQVTHEGSTVEKTVAPTECS (SEQ ID NO: 11, variable domain underscored; CDRs double underscored)

Light Chain Variable Domain (SEQ ID NO: 74)
QSVLTQPSSLSASPGASASLTCTLRSGINVDTYRIHWYQQKPGSPPQYL
LRYKSDSDKHQGSGVPSRFSGSKDPSANAGILLISGLQSEDEADYYCAI
WYSSTWVFGGGTQLTVL The present invention includes antibodies and antigen-binding fragments thereof wherein residue 1 of SEQ ID NO:11 or 74 is E instead of Q.

2A6 Light Chain CDRs

CDR-L1:
(SEQ ID NO: 25)
TLRSGINVDTYRIH

CDR-L2:
(SEQ ID NO: 26)
YKSDSDKHQGS

CDR-L3:
(SEQ ID NO: 27)
AIWYSSTWV

Antibodies and antigen-binding fragments thereof including the 2A6 heavy and light chain CDRs or the 2A6 V_H and V_L or the 2A6 heavy chain and light chain (or a variant thereof, e.g., as set forth herein) may be referred to as "2A6."

Antibody 3G7 (Q1E) Heavy Chain (IgG4)
Heavy Chain

EVQLVESGGGVVQPGRSLRLSCAASGETFSSYAMHWVRQAPGKGLEWV
AVISYDGSNKYYADSVKGRFTISRDNSKNTLYLQMNSLRAEDTAVYYC
ARVGEWIQLWSPFDYWGQGTLVTVSSASTKGPSVFPLAPCSRSTSEST
AALGCLVKDYFPEPVTVSWNSGALTSGVHTFPAVLQSSGLYSLSSVVT
VPSSSLGTKTYTCNVDHKPSNTKVDKRVESKYGPPCPPCPAPEFLGGP
SVFLFPPKPKDTLMISRTPEVTCVVVDVSQEDPEVQFNWYVDGVEVHN
AKTKPREEQFNSTYRVVSVLTVLHQDWLNGKEYKCKVSNKGLPSSIEK
TISKAKGQPREPQVYTLPPSQEEMTKNQVSLTCLVKGFYPSDIAVEWE
SNGQPENNYKTTPPVLDSDGSFFLYSRLTVDKSRWQEGNVFSCSVMHE
ALHNHYTQKSLSLSLGK (SEQ ID NO: 12, variable domain underscored; CDRs double underscored).

Heavy Chain Variable Domain (SEQ ID NO: 67)
EVQLVESGGGVVQPGRSLRLSCAASGETFSSYAMHWVRQAPGKGLEWV
AVISYDGSNKYYADSVKGRFTISRDNSKNTLYLQMNSLRAEDTAVYYC
ARVGEWIQLWSPFDYWGQGTLVTVSS The present invention includes antibodies and antigen-binding fragments thereof wherein residue 1 of SEQ ID NO:12 or 67 is Q instead of E.

3G7 Heavy Chain CDRs

CDR-H1:
(SEQ ID NO: 28)
SYAMH

CDR-H2:
(SEQ ID NO: 29)
VISYDGSNKYYADSVKG

CDR-H3:
(SEQ ID NO: 30)
VGEWIQLWSPFDY

Antibody 3G7 Light Chain (Kappa)
Light Chain

DIQMTQSPSSVSASVGDRVTITCRASQGISSWLAWYQQKPGKAPKFLI
YAASSLQSGVPSKFSGSGSGTDFTLTISSLQPEDFATYYCQQYNSYPP
TFGGGTKVEIKRtVAAPSVFIFPPSDEQLKSGTASVVCLLNNEYPREA
KVQWKVDNALQSGNSQESVTEQDSKDSTYSLSSTLTLSKADYEKHKVY
ACEVTHQGLSSPVTKSFNRGEC (SEQ ID NO: 13, variable domain underscored; CDRs double underscored)

Light Chain Variable Domain (SEQ ID NO: 75)
DIQMTQSPSSVSASVGDRVTITCRASQGISSWLAWYQQKPGKAPKFLI
YAASSLQSGVPSKFSGSGSGTDFTLTISSLQPEDFATYYCQQYNSYPP
TFGGGTKVEIK 3G7 Light Chain CDRs

CDR-L1:
RASQGISSWLA (SEQ ID NO: 31)

CDR-L2:
AASSLQS (SEQ ID NO: 32)

CDR-L3:
QQYNSYPPT (SEQ ID NO: 33)

Antibodies and antigen-binding fragments thereof including the 3G7 heavy and light chain CDRs or the 3G7 $V_H$ and $V_L$ or the 3G7 heavy chain and light chain (or a variant thereof, e.g., as set forth herein) may be referred to as "3G7."

Antibody 2C1 (Q1E) Heavy Chain (IgG4)
Heavy Chain (SEQ ID NO: 14, variable domain underscored; CDRs double underscored)

EVQLVQSGAEVKKPGASVKVSCKVSGYTLTELSMHWVRQAPGKGLEWMGG
FDPEDGETIYAQKFQGRVTMTEDTSTDTAYMELSSLRSEDTAVYYCARAG
PLYTIFGVVIIPDNWFDPWGQGTLVTVSSASTKGPSVFPLAPCSRSTSES
TAALGCLVKDYFPEPVTVSWNSGALTSGVHTFPAVLQSSGLYSLSSVVTV
PSSSLGTKTYTCNVDHKPSNTKVDKRVESKYGPPCPPCPAPEFLGGPSVF
LFPPKPKDTLMISRTPEVTCVVVDVSQEDPEVQFNWYVDGVEVHNAKTKP
REEQFNSTYRVVSVLTVLHQDWLNGKEYKCKVSNKGLPSSIEKTISKAKG
QPREPQVYTLPPSQEEMTKNQVSLTCLVKGFYPSDIAVEWESNGQPENNY
KTTPPVLDSDGSFFLYSRLTVDKSRWQEGNVFSCSVMHEALHNHYTQKSL
SLSLGK

Heavy Chain Variable Domain (SEQ ID NO: 68)
EVQLVQSGAEVKKPGASVKVSCKVSGYTLTELSMHWVRQAPGKGLEWMGG
FDPEDGETIYAQKFQGRVTMTEDTSTDTAYMELSSLRSEDTAVYYCARAG
PLYTIFGVVIIPDNWFDPWGQGTLVTVSS The present invention includes antibodies and antigen-binding fragments thereof wherein residue 1 of SEQ ID NO:14 or 68 is Q instead of E.

2C1 Heavy Chain CDRs

CDR-H1: ELSMH (SEQ ID NO: 34)

CDR-H2: GFDPEDGETIYAQKFQG (SEQ ID NO: 35)

CDR-H3: AGPLYTIFGVVIIPDNWFDP (SEQ ID NO: 36)

Antibody 2C1 Light Chain (Q1E) (Lambda)
Light Chain

ESVLTQPPSVSGAPGQRVTISCTGSSSNIGAGYDVHWYQQLPGTAPKLLI
YGNSNRPSGVPDRFSGSKSGTSASLAITGLQAEDEADYYCQSYDSSLSGS
GVVFGGGTQLIILGQPKAAPSVTLFPPSSEELQANKATLVCLISDFYPGA
VTVAWKADSSPVKAGVETTTPSKQSNNKYAASSYLSLTPEQWKSHRSYSC
QVTHEGSTVEKTVAPTECS (SEQ ID NO: 15, variable domain underscored; CDRs double underscored)

Light Chain Variable Domain (SEQ ID NO: 76)
ESVLTQPPSVSGAPGQRVTISCTGSSSNIGAGYDVHWYQQLPGTAPKLLI
YGNSNRPSGVPDRFSGSKSGTSASLAITGLQAEDEADYYCQSYDSSLSGS
GVVFGGGTQLIIL The present invention includes antibodies and antigen-binding fragments thereof wherein residue 1 of SEQ ID NO:15 or 76 is Q instead of E.

2C1 Light Chain CDRs

CDR-L1:
TGSSSNIGAGYDVH (SEQ ID NO: 37)

CDR-L2:
GNSNRPS (SEQ ID NO: 38)

CDR-L3:
QSYDSSLSGSGVV (SEQ ID NO: 39)

Antibodies and antigen-binding fragments thereof including the 2C1 heavy and light chain CDRs or the 2C1 $V_H$ and $V_L$ or the 2C1 heavy chain and light chain (or a variant thereof, e.g., as set forth herein) may be referred to as "2C1."

In various embodiments of the antibody or antigen-binding fragment thereof, a C-terminal lysine of a heavy chain immunoglobulin is absent.

Thus, in some embodiments, the antibody or antigen-binding fragment thereof comprises a light chain immunoglobulin, a heavy chain immunoglobulin, or both a light and heavy chain immunoglobulin, wherein the light chain immunoglobulin comprises the amino acid sequence set forth in SEQ ID NO:3, 4, 5, 6, 7, 11, 13, 15, or 45; and/or the heavy chain immunoglobulin comprises the amino acid sequence set forth in SEQ ID NO: 1, 2, 8, 9, 10, 12, 14, 44, 79, 80, 81, 82, 83, 84, 85, or 86.

In certain embodiments, the antibody or antigen-binding fragment thereof comprises: a heavy chain immunoglobulin comprising the amino acid sequence set forth in SEQ ID NO: 1 or 79; and a light chain immunoglobulin comprising the amino acid sequence set forth in SEQ ID NO: 3.

In some embodiments, the antibody or antigen-binding fragment thereof comprises: a heavy chain immunoglobulin comprising the amino acid sequence set forth in SEQ ID NO: 2 or 80; and a light chain immunoglobulin comprising the amino acid sequence set forth in SEQ ID NO: 4.

In other embodiments, the antibody or antigen-binding fragment thereof comprises: a heavy chain immunoglobulin comprising the amino acid sequence set forth in SEQ ID NO: 2 or 80; and a light chain immunoglobulin comprising the amino acid sequence set forth in SEQ ID NO: 5.

In yet other embodiments, the antibody or antigen-binding fragment thereof comprises: a heavy chain immunoglobulin comprising the amino acid sequence set forth in SEQ ID NO: 2 or 80; and a light chain immunoglobulin comprising the amino acid sequence set forth in SEQ ID NO: 6.

In still other embodiments, the antibody or antigen-binding fragment thereof comprises: a heavy chain immunoglobulin comprising the amino acid sequence set forth in SEQ ID NO: 2 or 80; and a light chain immunoglobulin comprising the amino acid sequence set forth in SEQ ID NO: 7.

In certain embodiments, the antibody or antigen-binding fragment thereof comprises: a heavy chain immunoglobulin comprising the amino acid sequence set forth in SEQ ID NO: 2 or 80; and a light chain immunoglobulin comprising the amino acid sequence set forth in SEQ ID NO: 3.

In some embodiments, the antibody or antigen-binding fragment thereof comprises: a heavy chain immunoglobulin comprising the amino acid sequence set forth in SEQ ID NO: 8 or 82; and a light chain immunoglobulin comprising the amino acid sequence set forth in SEQ ID NO: 11.

In other embodiments, the antibody or antigen-binding fragment thereof comprises: a heavy chain immunoglobulin comprising the amino acid sequence set forth in SEQ ID NO: 9 or 83; and a light chain immunoglobulin comprising the amino acid sequence set forth in SEQ ID NO: 11.

In yet other embodiments, the antibody or antigen-binding fragment thereof comprises: a heavy chain immunoglobulin comprising the amino acid sequence set forth in SEQ ID NO: 10 or 84; and a light chain immunoglobulin comprising the amino acid sequence set forth in SEQ ID NO: 11.

In still other embodiments, the antibody or antigen-binding fragment thereof comprises: a heavy chain immunoglobulin comprising the amino acid sequence set forth in SEQ ID NO: 12 or 85; and a light chain immunoglobulin comprising the amino acid sequence set forth in SEQ ID NO: 13.

In yet still embodiments, the antibody or antigen-binding fragment thereof comprises: a heavy chain immunoglobulin comprising the amino acid sequence set forth in SEQ ID NO: 14 or 86; and a light chain immunoglobulin comprising the amino acid sequence set forth in SEQ ID NO: 15.

In certain other embodiments, the antibody or antigen-binding fragment thereof comprises a light chain immunoglobulin, a heavy chain immunoglobulin, or both a light and heavy chain immunoglobulin, wherein the light chain variable domain comprises the amino acid sequence set forth in SEQ ID NO:70, 71, 72, 73, 58, 74, 75, 76, or 77, and/or the heavy chain variable domain comprise the amino acid sequence set forth in SEQ ID NO:63, 57, 64, 65, 66, 67, 68, or 69.

In certain embodiments, the antibody or antigen-binding fragment thereof comprises: a heavy chain variable domain comprising the amino acid sequence set forth in SEQ ID NO:63; and a light chain variable domain comprising the amino acid sequence set forth in SEQ ID NO:70.

In some embodiments, the antibody or antigen-binding fragment thereof comprises: a heavy chain variable domain comprising the amino acid sequence set forth in SEQ ID NO:57; and a light chain variable domain comprising the amino acid sequence set forth in SEQ ID NO:71.

In other embodiments, the antibody or antigen-binding fragment thereof comprises: a heavy chain variable domain comprising the amino acid sequence set forth in SEQ ID NO:57; and a light chain variable domain comprising the amino acid sequence set forth in SEQ ID NO:72.

In yet other embodiments, the antibody or antigen-binding fragment thereof comprises: a heavy chain variable domain comprising the amino acid sequence set forth in SEQ ID NO:57; and a light chain variable domain comprising the amino acid sequence set forth in SEQ ID NO:73.

In still other embodiments, the antibody or antigen-binding fragment thereof comprises: a heavy chain variable domain comprising the amino acid sequence set forth in SEQ ID NO:57; and a light chain variable domain comprising the amino acid sequence set forth in SEQ ID NO:58.

In certain embodiments, the antibody or antigen-binding fragment thereof comprises: a heavy chain variable domain comprising the amino acid sequence set forth in SEQ ID NO:57; and a light chain variable domain comprising the amino acid sequence set forth in SEQ ID NO:70.

In some embodiments, the antibody or antigen-binding fragment thereof comprises:
a heavy chain variable domain comprising the amino acid sequence set forth in SEQ ID NO:64; and a light chain variable domain comprising the amino acid sequence set forth in SEQ ID NO:74.

In other embodiments, the antibody or antigen-binding fragment thereof comprises: a heavy chain variable domain comprising the amino acid sequence set forth in SEQ ID NO:65; and a light chain variable domain comprising the amino acid sequence set forth in SEQ ID NO:74.

In yet other embodiments, the antibody or antigen-binding fragment thereof comprises: a heavy chain variable domain comprising the amino acid sequence set forth in SEQ ID NO:66; and a light chain variable domain comprising the amino acid sequence set forth in SEQ ID NO:74.

In still other embodiments, the antibody or antigen-binding fragment thereof comprises: a heavy chain variable domain comprising the amino acid sequence set forth in SEQ ID NO:67; and a light chain variable domain comprising the amino acid sequence set forth in SEQ ID NO:75.

In yet still other embodiments, the antibody or antigen-binding fragment thereof comprises: a heavy chain variable domain comprising the amino acid sequence set forth in SEQ ID NO:68; and a light chain variable domain comprising the amino acid sequence set forth in SEQ ID NO:76.

In a further embodiment, the antibody or antigen-binding fragment thereof that binds ILT4 comprises an immunoglobulin light chain variable ($V_L$) domain comprising a CDR-L1, CDR-L2 and CDR-L3 of 1E1 (e.g., SEQ ID NOs: 19-21); and an immunoglobulin heavy chain variable ($V_H$) domain comprising a CDR-H1, CDR-H2 and CDR-H3 of 1E1 (e.g., SEQ ID NOs: 16-18).

In a further embodiment, the antibody or antigen-binding fragment thereof that binds ILT4 comprises an immunoglobulin light chain variable ($V_L$) domain comprising a CDR-L1, CDR-L2 and CDR-L3 of 2A6 (e.g., SEQ ID NOs: 25-27); and an immunoglobulin heavy chain variable ($V_H$) domain comprising a CDR-H1, CDR-H2 and CDR-H3 of 2A6 (e.g., SEQ ID NOs: 22-24).

In a further embodiment, the antibody or antigen-binding fragment thereof that binds ILT4 comprises an immunoglobulin light chain variable ($V_L$) domain comprising a CDR-L1, CDR-L2 and CDR-L3 of 3G7 (e.g., SEQ ID NOs: 31-33); and an immunoglobulin heavy chain variable ($V_H$) domain comprising a CDR-H1, CDR-H2 and CDR-H3 of 3G7 (e.g., SEQ ID NOs: 28-30).

In a further embodiment, the antibody or antigen-binding fragment thereof that binds ILT4 comprises an immunoglobulin light chain variable ($V_L$) domain comprising a CDR-L1, CDR-L2 and CDR-L3 of 2C1 (e.g., SEQ ID NOs: 37-39); and an immunoglobulin heavy chain variable ($V_H$) domain comprising a CDR-H1, CDR-H2 and CDR-H3 of 2C1 (e.g., SEQ ID NOs: 34-36).

In one embodiment, the antibody or antigen-binding fragment comprises: a V$_H$ domain comprising: CDR-H1: GYYWS (SEQ ID NO: 16), CDR-H2: EINHSG-STNYNPSLKS (SEQ ID NO: 47), and CDR-H3: LPTRWVTTRYFDL (SEQ ID NO: 18); and/or, a V$_L$ domain comprising: CDR-L1: TGSSSNIGAGYDVH (SEQ ID NO: 19), CDR-L2: GNSNRPS(SEQ ID NO: 49), and CDR-L3: QSFDNSLSAYV (SEQ ID NO: 21).

In another embodiment, the antibody or antigen-binding fragment comprises: a V$_H$ domain comprising: CDR-H1: GYYWS (SEQ ID NO: 16), CDR-H2: EINHSG-STNYNPSLKS (SEQ ID NO: 47), and CDR-H3: LPTRWVTTRYFDL (SEQ ID NO: 18); and/or, a V$_L$ domain comprising: CDR-L1: TGSSSNIGAGYDVH (SEQ ID NO: 19), CDR-L2: GQSNRPS(SEQ ID NO: 50), and CDR-L3: QSFDNSLSAYV (SEQ ID NO: 21).

In yet another embodiment, the antibody or antigen-binding fragment thereof comprises: a V$_H$ domain comprising: CDR-H1: GYYWS (SEQ ID NO: 16), CDR-H2: EINHSGSTNYNPSLKS (SEQ ID NO: 47), and CDR-H3: LPTRWVTTRYFDL (SEQ ID NO: 18); and/or, a V$_L$ domain comprising: CDR-L1: TGSSSNIGAGYDVH (SEQ ID NO: 19), CDR-L2: GESNRPS(SEQ ID NO: 51), and CDR-L3: QSFDNSLSAYV (SEQ ID NO: 21).

In still another embodiment, the antibody or antigen-binding fragment thereof comprises: a V$_H$ domain comprising: CDR-H1: GYYWS (SEQ ID NO: 16), CDR-H2: EINHSGSTNYNPSLKS (SEQ ID NO: 47), and CDR-H3: LPTRWVTTRYFDL (SEQ ID NO: 18); and/or, a V$_L$ domain comprising: CDR-L1: TGSSSNIGAGYDVH (SEQ ID NO: 19), CDR-L2: GDSNRPS(SEQ ID NO: 52), and CDR-L3: QSFDNSLSAYV (SEQ ID NO: 21).

In one embodiment, the antibody or antigen-binding fragment thereof comprises: a V$_H$ domain comprising: CDR-H1: GYYWS (SEQ ID NO: 16), CDR-H2: EINHSG-STNYNPSLKS (SEQ ID NO: 47), and CDR-H3: LPTRWVTTRYFDL (SEQ ID NO: 18); and/or, a V$_L$ domain comprising: CDR-L1: TGSSSNIGAGYDVH (SEQ ID NO: 19), CDR-L2: GNANRPS(SEQ ID NO: 53), and CDR-L3: QSFDNSLSAYV (SEQ ID NO: 21).

In another embodiment, the antibody or antigen-binding fragment thereof comprises: a V$_H$ domain comprising: CDR-H1: GYYWS (SEQ ID NO: 16), CDR-H2: EINHSG-STNYNPSLKS (SEQ ID NO: 47), and CDR-H3: LPTRWVTTRYFDL (SEQ ID NO: 18); and/or, a V$_L$ domain comprising: CDR-L1: TGSSSNIGAGYDVH (SEQ ID NO: 19), CDR-L2: GQANRPS(SEQ ID NO: 54), and CDR-L3: QSFDNSLSAYV (SEQ ID NO: 21).

In yet another embodiment, the antibody or antigen-binding fragment thereof comprises: a V$_H$ domain comprising: CDR-H1: GYYWS (SEQ ID NO: 16), CDR-H2: EINHSGSTNYNPSLKS (SEQ ID NO: 47), and CDR-H3: LPTRWVTTRYFDL (SEQ ID NO: 18); and/or, a V$_L$ domain comprising: CDR-L1: TGSSSNIGAGYDVH (SEQ ID NO: 19), CDR-L2: GEANRPS(SEQ ID NO: 55), and CDR-L3: QSFDNSLSAYV (SEQ ID NO: 21).

In still another embodiment, the antibody or antigen-binding fragment thereof comprises: a V$_H$ domain comprising: CDR-H1: GYYWS (SEQ ID NO: 16), CDR-H2: EINHSGSTNYNPSLKS (SEQ ID NO: 47), and CDR-H3: LPTRWVTTRYFDL (SEQ ID NO: 18); and/or, a V$_L$ domain comprising: CDR-L1: TGSSSNIGAGYDVH (SEQ ID NO: 19), CDR-L2: GDANRPS(SEQ ID NO: 56), and CDR-L3: QSFDNSLSAYV (SEQ ID NO: 21).

In one embodiment, the antibody or antigen-binding fragment thereof comprises: a V$_H$ domain comprising: CDR-H1: GYYWS (SEQ ID NO: 16), CDR-H2: EINHAG-STNYNPSLKS (SEQ ID NO: 48), and CDR-H3: LPTRWVTTRYFDL (SEQ ID NO: 18); and/or, a V$_L$ domain comprising: CDR-L1: TGSSSNIGAGYDVH (SEQ ID NO: 19), CDR-L2: GNSNRPS(SEQ ID NO: 49), and CDR-L3: QSFDNSLSAYV (SEQ ID NO: 21).

In another embodiment, the antibody or antigen-binding fragment thereof comprises: a V$_H$ domain comprising: CDR-H1: GYYWS (SEQ ID NO: 16), CDR-H2: EINHAG-STNYNPSLKS (SEQ ID NO: 48), and CDR-H3: LPTRWVTTRYFDL (SEQ ID NO: 18); and/or, a V$_L$ domain comprising: CDR-L1: TGSSSNIGAGYDVH (SEQ ID NO: 19), CDR-L2: GQSNRPS(SEQ ID NO: 50), and CDR-L3: QSFDNSLSAYV (SEQ ID NO: 21).

In yet another embodiment, the antibody or antigen-binding fragment thereof comprises: a V$_H$ domain comprising: CDR-H1: GYYWS (SEQ ID NO: 16), CDR-H2: EINHAGSTNYNPSLKS (SEQ ID NO: 48), and CDR-H3: LPTRWVTTRYFDL (SEQ ID NO: 18); and/or, a V$_L$ domain comprising: CDR-L1: TGSSSNIGAGYDVH (SEQ ID NO: 19), CDR-L2: GESNRPS(SEQ ID NO: 51), and CDR-L3: QSFDNSLSAYV (SEQ ID NO: 21).

In still another embodiment, the antibody or antigen-binding fragment thereof comprises: a V$_H$ domain comprising: CDR-H1: GYYWS (SEQ ID NO: 16), CDR-H2: EINHAGSTNYNPSLKS (SEQ ID NO: 48), and CDR-H3: LPTRWVTTRYFDL (SEQ ID NO: 18); and/or, a V$_L$ domain comprising: CDR-L1: TGSSSNIGAGYDVH (SEQ ID NO: 19), CDR-L2: GDSNRPS(SEQ ID NO: 52), and CDR-L3: QSFDNSLSAYV (SEQ ID NO: 21).

In one embodiment, the antibody or antigen-binding fragment thereof comprises: a V$_H$ domain comprising: CDR-H1: GYYWS (SEQ ID NO: 16), CDR-H2: EINHAG-STNYNPSLKS (SEQ ID NO: 48), and CDR-H3: LPTRWVTTRYFDL (SEQ ID NO: 18); and/or, a V$_L$ domain comprising: CDR-L1: TGSSSNIGAGYDVH (SEQ ID NO: 19), CDR-L2: GNANRPS(SEQ ID NO: 53), and CDR-L3: QSFDNSLSAYV (SEQ ID NO: 21).

In another embodiment, the antibody or antigen-binding fragment thereof comprises: a V$_H$ domain comprising: CDR-H1: GYYWS (SEQ ID NO: 16), CDR-H2: EINHAG-STNYNPSLKS (SEQ ID NO: 48), and CDR-H3: LPTRWVTTRYFDL (SEQ ID NO: 18); and/or, a V$_L$ domain comprising: CDR-L1: TGSSSNIGAGYDVH (SEQ ID NO: 19), CDR-L2: GQANRPS(SEQ ID NO: 54), and CDR-L3: QSFDNSLSAYV (SEQ ID NO: 21).

In yet another embodiment, the antibody or antigen-binding fragment thereof comprises: a V$_H$ domain comprising: CDR-H1: GYYWS (SEQ ID NO: 16), CDR-H2: EINHAGSTNYNPSLKS (SEQ ID NO: 48), and CDR-H3: LPTRWVTTRYFDL (SEQ ID NO: 18); and/or, a V$_L$ domain comprising: CDR-L1: TGSSSNIGAGYDVH (SEQ ID NO: 19), CDR-L2: GEANRPS(SEQ ID NO: 55), and CDR-L3: QSFDNSLSAYV (SEQ ID NO: 21).

In still another embodiment, the antibody or antigen-binding fragment thereof comprises: a V$_H$ domain comprising: CDR-H1: GYYWS (SEQ ID NO: 16), CDR-H2: EINHAGSTNYNPSLKS (SEQ ID NO: 48), and CDR-H3: LPTRWVTTRYFDL (SEQ ID NO: 18); and/or, a V$_L$ domain comprising: CDR-L1: TGSSSNIGAGYDVH (SEQ ID NO: 19), CDR-L2: GDANRPS(SEQ ID NO: 56), and CDR-L3: QSFDNSLSAYV (SEQ ID NO: 21).

The present invention further provides an antibody or antigen-binding fragment thereof that binds ILT4 and comprises the V$_L$ domain of antibody 1E1 (e.g., SEQ ID NO:70, 71, 72, 73, 58 or 77) and/or the V$_H$ domain of antibody 1E1 (e.g., SEQ ID NO:63, 57 or 69).

The present invention further provides an antibody or antigen-binding fragment thereof that binds ILT4 and comprises the V$_L$ domain of antibody 2A6 (e.g., SEQ ID NO:74) and/or the V$_H$ domain of antibody 2A6 (e.g., SEQ ID NO:64, 65 or 66).

The present invention further provides an antibody or antigen-binding fragment thereof that binds ILT4 and comprises the V$_L$ domain of antibody 3G7 (e.g., SEQ ID NO:75) and/or the V$_H$ domain of antibody 3G7 (e.g., SEQ ID NO:67).

The present invention further provides an antibody or antigen-binding fragment thereof that binds ILT4 and comprises the V$_L$ domain of antibody 2C1 (e.g., SEQ ID NO:76) and/or the V$_H$ domain of antibody 2C1 (e.g., SEQ ID NO:68).

The present invention further provides an antibody or antigen-binding fragment thereof that binds ILT4 and comprises the light chain immunoglobulin of antibody 1E1 (e.g., SEQ ID NO:3, 4, 5, 6, 7 or 45) and/or the heavy chain immunoglobulin of antibody 1E1 (e.g., SEQ ID NO:1, 2, 44, 79, 80, or 81).

The present invention further provides an antibody or antigen-binding fragment thereof that binds ILT4 and comprises the light chain immunoglobulin of antibody 2A6 (e.g., SEQ ID NO:11) and/or the heavy chain immunoglobulin of antibody 2A6 (e.g., SEQ ID NO:8, 9, 10, 82, 83, or 84).

The present invention further provides an antibody or antigen-binding fragment thereof that binds ILT4 and comprises the light chain immunoglobulin of antibody 3G7 (e.g., SEQ ID NO:13) and/or the heavy chain immunoglobulin of antibody 3G7 (e.g., SEQ ID NO:12 or 85).

The present invention further provides an antibody or antigen-binding fragment thereof that binds ILT4 and comprises the light chain immunoglobulin of antibody 2C1 (e.g., SEQ ID NO:15) and/or the heavy chain immunoglobulin of antibody 2C1 (e.g., SEQ ID NO:14 or 86).

The present invention further provides an antibody that consists of two heavy chains and two light chains, wherein each light chain comprises the V$_L$ or light chain immunoglobulin of antibody 1E1, 2A6, 3G7, or 2C1, and each heavy chain comprises the V$_H$ or heavy chain immunoglobulin of antibody 1E1, 2A6, 3G7, or 2C1.

In one embodiment, the antibody consists of two heavy chains and two light chains, wherein each light chain comprises the amino acid sequence set forth in SEQ ID NO:58 and each heavy chain comprises the amino acid sequence set forth in SEQ ID NO:57.

In another embodiment, the antibody consists of two heavy chains and two light chains, wherein each light chain comprises the amino acid sequence set forth in SEQ ID NO:58 and each heavy chain comprises the amino acid sequence set forth in SEQ ID NO:57, wherein the light chain further comprises the amino acid sequence set forth in SEQ ID NO:90.

In yet another embodiment, the antibody consists of two heavy chains and two light chains, wherein each light chain comprises the amino acid sequence set forth in SEQ ID NO:58 and each heavy chain comprises the amino acid sequence set forth in SEQ ID NO:57, wherein the heavy chain further comprises the amino acid sequence set forth in SEQ ID NO:89.

In still another embodiment, the antibody consists of two heavy chains and two light chains, wherein each light chain comprises the amino acid sequence set forth in SEQ ID NO:58 and each heavy chain comprises the amino acid sequence set forth in SEQ ID NO:57, wherein the light chain further comprises the amino acid sequence set forth in SEQ ID NO:90 and the heavy chain further comprises the amino acid sequence set forth in SEQ ID NO:89.

In one embodiment, the antibody consists of two heavy chains and two light chains, wherein each light chain comprises the amino acid sequence set forth in SEQ ID NO:7 and each heavy chain comprises the amino acid sequence set forth in SEQ ID NO:2.

In another embodiment, the antibody consists of two heavy chains and two light chains, wherein each light chain consists of the amino acid sequence set forth in SEQ ID NO:7 and each heavy chain consists of the amino acid sequence set forth in SEQ ID NO:2.

In an embodiment of the invention, the antibody or antigen-binding fragment of the present invention comprises a V$_L$ (with or without signal sequence), e.g., the V$_L$ in any of SEQ ID NO:58 or 70-77, having up to 1, 2, 3, 4, 5, 6, 7, 8, 9, 10 or more conservative or non-conservative amino acid substitutions; and/or a V$_H$ (with or without signal sequence), e.g., the V$_H$ in any of SEQ ID NO:57 or 63-69, having up to 1, 2, 3, 4, 5, 6, 7, 8, 9, 10 or more conservative or non-conservative amino acid substitutions, while still binding to ILT4.

The present invention also includes polypeptides comprising the amino acid sequences disclosed herein, e.g. SEQ ID NOs: 1-39, 44, 45, 47-58, 63-77, or 79-86, as well as polypeptides comprising such amino acid sequences with up to 1, 2, 3, 4, 5, 6, 7, 8, 9, 10, 12, 15, 20 or more conservative or non-conservative amino acid substitutions therein.

In certain embodiments, the antibody or antigen-binding fragment thereof comprises a light chain immunoglobulin, a heavy chain immunoglobulin, or both a light and heavy chain immunoglobulin, wherein the light chain immunoglobulin has at least 90% amino acid sequence identity to the amino acid sequence set forth in SEQ ID NO:3, 4, 5, 6, 7, 11, 13, 15, or 45, and/or the heavy chain immunoglobulin has at least 90% amino acid sequence identity to the amino acid sequence set forth in SEQ ID NO:1, 2, 8, 9, 10, 12, 14, 44, 79, 80, 81, 82, 83, 84, 85, or 86.

In some embodiments, the antibody or antigen-binding fragment thereof comprises a light chain immunoglobulin, a heavy chain immunoglobulin, or both a light and heavy chain immunoglobulin, wherein the light chain immunoglobulin comprises a light chain variable domain having at least 90% amino acid sequence identity to the amino acid sequence set forth in SEQ ID NO:70, 71, 72, 73, 58, 74, 75, 76, or 77, and/or the heavy chain immunoglobulin comprises a heavy chain variable domain having at least 90% amino acid sequence identity to the amino acid sequence set forth in SEQ ID NO:63, 57, 64, 65, 66, 67, 68, or 69.

In an embodiment of the invention, an immunoglobulin heavy chain of an anti-ILT4 antibody or antigen-binding fragment of the present invention is operably linked to a signal sequence, e.g., comprising the amino acid sequence MEWSWVFLFFLSVTTGVHS (SEQ ID NO:41) and/or an immunoglobulin light chain of an anti-ILT4 antibody or antigen-binding fragment of the present invention is operably linked to a signal sequence, e.g., comprising the amino acid sequence MSVPTQVLGLLLLWLTDARC (SEQ ID NO:42).

In an embodiment of the invention, an N-terminal glutamine (Q) of an immunoglobulin chain set forth herein (e.g., heavy and/or light) is replaced with a pyroglutamic acid. In one embodiment, an N-terminal Q of a heavy chain immunoglobulin is replaced with a pyroglutamic acid. In another embodiment, an N-terminal Q of a light chain immunoglobulin is replaced with a pyroglutamic acid. In yet another embodiment, an N-terminal Q of a heavy chain immunoglobulin and an N-terminal Q of a heavy chain immunoglobulin are replaced with a pyroglutamic acid.

Further provided herein are antibodies or antigen-binding fragments that bind to the same epitope of ILT4 (e.g., human ILT4) as any anti-ILT4 antibody or antigen-binding fragment thereof disclosed herein (e.g., 1E1, 2A6, 3G7 or 2C1). In one embodiment, the epitope is LYREKKSASW (SEQ ID NO:59). In another embodiment, the epitope is TRIRPEL (SEQ ID NO:60). In yet another embodiment, the epitope is NGQF (SEQ ID NO:61). In still another embodiment, the epitope is HTGRYGCQ (SEQ ID NO:62). In certain embodiments, the antibody or antigen-binding fragment thereof binds to the same epitope of human ILT4 as an antibody or antigen-binding fragment thereof comprising the heavy chain and light chain amino acid sequences set forth in SEQ ID NOs:1 and 3; 2 and 4; 2 and 5; 2 and 6; 2 and 7; 2 and 3; 8 and 11; 9 and 11; 10 and 11; 12 and 13; 14 and 15; 79 and 3; 80 and 4; 80 and 5; 80 and 6; 80 and 7; 80 and 3; 82 and 11; 83 and 11; 84 and 11; 85 and 13; and 86 and 15; respectively. In some embodiments, the antibody or antigen-binding fragment thereof binds to the same epitope of human ILT4 as an antibody or antigen-binding fragment thereof comprising the heavy chain variable domain and light chain variable domain amino acid sequences set forth in SEQ ID NOs:63 and 70; 57 and 71; 57 and 72; 57 and 73; 57 and 58; 57 and 70; 64 and 74; 65 and 74; 66 and 74; 67 and 75; 68 and 76; respectively.

The present invention include antibodies and antigen-binding fragments that cross-block the binding of any anti-ILT4 antibody or antigen-binding fragment thereof disclosed herein (e.g., 1E1, 2A6, 3G7 or 2C1) to ILT4 (e.g., human ILT4) or compete with any anti-ILT4 antibody or antigen-binding fragment thereof disclosed herein (e.g., 1E1, 2A6, 3G7 or 2C1) to ILT4 (e.g., human ILT4). The cross-blocking antibodies and antigen-binding fragments thereof discussed herein can be identified based on their ability to block any of the antibodies or fragments specifically set forth herein from binding to ILT4, in binding assays (e.g., bio-layer interferometry (BLI; for example FORTEBIO OCTET binding assay; Pall ForteBio Corp; Menlo Park, CA), surface plasmon resonance (SPR), BIACore, ELISA, flow cytometry). For example, in an embodiment of the invention, when using BLI, the tip of a fiber-optic probe is coated with ligand (e.g., ILT4) and acts as the biosensor wherein binding of anti-ILT4 antibody or antigen-binding fragment to the ILT4 alters the interference pattern of white light reflected from the probe layer bound to ILT4 and an internal reference layer. The shift is indicative of ILT4/anti-ILT4 binding. In an embodiment of the invention, the ILT4 coated tip is immersed in a solution of analyte containing antibody or antigen-binding fragment, e.g., in the well of either a 96- or 384-well plate. In an embodiment of the invention, the plate is shaken during reading to create orbital flow. To read the assay, white light is directed down the length of the fiber. As mentioned above, interference between light reflecting off the reference layer and immobilized surfaces containing ILT4 of the tip creates a distinctive pattern of light returning up the fiber. As molecules bind to the immobilized sensor surface, that pattern changes in proportion to the extent of binding. For example, assays can be used in which a ILT4 (e.g., human ILT4) protein is immobilized on a BLI probe or plate, a reference anti-ILT4 antibody or fragment binds to ILT4 (e.g., at saturating concentration) and a test anti-ILT4 antibody or fragment is added. The ability of the test antibody to compete with the reference antibody for ILT4 binding is then determined. In the BLI format, light interference of the ILT4 complex is monitored to determine if the test antibody effectively competes with the reference antibody, e.g., nanometers of light wavelength shift over time is monitored wherein a shift indicates additional binding of the test antibody and a lack of cross-blocking. In an embodiment of the invention, in the BLI format, cross-blocking is qualitatively deemed to have occurred between the antibodies if no additional binding of test antibody is observed. In an embodiment of the invention, as a control, cross-blocking of the reference antibody with itself is confirmed; wherein the assay is determined to be operating correctly if the reference antibody can cross-block itself from ILT4 binding. The ability of a test antibody to inhibit the binding of the anti-ILT4 antibody or fragment 1E1, 2A6, 3G7 or 2C1, to ILT4 (e.g., human ILT4) demonstrates that the test antibody can cross-block the antibody or fragment for binding to ILT4 (e.g., human ILT4) and thus, may, in some cases, bind to the same epitope on ILT4 (e.g., human ILT4) as 1E1, 2A6, 3G7 and/or 2C1. As stated above, antibodies and fragments that bind to the same epitope as any of the anti-ILT4 antibodies or fragments of the present invention also form part of the present invention. In an embodiment of the invention, BLI is conducted in a sandwich format wherein a reference anti-ILT4 antibody or antigen-binding fragment is immobilized to the probe and then bound with ILT4. Test anti-ILT4 antibody or antigen-binding fragment is then tested for the ability to block binding of the references antibody or fragment.

In certain embodiments, the antibody or antigen-binding fragment thereof competes for binding to human ILT4 with an antibody or fragment comprising the heavy chain and light chain amino acid sequences set forth in SEQ ID NOs:1 and 3; 2 and 4; 2 and 5; 2 and 6; 2 and 7; 2 and 3; 8 and 11; 9 and 11; 10 and 11; 12 and 13; 14 and 15; 79 and 3; 80 and 4; 80 and 5; 80 and 6; 80 and 7; 80 and 3; 82 and 11; 83 and 11; 84 and 11; 85 and 13; and 86 and 15; respectively. In some embodiments, the antibody or antigen-binding fragment thereof competes for binding to human ILT4 with an antibody or fragment comprising the heavy chain variable domain and light chain variable domain amino acid sequences set forth in SEQ ID NOs:63 and 70; 57 and 71; 57 and 72; 57 and 73; 57 and 58; 57 and 70; 64 and 74; 65 and 74; 66 and 74; 67 and 75; 68 and 76; respectively.

Figure 16:
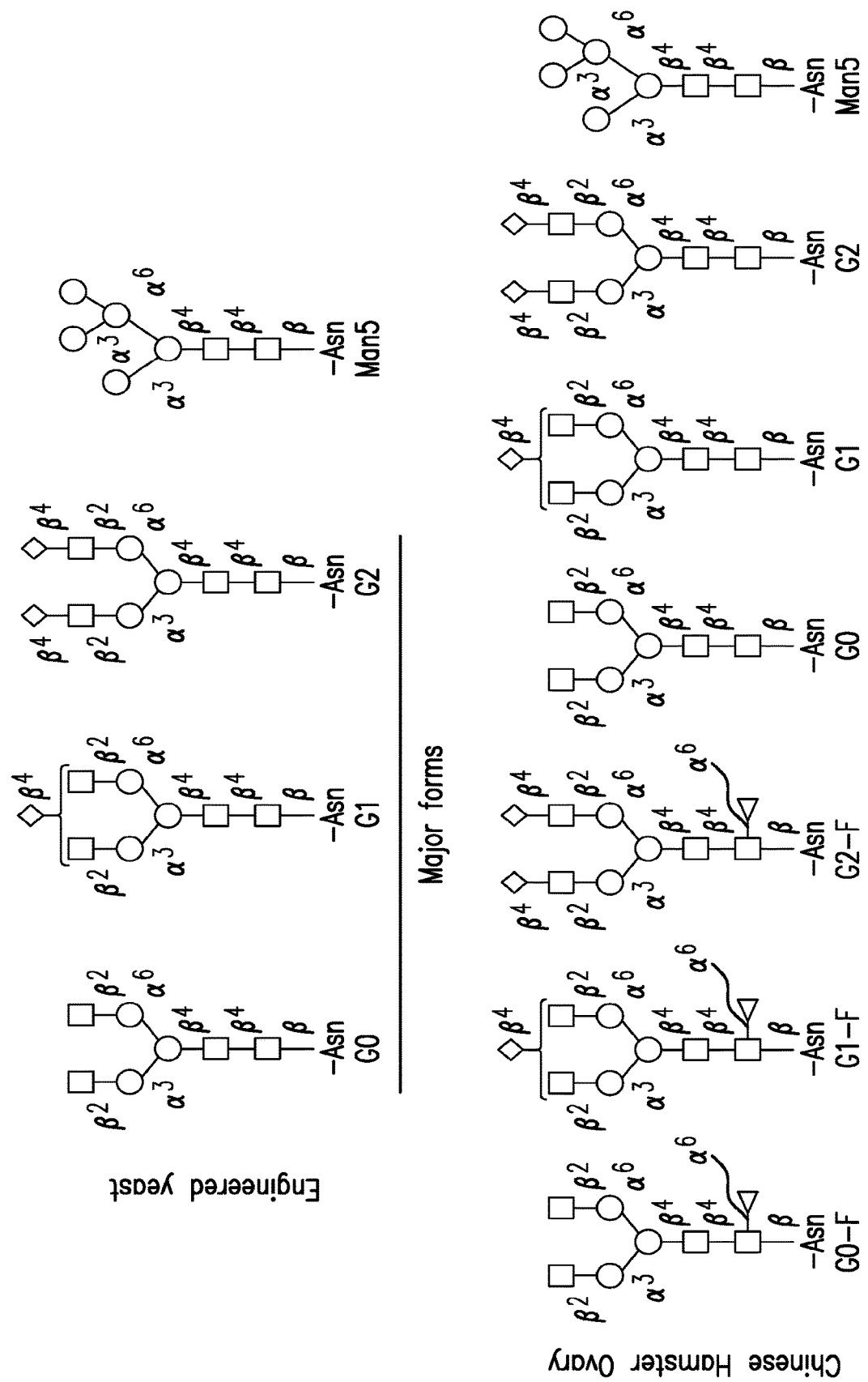
FIG. 16. Predominant N-linked glycans for monoclonal antibodies produced in Chinese hamster ovary cells (CHO N-linked glycans) and in engineered yeast cells (engineered yeast N-linked glycans): squares: N-acetylglucosamine (GlcNac); circles: mannose (Man); diamonds: galactose (Gal); triangles: fucose (Fuc).

The present invention includes anti-ILT4 antibodies and antigen-binding fragments thereof comprising N-linked glycans that are typically added to immunoglobulins produced in Chinese hamster ovary cells (CHO N-linked glycans) or to engineered yeast cells (engineered yeast N-linked glycans), such as, for example, *Pichia pastoris*. For example, in an embodiment of the invention, the anti-ILT4 antibodies and antigen-binding fragments thereof comprise one or more of the "engineered yeast N-linked glycans" or "CHO N-linked glycans" that are set forth in FIG. 16 (e.g., G0 and/or G0-F and/or G1 and/or G1-F and/or and/or G2-F and/or Man5). In an embodiment of the invention, the anti-ILT4 antibodies and antigen-binding fragments thereof comprise the engineered yeast N-linked glycans, i.e., G0 and/or G1 and/or G2, optionally, further including Man5. In an embodiment of the invention, the anti-ILT4 antibodies and antigen-binding fragments thereof comprise the CHO N-linked glycans, G0-F, G1-F and G2-F, optionally, further including G0 and/or G1 and/or G2 and/or Man5. In an embodiment of the invention, about 80% to about 95% (e.g., about 80-90%, about 85%, about 90% or about 95%) of all N-linked glycans on the anti-ILT4 antibodies and antigen-binding fragments thereof are engineered yeast N-linked glycans or CHO N-linked glycans. See Nett et al. Yeast. 28(3): 237-252 (2011); Hamilton et al. Science. 313(5792):

1441-1443 (2006); Hamilton et al. Curr Opin Biotechnol. 18(5): 387-392 (2007). For example, in an embodiment of the invention, an engineered yeast cell is GFI5.0 or YGLY8316 or strains set forth in U.S. Pat. No. 7,795,002 or Zha et al. Methods Mol Biol. 988:31-43 (2013). See also international patent application publication no. WO2013/066765.

Polynucleotides

The present invention comprises polynucleotides (e.g., DNA or RNA) encoding the immunoglobulin chains of anti-ILT4 antibodies and antigen-binding fragments thereof disclosed herein. For example, the present invention includes the nucleic acids encoding immunoglobulin heavy and/or light chains of antibodies 1E1, 2A6, 3G7 and 2C1 (e.g., SEQ ID NOs: 1-15, 44 and 45 or a variable domain thereof) as described herein as well as nucleic acids which hybridize thereto.

The present invention includes polynucleotides encoding an antibody light chain variable ($V_L$) domain comprising a CDR-L1, CDR-L2 and CDR-L3 of 1E1 (e.g., comprising the amino acids set forth in SEQ ID NOs: 19-21); and/or an antibody heavy chain variable ($V_H$) domain comprising a CDR-H1, CDR-H2 and CDR-H3 of 1E1 (e.g., comprising the amino acids set forth in SEQ ID NOs: 16-18).

The present invention includes polynucleotides encoding an antibody light chain variable ($V_L$) domain comprising a CDR-L1, CDR-L2 and CDR-L3 of 2A6 (e.g., comprising the amino acids set forth in SEQ ID NOs: 25-27); and/or an antibody heavy chain variable ($V_H$) domain comprising a CDR-H1, CDR-H2 and CDR-H3 of 2A6 (e.g., comprising the amino acids set forth in SEQ ID NOs: 22-24).

The present invention includes polynucleotides encoding an antibody light chain variable ($V_L$) domain comprising a CDR-L1, CDR-L2 and CDR-L3 of 3G7 (e.g., comprising the amino acids set forth in SEQ ID NOs: 31-33); and/or an antibody heavy chain variable ($V_H$) domain comprising a CDR-H1, CDR-H2 and CDR-H3 of 3G7 (e.g., comprising the amino acids set forth in SEQ ID NOs: 28-30).

The present invention includes polynucleotides encoding an antibody light chain variable ($V_L$) domain comprising a CDR-L1, CDR-L2 and CDR-L3 of 2C1 (e.g., comprising the amino acids set forth in SEQ ID NOs: 37-39); and/or an antibody heavy chain variable ($V_H$) domain comprising a CDR-H1, CDR-H2 and CDR-H3 of 2C1 (e.g., comprising the amino acids set forth in SEQ ID NOs: 34-36).

The present invention includes polynucleotides encoding the $V_L$ domain of antibody 1E1 (e.g., SEQ ID NO:70, 71, 72, 73, 58 or 77) and/or the $V_H$ domain of antibody 1E1 (e.g., SEQ ID NO:63, 57 or 69).

The present invention includes polynucleotides encoding the $V_L$ domain of antibody 2A6 (e.g., SEQ ID NO:74) and/or the $V_H$ domain of antibody 2A6 (e.g., SEQ ID NO:64, 65 or 66).

The present invention includes polynucleotides encoding the $V_L$ domain of antibody 3G7 (e.g., SEQ ID NO:75) and/or the $V_H$ domain of antibody 3G7 (e.g., SEQ ID NO:67).

The present invention includes polynucleotides encoding the $V_L$ domain of antibody 2C1 (e.g., SEQ ID NO:76) and/or the $V_H$ domain of antibody 2C1 (e.g., SEQ ID NO:68).

The present invention includes polynucleotides encoding the light chain immunoglobulin of antibody 1E1 (e.g., SEQ ID NO: 3, 4, 5, 6, 7 or 45) and/or the heavy chain immunoglobulin of antibody 1E1 (e.g., SEQ ID NO: 1, 2 or 44).

The present invention includes polynucleotides encoding the light chain immunoglobulin of antibody 2A6 (e.g., SEQ ID NO: 11) and/or the heavy chain immunoglobulin of antibody 2A6 (e.g., SEQ ID NO: 8, 9 or 10).

The present invention includes polynucleotides encoding the light chain immunoglobulin of antibody 3G7 (e.g., SEQ ID NO: 13) and/or the heavy chain immunoglobulin of antibody 3G7 (e.g., SEQ ID NO: 12).

The present invention includes polynucleotides encoding the light chain immunoglobulin of antibody 2C1 (e.g., SEQ ID NO: 15) and/or the heavy chain immunoglobulin of antibody 2C1 (e.g., SEQ ID NO: 14).

In one specific embodiment, the polynucleotide comprises nucleotide sequence set forth in SEQ ID NO:87. In another specific embodiment, the polynucleotide comprises nucleotide sequence set forth in SEQ ID NO:88. In yet another embodiment, the polynucleotide comprises nucleotide sequence set forth in SEQ ID NO:87 and nucleotide sequence set forth in SEQ ID NO:88.

This present invention also provides expression vectors comprising the isolated nucleic acids of the invention, wherein the nucleic acid is operably linked to one or more control sequences, e.g., that are recognized by a host cell when the host cell is transfected with the vector. Also provided are host cells comprising an expression vector of the present invention. In certain embodiments, the host cells are CHO cells.

Methods of Making Antibodies and Antigen-Binding Fragments Thereof

The anti-ILT4 antibodies and antigen-binding fragments disclosed herein (e.g., 1E1, 2A6, 3G7 and/or 2C1) may be produced recombinantly. In this embodiment, nucleic acids encoding one or more of the immunoglobulin chains of the antibodies and antigen-binding fragments of the invention (e.g., any one of SEQ ID NOs:1-15, 44, 45, or 79-86, or comprising a $V_H$ or $V_L$ of 1E1, 2A6, 3G7 or 2C1 as set forth in any one of SEQ ID Nos:57, 58, 63-77) may be inserted into a vector and/or into a host cell chromosome and expressed in a recombinant host cell. There are several methods by which to produce recombinant antibodies which are known in the art.

Antibodies (e.g., 1E1, 2A6, 3G7 or 2C1) can be recovered from the culture medium using standard protein purification methods. Further, expression of immunoglobulin chains of the invention from production cell lines can be enhanced using a number of known techniques. For example, the glutamine synthetase gene expression system (the GS system) is a common approach for enhancing expression under certain conditions. The present invention includes vectors comprising one or more polynucleotides encoding one or more of said immunoglobulin chains and a glutamine synthetase (GS) gene. In an embodiment of the invention, the vector is in a host cell that lacks functional glutamine synthetase. In an embodiment of the invention, the host cell is in a culture medium substantially lacking glutamine. Methods for making one or more of such immunoglobulin chains or an anti-ILT4 antibody or antigen-binding fragment thereof comprising culturing such a host cell in culture medium substantially lacking glutamine are within the scope of the present invention as well as such chains, antibodies and fragments produced by such a method.

In general, glycoproteins produced in a particular cell line or transgenic animal will have a glycosylation pattern that is characteristic for glycoproteins produced in the cell line or transgenic animal. Therefore, the particular glycosylation pattern of an immunoglobulin chain or antibody or antigen-binding fragment containing an immunoglobulin chain will depend on the particular cell line or transgenic animal used to produce the antibody. Antibodies and antigen-binding fragments with a glycosylation pattern comprising only non-fucosylated N-glycans may be advantageous, because these antibodies and antigen-binding fragments have been shown to typically exhibit more potent efficacy than their fucosylated counterparts both in vitro and in vivo (See for example, Shinkawa et al., J. Biol. Chem. 278: 3466-3473 (2003); U.S. Pat. Nos. 6,946,292 and 7,214,775). These anti-ILT4 antibodies and antigen-binding fragments (e.g., 1E1, 2A6, 3G7 or 2C1) with non-fucosylated N-glycans are part of the present invention.

The present invention further includes antibody fragments of the anti-ILT4 antibodies disclosed herein (e.g., 1E1, 2A6, 3G7 or 2C1). The antibody fragments include F(ab)$_2$ fragments, which may be produced by enzymatic cleavage of an IgG by, for example, pepsin. Fab fragments may be produced by, for example, reduction of F(ab)$_2$ with dithiothreitol or mercaptoethylamine. A Fab fragment is a $V_L$—CL chain appended to a $V_H$-CH1 chain by a disulfide bridge. A F(ab)$_2$ fragment is two Fab fragments which, in turn, are appended by two disulfide bridges. The Fab portion of an F(ab)$_2$ molecule includes a portion of the Fc region between which disulfide bridges are located. An FV fragment is a $V_L$ or $V_H$ region.

The present invention includes anti-ILT4 antibodies and antigen-binding fragments thereof (e.g., 1E1, 2A6, 3G7 or 2C1) which are of the IgA, IgD, IgE, IgG and IgM classification. In one embodiment, the anti-ILT4 antibody or antigen-binding fragment comprises a $V_H$ as set forth herein and a heavy chain constant region, e.g., a human constant region, such as γ1, γ2, γ3, or γ4 human heavy chain constant region or a variant thereof. In an embodiment of the invention, the antibody or antigen-binding fragment comprises a $V_H$ as set forth herein and a light chain constant region, e.g., a human light chain constant region, such as lambda or kappa human light chain region or variant thereof. By way of example, and not limitation the human heavy chain constant region can be γ1 or γ4 and the human light chain constant region can be kappa. By way of example, and not limitation the human heavy chain constant region can be γ1 or γ4 and the human light chain constant region can be lambda. In an embodiment of the invention, the Fc region of the antibody is γ4 with a Ser228Pro mutation (Schuurman, J et al., Mol. Immunol. 38: 1-8, 2001).

In some embodiments of the invention, different constant domains may be appended to $V_L$ and $V_H$ regions derived from the CDRs provided herein. For example, if a particular intended use of an antibody or antigen-binding fragment of the present invention were to call for altered effector functions, a heavy chain constant domain other than human IgG1 may be used, or hybrid IgG1/IgG4 may be utilized. Such anti-ILT4 antibodies and antigen-binding fragments thereof (e.g., 1E1, 2A6, 3G7 or 2C1) and hybrids thereof comprising IgG1 and IgG4 constant domains are part of the present invention.

In one embodiment, the IgG4 constant domain differs from the native human IgG4 constant domain (Swiss-Prot Accession No. P01861.1) at a position corresponding to position 228 in the EU system and position 241 in the KABAT system, where the native Sen 08 is replaced with Pro, in order to prevent a potential inter-chain disulfide bond between Cys106 and Cys109 (corresponding to positions Cys 226 and Cys 229 in the EU system and positions Cys 239 and Cys 242 in the KABAT system) that could interfere with proper intra-chain disulfide bond formation. See Angal et al. (1993) Mol. Imunol. 30:105. In other instances, a modified IgG1 constant domain which has been modified to increase half-life or reduce effector function can be used. Such anti-ILT4 antibodies and antigen-binding fragments thereof (e.g., 1E1, 2A6, 3G7 or 2C1), comprising a modified IgG4 constant domain are part of the present invention.

The present invention includes recombinant methods for making an anti-ILT4 antibody or antigen-binding fragment thereof of the present invention (e.g., 1E1, 2A6, 3G7 or 2C1, or an immunoglobulin chain thereof, comprising (i) introducing a polynucleotide encoding one or more immunoglobulin chains of the antibody or fragment (e.g., comprising an amino acid sequence that includes any one or more of the sequences set forth in SEQ ID NOs: 1-15, 44 and/or 45), for example, wherein the polynucleotide is in a vector and/or is operably linked to a promoter (e.g., a viral promoter, a CMV promoter or SV40 promoter); (ii) culturing the host cell (e.g., a mammalian host cell, a fungal host cell, a bacterial host cell, a Chinese hamster ovary (CHO) cell, an NSO cell, an SP2 cell, a HeLa cell, a baby hamster kidney (BHK) cell, a monkey kidney cell (COS), a human hepatocellular carcinoma cell (e.g., Hep G2), a A549 cell, a 3T3 cell, a HEK-293 cell, a *Pichia* cell or a *Pichia pastoris* cell) under condition favorable to expression of the polynucleotide(s) and, (iii) optionally, isolating the antibody or fragment or chain from the host cell and/or medium in which the host cell is grown. When making an antibody or antigen-binding fragment comprising more than one immunoglobulin chain, e.g., an antibody that comprises two heavy immunoglobulin chains and two light immunoglobulin chains, co-expression of the chains in a single host cell leads to association of the chains, e.g., in the cell or on the cell surface or outside the cell if such chains are secreted, so as to form the antibody or antigen-binding fragment molecule. The methods of the present invention include those wherein only a heavy immunoglobulin chain or only a light immunoglobulin chain (e.g., any of those discussed herein including mature fragments and/or variable domains thereof) is expressed. Such chains are useful, for example, as intermediates in the expression of an antibody or antigen-binding fragment that includes such a chain.

Antibody Engineering of the Fc Region

The anti-ILT4 antibodies and antigen-binding fragments of the present invention (e.g., 1E1, 2A6, 3G7 and/or 2C1) can also be engineered to include modifications within the Fc region, typically to alter one or more functional properties of the antibody, such as serum half-life, complement fixation, Fc receptor binding, and/or effector function (e.g., antigen-dependent cellular cytotoxicity). Furthermore, the antibodies and fragments disclosed herein can be chemically modified (e.g., one or more chemical moieties can be attached to the antibody) or be modified to alter its glycosylation, again to alter one or more functional properties of the antibody. Each of these embodiments is described in further detail below. The numbering of residues in the Fc region is that of the EU index of Kabat.

The antibodies and antigen-binding fragments disclosed herein (e.g., 1E1, 2A6, 3G7 and/or 2C1) also include antibodies with modified (or blocked) Fc regions to provide altered effector functions. See, e.g., U.S. Pat. No. 5,624,821; WO2003/086310; WO2005/120571; WO2006/0057702. Such modification can be used to enhance or suppress various reactions of the immune system, with possible beneficial effects in diagnosis and therapy. Alterations of the Fc region include amino acid changes (substitutions, deletions and/or insertions), glycosylation or deglycosylation, and adding multiple Fc domains. Changes to the Fc can also alter the half-life of antibodies in therapeutic antibodies, enabling less frequent dosing and thus increased convenience and decreased use of material. See Presta (2005) J. Allergy Clin. Immunol. 116:731 at 734-35.

In one embodiment of the invention, the anti-ILT4 antibody or antigen-binding fragment (e.g., 1E1, 2A6, 3G7 and/or 2C1) is an IgG4 isotype antibody or fragment comprising a serine to proline mutation at a position corresponding to position 228 (S228P; EU index) in the hinge region of the heavy chain constant region. This mutation has been reported to abolish the heterogeneity of inter-heavy chain disulfide bridges in the hinge region (Angal et al. supra; position 241 is based on the Kabat numbering system). In one embodiment of the invention, the hinge region of CH1 of an anti-ILT4 antibody or antigen-binding fragment thereof of the present invention (e.g., 1E1, 2A6, 3G7 and/or 2C1) is modified such that the number of cysteine residues in the hinge region is increased or decreased (e.g., by ±1, 2 or 3). This approach is described further in U.S. Pat. No. 5,677,425. The number of cysteine residues in the hinge region of CH1 is altered, for example, to facilitate assembly of the light and heavy chains or to increase or decrease the stability of the antibody.

In another embodiment, the Fc hinge region of an anti-ILT4 antibody or antigen-binding fragment (e.g., 1E1, 2A6, 3G7 and/or 2C1) is mutated to decrease the biological half-life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745.

In another embodiment, the anti-ILT4 antibody or antigen-binding fragment (e.g., 1E1, 2A6, 3G7 and/or 2C1) is modified to increase its biological half-life. Various approaches are possible. For example, one or more of the following mutations can be introduced: T252L, T254S, T256F, as described in U.S. Pat. No. 6,277,375. Alternatively, to increase the biological half-life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022.

In yet other embodiments, the Fc region is altered by replacing at least one amino acid residue with a different amino acid residue to alter the effector function(s) of the anti-ILT4 antibody or antigen-binding fragment (e.g., 1E1, 2A6, 3G7 and/or 2C1). For example, one or more amino acids selected from amino acid residues 234, 235, 236, 237, 297, 318, 320 and 322 can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260.

In another example, one or more amino acids selected from amino acid residues 329, 331 and 322 can be replaced with a different amino acid residue such that the anti-ILT4 antibody or antigen-binding fragment (e.g., 1E1, 2A6, 3G7 and/or 2C1) has altered C1q binding and/or reduced or abolished complement dependent cytotoxicity (CDC). This approach is described in further detail in U.S. Pat. No. 6,194,551.

In another example, one or more amino acid residues within amino acid positions 231 and 239 are altered to thereby alter the ability of the antibody to fix complement. This approach is described further in PCT Publication WO 94/29351.

In yet another example, the Fc region is modified to increase or decrease the ability of the anti-ILT4 antibody or antigen-binding fragment (e.g., 1E1, 2A6, 3G7 and/or 2C1) to mediate antibody dependent cellular cytotoxicity (ADCC) and/or to increase or decrease the affinity of the antibody or fragment for an Fcγ receptor by modifying one or more amino acids at the following positions: 238, 239, 243, 248, 249, 252, 254, 255, 256, 258, 264, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 329, 330, 331, 333, 334, 335, 337, 338, 340, 360, 373, 376, 378, 382, 388, 389, 398, 414, 416, 419, 430, 434, 435, 437, 438 or 439. This approach is described further in PCT Publication WO 00/42072. Moreover, the binding sites on human IgG1 for FcγR1, FcγRI I, FcγRIII and FcRn have been mapped and variants with improved binding have been described (see Shields et al. (2001) J. Biol. Chem. 276:6591-6604). Specific mutations at positions 256, 290, 298, 333, 334 and 339 were shown to improve binding to FcγRIII. Additionally, the following combination mutants were shown to improve FcγRIII binding: T256A/S298A, S298A/E333A, S298A/K224A and S298A/E333A/K334A.

In one embodiment, the Fc region is modified to decrease the ability of the anti-ILT4 antibody or antigen-binding fragment (e.g., 1E1, 2A6, 3G7 and/or 2C1) to mediate effector function and/or to increase anti-inflammatory properties by modifying residues 243 and 264. In one embodiment, the Fc region of the antibody is modified by changing the residues at positions 243 and 264 to alanine. In one embodiment, the Fc region is modified to decrease the ability of the antibody to mediate effector function and/or to increase anti-inflammatory properties by modifying residues 243, 264, 267 and 328.

Post-Translational Modifications

In still another embodiment, the antibody comprises a particular glycosylation pattern. For example, an aglycosylated anti-ILT4 antibody or antigen-binding fragment thereof (e.g., 1E1, 2A6, 3G7 and/or 2C1), which lacks glycosylation, is part of the present invention. The glycosylation pattern of an antibody or fragment may be altered to, for example, increase the affinity or avidity of the antibody for an antigen. Such modifications can be accomplished by, for example, altering one or more of the glycosylation sites within the antibody or fragment sequence. For example, one or more amino acid substitutions can be made that result removal of one or more of the variable region framework glycosylation sites to thereby eliminate glycosylation at that site. Such aglycosylation may increase the affinity or avidity of the antibody or fragment for antigen. See, e.g., U.S. Pat. Nos. 5,714,350 and 6,350,861.

An anti-ILT4 antibody or antigen-binding fragment (e.g., 1E1, 2A6, 3G7 and/or 2C1) of the invention may also be made in which the glycosylation pattern includes hypofucosylated or afucosylated glycans, such as hypofucosylated antibodies and antigen-binding fragments or afucosylated antibodies and fragments that have reduced amounts of fucosyl residues on the glycan. The antibody or antigen-binding fragment may also include glycans having an increased amount of bisecting GlcNac structures. Such altered glycosylation patterns have been demonstrated to increase the ADCC ability of antibodies. Such modifications can be accomplished by, for example, expressing the antibody or fragment in a host cell in which the glycosylation pathway was been genetically engineered to produce glycoproteins with particular glycosylation patterns. These cells have been described in the art and can be used as host cells in which to express recombinant antibodies of the invention to thereby produce an antibody with altered glycosylation. For example, the cell lines Ms704, Ms705, and Ms709 lack the fucosyltransferase gene, FUT8 (a (1,6)-fucosyltransferase), such that antibodies expressed in the Ms704, Ms705, and Ms709 cell lines lack fucose on their carbohydrates. The present invention includes anti-ILT4 antibodies and antigen-binding fragments lacking fucose or produced by a host cell that lacks FUT8. The Ms704, Ms705, and Ms709 FUT8$^{-/-}$ cell lines were created by the targeted disruption of the FUT8 gene in CHO/DG44 cells using two replacement vectors (see U.S. Patent Publication No. 20040110704 and Yamane-Ohnuki et al. (2004) Biotechnol Bioeng 87:614-22). As another example, EP 1176195 describes a cell line with a functionally disrupted FUT8 gene, which encodes a fucosyl transferase, such that antibodies expressed in such a cell line exhibit hypofucosylation by reducing or eliminating the α-1,6 bond-related enzyme. EP 1,176,195 also describes cell lines which have a low enzyme activity for adding fucose to the N-acetylglucosamine that binds to the Fc region of the antibody or does not have the enzyme activity, for example the rat myeloma cell line YB2/0 (ATCC CRL 1662). PCT Publication WO 03/035835 describes a variant CHO cell line, Lec13 cells, with reduced ability to attach fucose to Asn(297)-linked carbohydrates, also resulting in hypofucosylation of antibodies expressed in that host cell (see also Shields et al. (2002) J. Biol. Chem. 277:26733-26740). Antibodies with a modified glycosylation profile can also be produced in chicken eggs, as described in PCT Publication WO 06/089231. Alternatively, antibodies with a modified glycosylation profile can be produced in plant cells, such as Lemna (U.S. Pat. No. 7,632,983). Methods for production of antibodies in a plant system are disclosed in the U.S. Pat. Nos. 6,998,267 and 7,388,081. PCT Publication WO 99/54342 describes cell lines engineered to express glycoprotein-modifying glycosyl transferases (e.g., β(1,4)-N-acetylglucosaminyltransferase III (GnTIII)) such that antibodies expressed in the engineered cell lines exhibit increased bisecting GlcNac structures which results in increased ADCC activity of the antibodies (see also Umana et al. (1999) Nat. Biotech. 17:176-180). Anti-ILT4 antibodies an antigen-binding fragments thereof of the present invention which are produced by such host cells are part of the present invention.

Alternatively, the fucose residues of the anti-ILT4 antibody or antigen-binding fragment (e.g., 1E1, 2A6, 3G7 and/or 2C1) can be cleaved off using a fucosidase enzyme; e.g., the fucosidase α-L-fucosidase removes fucosyl residues from antibodies (Tarentino et al. (1975) Biochem. 14:5516-23). The present invention includes antibodies and fragments which have been treated with a fucosidase enzyme.

Anti-ILT4 antibody or antigen-binding fragments (e.g., 1E1, 2A6, 3G7 and/or 2C1) disclosed herein further include those produced in lower eukaryote host cells, in particular fungal host cells such as yeast and filamentous fungi have been genetically engineered to produce glycoproteins that have mammalian- or human-like glycosylation patterns (See for example, Choi et al, (2003) Proc. Natl. Acad. Sci. 100: 5022-5027; Hamilton et al., (2003) Science 301: 1244-1246; Hamilton et al., (2006) Science 313: 1441-1443). A particular advantage of these genetically modified host cells over currently used mammalian cell lines is the ability to control the glycosylation profile of glycoproteins that are produced in the cells such that compositions of glycoproteins can be produced wherein a particular N-glycan structure predominates (see, e.g., U.S. Pat. Nos. 7,029,872 and 7,449,308). These genetically modified host cells have been used to produce antibodies that have predominantly particular N-glycan structures (See for example, Li et al., (2006) Nat. Biotechnol. 24: 210-215).

Antibody Conjugates

The anti-ILT4 antibodies and antigen-binding fragments disclosed herein (e.g., 1E1, 2A6, 3G7 and/or 2C1) may also be conjugated to a peptide or chemical moiety. The chemical moiety may be, inter alia, a polymer, a radionuclide or a therapeutic or cytotoxic agent. In particular embodiments of the invention, the chemical moiety is a polymer which increases the half-life of the antibody molecule in the body of a subject. Polymers include, but are not limited to, hydrophilic polymers which include but are not limited to polyethylene glycol (PEG) (e.g., PEG with a molecular weight of 2 kDa, 5 kDa, 10 kDa, 12 kDa, 20 kDa, 30 kDa or 40 kDa), dextran and monomethoxypolyethylene glycol (mPEG). Lee, et al., (1999) (Bioconj. Chem. 10:973-981) discloses PEG conjugated single-chain antibodies. Wen, et al., (2001) (Bioconj. Chem. 12:545-553) disclose conjugating antibodies with PEG which is attached to a radiometal chelator (diethylenetriaminpentaacetic acid (DTPA)).

The antibodies and antigen-binding fragments disclosed herein (e.g., 1E1, 2A6, 3G7 and/or 201) may also be conjugated with labels, such as radiolabels. Labels include but are not limited to $^{99}$Tc, $^{90}$Y, $^{111}$In, $^{32}$P, $^{14}$C, $^{125}$I, $^{3}$H, $^{131}$I, $^{11}$C, $^{15}$O, $^{13}$N, $^{18}$F, $^{35}$S, $^{51}$Cr, $^{57}$To, $^{226}$Ra, $^{60}$Co, $^{59}$Fe, $^{57}$Se, $^{152}$Eu, $^{67}$Cu, $^{217}$Ci, $^{211}$At, $^{212}$Pb, $^{47}$Sc, $^{109}$Pd, $^{234}$Th, and $^{40}$K, $^{157}$Gd, $^{55}$Mn, $^{52}$Tr, and $^{56}$Fe.

The anti-ILT4 antibodies and antibody fragments disclosed herein (e.g., 1E1, 2A6, 3G7 and/or 2C1) may also be PEGylated (e.g., with 1 PEG or a 3 kDa, 12 kDa or 40 kDa PEG polymer molecule), for example to increase its biological (e.g., serum) half-life. To PEGylate an antibody or antigen-binding fragment thereof, the antibody or fragment typically is reacted with a reactive form of polyethylene glycol (PEG), such as a reactive ester or aldehyde derivative of PEG, under conditions in which one or more PEG groups become attached to the antibody or antigen-binding fragment. In particular embodiments, the PEGylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody to be PEGylated is an aglycosylated antibody. Methods for PEGylating proteins are known in the art and can be applied to the antibodies of the invention. See, e.g., EP 0 154 316 and EP 0 401 384.

The anti-ILT4 antibodies and antigen-binding fragments disclosed herein (e.g., 1E1, 2A6, 3G7 and/or 2C1) may also be conjugated with labels such as fluorescent or chemiluminescent labels, including fluorophores such as rare earth chelates, fluorescein and its derivatives, rhodamine and its derivatives, isothiocyanate, phycoerythrin, phycocyanin, allophycocyanin, o-phthaladehyde, fluorescamine, $^{152}$Eu, dansyl, umbelliferone, luciferin, luminal label, isoluminal label, an aromatic acridinium ester label, an imidazole label, an acridimium salt label, an oxalate ester label, an aequorin label, 2,3-dihydrophthalazinediones, biotin/avidin, spin labels and stable free radicals.

The anti-ILT4 antibodies and antigen-binding fragments disclosed herein (e.g., 1E1, 2A6, 3G7 and/or 2C1) may also be conjugated to a cytotoxic factor such as diptheria toxin, *Pseudomonas aeruginosa* exotoxin A chain, ricin A chain, abrin A chain, modeccin A chain, alpha-sarcin, *Aleurites fordii* proteins and compounds (e.g., fatty acids), dianthin proteins, *Phytoiacca americana* proteins PAPI, PAPII, and PAP-S, *Momordica charantia* inhibitor, curcin, crotin, *Saponaria officinalis* inhibitor, mitogellin, restrictocin, phenomycin, and enomycin.

Any method known in the art for conjugating the antibodies and antigen-binding to the various moieties may be employed, including those methods described by Hunter, et al., (1962) Nature 144:945; David, et al., (1974) Biochemistry 13:1014; Pain, et al., (1981) J. Immunol. Meth. 40:219; and Nygren, J., (1982) Histochem. and Cytochem. 30:407. Methods for conjugating antibodies are conventional and very well known in the art.

Pharmaceutical Compositions and Administration

The pharmaceutical compositions comprising the anti-ILT4 antibodies (e.g., fully human antibodies such as antagonist fully human antibodies (e.g., 1E1, 2A6, 3G7 and/or 2C1) and antigen-binding fragments thereof can be prepared for storage by mixing the antibodies or antigen-binding fragments thereof having the desired degree of purity with optionally physiologically acceptable carriers, excipients, or stabilizers (see, e.g., Remington, *Remington's Pharmaceutical Sciences* (18th ed. 1980)) in the form of aqueous solutions or lyophilized or other dried forms.

In one embodiment, the pharmaceutical composition comprises an antibody that consists of two heavy chains and two light chains, wherein each light chain consists of the amino acid sequence set forth in SEQ ID NO:7 and each heavy chain consists of the amino acid sequence set forth in SEQ ID NO:2.

In another embodiment, the pharmaceutical composition comprises: (i) an antibody that consists of two heavy chains and two light chains, wherein each light chain consists of the amino acid sequence set forth in SEQ ID NO:7 and each heavy chain consists of the amino acid sequence set forth in SEQ ID NO:2, and (ii) pembrolizumab.

Formulations of therapeutic and diagnostic agents may be prepared by mixing with acceptable carriers, excipients, or stabilizers in the form of, e.g., lyophilized powders, slurries, aqueous solutions or suspensions (see, e.g., Hardman, et al. (2001) Goodman and Gilman's The Pharmacological Basis of Therapeutics, McGraw-Hill, New York, NY; Gennaro (2000) Remington: The Science and Practice of Pharmacy, Lippincott, Williams, and Wilkins, New York, NY; Avis, et al. (eds.) (1993) Pharmaceutical Dosage Forms: Parenteral Medications, Marcel Dekker, NY; Lieberman, et al. (eds.) (1990) Pharmaceutical Dosage Forms: Tablets, Marcel Dekker, NY; Lieberman, et al. (eds.) (1990) Pharmaceutical Dosage Forms: Disperse Systems, Marcel Dekker, NY; Weiner and Kotkoskie (2000) Excipient Toxicity and Safety, Marcel Dekker, Inc., New York, NY).

Toxicity and therapeutic efficacy of the anti-ILT4 antibody or antigen-binding fragment (e.g., 1E1, 2A6, 3G7 and/or 2C1) compositions, administered alone or in combination with another therapeutic agent, can be determined by standard pharmaceutical procedures in cell cultures or experimental animals, e.g., for determining the $LD_{50}$ (the dose lethal to 50% of the population) and the $ED_{50}$ (the dose effective in 50% of the population). The dose ratio between toxic and therapeutic effects is the therapeutic index ($LD_{50}/ED_{50}$). In particular aspects, antibodies exhibiting high therapeutic indices are desirable. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration.

In a further embodiment, a further therapeutic agent that is administered to a subject in association with an anti-ILT4 antibody (e.g., fully human antibody such as antagonist fully human antibodies) or antigen-binding fragment thereof disclosed herein (e.g., 1E1, 2A6, 3G7 and/or 2C1) is administered to the subject in accordance with the Physicians' Desk Reference 2003 (Thomson Healthcare; 57th edition (Nov. 1, 2002)).

The mode of administration can vary. Routes of administration include oral, rectal, transmucosal, intestinal, parenteral; intramuscular, subcutaneous, intradermal, intramedullary, intrathecal, direct intraventricular, intravenous, intraperitoneal, intranasal, intraocular, inhalation, insufflation, topical, cutaneous, transdermal, or intra-arterial.

The present invention provided methods for administering an anti-ILT4 antibody or antigen-binding fragment thereof (e.g., 1E1, 2A6, 3G7 and/or 2C1) comprising introducing the antibody or fragment into the body of a subject. For example, the method comprises piercing the body of the subject with a needle of a syringe and injecting the antibody or fragment into the body of the subject, e.g., into the vein, artery, tumor, muscular tissue or subcutis of the subject.

The present invention provides a vessel (e.g., a plastic or glass vial, e.g., with a cap or a chromatography column, hollow bore needle or a syringe cylinder) comprising any of the anti-ILT4 antibodies or antigen-binding fragments (e.g., 1E1, 2A6, 3G7 and/or 2C1) set forth herein or a pharmaceutical composition thereof comprising a pharmaceutically acceptable carrier.

The present invention also provides an injection device comprising any of the anti-ILT4 antibodies or antigen-binding fragments (e.g., 1E1, 2A6, 3G7 and/or 2C1) set forth herein or a pharmaceutical composition thereof. An injection device is a device that introduces a substance into the body of a subject via a parenteral route, e.g., intramuscular, subcutaneous or intravenous. For example, an injection device may be a syringe (e.g., pre-filled with the pharmaceutical composition, such as an auto-injector) which, for example, includes a cylinder or barrel for holding fluid to be injected (e.g., comprising the antibody or fragment or a pharmaceutical composition thereof), a needle for piecing skin and/or blood vessels for injection of the fluid; and a plunger for pushing the fluid out of the cylinder and through the needle bore. In an embodiment of the invention, an injection device that comprises an antibody or antigen-binding fragment thereof of the present invention or a pharmaceutical composition thereof is an intravenous (IV) injection device. Such a device includes the antibody or fragment or a pharmaceutical composition thereof in a cannula or trocar/needle which may be attached to a tube which may be attached to a bag or reservoir for holding fluid (e.g., saline; or lactated ringer solution comprising NaCl, sodium lactate, KCl, CaCl$_2$) and optionally including glucose) introduced into the body of the subject through the cannula or trocar/needle.

The pharmaceutical compositions disclosed herein may also be administered with a needleless hypodermic injection device; such as the devices disclosed in U.S. Pat. Nos. 6,620,135; 6,096,002; 5,399,163; 5,383,851; 5,312,335; 5,064,413; 4,941,880; 4,790,824 or 4,596,556. Such needleless devices comprising the pharmaceutical composition are also part of the present invention. The pharmaceutical compositions disclosed herein may also be administered by infusion. Examples of well-known implants and modules for administering the pharmaceutical compositions include those disclosed in: U.S. Pat. No. 4,487,603, which discloses an implantable micro-infusion pump for dispensing medication at a controlled rate; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments. Many other such implants, delivery systems, and modules are well known to those skilled in the art and those comprising the pharmaceutical compositions of the present invention are within the scope of the present invention.

Antibodies (e.g., fully human antibodies such as antagonist fully human antibodies) or antigen-binding fragments thereof disclosed herein (e.g., 1E1, 2A6, 3G7 and/or 2C1) may be provided by continuous infusion, or by doses administered, e.g., daily, 1-7 times per week, weekly, bi-weekly, monthly, bimonthly, quarterly, semiannually, annually etc. Doses may be provided, e.g., intravenously, subcutaneously, topically, orally, nasally, rectally, intramuscular, intracerebrally, intraspinally, or by inhalation. An effective dose of an anti-ILT4 antibody or antigen-binding fragment thereof of the present invention, is from about 0.05 mg/kg (body weight) to about 30 mg/kg (body weight), e.g., for treatment or prevention of cancer or infectious diseases.

Determination of the appropriate dose is made by the clinician, e.g., using parameters or factors known or suspected in the art to affect treatment. Generally, in determining the dose, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced. In general, it is desirable that a biologic that will be used is derived from the same species as the animal targeted for treatment, thereby minimizing any immune response to the reagent. In the case of human subjects, for example, chimeric and fully human antibodies are may be desirable. Guidance in selecting appropriate doses of anti-ILT4 antibodies or fragments is available (see, e.g., Wawrzynczak (1996) Antibody Therapy, Bios Scientific Pub. Ltd, Oxfordshire, UK; Kresina (ed.) (1991) Monoclonal Antibodies, Cytokines and Arthritis, Marcel Dekker, New York, NY; Bach (ed.) (1993) Monoclonal Antibodies and Peptide Therapy in Autoimmune Diseases, Marcel Dekker, New York, NY; Baert et al. (2003) New Engl. J. Med. 348:601-608; Milgrom et al. (1999) New Engl. J. Med. 341:1966-1973; Slamon et al. (2001) New Engl. J. Med. 344:783-792; Beniaminovitz et al. (2000) New Engl. J. Med. 342:613-619; Ghosh et al. (2003) New Engl. J. Med. 348:24-32; Lipsky et al. (2000) New Engl. J. Med. 343:1594-1602).

Whether a disease symptom has been alleviated can be assessed by any clinical measurement typically used by physicians or other skilled healthcare providers to assess the severity or progression status of that symptom. While an embodiment of the present invention (e.g., a treatment method or article of manufacture) may not be effective in alleviating the target disease symptom(s) in every subject, it should alleviate the target disease symptom(s) in a statistically significant number of subjects as determined by any statistical test known in the art such as the Student's t-test, the chi$^2$-test, the U-test according to Mann and Whitney, the Kruskal-Wallis test (H-test), Jonckheere-Terpstra-test and the Wilcoxon-test.

Therapeutic Uses of Anti-ILT4 Antibodies

The present invention also provides methods for treating or preventing cancer in subjects, such as human subjects, in need of such treatment by administering an effective amount of the anti-ILT4 antibodies or antigen-binding fragments thereof of the present invention which are disclosed herein (e.g., 1E1, 2A6, 3G7 and/or 2C1) which may be effective for such treatment or prevention.

In certain embodiments, the cancer is solid tumor. In other embodiments, the cancer is hematologic cancer. In certain embodiments, the cancer is metastatic. In some embodiments, the cancer is relapsed. In other embodiments, the cancer is refractory. In yet other embodiments, the cancer is relapsed and refractory.

In some embodiments, the cancer is anaplastic astrocytoma, astrocytoma, bladder cancer, bone cancer, brain cancer, breast cancer (e.g., characterized by a mutation in BRCA1 and/or BRCA2), carcinoid cancer, cervical cancer, chondrosarcoma, choroid plexus papilloma, colorectal cancer, endometrial cancer, ependymoma, esophagus cancer, Ewing's sarcoma, gall bladder cancer, gastric cancer, glioblastoma, head and neck cancer, hepatoblastoma, hepatocellular carcinoma, idiopathic myelfibrosis, kidney cancer, leukemia, liver cancer, lung cancer (e.g., non-small cell lung cancer), lymphoma, medulloblastoma, melanoma, meningioma, Merkel cell cancer, mesothelioma, multiple myeloma, neuroblastoma, oligodendroglioma, osteosarcoma, ovarian cancer, pancreatic cancer, polycythemia vera, primitive neuroectodermal tumor, prostate cancer, renal cell cancer, renal transitional cell cancer, retinoblastoma, rhabdoid tumor of the kidney, rhabdomyosarcoma, salivary gland cancer, sarcoma, small intestine cancer, soft tissue sarcoma, squamous cell carcinoma (e.g., cutaneous squamous cell carcinoma), synovial sarcoma, thrombocythemia, thyroid cancer, uterine cancer, vestibular schwannoma, or Wilm's tumor. In an embodiment of the invention, the cancer is metastatic cancer, e.g., of the varieties described above.

In an embodiment of the invention, the cancer is a myeloid-rich tumor (e.g., mesothelioma, kidney cancer, lymphoma, sarcoma, melanoma, head & neck cancer, breast cancer, bladder cancer, gastric cancer, ovarian cancer or thyroid cancer; see e.g., Burt et al. Cancer. 117 (22):5234-44 (2011); Dannenmann et al. Oncoimmunology 2(3):e23562 (2013); Steidl et al. N. Engl. J. Med. 362:875-885 (2010); Fujiwara et al., Am. J. Pathol. 179(3):1157-70 (2011); Bronkhorst et al. Invest. Ophthalmol. Vis. Sci. 52(2):643-50 (2011); Balermpas et al. Br. J. Cancer 111(8):1509-18 (2014); and Zhang et al. PLoS One 7(12):e50946 (2012)). Since ILT4 is expressed primarily by myeloid cells and granulocytes, and myeloid cell infiltration into tumors is generally associated with poor prognosis due to the immunosuppressive effects of these cells that can antagonize anti-tumor responses by T-cells, treatment with an anti-ILT4 antibody or antigen-binding fragment of the present invention will benefit subjects with a high myeloid or immunosuppressive myeloid cell infiltration.

Thus, provided herein are methods of treating a cancer in a human subject in need thereof, comprising administering to the human subject an effective amount of the antibody or antigen-binding fragment thereof comprising (a) the CDR-L1, CDR-L2, and CDR-L3 of a light chain variable ($V_L$) domain of an immunoglobulin chain that comprises the amino acid sequence set forth in SEQ ID NO: 3-7, 11, 13, 15, or 45; and/or (b) the CDR-H1, CDR-H2, and CDR-H3 of a heavy chain variable ($V_H$) domain of an immunoglobulin chain that comprises the amino acid sequence set forth in SEQ ID NO: 1, 2, 8-10, 12, 14, 44, or 79-86.

In an embodiment of the invention, the method of treating a cancer in a human subject in need thereof, comprising administering to the human subject an effective amount of the antibody or antigen-binding fragment thereof comprising: (1) a $V_H$ domain comprising: complementarity determining region-H1 (CDR-H1): GYYWS (SEQ ID NO: 16), complementarity determining region-H2 (CDR-H2): EINHXGSTNYNPSLKS wherein X is S or A (SEQ ID NO: 17); and complementarity determining region-H3 (CDR-H3): LPTRWVTTRYFDL (SEQ ID NO: 18); and/or, a $V_L$ domain comprising: complementarity determining region-L1 (CDR-L1): TGSSSNIGAGYDVH (SEQ ID NO: 19), complementarity determining region-L2 (CDR-L2): GX$_1$X$_2$NRPS, wherein X$_1$ is S or A and X$_2$ is N, Q, E or D (SEQ ID NO: 20); and complementarity determining region-L3 (CDR-L3): QSFDNSLSAYV (SEQ ID NO: 21); (2) a $V_H$ domain comprising: CDR-H1: SYAIS (SEQ ID NO: 22); CDR-H2: GIIPIFGTANYAQKFQG (SEQ ID NO: 23); and CDR-H3: YFX$_1$X$_2$SGWYKGGAFDI, wherein X$_1$ is D or S and X$_2$ is S or A (SEQ ID NO: 24); and/or, a $V_L$ domain comprising: CDR-L1: TLRSGINVDTYRIH (SEQ ID NO: 25); CDR-L2: YKSDSDKHQGS (SEQ ID NO: 26); and CDR-L3: AIWYSSTWV (SEQ ID NO: 27); (3) a $V_H$ domain comprising: CDR-H1: SYAMH (SEQ ID NO: 28); CDR-H2: VISYDGSNKYYADSVKG (SEQ ID NO: 29); and CDR-H3: VGEWIQLWSPFDY (SEQ ID NO: 30); and/or, a $V_L$ domain comprising: CDR-L1: RASQGISSWLA (SEQ ID NO: 31); CDR-L2: AASSLQS (SEQ ID NO: 32); and CDR-L3: QQYNSYPPT (SEQ ID NO: 33); and/or (4) a $V_H$ domain comprising: CDR-H1: ELSMH (SEQ ID NO: 34); CDR-H2: GFDPEDGETIYAQKFQG (SEQ ID NO: 35); and CDR-H3: AGPLYTIFGVVIIPDNWFDP (SEQ ID NO: 36); and/or, a $V_L$ domain comprising: CDR-L1: TGSSSNIGAGYDVH (SEQ ID NO: 37); CDR-L2: GNSNRPS (SEQ ID NO: 38); and CDR-L3: QSYDSSLSGSGW (SEQ ID NO: 39).

In one embodiment, the method of treating a cancer in a human subject in need thereof, comprising administering to the human subject an effective amount of the antibody or antigen-binding fragment thereof comprising: CDR-H1: GYYWS (SEQ ID NO: 16), CDR-H2: EINHSG-STNYNPSLKS (SEQ ID NO: 47), and CDR-H3: LPTRWVTTRYFDL (SEQ ID NO: 18); and/or, a $V_L$ domain comprising: CDR-L1: TGSSSNIGAGYDVH (SEQ ID NO: 19), CDR-L2: GNSNRPS(SEQ ID NO: 49), and CDR-L3: QSFDNSLSAYV (SEQ ID NO: 21).

In another embodiment, the method of treating a cancer in a human subject in need thereof, comprising administering to the human subject an effective amount of the antibody or antigen-binding fragment thereof comprising: CDR-H1: GYYWS (SEQ ID NO: 16), CDR-H2: EINHSG-STNYNPSLKS (SEQ ID NO: 47), and CDR-H3: LPTRWVTTRYFDL (SEQ ID NO: 18); and/or, a $V_L$ domain comprising: CDR-L1: TGSSSNIGAGYDVH (SEQ ID NO: 19), CDR-L2: GQSNRPS(SEQ ID NO: 50), and CDR-L3: QSFDNSLSAYV (SEQ ID NO: 21).

In yet another embodiment, the method of treating a cancer in a human subject in need thereof, comprising administering to the human subject an effective amount of the antibody or antigen-binding fragment thereof comprising: GYYWS (SEQ ID NO: 16), CDR-H2: EINHSG-STNYNPSLKS (SEQ ID NO: 47), and CDR-H3: LPTRWVTTRYFDL (SEQ ID NO: 18); and/or, a $V_L$ domain comprising: CDR-L1: TGSSSNIGAGYDVH (SEQ ID NO: 19), CDR-L2: GESNRPS(SEQ ID NO: 51), and CDR-L3: QSFDNSLSAYV (SEQ ID NO: 21).

In still another embodiment, the method of treating a cancer in a human subject in need thereof, comprising administering to the human subject an effective amount of the antibody or antigen-binding fragment thereof comprising: CDR-H1: GYYWS (SEQ ID NO: 16), CDR-H2: EINHSGSTNYNPSLKS (SEQ ID NO: 47), and CDR-H3: LPTRWVTTRYFDL (SEQ ID NO: 18); and/or, a $V_L$ domain comprising: CDR-L1: TGSSSNIGAGYDVH (SEQ ID NO: 19), CDR-L2: GDSNRPS(SEQ ID NO: 52), and CDR-L3: QSFDNSLSAYV (SEQ ID NO: 21).

In one embodiment, the method of treating a cancer in a human subject in need thereof, comprising administering to the human subject an effective amount of the antibody or antigen-binding fragment thereof comprising: CDR-H1: GYYWS (SEQ ID NO: 16), CDR-H2: EINHSG-STNYNPSLKS (SEQ ID NO: 47), and CDR-H3: LPTRWVTTRYFDL (SEQ ID NO: 18); and/or, a $V_L$ domain comprising: CDR-L1: TGSSSNIGAGYDVH (SEQ ID NO: 19), CDR-L2: GNANRPS(SEQ ID NO: 53), and CDR-L3: QSFDNSLSAYV (SEQ ID NO: 21).

In another embodiment, the method of treating a cancer in a human subject in need thereof, comprising administering to the human subject an effective amount of the antibody or antigen-binding fragment thereof comprising: CDR-H1: GYYWS (SEQ ID NO: 16), CDR-H2: EINHSG-STNYNPSLKS (SEQ ID NO: 47), and CDR-H3: LPTRWVTTRYFDL (SEQ ID NO: 18); and/or, a $V_L$ domain comprising: CDR-L1: TGSSSNIGAGYDVH (SEQ ID NO: 19), CDR-L2: GQANRPS(SEQ ID NO: 54), and CDR-L3: QSFDNSLSAYV (SEQ ID NO: 21).

In yet another embodiment, the method of treating a cancer in a human subject in need thereof, comprising administering to the human subject an effective amount of the antibody or antigen-binding fragment thereof comprising: CDR-H1: GYYWS (SEQ ID NO: 16), CDR-H2: EINHSGSTNYNPSLKS (SEQ ID NO: 47), and CDR-H3: LPTRWVTTRYFDL (SEQ ID NO: 18); and/or, a $V_L$ domain comprising: CDR-L1: TGSSSNIGAGYDVH (SEQ ID NO: 19), CDR-L2: GEANRPS(SEQ ID NO: 55), and CDR-L3: QSFDNSLSAYV (SEQ ID NO: 21).

In still another embodiment, the method of treating a cancer in a human subject in need thereof, comprising administering to the human subject an effective amount of the antibody or antigen-binding fragment thereof comprising: CDR-H1: GYYWS (SEQ ID NO: 16), CDR-H2: EINHSGSTNYNPSLKS (SEQ ID NO: 47), and CDR-H3: LPTRWVTTRYFDL (SEQ ID NO: 18); and/or, a $V_L$ domain comprising: CDR-L1: TGSSSNIGAGYDVH (SEQ ID NO: 19), CDR-L2: GDANRPS(SEQ ID NO: 56), and CDR-L3: QSFDNSLSAYV (SEQ ID NO: 21).

In one embodiment, the method of treating a cancer in a human subject in need thereof, comprising administering to the human subject an effective amount of the antibody or antigen-binding fragment thereof comprising: CDR-H1: GYYWS (SEQ ID NO: 16), CDR-H2: EINHAGSTNYNPSLKS (SEQ ID NO: 48), and CDR-H3: LPTRWVTTRYFDL (SEQ ID NO: 18); and/or, a $V_L$ domain comprising: CDR-L1: TGSSSNIGAGYDVH (SEQ ID NO: 19), CDR-L2: GNSNRPS(SEQ ID NO: 49), and CDR-L3: QSFDNSLSAYV (SEQ ID NO: 21).

In another embodiment, the method of treating a cancer in a human subject in need thereof, comprising administering to the human subject an effective amount of the antibody or antigen-binding fragment thereof comprising: CDR-H1: GYYWS (SEQ ID NO: 16), CDR-H2: EINHAGSTNYNPSLKS (SEQ ID NO: 48), and CDR-H3: LPTRWVTTRYFDL (SEQ ID NO: 18); and/or, a $V_L$ domain comprising: CDR-L1: TGSSSNIGAGYDVH (SEQ ID NO: 19), CDR-L2: GQSNRPS(SEQ ID NO: 50), and CDR-L3: QSFDNSLSAYV (SEQ ID NO: 21).

In yet another embodiment, the method of treating a cancer in a human subject in need thereof, comprising administering to the human subject an effective amount of the antibody or antigen-binding fragment thereof comprising: CDR-H1: GYYWS (SEQ ID NO: 16), CDR-H2: EINHAGSTNYNPSLKS (SEQ ID NO: 48), and CDR-H3: LPTRWVTTRYFDL (SEQ ID NO: 18); and/or, a $V_L$ domain comprising: CDR-L1: TGSSSNIGAGYDVH (SEQ ID NO: 19), CDR-L2: GESNRPS(SEQ ID NO: 51), and CDR-L3: QSFDNSLSAYV (SEQ ID NO: 21).

In still another embodiment, the method of treating a cancer in a human subject in need thereof, comprising administering to the human subject an effective amount of the antibody or antigen-binding fragment thereof comprising: CDR-H1: GYYWS (SEQ ID NO: 16), CDR-H2: EINHAGSTNYNPSLKS (SEQ ID NO: 48), and CDR-H3: LPTRWVTTRYFDL (SEQ ID NO: 18); and/or, a $V_L$ domain comprising: CDR-L1: TGSSSNIGAGYDVH (SEQ ID NO: 19), CDR-L2: GDSNRPS(SEQ ID NO: 52), and CDR-L3: QSFDNSLSAYV (SEQ ID NO: 21).

In one embodiment, the method of treating a cancer in a human subject in need thereof, comprising administering to the human subject an effective amount of the antibody or antigen-binding fragment thereof comprising: CDR-H1: GYYWS (SEQ ID NO: 16), CDR-H2: EINHAGSTNYNPSLKS (SEQ ID NO: 48), and CDR-H3: LPTRWVTTRYFDL (SEQ ID NO: 18); and/or, a $V_L$ domain comprising: CDR-L1: TGSSSNIGAGYDVH (SEQ ID NO: 19), CDR-L2: GNANRPS(SEQ ID NO: 53), and CDR-L3: QSFDNSLSAYV (SEQ ID NO: 21).

In another embodiment, the method of treating a cancer in a human subject in need thereof, comprising administering to the human subject an effective amount of the antibody or antigen-binding fragment thereof comprising: CDR-H1: GYYWS (SEQ ID NO: 16), CDR-H2: EINHAGSTNYNPSLKS (SEQ ID NO: 48), and CDR-H3: LPTRWVTTRYFDL (SEQ ID NO: 18); and/or, a $V_L$ domain comprising: CDR-L1: TGSSSNIGAGYDVH (SEQ ID NO: 19), CDR-L2: GQANRPS(SEQ ID NO: 54), and CDR-L3: QSFDNSLSAYV (SEQ ID NO: 21).

In yet another embodiment, the method of treating a cancer in a human subject in need thereof, comprising administering to the human subject an effective amount of the antibody or antigen-binding fragment thereof comprising: CDR-H1: GYYWS (SEQ ID NO: 16), CDR-H2: EINHAGSTNYNPSLKS (SEQ ID NO: 48), and CDR-H3: LPTRWVTTRYFDL (SEQ ID NO: 18); and/or, a $V_L$ domain comprising: CDR-L1: TGSSSNIGAGYDVH (SEQ ID NO: 19), CDR-L2: GEANRPS(SEQ ID NO: 55), and CDR-L3: QSFDNSLSAYV (SEQ ID NO: 21).

In still another embodiment, the method of treating a cancer in a human subject in need thereof, comprising administering to the human subject an effective amount of the antibody or antigen-binding fragment thereof comprising: CDR-H1: GYYWS (SEQ ID NO: 16), CDR-H2: EINHAGSTNYNPSLKS (SEQ ID NO: 48), and CDR-H3: LPTRWVTTRYFDL (SEQ ID NO: 18); and/or, a $V_L$ domain comprising: CDR-L1: TGSSSNIGAGYDVH (SEQ ID NO: 19), CDR-L2: GDANRPS(SEQ ID NO: 56), and CDR-L3: QSFDNSLSAYV (SEQ ID NO: 21).

In still other embodiments, the method of treating a cancer in a human subject in need thereof, comprising administering to the human subject an effective amount of the antibody or antigen-binding fragment thereof comprising: a light chain immunoglobulin, a heavy chain immunoglobulin, or both a light and heavy chain immunoglobulin, wherein the light chain immunoglobulin comprises the amino acid sequence set forth in SEQ ID NO:3, 4, 5, 6, 7, 11, 13, 15, or 45; and/or the heavy chain immunoglobulin comprises the amino acid sequence set forth in SEQ ID NO: 1, 2, 8, 9, 10, 12, 14, 44, 79, 80, 81, 82, 83, 84, 85, or 86. In yet still other embodiments, the method of treating a cancer in a human subject in need thereof, comprising administering to the human subject an effective amount of the antibody or antigen-binding fragment thereof comprising: a light chain immunoglobulin, a heavy chain immunoglobulin, or both a light and heavy chain immunoglobulin, wherein the light chain variable domain comprises the amino acid sequence set forth in SEQ ID NO:70, 71, 72, 73, 58, 74, 75, 76, or 77, and/or the heavy chain variable domain comprise the amino acid sequence set forth in SEQ ID NO:63, 57, 64, 65, 66, 67, 68, or 69.

In more embodiments, the method of treating a cancer in a human subject in need thereof, comprising administering to the human subject an effective amount of the antibody or antigen-binding fragment thereof comprising: any of the following sets of heavy chain immunoglobulins and light chain immunoglobulins: (1) a heavy chain immunoglobulin comprising the amino acid sequence set forth in SEQ ID NO:1; a light chain immunoglobulin comprising the amino acid sequence set forth in SEQ ID NO:3; (2) a heavy chain immunoglobulin comprising the amino acid sequence set forth in SEQ ID NO:2; a light chain immunoglobulin comprising the amino acid sequence set forth in SEQ ID NO:4; (3) a heavy chain immunoglobulin comprising the amino acid sequence set forth in SEQ ID NO:2; a light chain immunoglobulin comprising the amino acid sequence set forth in SEQ ID NO:5; (4) a heavy chain immunoglobulin comprising the amino acid sequence set forth in SEQ ID NO:2; a light chain immunoglobulin comprising the amino acid sequence set forth in SEQ ID NO:6; (5) a heavy chain immunoglobulin comprising the amino acid sequence set forth in SEQ ID NO:2; a light chain immunoglobulin comprising the amino acid sequence set forth in SEQ ID NO:7; (6) a heavy chain immunoglobulin comprising the amino acid sequence set forth in SEQ ID NO:2; a light chain immunoglobulin comprising the amino acid sequence set forth in SEQ ID NO:3; (7) a heavy chain immunoglobulin comprising the amino acid sequence set forth in SEQ ID NO:8; a light chain immunoglobulin comprising the amino acid sequence set forth in SEQ ID NO:11; (8) a heavy chain immunoglobulin comprising the amino acid sequence set forth in SEQ ID NO:9; a light chain immunoglobulin comprising the amino acid sequence set forth in SEQ ID NO:11; (9) a heavy chain immunoglobulin comprising the amino acid sequence set forth in SEQ ID NO:10; a light chain immunoglobulin comprising the amino acid sequence set forth in SEQ ID NO:11; (10) a heavy chain immunoglobulin comprising the amino acid sequence set forth in SEQ ID NO:12; a light chain immunoglobulin comprising the amino acid sequence set forth in SEQ ID NO:13; (11) a heavy chain immunoglobulin comprising the amino acid sequence set forth in SEQ ID NO:14; a light chain immunoglobulin comprising the amino acid sequence set forth in SEQ ID NO:15; (12) a heavy chain immunoglobulin comprising the amino acid sequence set forth in SEQ ID NO:79; a light chain immunoglobulin comprising the amino acid sequence set forth in SEQ ID NO:3; (13) a heavy chain immunoglobulin comprising the amino acid sequence set forth in SEQ ID NO:80; a light chain immunoglobulin comprising the amino acid sequence set forth in SEQ ID NO:4; (14) a heavy chain immunoglobulin comprising the amino acid sequence set forth in SEQ ID NO:80; a light chain immunoglobulin comprising the amino acid sequence set forth in SEQ ID NO:5; (15) a heavy chain immunoglobulin comprising the amino acid sequence set forth in SEQ ID NO:80; a light chain immunoglobulin comprising the amino acid sequence set forth in SEQ ID NO:6; (16) a heavy chain immunoglobulin comprising the amino acid sequence set forth in SEQ ID NO:80; a light chain immunoglobulin comprising the amino acid sequence set forth in SEQ ID NO:7; (17) a heavy chain immunoglobulin comprising the amino acid sequence set forth in SEQ ID NO:80; a light chain immunoglobulin comprising the amino acid sequence set forth in SEQ ID NO:3; (18) a heavy chain immunoglobulin comprising the amino acid sequence set forth in SEQ ID NO:82; a light chain immunoglobulin comprising the amino acid sequence set forth in SEQ ID NO:11; (19) a heavy chain immunoglobulin comprising the amino acid sequence set forth in SEQ ID NO:83; a light chain immunoglobulin comprising the amino acid sequence set forth in SEQ ID NO:11; (20) a heavy chain immunoglobulin comprising the amino acid sequence set forth in SEQ ID NO:84; a light chain immunoglobulin comprising the amino acid sequence set forth in SEQ ID NO:11; (21) a heavy chain immunoglobulin comprising the amino acid sequence set forth in SEQ ID NO:85; a light chain immunoglobulin comprising the amino acid sequence set forth in SEQ ID NO:13; or (22) a heavy chain immunoglobulin comprising the amino acid sequence set forth in SEQ ID NO:86; a light chain immunoglobulin comprising the amino acid sequence set forth in SEQ ID NO:15.

In even more embodiments, the method of treating a cancer in a human subject in need thereof, comprising administering to the human subject an effective amount of the antibody or antigen-binding fragment thereof comprising: any of the following sets of heavy chain variable domain and light chain variable domain: (1) a heavy chain variable domain comprising the amino acid sequence set forth in SEQ ID NO:63; and a light chain variable domain comprising the amino acid sequence set forth in SEQ ID NO:70; (2) a heavy chain variable domain comprising the amino acid sequence set forth in SEQ ID NO:57; and a light chain variable domain comprising the amino acid sequence set forth in SEQ ID NO:71; (3) a heavy chain variable domain comprising the amino acid sequence set forth in SEQ ID NO:57; and a light chain variable domain comprising the amino acid sequence set forth in SEQ ID NO:72; (4) a heavy chain variable domain comprising the amino acid sequence set forth in SEQ ID NO:57; and a light chain variable domain comprising the amino acid sequence set forth in SEQ ID NO:73; (5) a heavy chain variable domain comprising the amino acid sequence set forth in SEQ ID NO:57; and a light chain variable domain comprising the amino acid sequence set forth in SEQ ID NO:58; (6) a heavy chain variable domain comprising the amino acid sequence set forth in SEQ ID NO:57; and a light chain variable domain comprising the amino acid sequence set forth in SEQ ID NO:70; (7) a heavy chain variable domain comprising the amino acid sequence set forth in SEQ ID NO:64; and a light chain variable domain comprising the amino acid sequence set forth in SEQ ID NO:74; (8) a heavy chain variable domain comprising the amino acid sequence set forth in SEQ ID NO:65; and a light chain variable domain comprising the amino acid sequence set forth in SEQ ID NO:74; (9) a heavy chain variable domain comprising the amino acid sequence set forth in SEQ ID NO:66; and a light chain variable domain comprising the amino acid sequence set forth in SEQ ID NO:74; (10) a heavy chain variable domain comprising the amino acid sequence set forth in SEQ ID NO:67; and a light chain variable domain comprising the amino acid sequence set forth in SEQ ID NO:75; or (11) a heavy chain variable domain comprising the amino acid sequence set forth in SEQ ID NO:68; and a light chain variable domain comprising the amino acid sequence set forth in SEQ ID NO:76.

In one preferred embodiment, the method of treating a cancer in a human subject in need thereof, comprising administering to the human subject an effective amount of the antibody or antigen-binding fragment thereof comprising: a $V_H$ domain comprising the amino acid sequence set forth in SEQ ID NO:57; and a $V_L$ domain comprising the amino acid sequence set forth in SEQ ID NO:58.

In another preferred embodiment, the method of treating a cancer in a human subject in need thereof, comprising administering to the human subject an effective amount of the antibody or antigen-binding fragment thereof comprising: a heavy chain immunoglobulin comprising the amino acid sequence set forth in SEQ ID NO:2; and a light chain immunoglobulin comprising the amino acid sequence set forth in SEQ ID NO:7. In yet another preferred embodiment, the method of treating a cancer in a human subject in need thereof, comprising administering to the human subject an effective amount of the antibody or antigen-binding fragment thereof comprising: a heavy chain immunoglobulin comprising the amino acid sequence set forth in SEQ ID NO:80; and a light chain immunoglobulin comprising the amino acid sequence set forth in SEQ ID NO:7.

Further provided herein are methods of blocking binding of ILT4 to HLA-G, HLA-A, HLA-B and/or HLA-F in a human subject in need thereof comprising administering to the human subject an effective amount of the antibody or antigen-binding fragment thereof comprising (a) the CDR-L1, CDR-L2, and CDR-L3 of a light chain variable ($V_L$) domain of an immunoglobulin chain that comprises the amino acid sequence set forth in SEQ ID NO: 3-7, 11, 13, 15, or 45; and/or (b) the CDR-H1, CDR-H2, and CDR-H3 of a heavy chain variable ($V_H$) domain of an immunoglobulin chain that comprises the amino acid sequence set forth in SEQ ID NO: 1, 2, 8-10, 12, 14, 44, or 79-86.

In an embodiment of the invention, the method of blocking binding of ILT4 to HLA-G, HLA-A, HLA-B and/or HLA-F in a human subject in need thereof, comprising administering to the human subject an effective amount of the antibody or antigen-binding fragment thereof comprising: (1) a $V_H$ domain comprising: complementarity determining region-H1 (CDR-H1): GYYWS (SEQ ID NO: 16), complementarity determining region-H2 (CDR-H2): EINHXGSTNYNPSLKS wherein X is S or A (SEQ ID NO:

17); and complementarity determining region-H3 (CDR-H3): LPTRWVTTRYFDL (SEQ ID NO: 18); and/or, a $V_L$ domain comprising: complementarity determining region-L1 (CDR-L1): TGSSSNIGAGYDVH (SEQ ID NO: 19), complementarity determining region-L2 (CDR-L2): GX$_1$X$_2$NRPS, wherein X$_1$ is S or A and X$_2$ is N, Q, E or D (SEQ ID NO: 20); and complementarity determining region-L3 (CDR-L3): QSFDNSLSAYV (SEQ ID NO: 21); (2) a $V_H$ domain comprising: CDR-H1: SYAIS (SEQ ID NO: 22); CDR-H2: GIIPIFGTANYAQKFQG (SEQ ID NO: 23); and CDR-H3: YFX$_1$X$_2$SGWYKGGAFDI, wherein X$_1$ is D or S and X$_2$ is S or A (SEQ ID NO: 24); and/or, a $V_L$ domain comprising: CDR-L1: TLRSGINVDTYRIH (SEQ ID NO: 25); CDR-L2: YKSDSDKHQGS (SEQ ID NO: 26); and CDR-L3: AIWYSSTWV (SEQ ID NO: 27); (3) a $V_H$ domain comprising: CDR-H1: SYAMH (SEQ ID NO: 28); CDR-H2: VISYDGSNKYYADSVKG (SEQ ID NO: 29); and CDR-H3: VGEWIQLWSPFDY (SEQ ID NO: 30); and/or, a $V_L$ domain comprising: CDR-L1: RASQGISS-WLA (SEQ ID NO: 31); CDR-L2: AASSLQS (SEQ ID NO: 32); and CDR-L3: QQYNSYPPT (SEQ ID NO: 33); and/or (4) a $V_H$ domain comprising: CDR-H1: ELSMH (SEQ ID NO: 34); CDR-H2: GFDPEDGETIYAQKFQG (SEQ ID NO: 35); and CDR-H3: AGPLYTIFGVVIIPDNWFDP (SEQ ID NO: 36); and/or, a $V_L$ domain comprising: CDR-L1: TGSSSNIGAGYDVH (SEQ ID NO: 37); CDR-L2: GNSNRPS (SEQ ID NO: 38); and CDR-L3: QSYDSSLSGSGW (SEQ ID NO: 39).

In one embodiment, the method of blocking binding of ILT4 to HLA-G, HLA-A, HLA-B and/or HLA-F in a human subject in need thereof, comprising administering to the human subject an effective amount of the antibody or antigen-binding fragment thereof comprising: CDR-H1: GYYWS (SEQ ID NO: 16), CDR-H2: EINHSG-STNYNPSLKS (SEQ ID NO: 47), and CDR-H3: LPTRWVTTRYFDL (SEQ ID NO: 18); and/or, a $V_L$ domain comprising: CDR-L1: TGSSSNIGAGYDVH (SEQ ID NO: 19), CDR-L2: GNSNRPS(SEQ ID NO: 49), and CDR-L3: QSFDNSLSAYV (SEQ ID NO: 21).

In another embodiment, the method of blocking binding of ILT4 to HLA-G, HLA-A, HLA-B and/or HLA-F in a human subject in need thereof, comprising administering to the human subject an effective amount of the antibody or antigen-binding fragment thereof comprising: CDR-H1: GYYWS (SEQ ID NO: 16), CDR-H2: EINHSG-STNYNPSLKS (SEQ ID NO: 47), and CDR-H3: LPTRWVTTRYFDL (SEQ ID NO: 18); and/or, a $V_L$ domain comprising: CDR-L1: TGSSSNIGAGYDVH (SEQ ID NO: 19), CDR-L2: GQSNRPS(SEQ ID NO: 50), and CDR-L3: QSFDNSLSAYV (SEQ ID NO: 21).

In yet another embodiment, the method of blocking binding of ILT4 to HLA-G, HLA-A, HLA-B and/or HLA-F in a human subject in need thereof, comprising administering to the human subject an effective amount of the antibody or antigen-binding fragment thereof comprising: GYYWS (SEQ ID NO: 16), CDR-H2: EINHSGSTNYNPSLKS (SEQ ID NO: 47), and CDR-H3: LPTRWVTTRYFDL (SEQ ID NO: 18); and/or, a $V_L$ domain comprising: CDR-L1: TGSSSNIGAGYDVH (SEQ ID NO: 19), CDR-L2: GESNRPS(SEQ ID NO: 51), and CDR-L3: QSFDNSLSAYV (SEQ ID NO: 21).

In still another embodiment, the method of blocking binding of ILT4 to HLA-G, HLA-A, HLA-B and/or HLA-F in a human subject in need thereof, comprising administering to the human subject an effective amount of the antibody or antigen-binding fragment thereof comprising: CDR-H1: GYYWS (SEQ ID NO: 16), CDR-H2: EINHSG-STNYNPSLKS (SEQ ID NO: 47), and CDR-H3: LPTRWVTTRYFDL (SEQ ID NO: 18); and/or, a $V_L$ domain comprising: CDR-L1: TGSSSNIGAGYDVH (SEQ ID NO: 19), CDR-L2: GDSNRPS(SEQ ID NO: 52), and CDR-L3: QSFDNSLSAYV (SEQ ID NO: 21).

In one embodiment, the method of blocking binding of ILT4 to HLA-G, HLA-A, HLA-B and/or HLA-F in a human subject in need thereof, comprising administering to the human subject an effective amount of the antibody or antigen-binding fragment thereof comprising: CDR-H1: GYYWS (SEQ ID NO: 16), CDR-H2: EINHSG-STNYNPSLKS (SEQ ID NO: 47), and CDR-H3: LPTRWVTTRYFDL (SEQ ID NO: 18); and/or, a $V_L$ domain comprising: CDR-L1: TGSSSNIGAGYDVH (SEQ ID NO: 19), CDR-L2: GNANRPS(SEQ ID NO: 53), and CDR-L3: QSFDNSLSAYV (SEQ ID NO: 21).

In another embodiment, the method of blocking binding of ILT4 to HLA-G, HLA-A, HLA-B and/or HLA-F in a human subject in need thereof, comprising administering to the human subject an effective amount of the antibody or antigen-binding fragment thereof comprising: CDR-H1: GYYWS (SEQ ID NO: 16), CDR-H2: EINHSG-STNYNPSLKS (SEQ ID NO: 47), and CDR-H3: LPTRWVTTRYFDL (SEQ ID NO: 18); and/or, a $V_L$ domain comprising: CDR-L1: TGSSSNIGAGYDVH (SEQ ID NO: 19), CDR-L2: GQANRPS(SEQ ID NO: 54), and CDR-L3: QSFDNSLSAYV (SEQ ID NO: 21).

In yet another embodiment, the method of blocking binding of ILT4 to HLA-G, HLA-A, HLA-B and/or HLA-F in a human subject in need thereof, comprising administering to the human subject an effective amount of the antibody or antigen-binding fragment thereof comprising: CDR-H1: GYYWS (SEQ ID NO: 16), CDR-H2: EINHSG-STNYNPSLKS (SEQ ID NO: 47), and CDR-H3: LPTRWVTTRYFDL (SEQ ID NO: 18); and/or, a $V_L$ domain comprising: CDR-L1: TGSSSNIGAGYDVH (SEQ ID NO: 19), CDR-L2: GEANRPS(SEQ ID NO: 55), and CDR-L3: QSFDNSLSAYV (SEQ ID NO: 21).

In still another embodiment, the method of blocking binding of ILT4 to HLA-G, HLA-A, HLA-B and/or HLA-F in a human subject in need thereof, comprising administering to the human subject an effective amount of the antibody or antigen-binding fragment thereof comprising: CDR-H1: GYYWS (SEQ ID NO: 16), CDR-H2: EINHSG-STNYNPSLKS (SEQ ID NO: 47), and CDR-H3: LPTRWVTTRYFDL (SEQ ID NO: 18); and/or, a $V_L$ domain comprising: CDR-L1: TGSSSNIGAGYDVH (SEQ ID NO: 19), CDR-L2: GDANRPS(SEQ ID NO: 56), and CDR-L3: QSFDNSLSAYV (SEQ ID NO: 21).

In one embodiment, the method of blocking binding of ILT4 to HLA-G, HLA-A, HLA-B and/or HLA-F in a human subject in need thereof, comprising administering to the human subject an effective amount of the antibody or antigen-binding fragment thereof comprising: CDR-H1: GYYWS (SEQ ID NO: 16), CDR-H2: EINHAG-STNYNPSLKS (SEQ ID NO: 48), and CDR-H3: LPTRWVTTRYFDL (SEQ ID NO: 18); and/or, a $V_L$ domain comprising: CDR-L1: TGSSSNIGAGYDVH (SEQ ID NO: 19), CDR-L2: GNSNRPS(SEQ ID NO: 49), and CDR-L3: QSFDNSLSAYV (SEQ ID NO: 21).

In another embodiment, the method of blocking binding of ILT4 to HLA-G, HLA-A, HLA-B and/or HLA-F in a human subject in need thereof, comprising administering to the human subject an effective amount of the antibody or antigen-binding fragment thereof comprising: CDR-H1: GYYWS (SEQ ID NO: 16), CDR-H2: EINHAG-STNYNPSLKS (SEQ ID NO: 48), and CDR-H3:

LPTRWVTTRYFDL (SEQ ID NO: 18); and/or, a $V_L$ domain comprising: CDR-L1: TGSSSNIGAGYDVH (SEQ ID NO: 19), CDR-L2: GQSNRPS(SEQ ID NO: 50), and CDR-L3: QSFDNSLSAYV (SEQ ID NO: 21).

In yet another embodiment, the method of blocking binding of ILT4 to HLA-G, HLA-A, HLA-B and/or HLA-F in a human subject in need thereof, comprising administering to the human subject an effective amount of the antibody or antigen-binding fragment thereof comprising: CDR-H1: GYYWS (SEQ ID NO: 16), CDR-H2: EINHAGSTNYNPSLKS (SEQ ID NO: 48), and CDR-H3: LPTRWVTTRYFDL (SEQ ID NO: 18); and/or, a $V_L$ domain comprising: CDR-L1: TGSSSNIGAGYDVH (SEQ ID NO: 19), CDR-L2: GESNRPS(SEQ ID NO: 51), and CDR-L3: QSFDNSLSAYV (SEQ ID NO: 21).

In still another embodiment, the method of blocking binding of ILT4 to HLA-G, HLA-A, HLA-B and/or HLA-F in a human subject in need thereof, comprising administering to the human subject an effective amount of the antibody or antigen-binding fragment thereof comprising: CDR-H1: GYYWS (SEQ ID NO: 16), CDR-H2: EINHAGSTNYNPSLKS (SEQ ID NO: 48), and CDR-H3: LPTRWVTTRYFDL (SEQ ID NO: 18); and/or, a $V_L$ domain comprising: CDR-L1: TGSSSNIGAGYDVH (SEQ ID NO: 19), CDR-L2: GDSNRPS(SEQ ID NO: 52), and CDR-L3: QSFDNSLSAYV (SEQ ID NO: 21).

In one embodiment, the method of blocking binding of ILT4 to HLA-G, HLA-A, HLA-B and/or HLA-F in a human subject in need thereof, comprising administering to the human subject an effective amount of the antibody or antigen-binding fragment thereof comprising: CDR-H1: GYYWS (SEQ ID NO: 16), CDR-H2: EINHAGSTNYNPSLKS (SEQ ID NO: 48), and CDR-H3: LPTRWVTTRYFDL (SEQ ID NO: 18); and/or, a $V_L$ domain comprising: CDR-L1: TGSSSNIGAGYDVH (SEQ ID NO: 19), CDR-L2: GNANRPS(SEQ ID NO: 53), and CDR-L3: QSFDNSLSAYV (SEQ ID NO: 21).

In another embodiment, the method of blocking binding of ILT4 to HLA-G, HLA-A, HLA-B and/or HLA-F in a human subject in need thereof, comprising administering to the human subject an effective amount of the antibody or antigen-binding fragment thereof comprising: CDR-H1: GYYWS (SEQ ID NO: 16), CDR-H2: EINHAGSTNYNPSLKS (SEQ ID NO: 48), and CDR-H3: LPTRWVTTRYFDL (SEQ ID NO: 18); and/or, a $V_L$ domain comprising: CDR-L1: TGSSSNIGAGYDVH (SEQ ID NO: 19), CDR-L2: GQANRPS(SEQ ID NO: 54), and CDR-L3: QSFDNSLSAYV (SEQ ID NO: 21).

In yet another embodiment, the method of blocking binding of ILT4 to HLA-G, HLA-A, HLA-B and/or HLA-F in a human subject in need thereof, comprising administering to the human subject an effective amount of the antibody or antigen-binding fragment thereof comprising: CDR-H1: GYYWS (SEQ ID NO: 16), CDR-H2: EINHAGSTNYNPSLKS (SEQ ID NO: 48), and CDR-H3: LPTRWVTTRYFDL (SEQ ID NO: 18); and/or, a $V_L$ domain comprising: CDR-L1: TGSSSNIGAGYDVH (SEQ ID NO: 19), CDR-L2: GEANRPS(SEQ ID NO: 55), and CDR-L3: QSFDNSLSAYV (SEQ ID NO: 21).

In still another embodiment, the method of blocking binding of ILT4 to HLA-G, HLA-A, HLA-B and/or HLA-F in a human subject in need thereof, comprising administering to the human subject an effective amount of the antibody or antigen-binding fragment thereof comprising: CDR-H1: GYYWS (SEQ ID NO: 16), CDR-H2: EINHAGSTNYNPSLKS (SEQ ID NO: 48), and CDR-H3: LPTRWVTTRYFDL (SEQ ID NO: 18); and/or, a $V_L$ domain comprising: CDR-L1: TGSSSNIGAGYDVH (SEQ ID NO: 19), CDR-L2: GDANRPS(SEQ ID NO: 56), and CDR-L3: QSFDNSLSAYV (SEQ ID NO: 21).

In still other embodiments, the method of blocking binding of ILT4 to HLA-G, HLA-A, HLA-B and/or HLA-F in a human subject in need thereof, comprising administering to the human subject an effective amount of the antibody or antigen-binding fragment thereof comprising: a light chain immunoglobulin, a heavy chain immunoglobulin, or both a light and heavy chain immunoglobulin, wherein the light chain immunoglobulin comprises the amino acid sequence set forth in SEQ ID NO:3, 4, 5, 6, 7, 11, 13, 15, or 45; and/or the heavy chain immunoglobulin comprises the amino acid sequence set forth in SEQ ID NO: 1, 2, 8, 9, 10, 12, 14, 44, 79, 80, 81, 82, 83, 84, 85, or 86.

In yet still other embodiments, the method of blocking binding of ILT4 to HLA-G, HLA-A, HLA-B and/or HLA-F in a human subject in need thereof, comprising administering to the human subject an effective amount of the antibody or antigen-binding fragment thereof comprising: a light chain immunoglobulin, a heavy chain immunoglobulin, or both a light and heavy chain immunoglobulin, wherein the light chain variable domain comprises the amino acid sequence set forth in SEQ ID NO:70, 71, 72, 73, 58, 74, 75, 76, or 77, and/or the heavy chain variable domain comprise the amino acid sequence set forth in SEQ ID NO:63, 57, 64, 65, 66, 67, 68, or 69.

In more embodiments, the method of blocking binding of ILT4 to HLA-G, HLA-A, HLA-B and/or HLA-F in a human subject in need thereof, comprising administering to the human subject an effective amount of the antibody or antigen-binding fragment thereof comprising: any of the following sets of heavy chain immunoglobulins and light chain immunoglobulins: (1) a heavy chain immunoglobulin comprising the amino acid sequence set forth in SEQ ID NO:1; a light chain immunoglobulin comprising the amino acid sequence set forth in SEQ ID NO:3; (2) a heavy chain immunoglobulin comprising the amino acid sequence set forth in SEQ ID NO:2; a light chain immunoglobulin comprising the amino acid sequence set forth in SEQ ID NO:4; (3) a heavy chain immunoglobulin comprising the amino acid sequence set forth in SEQ ID NO:2; a light chain immunoglobulin comprising the amino acid sequence set forth in SEQ ID NO:5; (4) a heavy chain immunoglobulin comprising the amino acid sequence set forth in SEQ ID NO:2; a light chain immunoglobulin comprising the amino acid sequence set forth in SEQ ID NO:6; (5) a heavy chain immunoglobulin comprising the amino acid sequence set forth in SEQ ID NO:2; a light chain immunoglobulin comprising the amino acid sequence set forth in SEQ ID NO:7; (6) a heavy chain immunoglobulin comprising the amino acid sequence set forth in SEQ ID NO:2; a light chain immunoglobulin comprising the amino acid sequence set forth in SEQ ID NO:3; (7) a heavy chain immunoglobulin comprising the amino acid sequence set forth in SEQ ID NO:8; a light chain immunoglobulin comprising the amino acid sequence set forth in SEQ ID NO:11, (8) a heavy chain immunoglobulin comprising the amino acid sequence set forth in SEQ ID NO:9; a light chain immunoglobulin comprising the amino acid sequence set forth in SEQ ID NO:11; (9) a heavy chain immunoglobulin comprising the amino acid sequence set forth in SEQ ID NO:10; a light chain immunoglobulin comprising the amino acid sequence set forth in SEQ ID NO:11; (10) a heavy chain immunoglobulin comprising the amino acid sequence set forth in SEQ ID NO:12; a light chain immunoglobulin comprising the amino acid sequence set forth in SEQ ID NO:13; (11) a heavy chain immunoglobulin comprising the amino acid sequence set forth in SEQ ID NO:14; a light chain immunoglobulin comprising the amino acid sequence set forth in SEQ ID NO:15; (12) a heavy chain immunoglobulin comprising the amino acid sequence set forth in SEQ ID NO:79; a light chain immunoglobulin comprising the amino acid sequence set forth in SEQ ID NO:3; (13) a heavy chain immunoglobulin comprising the amino acid sequence set forth in SEQ ID NO:80; a light chain immunoglobulin comprising the amino acid sequence set forth in SEQ ID NO:4; (14) a heavy chain immunoglobulin comprising the amino acid sequence set forth in SEQ ID NO:80; a light chain immunoglobulin comprising the amino acid sequence set forth in SEQ ID NO:5; (15) a heavy chain immunoglobulin comprising the amino acid sequence set forth in SEQ ID NO:80; a light chain immunoglobulin comprising the amino acid sequence set forth in SEQ ID NO:6; (16) a heavy chain immunoglobulin comprising the amino acid sequence set forth in SEQ ID NO:80; a light chain immunoglobulin comprising the amino acid sequence set forth in SEQ ID NO:7; (17) a heavy chain immunoglobulin comprising the amino acid sequence set forth in SEQ ID NO:80; a light chain immunoglobulin comprising the amino acid sequence set forth in SEQ ID NO:3; (18) a heavy chain immunoglobulin comprising the amino acid sequence set forth in SEQ ID NO:82; a light chain immunoglobulin comprising the amino acid sequence set forth in SEQ ID NO:11, (19) a heavy chain immunoglobulin comprising the amino acid sequence set forth in SEQ ID NO:83; a light chain immunoglobulin comprising the amino acid sequence set forth in SEQ ID NO:11; (20) a heavy chain immunoglobulin comprising the amino acid sequence set forth in SEQ ID NO:84; a light chain immunoglobulin comprising the amino acid sequence set forth in SEQ ID NO:11; (21) a heavy chain immunoglobulin comprising the amino acid sequence set forth in SEQ ID NO:85; a light chain immunoglobulin comprising the amino acid sequence set forth in SEQ ID NO:13; or (22) a heavy chain immunoglobulin comprising the amino acid sequence set forth in SEQ ID NO:86; a light chain immunoglobulin comprising the amino acid sequence set forth in SEQ ID NO:15.

In even more embodiments, the method of blocking binding of ILT4 to HLA-G, HLA-A, HLA-B and/or HLA-F in a human subject in need thereof, comprising administering to the human subject an effective amount of the antibody or antigen-binding fragment thereof comprising: any of the following sets of heavy chain variable domain and light chain variable domain: (1) a heavy chain variable domain comprising the amino acid sequence set forth in SEQ ID NO:63; and a light chain variable domain comprising the amino acid sequence set forth in SEQ ID NO:70; (2) a heavy chain variable domain comprising the amino acid sequence set forth in SEQ ID NO:57; and a light chain variable domain comprising the amino acid sequence set forth in SEQ ID NO:71; (3) a heavy chain variable domain comprising the amino acid sequence set forth in SEQ ID NO:57; and a light chain variable domain comprising the amino acid sequence set forth in SEQ ID NO:72; (4) a heavy chain variable domain comprising the amino acid sequence set forth in SEQ ID NO:57; and a light chain variable domain comprising the amino acid sequence set forth in SEQ ID NO:73; (5) a heavy chain variable domain comprising the amino acid sequence set forth in SEQ ID NO:57; and a light chain variable domain comprising the amino acid sequence set forth in SEQ ID NO:58; (6) a heavy chain variable domain comprising the amino acid sequence set forth in SEQ ID NO:57; and a light chain variable domain comprising the amino acid sequence set forth in SEQ ID NO:70; (7) a heavy chain variable domain comprising the amino acid sequence set forth in SEQ ID NO:64; and a light chain variable domain comprising the amino acid sequence set forth in SEQ ID NO:74; (8) a heavy chain variable domain comprising the amino acid sequence set forth in SEQ ID NO:65; and a light chain variable domain comprising the amino acid sequence set forth in SEQ ID NO:74; (9) a heavy chain variable domain comprising the amino acid sequence set forth in SEQ ID NO:66; and a light chain variable domain comprising the amino acid sequence set forth in SEQ ID NO:74; (10) a heavy chain variable domain comprising the amino acid sequence set forth in SEQ ID NO:67; and a light chain variable domain comprising the amino acid sequence set forth in SEQ ID NO:75; or (11) a heavy chain variable domain comprising the amino acid sequence set forth in SEQ ID NO:68; and a light chain variable domain comprising the amino acid sequence set forth in SEQ ID NO:76.

In one preferred embodiment, the method of blocking binding of ILT4 to HLA-G, HLA-A, HLA-B and/or HLA-F in a human subject in need thereof, comprising administering to the human subject an effective amount of the antibody or antigen-binding fragment thereof comprising: a $V_H$ domain comprising the amino acid sequence set forth in SEQ ID NO:57; and a $V_L$ domain comprising the amino acid sequence set forth in SEQ ID NO:58.

In another preferred embodiment, the method of blocking binding of ILT4 to HLA-G, HLA-A, HLA-B and/or HLA-F in a human subject in need thereof, comprising administering to the human subject an effective amount of the antibody or antigen-binding fragment thereof comprising: a heavy chain immunoglobulin comprising the amino acid sequence set forth in SEQ ID NO:2; and a light chain immunoglobulin comprising the amino acid sequence set forth in SEQ ID NO:7.

In yet another preferred embodiment, the method of blocking binding of ILT4 to HLA-G, HLA-A, HLA-B and/or HLA-F in a human subject in need thereof, comprising administering to the human subject an effective amount of the antibody or antigen-binding fragment thereof comprising: a heavy chain immunoglobulin comprising the amino acid sequence set forth in SEQ ID NO:80; and a light chain immunoglobulin comprising the amino acid sequence set forth in SEQ ID NO:7.

The present invention also provides methods for treating or preventing an infectious disease in a subject by administering an effective amount of anti-ILT4 antibodies or antigen-binding fragments thereof disclosed herein (e.g., 1E1, 2A6, 3G7 and/or 2C1) to the subject which may be effective for such treatment or prevention. In an embodiment of the invention, the infectious disease is viral infection. In an embodiment of the invention, the infectious disease is bacterial infection. In an embodiment of the invention, the infectious disease is parasitic infection. In an embodiment of the invention, the infectious disease is fungal infection.

The present invention includes methods of treating any of the cancers or infectious diseases discussed herein by administering a therapeutically effective amount of an anti-ILT4 antibody or antigen-binding fragment thereof (e.g., 1E1, 2A6, 3G7 and/or 2C1) optionally in association with any of the further chemotherapeutic agents or therapeutic procedures discussed herein as well as compositions including such an antibody or fragment in association with such a further chemotherapeutic agent (e.g., co-formulated antibody or fragment and further chemotherapeutic agent).

A "subject" is a mammal such as, for example, a human, dog, cat, horse, cow, mouse, rat, monkey (e.g., cynomolgus monkey, e.g., *Macaca fascicularis* or *Macaca mulatta*) or rabbit.

In an embodiment of the invention, an anti-ILT4 antibody (e.g., fully human antibody such as antagonist fully human antibodies) or antigen-binding fragment thereof of the present invention (e.g., 1E1, 2A6, 3G7 and/or 2C1) is in association with a further chemotherapeutic agent such as an antibody or antigen-binding fragment thereof. In an embodiment of the invention, the further chemotherapeutic agent is an antiemetic, erythropoietin, GM-CSF, a vaccine, an anti-PD-L1 antibody or antigen-binding fragment thereof, an anti-PD-L2 antibody or antigen-binding fragment thereof, an anti-PD1 antibody or antigen-binding fragment thereof (e.g., pembrolizumab or nivolumab), 5-fluorouracil (5-FU), a platinum compound, bevacizumab, daunorubicin, doxorubicin, temozolomide topotecan, irinotecan, paclitaxel, docetaxel, imatinib or rituximab.

The term "in association with" indicates that the components, an anti-ILT4 antibody (e.g., fully human antibody such as antagonist fully human antibodies) or antigen-binding fragment thereof of the present invention (e.g., 1E1, 2A6, 3G7 and/or 2C1) along with another agent such as pembrolizumab or nivolumab, can be formulated into a single composition, e.g., for simultaneous delivery, or formulated separately into two or more compositions (e.g., a kit). Each component can be administered to a subject at a different time than when the other component is administered; for example, each administration may be given non-simultaneously (e.g., separately or sequentially) at intervals over a given period of time. Moreover, the separate components may be administered to a subject by the same or by a different route (e.g., wherein an anti-ILT4 antibody (e.g., fully human antibody such as antagonist fully human antibodies) or antigen-binding fragment thereof (e.g., 1E1, 2A6, 3G7 and/or 2C1 is administered parenterally and paclitaxel is administered orally).

Assays and Experimental and Diagnostic Uses

The present invention includes any method for forming a complex between an anti-ILT4 antibody or antigen-binding fragment thereof of the present invention and ILT4 or a fragment thereof comprising contacting the ILT4 polypeptide or fragment with the anti-ILT4 antibody or antigen-binding fragment under conditions suitable for binding and complex formation.

The anti-ILT4 antibodies (e.g., fully human antibodies such as antagonist fully human antibodies) and antigen-binding fragments thereof disclosed herein (e.g., 1E1, 2A6, 3G7 and/or 2C1) may be used as affinity purification agents. In this process, the anti-ILT4 antibodies and antigen-binding fragments thereof are immobilized on a solid phase such a sephadex, glass or agarose resin or filter paper, using methods well known in the art. The immobilized antibody or fragment is contacted with a sample containing the ILT4 protein (or a fragment thereof) to be purified, and, thereafter, the support is washed with a suitable solvent that will remove the material in the sample except the ILT4 protein which is bound to the immobilized antibody or fragment. Finally, the support is washed with a solvent which elutes the bound ILT4 (e.g., protein A). Such immobilized antibodies and fragments form part of the present invention.

The present invention includes cell-based ELISA methods using the anti-ILT4 antibodies and antigen-binding fragments thereof of the present invention (e.g., 1E1, 2A6, 3G7 and/or 2C1). In an embodiment of the invention, the method is for determining whether cells contain ILT4 and the method includes the steps: (i) contacting said cells immobilized to a solid surface (e.g., a microplate), which are to be tested for the presence of ILT4, with an anti-ILT4 antibody or antigen-binding fragment thereof of the present invention, (ii) optionally, washing the mixture to remove unbound anti-ILT4 antibody or fragment, (iii) contacting the anti-ILT4 antibody or fragment with a labeled secondary antibody or antigen-binding fragment thereof that binds to the anti-ILT4 antibody or fragment, (iv) optionally washing the complex to remove unbound antibodies or fragments and (v) detecting the presence of the label on the secondary antibody or fragment; wherein detection of the label indicates that cells containing ILT4 are immobilized to the solid surface.

The present invention includes ELISA assays (enzyme-linked immunosorbent assay) incorporating the use of an anti-ILT4 antibody (e.g., fully human antibodies such as antagonist fully human antibodies) or antigen-binding fragment thereof disclosed herein (e.g., 1E1, 2A6, 3G7 and/or 2C1). For example, such a method, for determining if a sample contains ILT4 or a fragment thereof, comprises the following steps:

(a) coating a substrate (e.g., surface of a microtiter plate well, e.g., a plastic plate) with anti-ILT4 antibody (e.g., fully human antibodies such as antagonist fully human antibodies) or antigen-binding fragment thereof (e.g., 1E1, 2A6, 3G7 and/or 2C1);

(b) applying a sample to be tested for the presence of ILT4 to the substrate;

(c) washing the substrate, so that unbound material in the sample is removed;

(d) applying detectably labeled antibodies (e.g., enzyme-linked antibodies) which are also specific to the ILT4 antigen;

(e) washing the substrate, so that the unbound, labeled antibodies are removed;

(f) detecting the label on the antibodies; if the labeled antibodies are enzyme linked, apply a chemical which is converted by the enzyme into a detectable, e.g., fluorescent, signal; and Detection of the label, e.g., associated with the substrate, indicates the presence of the ILT4 protein.

In an embodiment of the invention, the labeled antibody or antigen-binding fragment thereof is labeled with peroxidase which reacts with ABTS (e.g., 2,2'-azino-bis(3-ethylbenzthiazoline-6-sulphonic acid)) or 3,3',5,5'-Tetramethylbenzidine to produce a color change which is detectable. Alternatively, the labeled antibody or fragment is labeled with a detectable radioisotope (e.g., $^3$H) which can be detected by scintillation counter in the presence of a scintillant.

An anti-ILT4 antibody (e.g., fully human antibodies such as antagonist fully human antibodies) or antigen-binding fragment thereof of the invention (e.g., 1E1, 2A6, 3G7 and/or 2C1) may be used in a Western blot or immune-protein blot procedure. Such a procedure forms part of the present invention and includes e.g.:

(1) providing a membrane or other solid substrate comprising a sample to be tested for the presence of ILT4 or fragment thereof, e.g., optionally including the step of transferring proteins from a sample to be tested for the presence of ILT4 (e.g., from a PAGE or SDS-PAGE electrophoretic separation of the proteins in the sample) onto a membrane or other solid substrate (e.g., using methods known in the art (e.g., semi-dry blotting or tank blotting)); and contacting the membrane or other solid substrate to be tested for the presence of bound ILT4 or a fragment thereof with an anti-ILT4 antibody or antigen-binding fragment thereof of the invention (e.g., 1E1, 2A6, 3G7 and/or 2C1); (2) washing the membrane one or more times to remove unbound anti-ILT4 antibody or fragment and other unbound substances; and
(3) detecting the bound anti-ILT4 antibody or fragment.

Such a membrane may take the form, for example, of a nitrocellulose or vinyl-based (e.g., polyvinylidene fluoride (PVDF)) membrane to which the proteins to be tested for the presence of ILT4 in a non-denaturing PAGE (polyacrylamide gel electrophoresis) gel or SDS-PAGE (sodium dodecyl sulfate polyacrylamide gel electrophoresis) gel have been transferred (e.g., following electrophoretic separation in the gel). Before contacting the membrane with the anti-ILT4 antibody or fragment, the membrane is optionally blocked, e.g., with non-fat dry milk or the like so as to bind non-specific protein binding sites on the membrane.

Detection of the bound anti-ILT4 antibody or fragment indicates that the ILT4 protein is present on the membrane or substrate and in the sample. Detection of the bound antibody or fragment may be by binding the antibody or fragment with a secondary antibody (an anti-immunoglobulin antibody) which is detectably labeled and, then, detecting the presence of the secondary antibody label.

The anti-ILT4 antibodies (e.g., fully human antibodies such as antagonist fully human antibodies) and antigen-binding fragments thereof disclosed herein (e.g., 1E1, 2A6, 3G7 and/or 2C1) may also be used for immunohistochemistry. Such a method forms part of the present invention and comprises, e.g.,
(1) contacting cells (e.g., myeloid lineage cells such as monocytes, macrophages or dendtritic cells) to be tested for the presence of ILT4 protein with an anti-ILT4 antibody or antigen-binding fragment thereof of the invention (e.g., 1E1, 2A6, 3G7 and/or 2C1), and
(2) detecting the antibody or fragment on or in the cells.

If the antibody or fragment itself is detectably labeled, it can be detected directly. Alternatively, the antibody or fragment may be bound by a detectably labeled secondary antibody wherein the label is then detected.

EXAMPLES

These examples are intended to exemplify the present invention and are not a limitation thereof. Compositions and methods set forth in the Examples form part of the present invention.

As used herein the term "p1E1 (C1)" refers to a fully human anti-ILT4 1E1 mAb which is derived from the germline V genes, IGHV4-34*0 and IGLV1-40*01, respectively; having the human IgG1 and human lambda constant domains.

>heavy chain
(SEQ ID NO: 44)
QVQLQQWGAGLLKPSETLSLTCAVYGGSFSGYYWSWIRQPPGKGLEWIGE

INHSGSTNYNPSLKSRVTISVDTSKNQFSLKLSSVTAADTAVYYCARLPT

RWVTTRYFDLWGRGTLVTVSSASTKGPSVFPLAPSSKSTSGGTAALGCLV

KDYFPEPVTVSWNSGALTSGVHTFPAVLQSSGLYSLSSVVTVPSSSLGTQ

TYICNVNHKPSNTKVDKRVEPKSCDKTHTCPPCPAPELLGGPSVFLFPPK

PKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREP

QVYTLPPSREEMTKNQVSLTCLVKGFYPSDIAVEWESNGQPENNYKTTPP

VLDSDGSFFLYSKLTVDKSRWQQGNVFSCSVMHEALHNHYTQKSLSLSPG

K

>light chain
(SEQ ID NO: 45)
QSVLTQPPSVSGAPGQRVTISCTGSSSNIGAGYDVHWYQQLPGTAPKLLI

YGNSNRPSGVPDRFSVSKSGASASLAITGLQAEDEADYYCQSFDNSLSAY

VFGGGTQLTVLGQPKAAPSVTLFPPSSEELQANKATLVCLISDFYPGAVT

VAWKADSSPVKAGVETTTPSKQSNNKYAASSYLSLTPEQWKSHRSYSCQV

THEGSTVEKTVAPTECS

As used herein "p1E1(G4)" refers to a fully human anti-ILT4 1E1 (having the mutations Q1E in heavy chain and Q1E in light chain) mAb which is derived from the germline V genes, IGHV4-34*0 and IGLV1-40*01, respectively; having the human IgG4 (S228P) and human lambda constant domains.

> heavy chain
(SEQ ID NO: 1)
EVQLQQWGAGLLKPSETLSLTCAVYGGSFSGYYWSWIRQPPGKGLEWIGE

INHSGSTNYNPSLKSRVTISVDTSKNQFSLKLSSVTAADTAVYYCARLPT

RWVTTRYFDLWGRGTLVTVSSASTKGPSVFPLAPCSRSTSESTAALGCLV

KDYFPEPVTVSWNSGALTSGVHTFPAVLQSSGLYSLSSVVTVPSSSLGTK

TYTCNVDHKPSNTKVDKRVESKYGPPCPPCPAPEFLGGPSVFLFPPKPKD

TLMISRTPEVTCVVVDVSQEDPEVQFNWYVDGVEVHNAKTKPREEQFNST

YRVVSVLTVLHQDWLNGKEYKCKVSNKGLPSSIEKTISKAKGQPREPQVY

TLPPSQEEMTKNQVSLTCLVKGFYPSDIAVEWESNGQPENNYKTTPPVLD

SDGSFFLYSRLTVDKSRWQEGNVFSCSVMHEALHNHYTQKSLSLSLGK

> human IgG4 (S228P) constant domain
(SEQ ID NO: 89)
ASTKGPSVFPLAPCSRSTSESTAALGCLVKDYFPEPVTVSWNSGALTSGV

HTFPAVLQSSGLYSLSSVVTVPSSSLGTKTYTCNVDHKPSNTKVDKRVES

KYGPPCPPCPAPEFLGGPSVFLFPPKPKDTLMISRTPEVTCVVVDVSQED

PEVQFNWYVDGVEVHNAKTKPREEQFNSTYRVVSVLTVLHQDWLNGKEYK

CKVSNKGLPSSIEKTISKAKGQPREPQVYTLPPSQEEMTKNQVSLTCLVK

GFYPSDIAVEWESNGQPENNYKTTPPVLDSDGSFFLYSRLTVDKSRWQEG

NVFSCSVMHEALHNHYTQKSLSLSLGK

> light chain
(SEQ ID NO: 3)
ESVLTQPPSVSGAPGQRVTISCTGSSSNIGAGYDVHWYQQLPGTAPKLLI

YGNSNRPSGVPDRFSVSKSGASASLAITGLQAEDEADYYCQSFDNSLSAY

VEGGGTQLTVLGQPKAAPSVTLEPPSSEELQANKATLVCLISDFYPGAVT

VAWKADSSPVKAGVETTTPSKQSNNKYAASSYLSLTPEQWKSHRSYSCQV

THEGSTVEKTVAPTECS

```
> human lambda constant domain
                                      (SEQ ID NO: 90)
GQPKAAPSVTLFPPSSEELQANKATLVCLISDFYPGAVTVAWKADSSPVK

AGVETTTPSKQSNNKYAASSYLSLTPEQWKSHRSYSCQVTHEGSTVEKTV

APTECS
```

As used herein "1E1(G4)" refers to a fully human anti-ILT4 1E1 (having the mutations Q1E and N53D in light chain and Q1E and S54A in heavy chain) mAb which is derived from the germline V genes, IGHV4-34*0 and IGLV1-40*01, respectively; having human IgG4 (S228P) and human lambda constant domains.

```
> heavy chain
                                      (SEQ ID NO: 2)
EVQLQQWGAGLLKPSETLSLTCAVYGGSFSGYYWSWIRQPPGKGLEWIGE

INHAGSTNYNPSLKSRVTISVDTSKNQFSLKLSSVTAADTAVYYCARLPT

RWVTTRYFDLWGRGTLVTVSSASTKGPSVFPLAPCSRSTSESTAALGCLV

KDYFPEPVTVSWNSGALTSGVHTFPAVLQSSGLYSLSSVVTVPSSSLGTK

TYTCNVDHKPSNTKVDKRVESKYGPPCPPCPAPEFLGGPSVFLFPPKPKD

TLMISRTPEVTCVVVDVSQEDPEVQFNWYVDGVEVHNAKTKPREEQFNST

YRVVSVLTVLHQDWLNGKEYKCKVSNKGLPSSIEKTISKAKGQPREPQVY

TLPPSQEEMTKNQVSLTCLVKGFYPSDIAVEWESNGQPENNYKTTPPVLD

SDGSFFLYSRLTVDKSRWQEGNVFSCSVMHEALHNHYTQKSLSLSLGK

> light chain
                                      (SEQ ID NO: 7)
ESVLTQPPSVSGAPGQRVTISCTGSSSNIGAGYDVHWYQQLPGTAPKLLI

YGDSNRPSGVPDRFSVSKSGASASLAITGLQAEDEADYYCQSFDNSLSAY

VFGGGTQLTVLGQPKAAPSVTLFPPSSEELQANKATLVCLISDFYPGAVT

VAWKADSSPVKAGVETTTPSKQSNNKYAASSYLSLTPEQWKSHRSYSCQV

THEGSTVEKTVAPTECS
```

Example 1: Anti-ILT4 Antibody Identification and Characterization

Antibody Generation and Identification

The anti-ILT4 parental human mAb 1E1 was identified using the RETROCYTE DISPLAY platform (Breous-Nystroma et al., Methods 65(1): 57-67 (2014)). The RETROCYTE DISPLAY platform utilizes retroviral gene transfer of human antibody genes into mammalian pre-B cells to generate stable high diversity antibody display libraries. Human cord blood containing naïve B cells were used as the source material for antibody heavy and light chains. The cellular antibody libraries typically expressed>$10^8$ different full length (hIgG1-4 isotypes) monoclonal human antibodies on the cell surface of the pre-B cell.

Antibody Pre-panels were compiled from antibody hits identified in 3 separate RETROCYTE DISPLAY screening campaigns. Candidates were enriched based on FACS detection of recombinant human ILT4 antigen-binding to B-cell clones. Putative B-cell clones were sorted out and their antibody sequences determined. These sequences were then used to produce antibody candidates and ILT4 binding was confirmed using ILT4 CHO transfectant cell binding assays, with parental CHO cells serving as a negative control. Candidates were also counter-screened for ILT4 specificity against closely related ILT family members (human ILT2, LILRA1, and LILRA2 CHO transfectant FACS) and against ILT family members by flow cytometric evaluation (LILRA1, LILRA2, LILRA4, LILRA5, LILRA6, ILT2, ILT5, and ILT3).

Monoclonal antibodies were further tested for their ability to bind cynomolgous monkey ILT4 (predicted sequence from NCBI) CHO transfectants via FACS. Candidate mAbs were also screened for their ability to block recombinant HLA-G Fc ligand binding to recombinant ILT4 protein in Luminex-based assays or to ILT4-expressing CHO cells in FACS-based assays. Candidate antibody functional activity was assessed by three methods: 1) Rescue of spontaneous I L2 suppression in ILT4-transfected mouse 3A9 T-cells; 2) Rescue of HLA-G-dependent suppression of CD200RLa-stimulated mast cell degranulation in mouse WTMC ILT4 transfectants; and 3) Cytokine modulation in whole PBMC mixed lymphocyte reactions.

Based on the above screening criteria, eight anti-ILT4 antibodies (1E1, 1G2, 2A6, 2D5, 3E6, 3G7, 2C1 and 5A6) were selected based on their functional and biophysical properties. Antibodies were further analyzed and re-evaluated in a set of bio-functional, biophysical, and physicochemical assays. Functional assays assessed antibody-mediated dose-dependent rescue of I L-2 suppression of 3A9 cells and mast cell degranulation described above. Luminex and cell-based ligand blocking and ligand competition assays were performed and binding properties and affinities to the ILT4 target antigen, off-target antigens, and PBMC subsets were determined using Biacore and flow cytometry based assays, respectively. Biophysical assays assessed antibody stability (temperature, pH) and degradation and aggregation behavior. Sequence liabilities and potential post-translational modification motifs were addressed in order to exclude potential antibody production risks. Finally, candidates were tested in an in vivo, tumor regression study using SKMEL5 melanoma-challenged humanized mice.

Biophysical Properties

Studies were conducted on human 1E1 sequence (human IgG4 backbone with S228P mutation) transiently expressed in CHO cells. 1E1 presented the following physicochemical characteristics: calculated and experimentally determined isoelectric point (PI) were respectively ~7.29 and ~7.2, aggregation level (HMW species) was <5%, Tm onset>60° C., Tm1~65.2° C., Tm2~78.8° C., and was stable for at least 5 freeze/thaw cycles. The sequence of 1E1 originally had a N-glycosylation site in $V_H$-CDR2 which was successfully corrected with the S54A mutation without negative impact on binding by BIACORE and in functional assay. Stress studies showed deamidation of the N53 residue in $V_L$-CDR3 (>13% under high PH conditions). N53 was successfully corrected (N53D) without a negative impact on binding and in a functional assay (rescue of IL-2 release from ILT4 3A9 T cell transfectants with 1E1). Both N-terminal Q residues in the 1E1 $V_H$ and $V_L$ were mutated to E ($V_H$-Q1E and $V_L$-Q1E) to reduce risk of heterogeneity due to deamidation. Stress studies conducted on the mutated 1E1 sequence (1E1 $V_H$ Q1E, S54A/$V_L$ Q1E, N53D) IgG4 S228P/Lambda) showed ~17% oxidation of the W102 residue in $V_H$-CDR3 under forced oxidation with AAPH (2,2'-Azobis(2-amidinopropane) dihydrochloride) at 6 hours with minimal impact on binding and function. AAPH is used to force oxidation of Trp and Met residues. Under the same condition, ~8% oxidation of W7 in $V_H$ framework was detected with no impact on binding and function. Around 8% afucosylated antibody was detected by peptide mapping. This finding might be associated with the molecule being expressed in transiently transfected CHO cells.

Epitope Mapping

The epitope on ILT4 of the antibody clone, p1E1(G1), was identified by Hydrogen-Deuterium Exchange Mass Spectrometry. The antibody p1E1(G1) was premixed with the recombinant histidine tagged, extracellular domain of ILT4, then the complex was incubated in deuterium buffer. The amount of deuterium incorporation was measured by mass spectrometry. ILT4 residues LYREKKSASW (39-48 of ILT4 without signal sequence) (SEQ ID NO:59) and TRIRPEL (50-56 of ILT4 without signal sequence) (SEQ ID NO:60) and to less extent NGQF (59-62 of ILT4 without signal sequence) (SEQ ID NO:61) and HTGRYGCQ (71-78 of ILT4 without signal sequence) (SEQ ID NO:62) were identified as showing the largest difference in deuterium labeling compared to an antigen-only sample, indicating they are likely the residues interacting with p1E1(G1) (FIG. 1). These peptides are on domain 1 of ILT4. Other peptides on domain 1 and 2 that showed less deuterium labeling differences are likely protected due to conformational stability upon antibody binding. No significant differences in labeling were seen in domains 3 and 4.

Figure 2A:
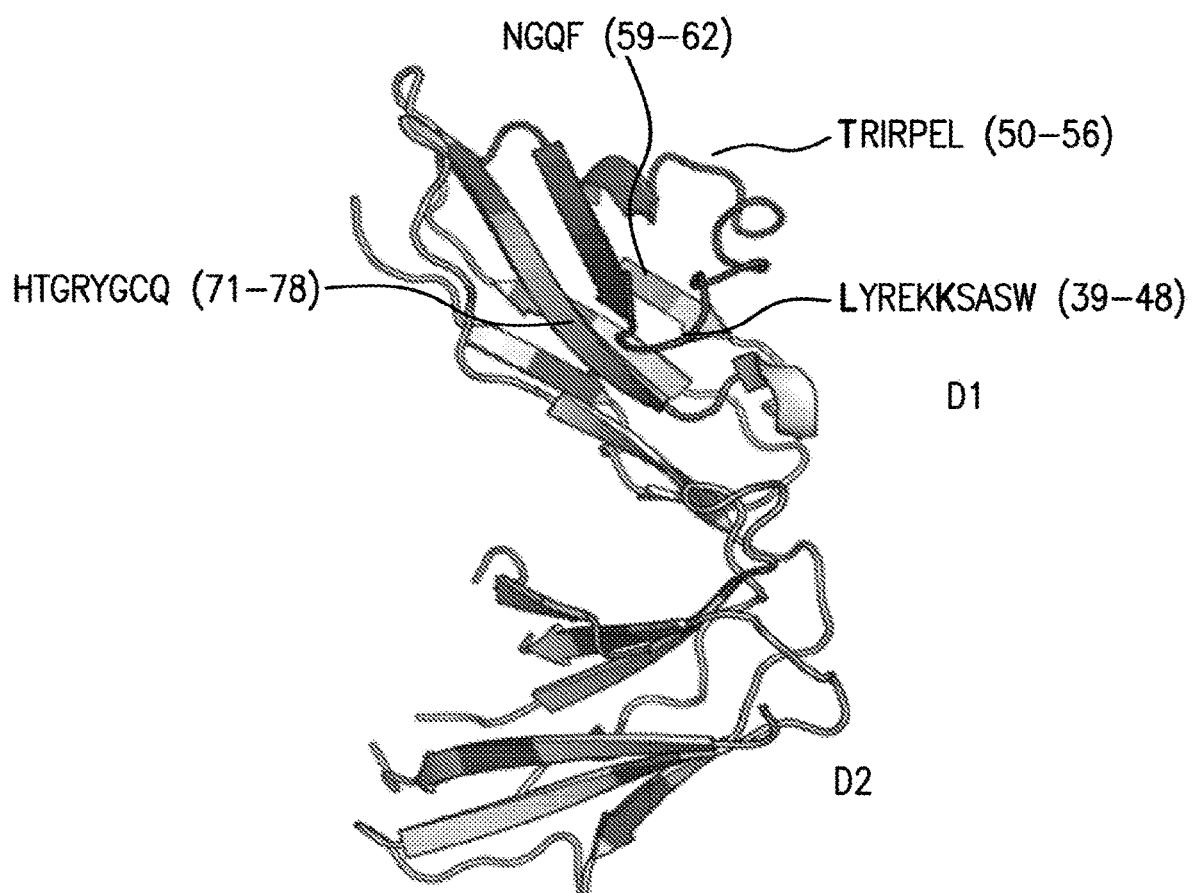
FIGS. 2A and 2B show the crystal structure of human ILT4.

When mapped onto the crystal structure of human ILT4, the residues protected by p1E1(G4) are forming non-linear conformational epitope comprising three beta-strands and a loop (FIG. 2A).

Figure 2B:
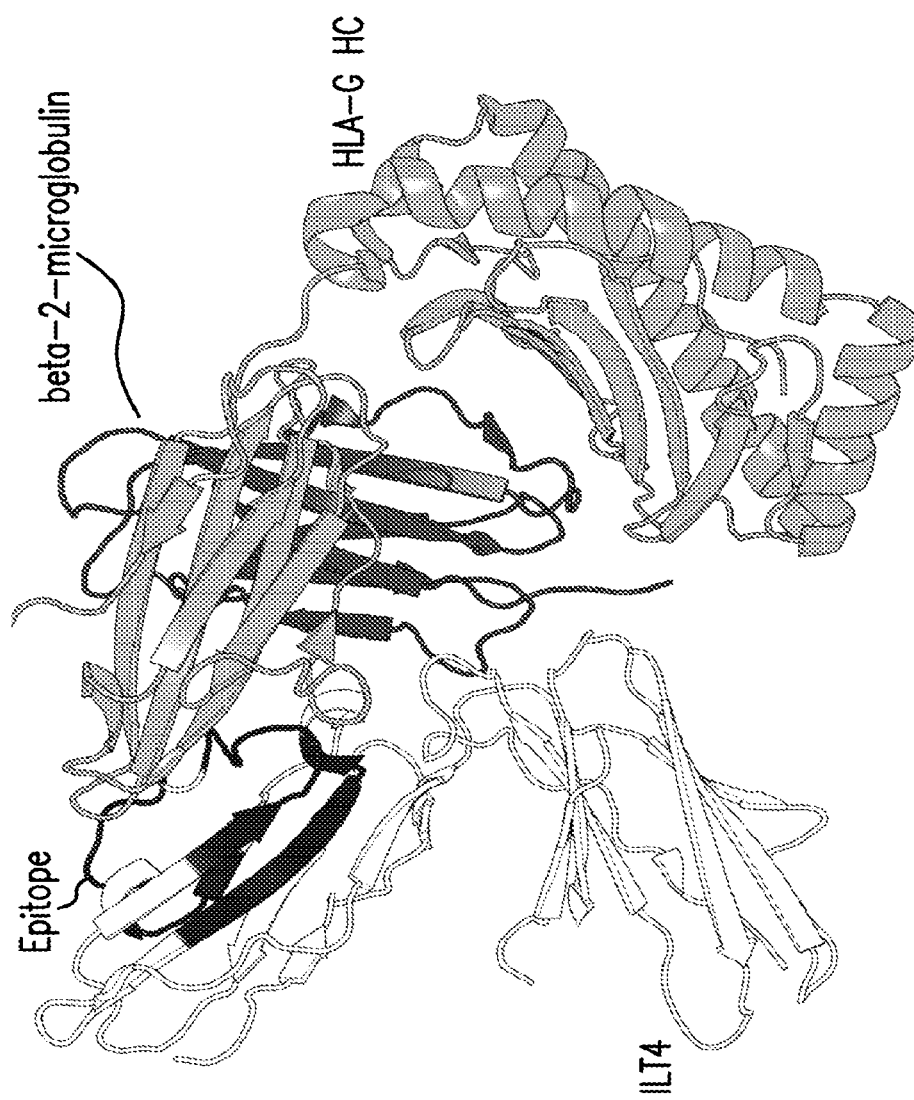

ILT4 uses two binding interfaces to engage its ligand HLA-G (Shiroishi et al, 2006): site 1 for beta-2-microglobulin binding, located in domain 2 of ILT4, and site 2 for HLA-G heavy chain binding, located in domain 1 of ILT4 (FIG. 2B). Site 1 includes ILT4 residues Trp-67, Asp-177, Asn-179, and Val-183 (numbering according to Shiroishi et al, 2006). Site 2 includes ILT4 residues Arg-36, Tyr-38, Lys-42, Ile-47, and Thr-48 (numbering according to Shiroishi et al, 2006). The HDX-MS data of this application show that Tyr-38, Lys-42, and Thr-48 (numbering according to Shiroishi et al, 2006) are part of the p1E1(G1) epitope on ILT4 domain 1 as residues Tyr-40, Lys-44, and Thr-50 of human ILT4 (FIG. 2A). This indicates that the human ILT4 epitope bound by p1E1(G1) overlaps with the site 2 epitope bound by the HLA-G ligand.

Example 2: Affinity, Binding and Blocking Properties of Anti-ILT4 mAb 1E1

Binding Affinities of 1E1(G4) and HLA-G1 to Human ILT4 Determined by Surface Plasmon Resonance (SPR)

Binding of 1E1(G4) and HLA-G1 Fc (recombinant extracellular domain of HLA-G (isoform 1) fused to the human IgG1 Fc domain to make soluble HLA-G1 protein) to ILT4-His (recombinant extracellular domain of human ILT4 fused to a poly-Histidine tag to make soluble ILT4 protein) was assessed via Biacore. Either 1E1(G4) or HLA-G1 Fc was captured on a Biacore chip via Fc capture. Monomeric ILT4-His was then tested for binding and data indicated ILT4-His bound 1E1(G4) with a greater than 600-fold higher affinity than HLA-G1 Fc (Table 3).

TABLE 3

ILT4-His binds 1E1(G4) with a greater than 600-fold tighter affinity than HLA-G1 Fc. 1:1 binding kinetics and steady-state analyses indicate 630- and 670-fold differences.

| n | Ligand | ka (1/M$^{-1}$s$^{-1}$) | kd (1/s) | K$_D$ (M) | K$_D$ Ratio |
|---|---|---|---|---|---|
| 2 | 1E1 (G4) | 5.5E+05 | 9.0E−03 | 1.7E−08 | 1 |
| 2 | HLA-G1 Fc (Kinetics) | 1.1E+05 | 1.1E+00 | 1.1E−05 | 630 |
|   | HLA-G1 Fc (SSA) | — | — | 1.1E−05 | 670 |

A surface plasmon resonance (SPR) assay on a Biacore T200 (GE HEALTHCARE) instrument was used to determine the monovalent affinities of anti-human ILT4 IgG4 mAb (1E1(G4)) and HLA-G1 Fc fusion (HLA-G1-Fc) against polyhistidine-tagged human ILT4 (ILT4-His). Either mAb or Fc fusion protein was captured on a CM5 sensor chip prepared using a Human Fc Capture kit (GE HEATHCARE) and a titrating concentration series of ILT4-His was injected over this surface. Biacore T200 Evaluation Software was used to fit each titration series to a 1:1 binding model. The association (ka, M$^{-1}$ s$^{-1}$) and dissociation (kd, s$^{-1}$) rate constants were determined for each set of titrations and used to calculate the dissociation constant, K$_D$ (M)=koff/kon, for each titration. As shown in Table 1, the monovalent affinities (K$_D$) of 1E1(G4) mAb and HLA-G1-Fc against human ILT4-His were 17 nM and 11 uM, respectively, with a 630-fold difference indicated by the K$_D$ ratio. Because of the fast ka and kd kinetics constants, steady-state approximation (SSA) was also used to confirm the low affinity of HLA-G1-Fc for ILT4-His.

Blocking of HLA-G Binding to ILT4 3A9 T Cell Transfectants with 1E1(G4)

Figure 3A:
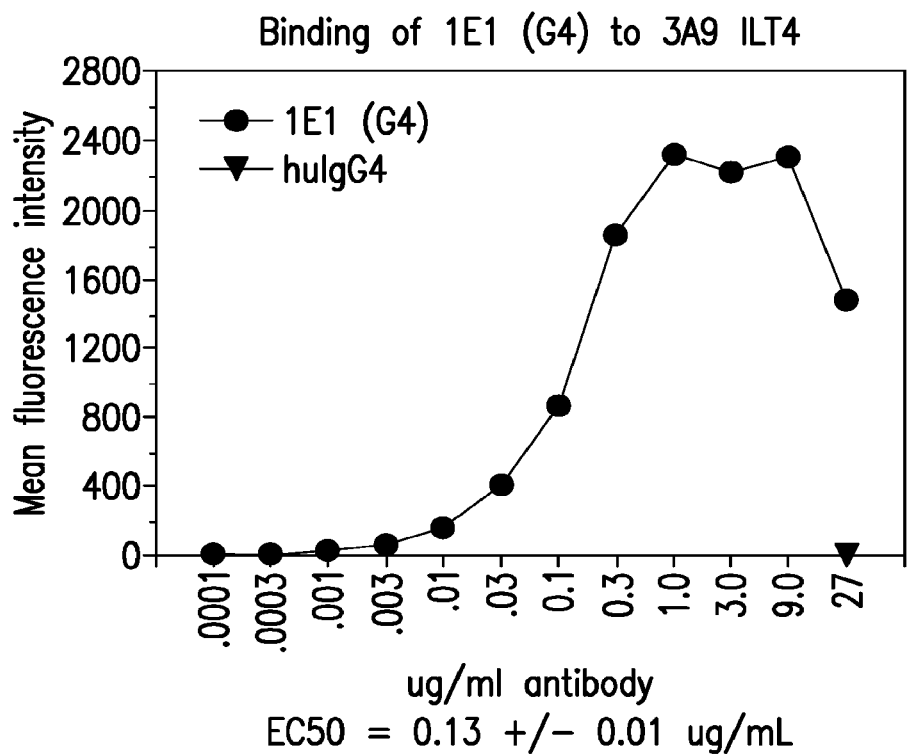
FIGS. 3A and 3B show ILT4 HLA-G binding and 1E1 (G4) blockade. Mouse 3A9 T cells transfected with human ILT4 were blocked with Fc block, then incubated with titrated concentrations of 1E1(G4) (starting at 27 ug/mL, 1:3 dilutions), or with hIgG4 isotype control (27 ug/mL).
Figure 3B:
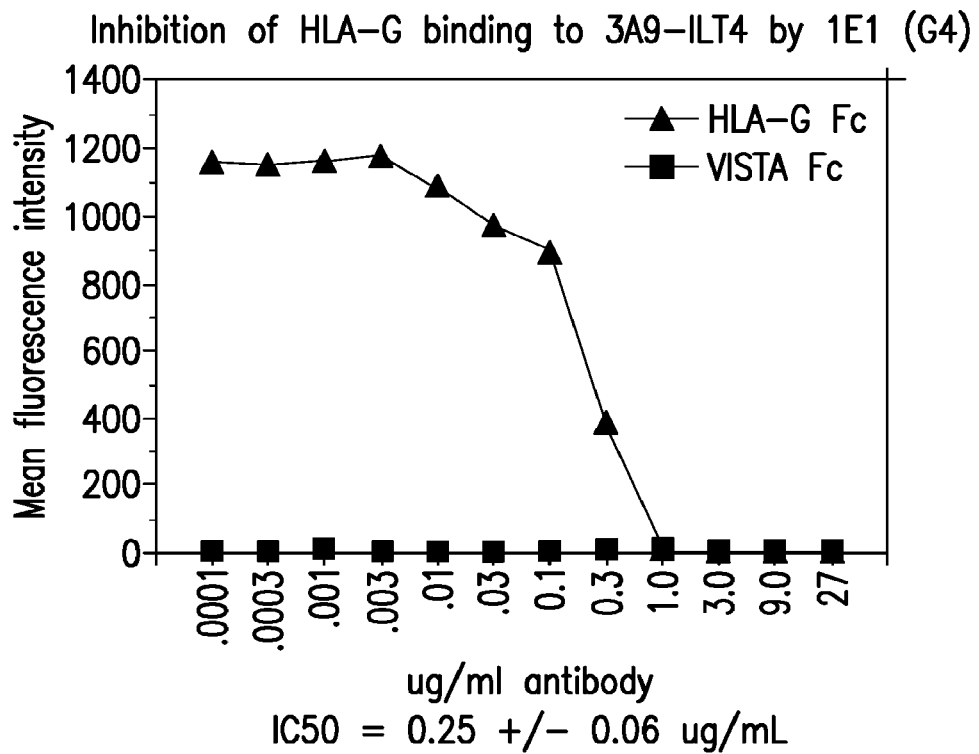

ILT4 3A9 T cell transfectants were pre-treated with 1E1 (G4) or isotype control at various doses, followed by secondary detection of 1E1(G4) (FIG. 3A) or by treatment with a fixed concentration of biotinylated HLA-G1 Fc chimera to assess the ability of 1E1(G4) to block cognate ligand (FIG. 3B). 1E1(G4) and HLA-G Fc was detected via flow cytometry. The data show 1E1(G4) blocked HLA-G1 Fc binding in a dose-dependent manner.

Luminex- and Cell-Based Ligand Blocking and Competition Assays

Antibodies 1E1, 2A6, 2C1, and 3G7 were tested in Luminex- and cell-based ligand blocking and ligand competition assays for their potential of inhibiting the interaction of recombinant dimeric HLA-G with ILT4 antigen coupled to beads or expressed by CHO/ILT4+ cells.

The Luminex based ligand blocking and competition assays used recombinant human ILT4 antigen chemically coupled to Luminex beads. In the blocking assay, the beads were pre-incubated with a dose range (0.5-9,000 ng/mL in 1:3 serial dilutions) of hIgG4 variants of the anti-ILT4 antibody 1E1, 2A6, 2C1, or 3G7. Bead-bound ILT4 antigen was then tested for binding to soluble biotinylated HLA-G/Fc fusion protein at a concentration of 50 nM. In the Luminex ligand competition assay, antigen-coupled Luminex beads were pre-incubated with soluble biotinylated HLA-G/Fc fusion protein at a concentration of 50 nM before dose-titrations (0.5-9,000 ng/mL in 1:3 serial dilutions) of hIgG4 variants of the anti-ILT4 antibody 1E1, 2A6, 2C1, or 3G7. In both assay setups, ILT4:HLA-G interaction was detected with an anti-streptavidin-PE antibody and IC$_{50}$ values were determined. All tested antibodies showed dose-dependent blocking of HLA-G binding to Luminex bead-coupled ILT4/Fc and $IC_{50}$ values are summarized in Table 4. All tested antibodies also showed dose-dependent competition with HLA-G for binding to Luminex bead-coupled ILT4/Fc (data not shown).

TABLE 4

Luminex Ligand Blocking Assay

| Antibody | IC50 (ng/mL) |
| --- | --- |
| 1E1 | 19.2 |
| 2A6 | 17.7 |
| 2C1 | 10.2 |
| 3G7 | 40.0 |

The cell-based ligand blocking and ligand competition assays followed a similar principle as described for the Luminex-based assays and used a CHO/ILT4 cell line for surface expression of the antigen. In the blocking assay, cells were pre-incubated with the tested antibody using a dose range of 1-20,000 ng/mL in 1:3 serial dilutions. ILT4 antigens were then tested for binding to soluble biotinylated HLA-G/Fc fusion protein at a concentration of 5 pg/ml. The competition assay used a reverse setup. Cells were pre-incubated with soluble biotinylated HLA-G/Fc fusion protein at a concentration of 5 pg/ml before dose titrations of the tested antibody were added in a range of 1-20,000 ng/mL in 1:3 serial dilutions. ILT4:HLA-G interaction was detected with an anti-streptavidin-PE antibody. All tested antibodies showed dose-dependent blocking of HLA-G binding to CHO-expressed ILT4 and $IC_{50}$ values are summarized in Table 5. All tested antibodies also showed dose-dependent competition with HLA-G for binding to CHO-expressed ILT4 (data not shown).

TABLE 5

Cell-based Ligand Blocking Assay

| Antibody | IC50 (ng/mL) |
| --- | --- |
| 1E1 | 98.4 |
| 2A6 | 232.6 |
| 2C1 | 56.1 |
| 3G7 | 374.3 |

Blockade of Non-HLA-G MHC Class I Ligand Binding to ILT4 3A9 T Cell Transfectants with p1E1(G1)

Figure 4:
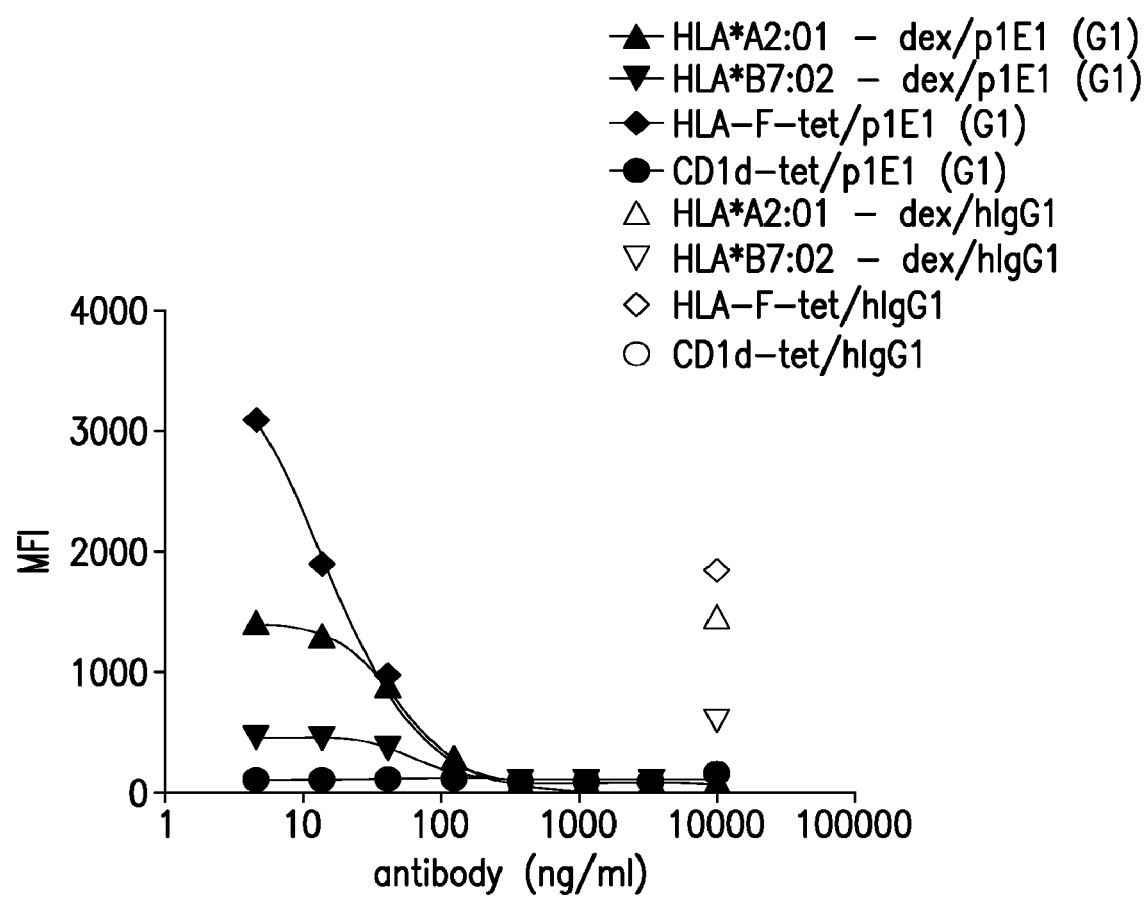
FIG. 4. Non-HLA-G MHC class I ligand binding to ILT4 and p1E1(G1) blockade. Mouse 3A9 T cells transfected with human ILT4 were pretreated with titrated concentrations of p1E1(G1) (starting at 10 ug/mL, 1:3 dilutions), or with hIgG1 isotype control (10 ug/mL) before incubation with fluorochrome labeled tetramers of HLA-F or CD1d, or fluorochrome labeled dexamers of HLA*A2:01 or HLA*B7:02. Tetramer/dexamer binding was determined by flow cytometry and the mean fluorescence intensity of each was plotted. The dilutions/concentrations used for each dexamer/tetramer are as follows: HLA*A2:01-dex PE: 1:25; HLA*B7:02-dex FITC: 1:25; CD1d-tet PE: 1:50; HLA-F-tet PE: 1 ug/mL.

ILT4 3A9 T cell transfectants were pre-treated with p1E1(G1) or hIgG1 isotype control at various doses, followed by treatment with a fixed concentration of fluorochrome labeled HLA-F or CD1d tetramers, or HLA-A02:01 or HLA*B7:02 dexamers to assess the ability of p1E1(G1) to block non-HLA-G MHC class I ligands. HLA-A, HLA-B, and HLA-F binding to ILT4 was inhibited by p1E1(G1) in a dose titratable fashion (FIG. 4), indicating the ability of p1E1(G1) to block other reported MHC class I ligands.

Blockade of ANGPTL Binding to ILT4 3A9 T Cell Transfectants with p1E1(G1)

Angiopoietin-like (ANGPTL) proteins were recently reported to bind to ILT4 expressed by human hematopoietic stem cells (Zheng et al., Nature. 2012 May 30; 485(7400): 656-60 and Deng et al. Blood. 2014 Aug. 7; 124(6):924-35). To test whether p1E1(G1) could block ANGPTL family member binding to ILT4, commercially available ANGPTL proteins or protein fragments were purchased and tested for binding to ILT4 3A9 T cell transfectants that were pre-treated with p1E1(G1). Binding data indicate that ANGPTL1, 4, and potentially 7 could bind to ILT4 and not vector control cells at the concentration of protein tested. p1E1(G1) was able to fully block ANGPTL protein binding at a saturating dose (FIG. 5).

ILT Family Specificity Binding of 1E1(G4) to Human ILT 3A9 T Cell Transfectants

Figure 6A:
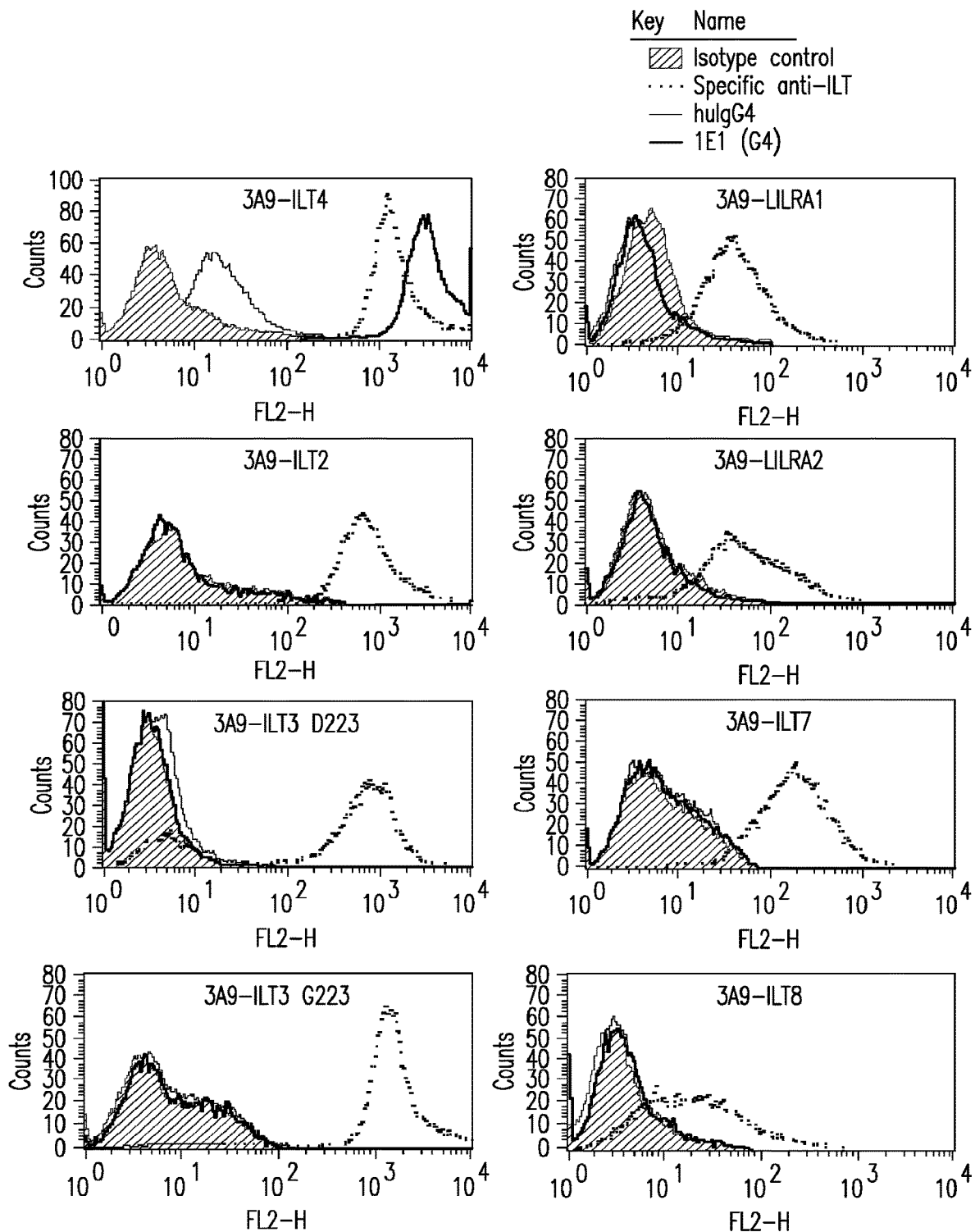
FIGS. 6A and 6B. ILT family 1E1(G4) binding specificity. Mouse 3A9 T cells transfected with human ILT family members derived from consensus sequences published in the Uniprot database were used to test binding of hIgG4 isotype control antibody or 1E1 (G4) at a fixed dose of 10 ug/mL. Vector control 3A9 T cells were used as an additional negative control. Also shown is binding of commercially available ILT-reactive antibodies compared to their respective isotype control to demonstrate ILT-family member expression. Data shown is representative of two experiments with similar results. See the legend embedded in the figure.
Figure 6B:
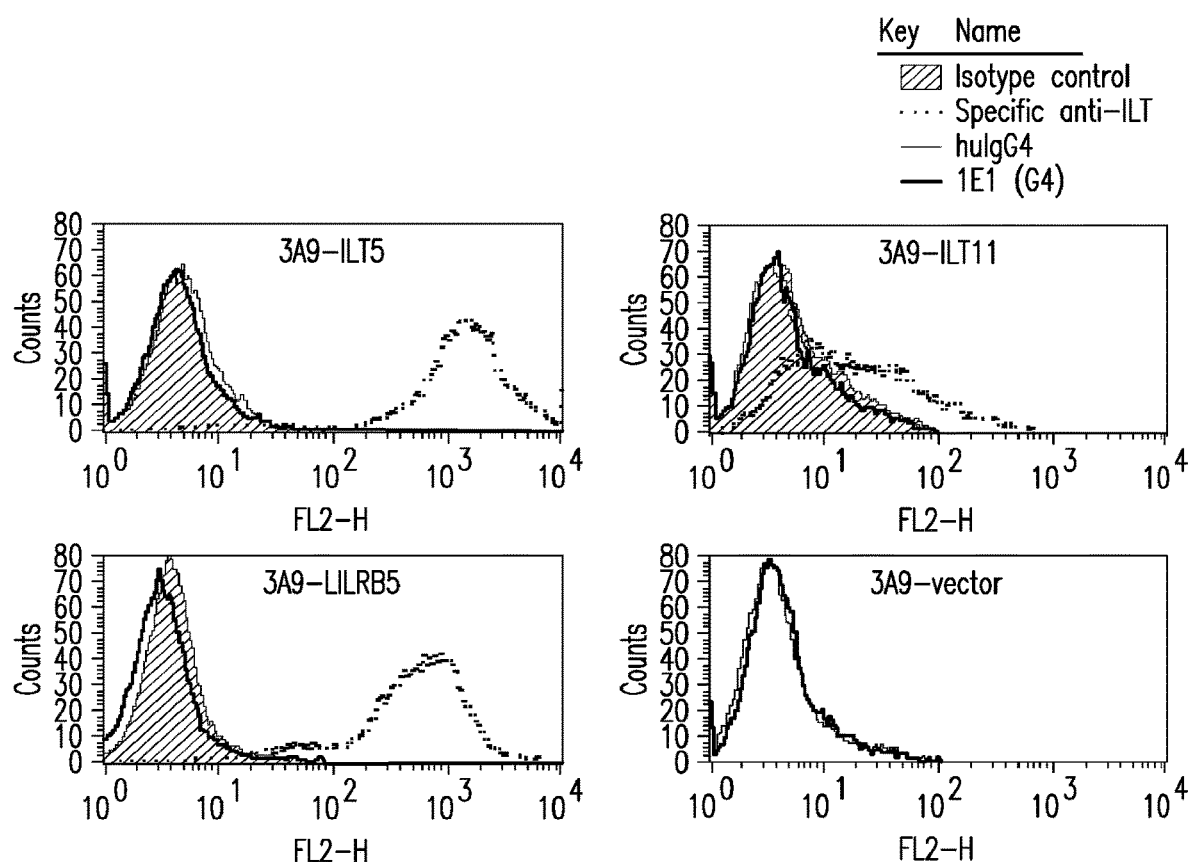

ILT family specificity binding of 1E1(G4) to human ILT family members was assessed by cell-based flow cytometry using 3A9 T cell lines transfected to express human ILT4, ILT2, ILT3 (two variants), ILT5, LILRB5, LILRA1, LILRA2, ILT7, ILT8, or ILT11. 1E1(G4) specifically bound human ILT4 and did not have cross-reactivity to any other ILT family member tested (FIGS. 6A and 6B).

Example 3: Bioactivity of Anti-ILT4 mAb 1E1 in Engineered and Primary Cells

Ability of 1E1(G4), 2A6, 2C1, and 3G7 to Reverse Interleukin 2 Suppression in Engineered ILT4 3A9 Cell-Based Assays An anti-CD3 antibody was used to stimulate control mouse 3A9 T-cells resulting in an increase of IL-2 release. In contrast, ILT4 3A9 T-cell transfectants could not express IL-2 in the presence of CD3 stimulation, possibly due to cross-reactivity with ILT4 with mouse MHC class I molecules or through an unknown xeno-ligand(s). This interaction appeared to lead to spontaneous multimerization/activation of the ILT4 receptor, resulting in suppression of the anti-CD3 mediated IL-2 release. Accordingly, antibodies that functionally bind to ILT4 and block the interaction of ILT4 with the xeno-ligand(s) and/or inhibit receptor multimerization should restore IL-release.

Figure 7:
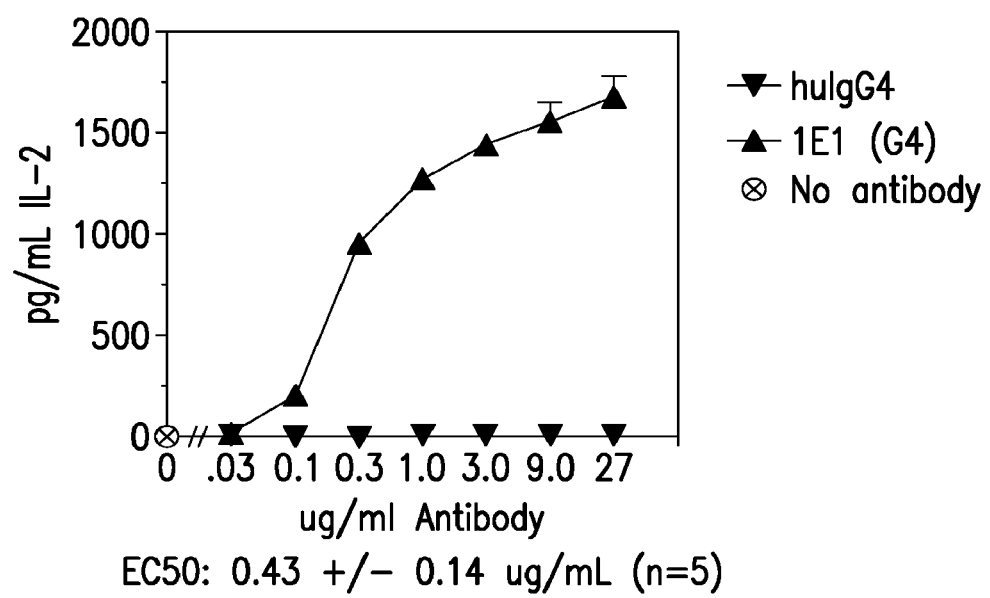
FIG. 7. Rescue of IL-2 release from ILT4 3A9 T cell transfectants with 1E1(G4). Mouse 3A9 T cells transfected with human ILT4 were treated with platebound anti-CD3 antibody in the presence of soluble 1E1(G4) or isotype control (huIgG4), starting at 27 ug/mL and serially diluted 3-fold to 0.3 ug/mL. After 24 hrs of incubation, supernatants are removed and mouse IL-2 is measured by ELISA. Plot shown is representative of 5 independent experiments. EC50 value shown is the average of these experiments+/−standard deviation.

1E1(G4), 2A6, 2C1, and 3G7 were tested for mediating IL-2 release of ILT4 mouse 3A9 T-cell transfectants. 1E1(G4), 2A6, 2C1, or 3G7 was added to ILT4+ mouse 3A9 T-cell transfectants and IL-2 release was measured photometrically by ELISA following 24 hours of anti-CD3 mediated cell stimulation. The representative dose response curve of 1E1(G4) is shown in FIG. 7. $EC_{50}$ values of the tested antibodies were determined from the dose response curves and shown in Table 6.

TABLE 6

IL-2 Repression Assay

| Antibody | EC50 (µg/mL) |
| --- | --- |
| 1E1 | 0.43 |
| 2A6 | 1.2 |
| 2C1 | 0.24 |
| 3G7 | 0.26 |

Figure 8:
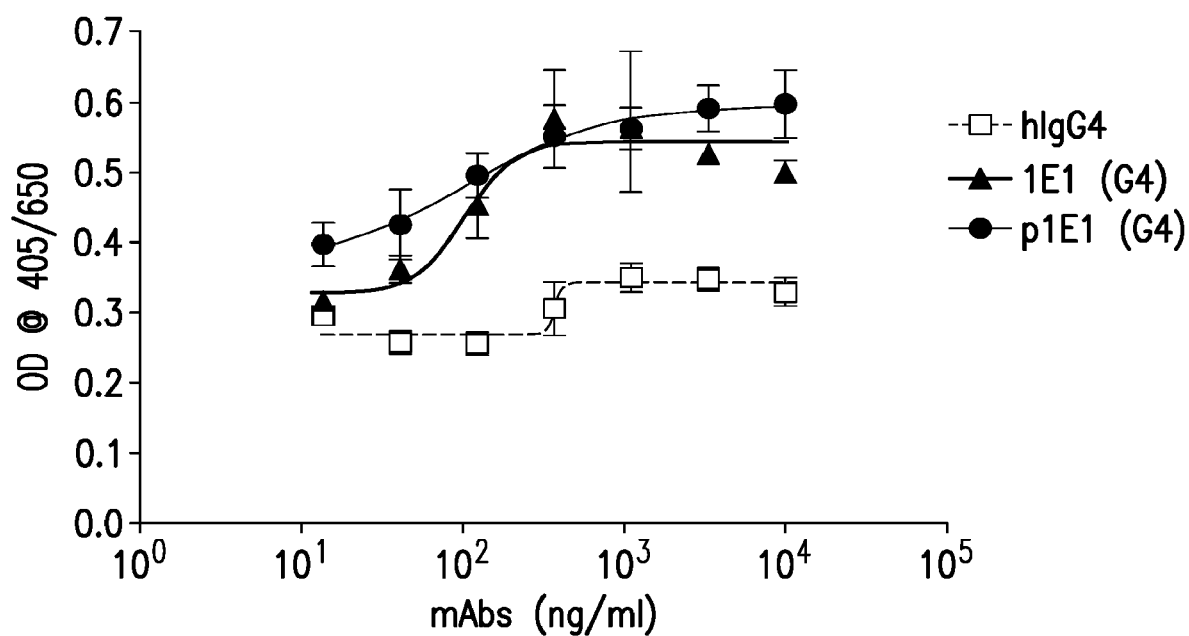
FIG. 8. p1E1(G4) and 1E1(G4) rescued ILT4:HLA-G induced suppression of mast cell degranulation. Mouse WTMC mast cells were transfected with human ILT4 and pretreated with titrated concentrations of 1E1(G4), p1E1 (G4), or hIgG4 isotype control (starting at 10 ug/mL, 1:3 dilutions) before stimulating with platebound anti-CD200Rla (Clone DX89; 1 ug/mL) and platebound HLA-G tetramer (0.625 ug/mL). Following stimulation for 1 hour, degranulation was assessed by collecting supernatants from the mast cells to measure the release of β-hexoseaminidase using a colorimetric enzymatic assay. Data shown is representative of 2 independent experiments with 3 technical replicates per data point.

WTMC (Wild-Type Mast Cell) Mouse Cell Degranulation Assay (Qualitative Only)

p1E1(G4) and 1E1(G4) were tested for rescue of ILT4:HLA-G dependent mast cell degranulation. Mouse WTMC mast cells were transfected with human ILT4 and stimulated with plate-bound antibody raised against CD200RLa. Antibody-mediated cross-linking of CD200RLa led to mast cell degranulation by activation of ITAM motifs found in the intracellular domain of CD220RLa. Degranulation can be measured colorimetrically by assaying granule content release in assay supernatants. In the presence of plate-bound HLA-G tetramer, CD200RLa-mediated mast cell degranulation was inhibited in ILT4 transfectants. Pretreatment of ILT4 WTMC transfectants with p1E1(G4) or 1E1(G4)

before stimulation with platebound anti-CD200RLa and HLA-G tetramer reversed degranulation inhibition in a dose titratable manner (FIG. 8).

Effect of 1E1(G4) on Myeloid Derived Cytokine Secretion by Primary Human Peripheral Blood Mononuclear Cells (PBMC)

Assessment of 1E1(G4) in Human Primary PBMC LPS Stimulation Assays

Figure 9A:
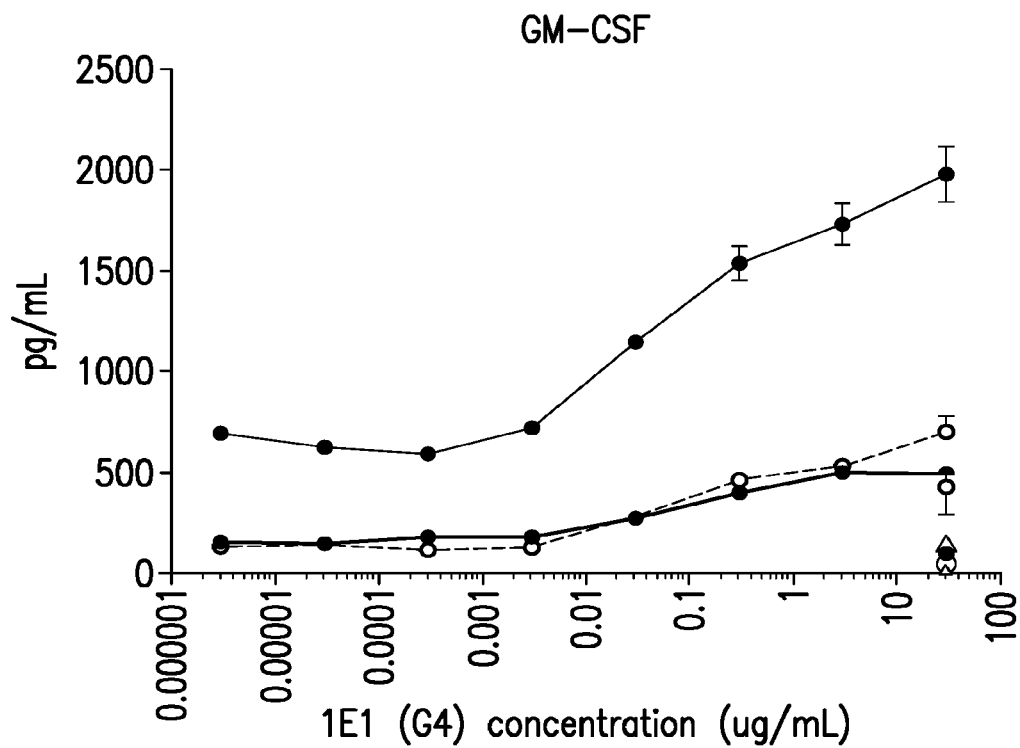
FIGS. 9A and 9B. 1E1(G4) enhanced LPS-induced expression of pro-inflammatory myeloid cytokines. Whole PBMCs from healthy patients were isolated from leukoreduction chambers and treated with 0.25 ug/mL LPS in the presence of either hIgG4 (30 ug/mL; open circles) or 1E1 (G4) (marked as "1E1" in figure) (between 30 ug/mL and 3 pg/mL; closed circles) for 3 days. Following stimulation, supernatants were assayed for cytokine expression ((FIG. 9A) GM-CSF and (FIG. 9B) TNFa) using a Meso Scale Discovery multi-cytokine assay kit. Each color represents data from an individual patient. Conditions without any stimulation are also shown (closed triangles).
Figure 9B:
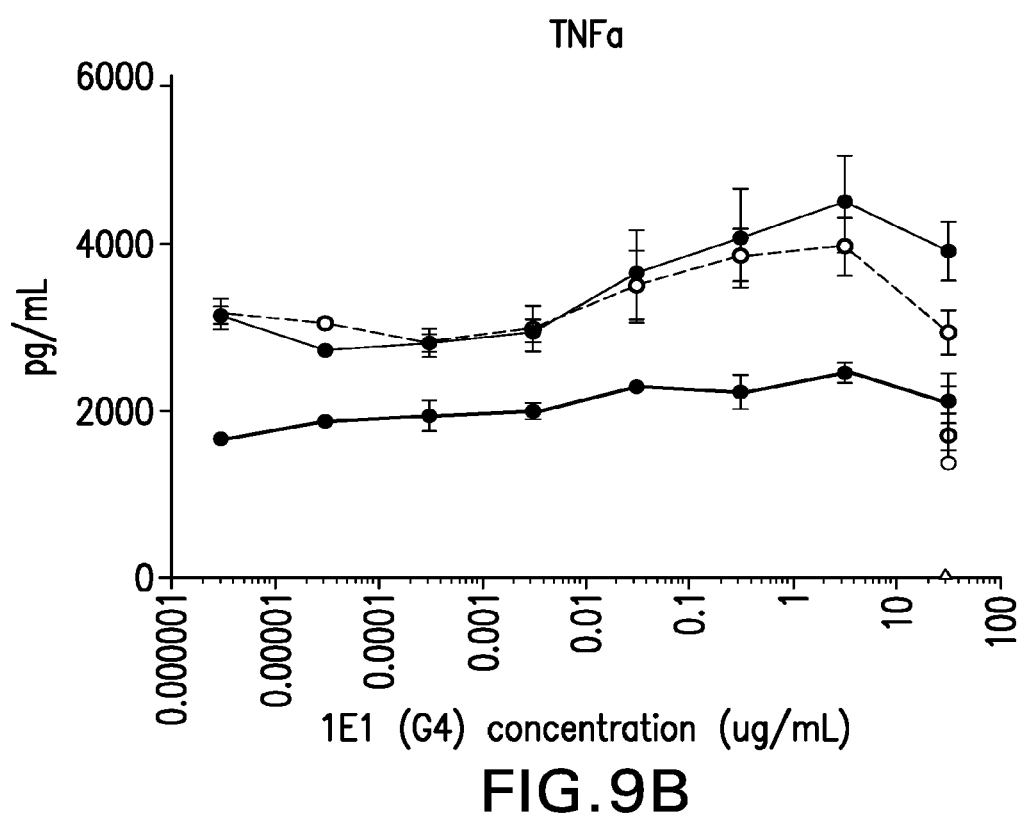

Expression of TNFa, a prototypical myeloid derived proinflammatory cytokine, was reported to be expressed by monocytes expressing low levels of ILT4 when stimulated with LPS. Monocytes with high expression of ILT4 did not express as much TNFa, and the lack of ILT4 expression was found to be a hallmark of monocytes isolated from patients with psoriatic arthritis (Bergamini et al., PLoS One. 2014 Mar. 27; 9(3):e92018). ILT4 expression on monocytes could inhibit myeloid cell effector activity and antagonize proinflammatory cytokine induction (e.g., TNFα) in the presence of proinflammatory stimuli (e.g., LPS). As such, whole PBMCs isolated from healthy human donors were treated with LPS and the ability of ILT4 antagonism to enhance proinflammatory myeloid cytokine expression was evaluated with 1E1(G4). FIGS. 9A and 9B show data from one of three experiments, with 3 donors each, demonstrating that 1E1(G4) enhanced LPS-dependent expression of both GM-CSF and TNFa (both myeloid-derived cytokines) in a dose titratable fashion.

Assessment of 1E1(G4) in Human Primary PBMC Anti-CD3 Stimulation Assays

Figure 10A:
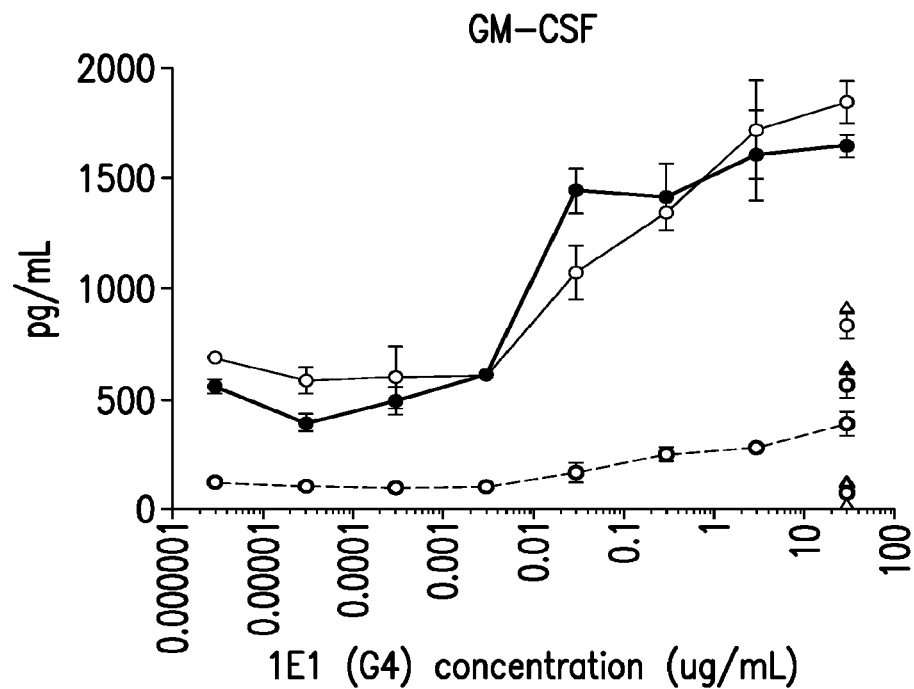
FIGS. 10A and 10B. 1E1(G4) enhanced anti-CD3-induced expression of pro-inflammatory myeloid cytokines. (A-B) Whole PBMCs from healthy patients were isolated from leukoreduction chambers and treated with 0.01 ug/mL anti-CD3 (HIT3a) in the presence of either hIgG4 (30 ug/mL; open circles) or 1E1(G4) (marked as "1E1" in figure) (between 30 ug/mL and 3 pg/mL; closed circles) for 3 days. Following stimulation, supernatants were assayed for cytokine expression ((FIG. 10A) GM-CSF and (FIG. 10B) TNFa) using a Meso Scale Discovery multi-cytokine assay kit. Each color represents data from an individual patient. Conditions without any stimulation are also shown (closed triangles).
Figure 10B:
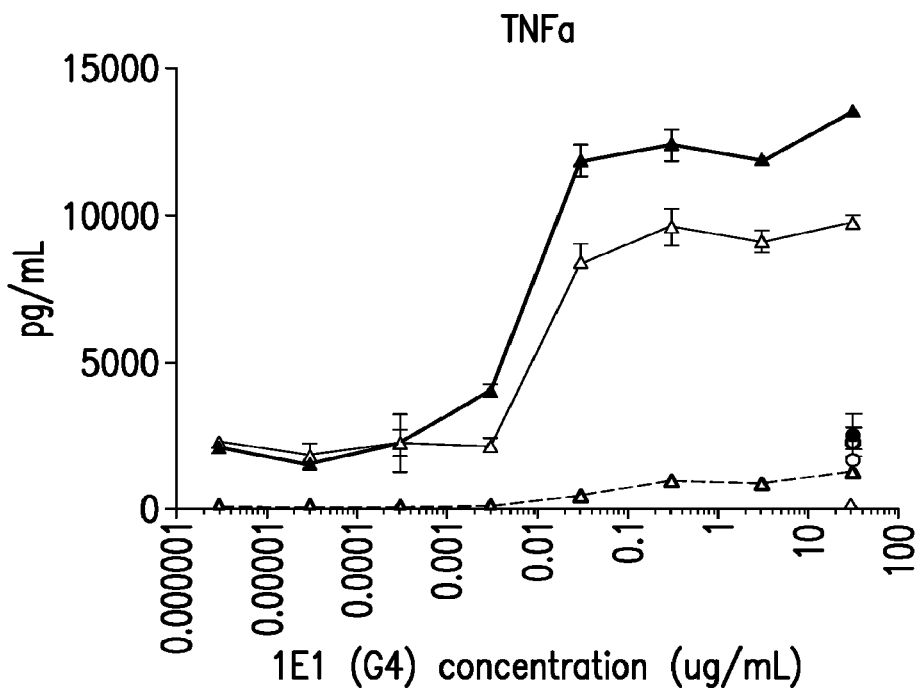

To assess whether 1E1(G4) treatment could enhance T-cell or myeloid effector cytokine expression in the presence of a sub-optimal T cell stimulus, whole PBMCs isolated from healthy human donors were treated with anti-CD3 to induce T-cell proliferation, and the ability of ILT4-antagonism to modify cytokine expression was evaluated with 1E1(G4). FIGS. 10A and 10B show data from one of three experiments, with 3 donors each, demonstrating that 1E1(G4) enhanced anti-CD3 dependent expression of GM-CSF and TNFa in a dose titratable fashion.

Figure 17:
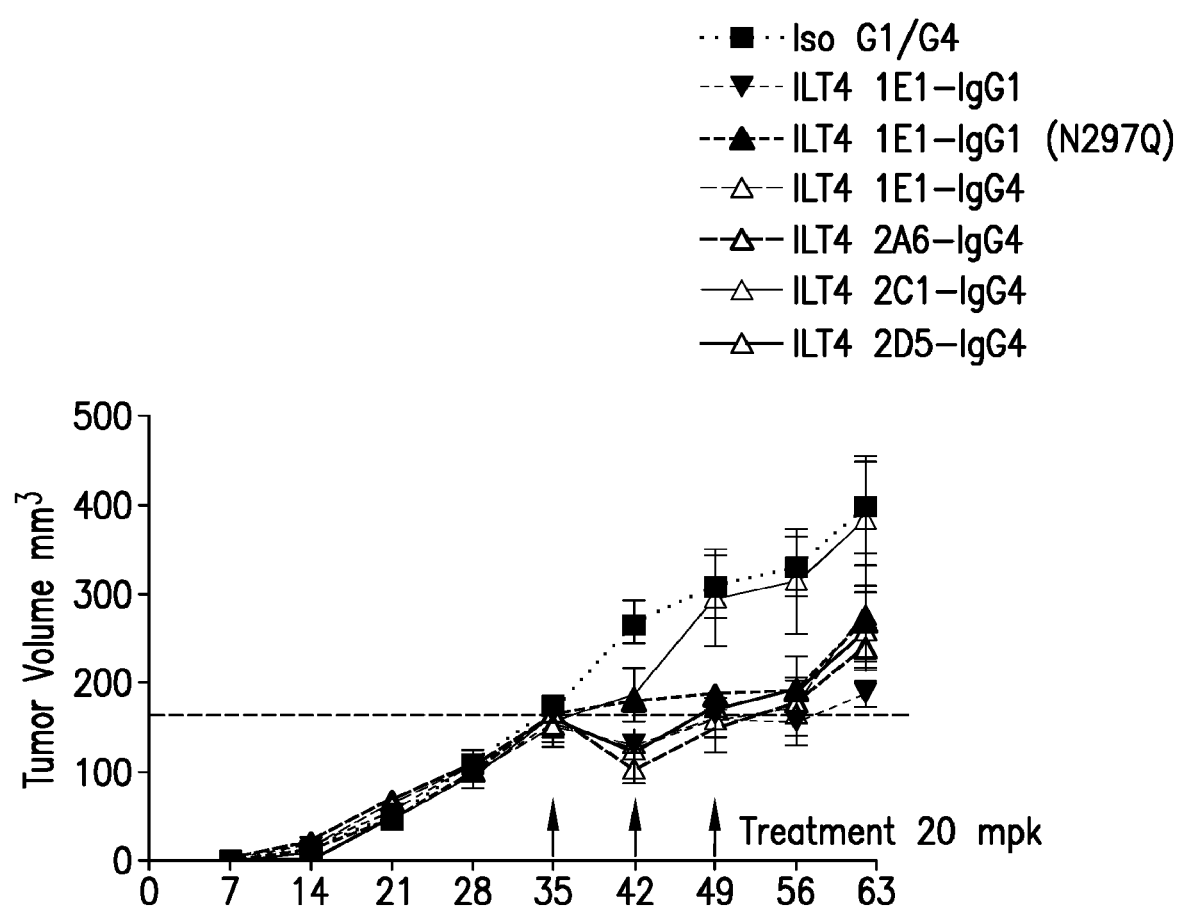
FIG. 17 shows anti-tumor efficacy of various anti-ILT4 antibodies in a humanized mouse SK-MEL-5 tumor model.

Example 4: Anti-Tumor Efficacy of Anti-ILT4 Antibodies in the Humanized Mouse SK-MEL-5 Tumor Model Anti-Tumor Efficacy of 1E1, 2A6, 2C1, and 2D5 in the Humanized Mouse Tumor Model Antibodies 1E1, 2A6, 2C1 and 2D5 were tested in an in vivo tumor regression assay. Humanized mice (NSG mice reconstituted with human hematopoeitic stem cells to establish human immune cell constitution) were inoculated with $1 \times 10^6$ SKMEL5 melanoma cells (HLA class A*02:01) and tumor growth was monitored until an average size of 150 mm³ after approximately 35 days was observed. Seven randomized groups of mice, each containing six animals, were subcutaneously dosed with isotype control antibody (hIgG1+hIgG4, 20 mg/kg of each), or 20 mg/kg of of either of the following anti-ILT4 antibodies: 1E1-IgG1, 1E1-IgG1 (N297Q) (Fc null mutant), 1E1-IgG4, 2A6-IgG4, 2C1-IgG4, and 2D5-IgG4. Mice were dosed every seven days (day 35, 42, and 49; total of three doses) and tumor size was measured until day 63. Results indicated impaired tumor growth in mice treated with 1E1 (IgG1, IgG1-(N297Q), IgG4), 2A6-IgG4, and 2D5-IgG4 compared to animals dosed with the isotype control (FIG. 17). In contrast, mice treated with either isotype control or anti-ILT4 candidate 2C1 failed to demonstrate impaired tumor growth.

Anti-Tumor Efficacy of p1E1(G4) in the Humanized Mouse Tumor Model

A humanized mouse tumor model was developed to test in vivo efficacy of p1E1(G4) for tumor growth inhibition. Immuno-deficient NSG mice were reconstituted with human hematopoietic stem cells. After mice were confirmed to harbor peripheral human CD45+ immune cells (≥25% of PBMCs), they were inoculated with SK-MEL-5 tumor cells, a human skin melanoma derived tumor line. These cells were selected for their genetic expression of HLA-G. Following inoculation, tumors were allowed to grow to an approximate size of 150 mm³. Mice were randomized into groups and challenged with either hIgG4 isotype control or p1E1(G4).

Figure 11A:
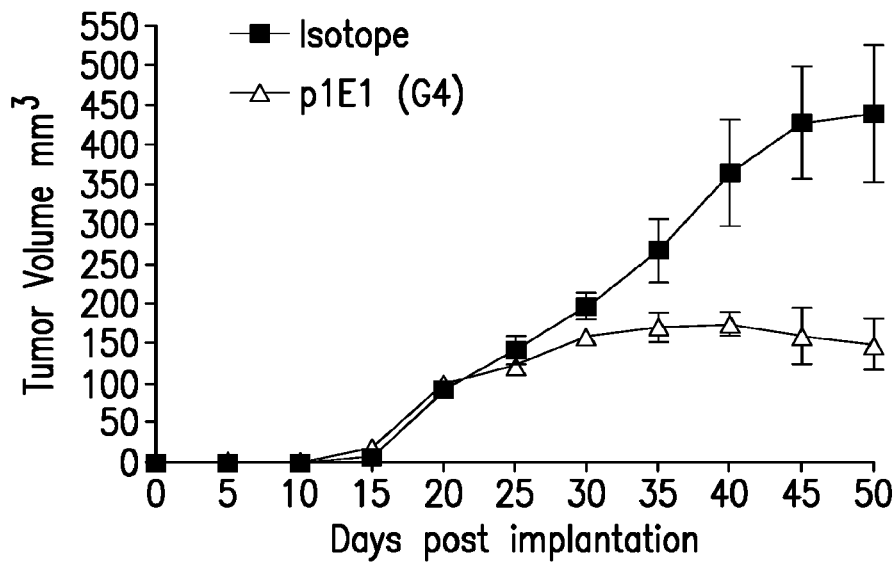
FIGS. 11A-11E. p1E1(G4) treatment leads to tumor growth inhibition in a humanized mouse SKMEL5 tumor model. CD34+Cord blood-engrafted humanized NSG mice, from 2 different cord blood donors, were subcutaneously inoculated with 1×10$^6$ SKMEL5 tumor cells in their left flanks. Following inoculation, tumors were allowed to grow and those which reached an average size of 150 mm$^3$ were randomized into groups of 6 (3 from each stem cell donor, n=6 per group total). Mice were then challenged with either hIgG4 isotype control or p1E1(G4) (20 mgs/kg each) every 5 days, with tumors and weights measured weekly, until the end of the study. Tumor growth in the isotype control and p1E1(G4) treated mice were tracked over time.
Figure 11B:
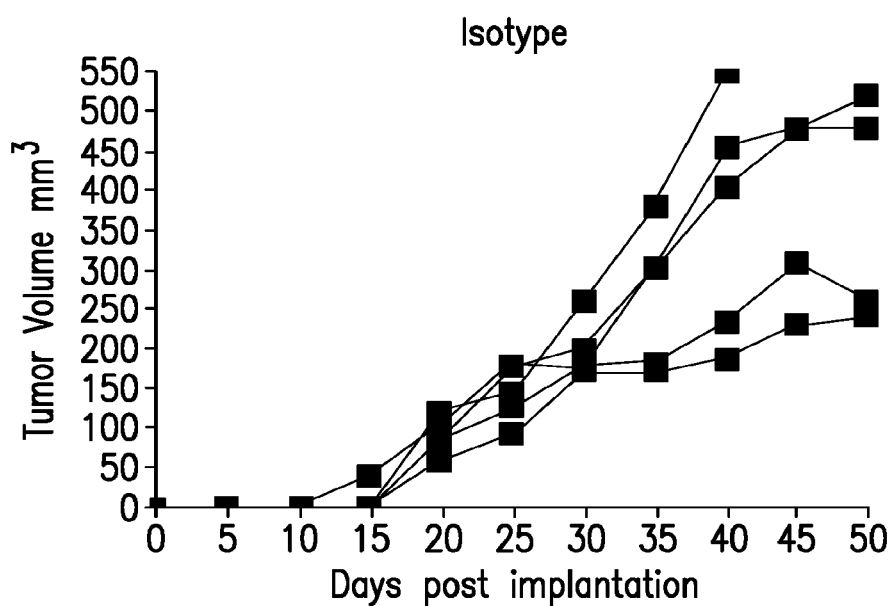
Figure 11C:
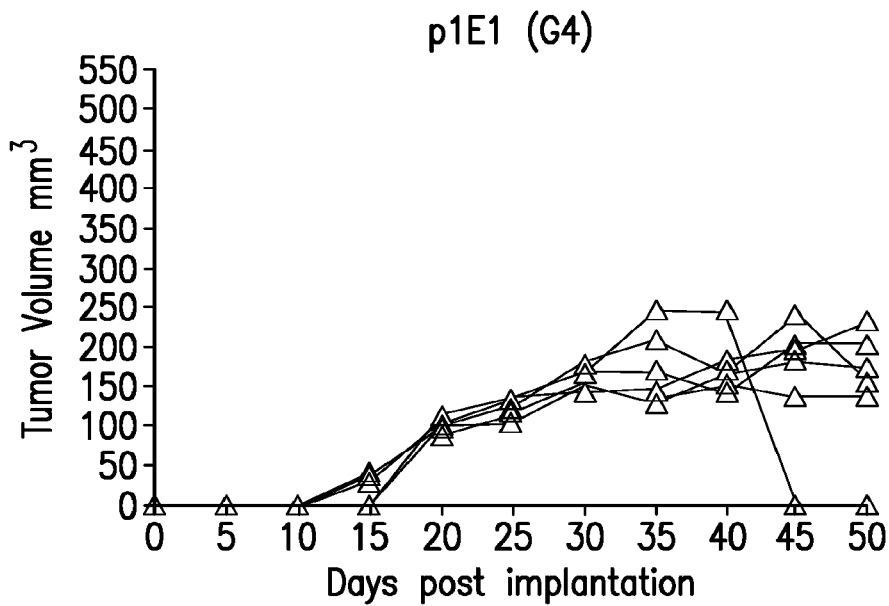
Figure 11D:
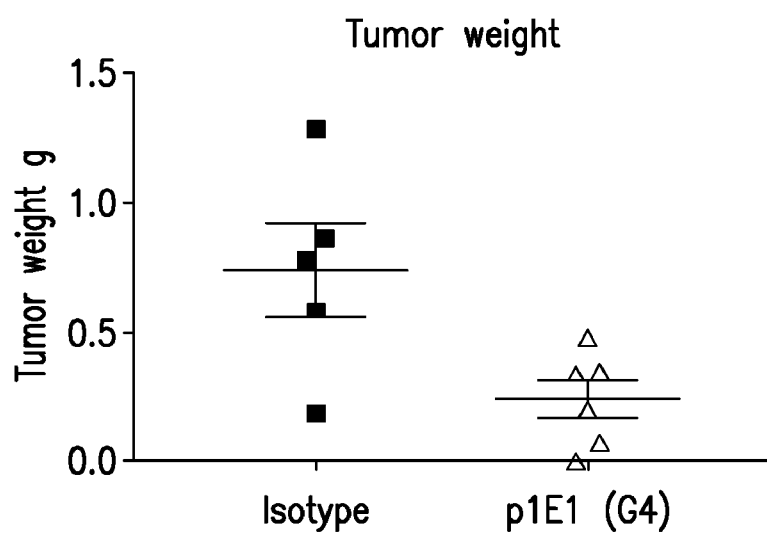
Figure 11E:
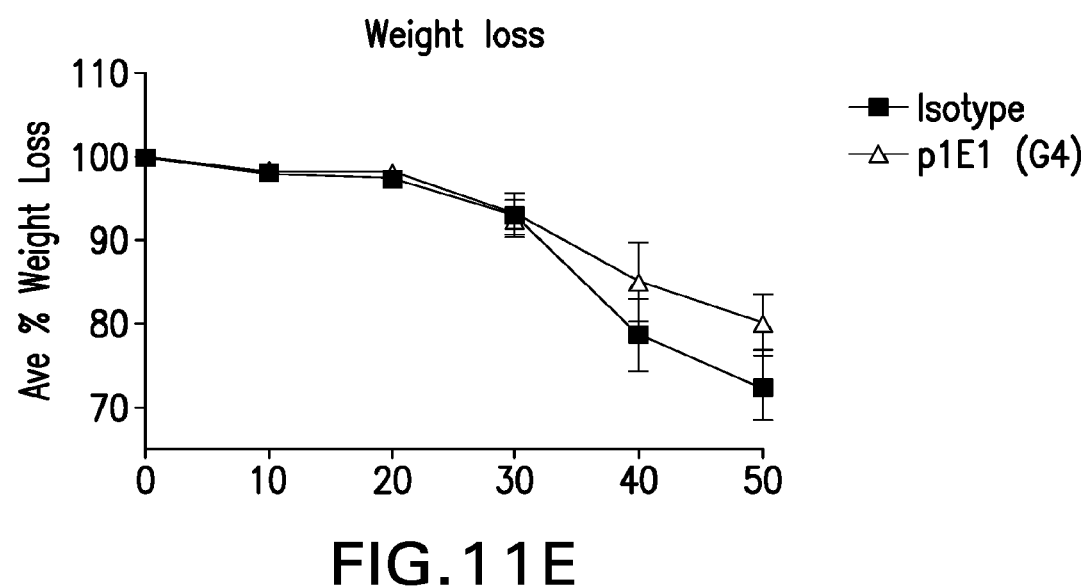

Mice treated with p1E1(G4) displayed tumor growth inhibition over the course of the study (FIG. 11A). One complete and one partial regression were observed with p1E1(G4) (FIG. 11C).

Anti-Tumor Efficacy of 1E1(G4) in the Humanized Mouse Tumor Model

The anti-tumor activity of 1E1(G4) was tested in the humanized mouse SK-MEL-5 tumor model. In this model, immunodeficient NSG (NOD·Cg-Prkdc$^{scid}$//2rg$^{tm1Wji}$/SzJ) mice are irradiated and injected with human CD34+ hematopoietic stem cells isolated from umbilical cord blood. After several months of engraftment, human immune cells can be detected in mouse blood. The mice were then implanted subcutaneously (SC) with the human melanoma-derived SK-MEL-5 cell line.

For this study, NSG mice transplanted at 3 to 4 weeks of age with human cord blood-derived CD34+ cells from 3 separate donors were injected SC with $1 \times 10^6$ SK-MEL-5 cells at approximately 20 weeks of age. Humanized NSG mice bearing SK-MEL-5 tumors were assigned to 2 treatment groups at 6 mice per group (3 mice from each human CD34+ donor cohort per treatment group) when mean tumor size was approximately 100 mm³, 21 days following tumor inoculation (DO tumor randomization). Tumor-bearing mice were injected SC with 20 mg/kg 1E1(G4) or a hIgG4 isotype control mAb every 7 days for 4 doses. Tumor volumes were monitored every 7 days following the initiation of treatment. Anti-tumor efficacy in the 1E1(G4) treatment group was significantly greater than the isotype control group (p 0.001 from Day 28 through Day 49) (FIG. 12A). The endpoint tumor weight in 1E1(G4)-treated mice was lower than that in isotype-treated mice (FIG. 12C). Overall, the results revealed significant anti-tumor efficacy of 1E1(G4) at 20 mg/kg in the humanized mouse SK-MEL-5 tumor model. No effect was observed on body weight (FIG. 12B) and splenic weight (FIG. 12D) with 1E1(G4) treatment.

Figure 13:
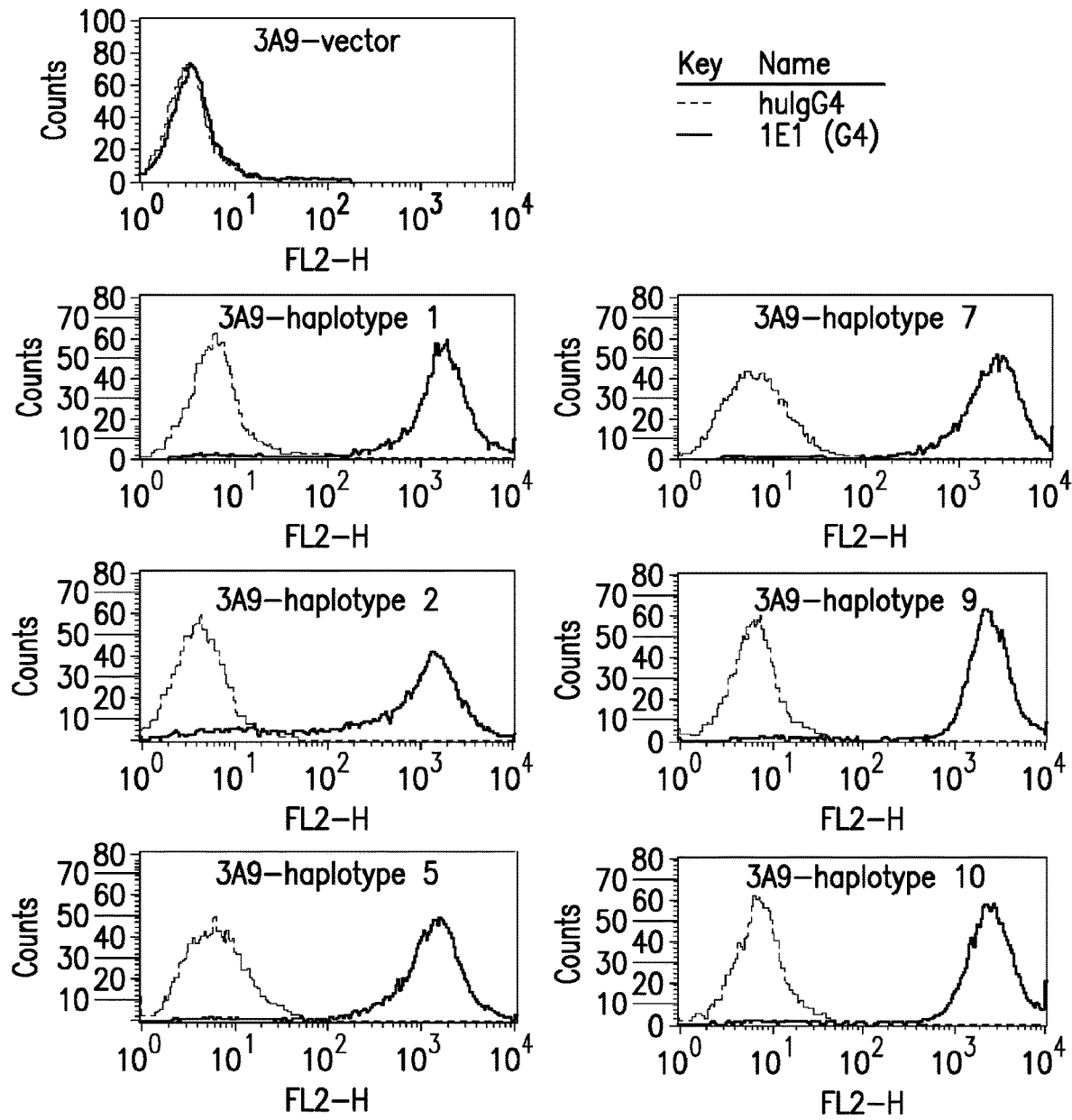
FIG. 13. ILT4 haplotype binding. Mouse 3A9 T cells transfected with human ILT4 allelic variants were used to test binding of hIgG4 isotype control antibody or 1E1(G4) at a fixed dose of 10 ug/mL. Vector control 3A9 T cells were used as an additional negative control. Haplotypes are explained in Table 2. Data shown is representative of two experiments with similar results.

Example 5: ILT4 Haplotype Binding of 1E1(G4) to Human ILT 3A9 T Cell Transfectants Single nucleotide polymorphism data from publicly available sources (1K Genome Project Phase 3) was used to determine ILT4 allelic frequencies for African, European, Asian, and South Asian populations. Sequences for haplotypes that were expressed with a 5% or greater prevalence in any population (haplotypes 1, 2, 5, 7, 9 and 10 in Table 7) were determined and expressed in 3A9 T cells. 1E1(G4) bound all haplotypes tested using saturating doses of the antibody (FIG. 13). Haplotype 2 corresponded to the consensus sequence reported in Uniprot. Haplotype 5 was used in functional and ligand-based assays. Haplotype binding data indicates that 1E1(G4) binds all major allelic variants tested.

TABLE 7

Haplotype frequencies for ILT4 across human populations.

| Haplotype | | rs373032 p.Glu61Asp c.483A > T | rs386056 p.Val235Met c.703G > A | rs7247538 p.His300Tyr c.898C > T | rs7247451 p.Cys306Trp c.918C > G | rs1128646 p.Arg322His c.965G > A | Haplotype frequencies by ethnicity | | | | SOUTH ASIAN |
|---|---|---|---|---|---|---|---|---|---|---|---|
| | | | | | | | All | AFRICAN | EUROPEAN | ASIAN | |
| 1 | ATGGC | D | M | H | C | R | 0.23 | 0.09 | 0.15 | 0.60 | 0.15 |
| 2 | TCGGC | E | V | H | C | R | 0.14 | 0.04 | 0.22 | 0.08 | 0.28 |
| 3 | ATAGC | D | M | Y | C | R | | | 0.03 | | |
| 4 | TCGCC | E | M | H | W | R | | | 0.02 | | |
| 5 | ACACT | D | V | Y | W | H | 0.30 | 0.17 | 0.58 | 0.08 | 0.37 |
| 6 | ACACC | D | V | Y | W | R | 0.02 | 0.04 | | | 0.02 |
| 7 | ACGCT | D | V | H | W | H | 0.02 | 0.06 | | | |
| 8 | ACGGT | D | V | H | C | H | | 0.02 | | | |
| 9 | ACGCC | D | V | H | W | R | 0.02 | | | 0.01 | 0.11 |
| 10 | ACGGC | D | V | H | C | R | 0.23 | 0.54 | | 0.20 | 0.06 |
| f(SNP) | | 0.80 | 0.24 | 0.45 | 0.46 | 0.46 | | | | | |

*Haplotypes for each population were based on the phase 3 data from the 1000 genome project and were determined using PLINK to analyze non-synonymous SNPs listed in the EXAC database.

Figure 14A:
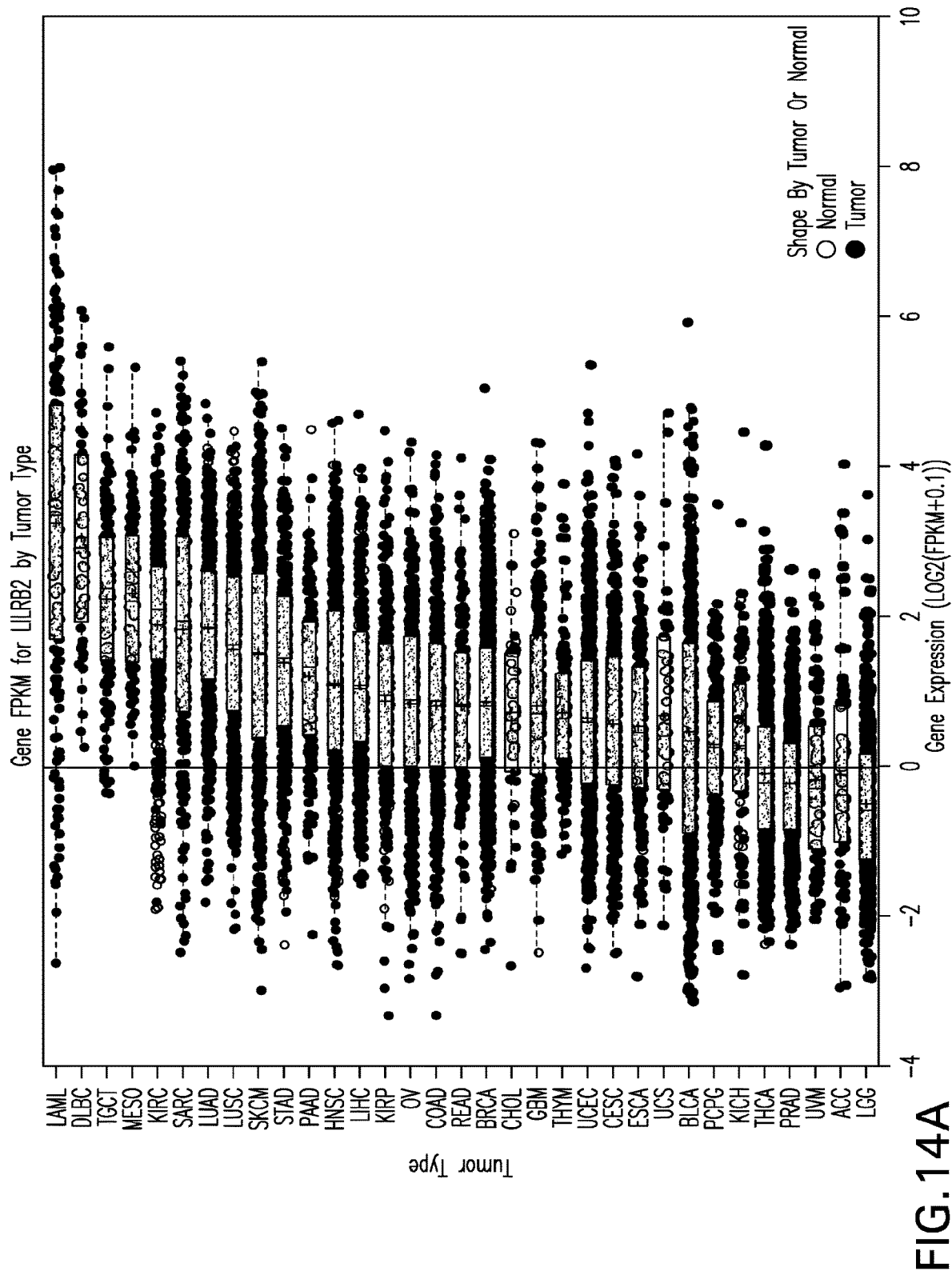
FIGS. 14A and 14B. ILT4 RNA expression in different tumor types or cell types according to public databases.
Figure 14B:
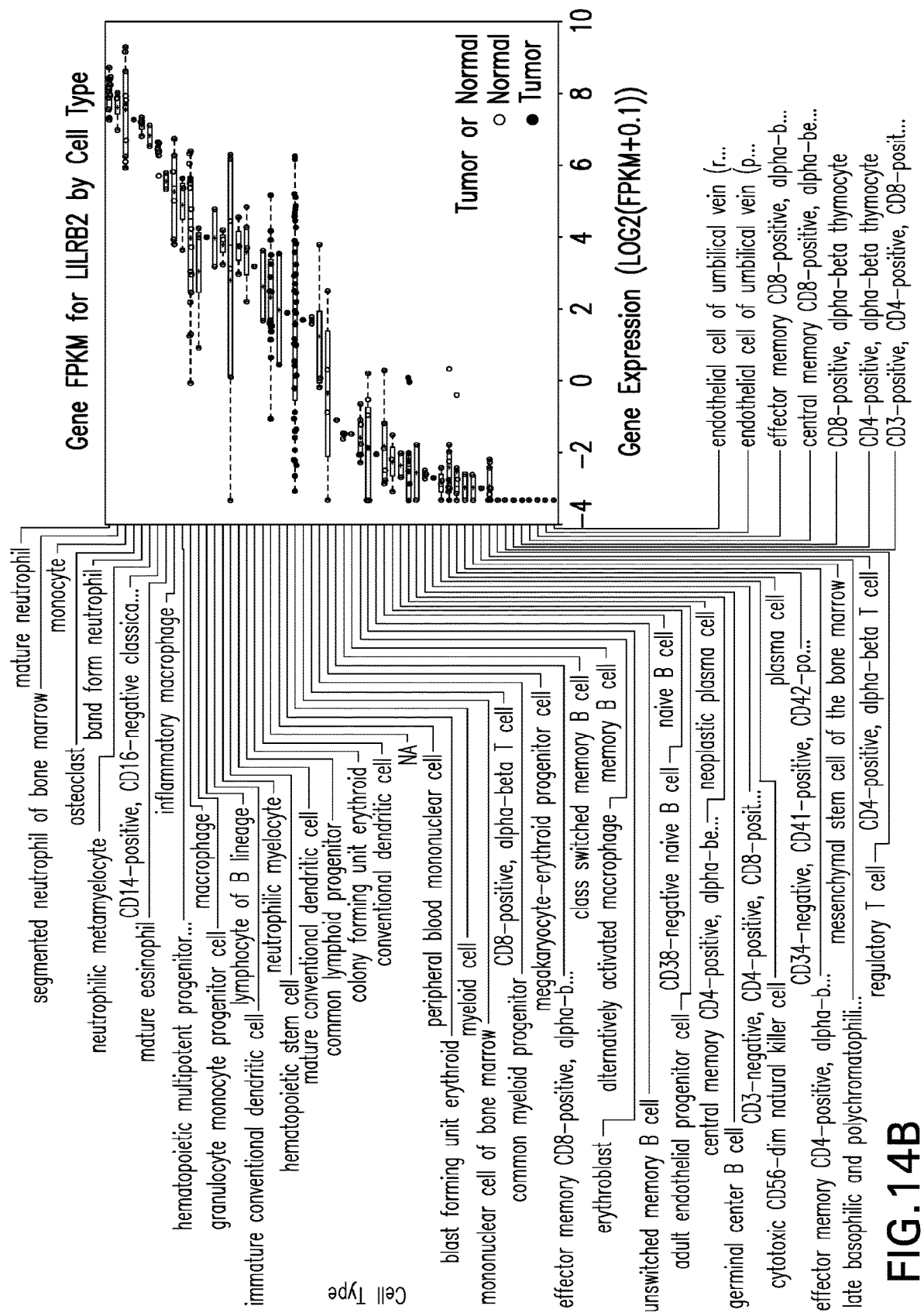

Example 6: RNA Expression of ILT4 in Tumor and Cell Types Based on TCGA and Blueprint Databases Expression of ILT4 across tumor types and cell populations was determined using publicly available RNAseq datasets, through Omicsoft (Qiagen, Cary, NC). The TOGA dataset (TCGA_B38_20171002_v4, https://gdc-portal.nci.nih.gov/) is comprised of 11,292 samples with RNA-Seq data. The Blueprint dataset (Blueprint_B38_20170216_v2, http://www.blueprint-epigenome.eu/) is comprised of 258 normal blood samples from 55 cell types with RNA-Seq data. The tumor types with highest expression of ILT4, at the RNA level, include LAML (i.e., AML), DLBC (i.e., DLBCL), TGCT, MESO, KIRC (FIG. 14A). The cell types with highest expression of ILT4, at the RNA level, include neutrophils, monocytes, osteoclasts, eosinophils, macrophages, and dendritic cells (FIG. 14B). Lymphocytes had low to no expression of ILT4, in this dataset. FPKM of 1 (or LOG2(FPKM+0.1) of 0) is the most widely accepted heuristic fixed threshold, although lower FPKM values could report on "low expressed" genes within a sample.

Figure 15A:
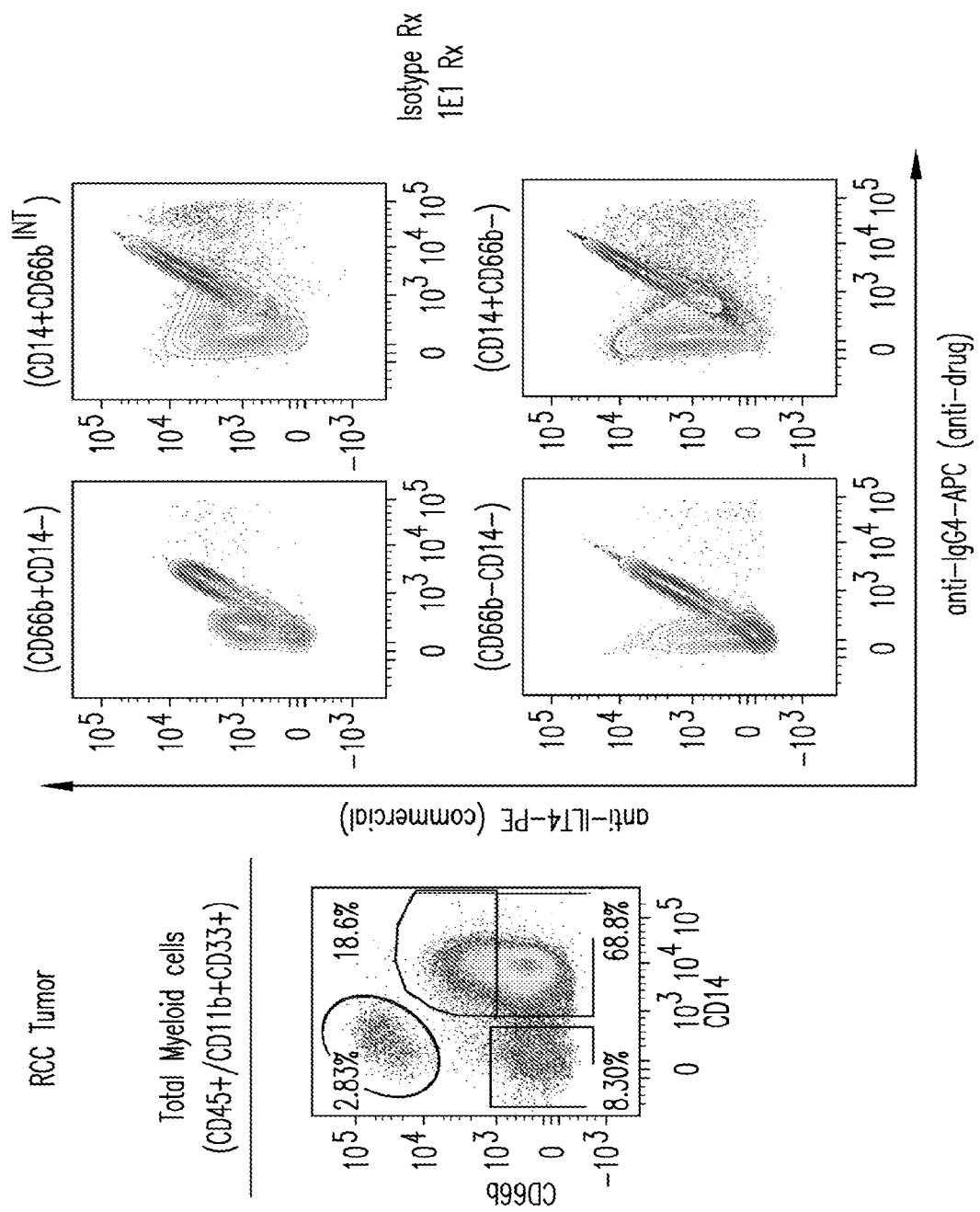
FIGS. 15A and 15B show 1E1(G4) binding to myeloid cells from renal cell carcinoma (RCC) (FIG. 15A) and colorectal cancer (CRC) (FIG. 15B) tumor histoculture samples.
Figure 15B:
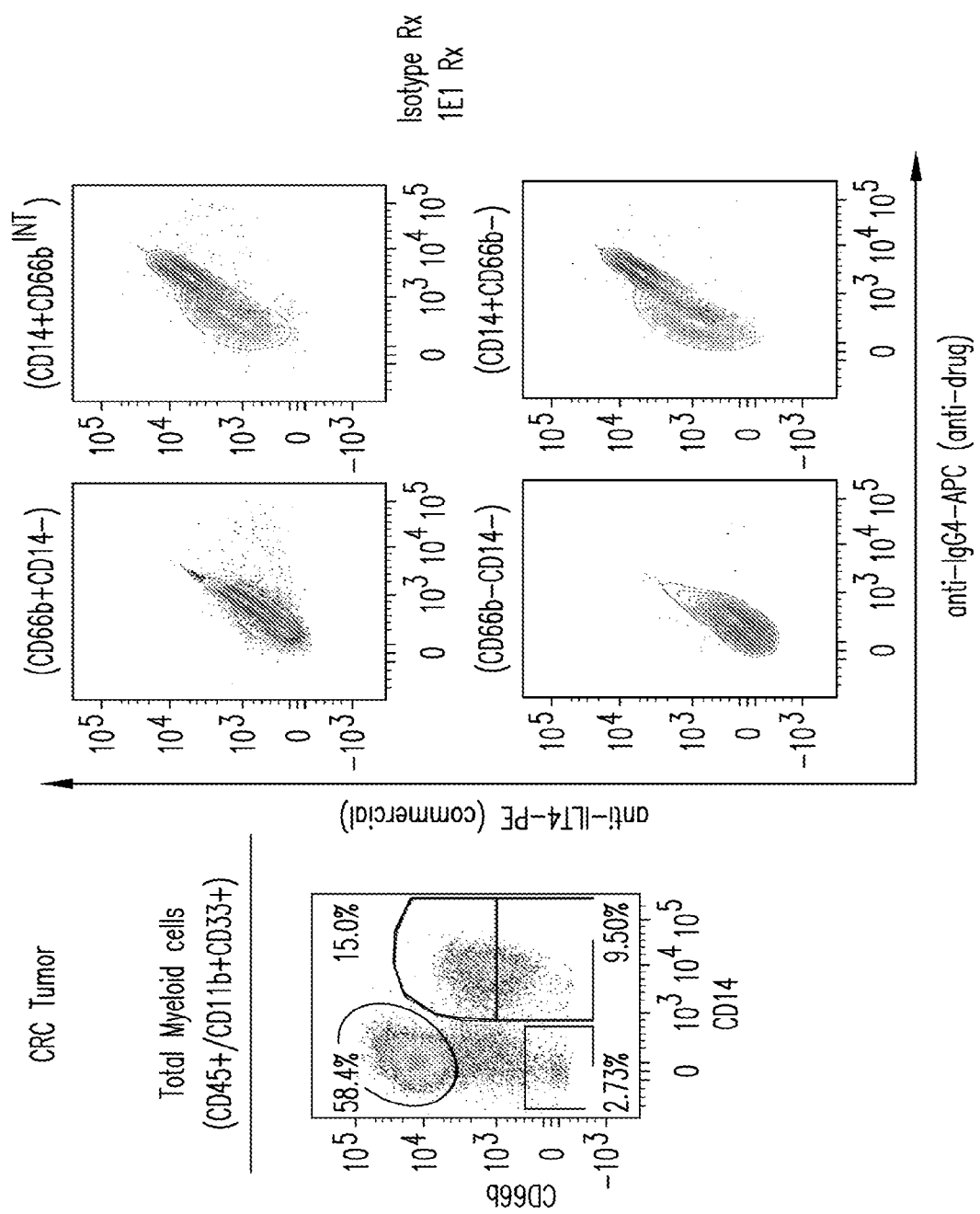

Example 7: Binding of 1E1(G4) to Myeloid Cells from Tumor Histoculture Samples Histocultures were prepared from fresh human tumor samples (surgical resections), and were treated with either anti-RSV IgG4 (isotype control) or 1E1(G4) at 20 pg/mL for 18-24 hours at 37° C. After treatment, tumor slices were digested into single cell suspensions and stained for FACS. Dot plots and contour plots represent FACS data from either RCC (FIG. 15A) or CRC (FIG. 15B) tumor histoculture single cell suspensions. Total myeloid cells can be subdivided into four subsets based on the expression of CD66b and/or CD14. These four myeloid subsets were simultaneously analyzed for ILT4 expression, using a non-competing commercial anti-ILT4-PE (BioLegend, cat #338706, San Diego, CA), and cell surface-bound 1E1(G4), using an anti-IgG4 secondary antibody. Good correlation between ILT4+ cells and 1E1(G4)+ cells was observed in 1E1(G4)-treated histocultures. Tumor-infiltrating lymphocytes were observed to be ILT4- and 1E1(G4)— in these samples.

The present invention is not to be limited in scope by the specific embodiments described herein. Indeed, the scope of the present invention includes embodiments specifically set forth herein and other embodiments not specifically set forth herein; the embodiments specifically set forth herein are not necessarily intended to be exhaustive. Various modifications of the invention in addition to those described herein will become apparent to those skilled in the art from the foregoing description. Such modifications are intended to fall within the scope of the claims.

Patents, patent applications, publications, product descriptions, and protocols are cited throughout this application, the disclosures of which are incorporated herein by reference in their entireties for all purposes.

SEQUENCE LISTING

The present specification is being filed with a computer readable form (CRF) copy of the Sequence Listing. The CRF entitled 24443USDIV1_SEQLIST.txt, which was created on Jun. 2, 2021 126 KB bytes in size, is incorporated herein by reference in its entirety.

We claim:

1. A polynucleotide comprising a nucleotide sequence encoding a VH, a VL, both a VH and a VL, a heavy chain immunoglobulin, a light chain immunoglobulin, or both a heavy chain and a light chain immunoglobulin of an antibody or antigen-binding fragment thereof that binds human ILT4, wherein the antibody or antigen-binding fragment thereof comprises a heavy chain variable domain comprising: a CDR-H1 having an amino acid sequence of GYYWS (SEQ ID NO: 16), a CDR-H2 having an amino acid sequence of EINHSGSTNYNPSLKS (SEQ ID NO: 47) or EINHAGSTNYNPSLKS (SEQ ID NO: 48), and a CDR-H3 having an amino acid sequence of LPTRWVTTRYFDL (SEQ ID NO: 18); and a light chain variable domain comprising: a CDR-L1 having an amino acid sequence of TGSSSNIGAGYDVH (SEQ ID NO: 19), a CDR-L2 having an amino acid sequence of GNSNRPS(SEQ ID NO: 49), GQSNRPS(SEQ ID NO: 50), GESNRPS(SEQ ID NO: 51), GDSNRPS(SEQ ID NO: 52), GNANRPS(SEQ ID NO: 53), GQANRPS(SEQ ID NO: 54), GEANRPS(SEQ ID NO: 55), or GDANRPS(SEQ ID NO: 56), and a CDR-L3 having an amino acid sequence of QSFDNSLSAYV (SEQ ID NO: 21).

2. The polynucleotide of claim 1, wherein the antibody or antigen-binding fragment thereof comprises a light chain variable domain comprising an amino acid sequence that is at least 90% identical to the amino acid sequence set forth in SEQ ID NO:58, 70, 71, 72, 73, or 77, and a heavy chain variable domain comprising an amino acid sequence that is at least 90% identical to the amino acid sequence set forth in SEQ ID NO:57, 63, or 69.

3. The polynucleotide of claim 1, wherein the antibody or antigen-binding fragment thereof comprises a light chain variable domain comprising the amino acid sequence set forth in SEQ ID NO:58, 70, 71, 72, 73, or 77, and a heavy chain variable domain comprising the amino acid sequence set forth in SEQ ID NO:57, 63, or 69.

4. The polynucleotide of claim 1, wherein the antibody or antigen-binding fragment thereof comprises a light chain comprising an amino acid sequence that is at least 90% identical to the amino acid sequence set forth in SEQ ID NO:3, 4, 5, 6, 7, or 45, and a heavy chain comprising an amino acid sequence that is at least 90% identical to the amino acid sequence set forth in SEQ ID NO:1, 2, 79, 80, or 81.

5. The polynucleotide of claim 1, wherein the antibody or antigen-binding fragment thereof comprises a light chain comprising the amino acid sequence set forth in SEQ ID NO:3, 4, 5, 6, 7, or 45, and a heavy chain comprising the amino acid sequence set forth in SEQ ID NO:1, 2, 79, 80, or 81.

6. A polynucleotide comprising a nucleotide sequence encoding a VH, a VL, both a VH and a VL, a heavy chain immunoglobulin, a light chain immunoglobulin, or both a heavy chain and a light chain immunoglobulin of an antibody or antigen-binding fragment thereof that binds human ILT4, wherein the antibody or antigen-binding fragment thereof comprises a heavy chain variable domain comprising: a CDR-H1 having an amino acid sequence of GYYWS (SEQ ID NO: 16), a CDR-H2 having an amino acid sequence of EINHAGSTNYNPSLKS (SEQ ID NO: 48), and a CDR-H3 having an amino acid sequence of LPTRWVTTRYFDL (SEQ ID NO: 18); and a light chain variable domain comprising: a CDR-L1 having an amino acid sequence of TGSSSNIGAGYDVH (SEQ ID NO: 19), a CDR-L2 having an amino acid sequence of GDSNRPS (SEQ ID NO: 52), and a CDR-L3 having an amino acid sequence of QSFDNSLSAYV (SEQ ID NO: 21).

7. The polynucleotide of claim 6, wherein the antibody or antigen-binding fragment thereof comprises a light chain variable domain comprising an amino acid sequence that is at least 90% identical to the amino acid sequence set forth in SEQ ID NO:58, and a heavy chain variable domain comprising an amino acid sequence that is at least 90% identical to the amino acid sequence set forth in SEQ ID NO:57.

8. The polynucleotide of claim 6, wherein the antibody or antigen-binding fragment thereof comprises a light chain variable domain comprising the amino acid sequence set forth in SEQ ID NO:58 and a heavy chain variable domain comprising the amino acid sequence set forth in SEQ ID NO:57.

9. The polynucleotide of claim 6, wherein the antibody or antigen-binding fragment thereof comprises a light chain comprising an amino acid sequence that is at least 90% identical to the amino acid sequence set forth in SEQ ID NO:7 and a heavy chain comprising an amino acid sequence that is at least 90% identical to the amino acid sequence set forth in SEQ ID NO:2.

10. The polynucleotide of claim 6, wherein the antibody or antigen-binding fragment thereof comprises a light chain comprising the amino acid sequence set forth in SEQ ID NO:7 and a heavy chain comprising the amino acid sequence set forth in SEQ ID NO:2.

11. The polynucleotide of claim 6, wherein the antibody or antigen-binding fragment thereof comprises a light chain comprising the amino acid sequence set forth in SEQ ID NO:7 and a heavy chain comprising the amino acid sequence set forth in SEQ ID NO:80.

12. The polynucleotide of claim 6, the nucleotide sequence encodes a light chain comprising the amino acid sequence set forth in SEQ ID NO:7.

13. The polynucleotide of claim 6, the nucleotide sequence encodes a heavy chain comprising the amino acid sequence set forth in SEQ ID NO:2.

14. The polynucleotide of claim 6, the nucleotide sequence encodes a heavy chain comprising the amino acid sequence set forth in SEQ ID NO:80.

15. The polynucleotide of claim 6, comprising the nucleotide sequence set forth in SEQ ID NO:87.

16. The polynucleotide of claim 6, comprising the nucleotide sequence set forth in SEQ ID NO:88.

17. A vector comprising the polynucleotide of claim 6.

18. A host cell comprising the vector of claim 17.

* * * * *